United States Patent
Cotterman et al.

(10) Patent No.: US 7,138,361 B2
(45) Date of Patent: Nov. 21, 2006

(54) HERBICIDAL HETEROCYCLES

(75) Inventors: Clifford Daniel Cotterman, Newark, DE (US); Chi-Ping Tseng, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 386 days.

(21) Appl. No.: 10/432,964

(22) PCT Filed: Nov. 20, 2001

(86) PCT No.: PCT/US01/43357

§ 371 (c)(1), (2), (4) Date: May 28, 2003

(87) PCT Pub. No.: WO02/44173

PCT Pub. Date: Jun. 6, 2002

(65) Prior Publication Data

US 2004/0106520 A1    Jun. 3, 2004

Related U.S. Application Data

(60) Provisional application No. 60/284,616, filed on Apr. 18, 2001, provisional application No. 60/273,469, filed on Mar. 5, 2001, provisional application No. 60/250,678, filed on Dec. 1, 2000.

(51) Int. Cl.
   *A01N 43/56* (2006.01)
   *C07D 401/04* (2006.01)
   *C07D 403/04* (2006.01)

(52) U.S. Cl. .................. 504/253; 504/280; 546/275.4; 548/364.1; 548/365.7

(58) Field of Classification Search ............. 548/364.1, 548/365.7; 546/275.4; 504/280, 253
See application file for complete search history.

(56) References Cited

FOREIGN PATENT DOCUMENTS

WO    WO 95 33719 A    12/1995

OTHER PUBLICATIONS

Patent Abstracts of Japan vol. 011, No. 394 (C-465), Dec. 23, 1987 and JP 62 153283 A (Tokuyama Soda Co Ltd) Jul. 8, 1987 abstract; example 51.

*Primary Examiner*—Kamal A. Saeed
*Assistant Examiner*—Rebecca Anderson

(57) ABSTRACT

Compounds of Formula (1), their N-oxides and agriculturally suitable salts, are disclosed which are useful for controlling undesired vegetation

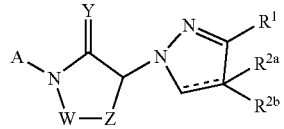

wherein
A, $R^1$, $R^{2a}$, $R^{2b}$, W, Y, and Z are as defined in the disclosure. Also disclosed are compositions containing the compounds of Formula (1) and a method for controlling undesired vegetation which involves contacting the vegetation or its environment with an effective amount of a compound of Formula (1).

20 Claims, No Drawings

HERBICIDAL HETEROCYCLES

CROSS-REFERENCE TO RELATED APPLICATIONS

This application is a national phase entry under 35 U.S.C. 371 from International Application No. PCT/US01/43357, filed 20 Nov. 2001, which claims priority benefit from U.S. Provisional Application No. 60/250,678, filed 01 Dec. 2000, U.S. Provisional Application No. 60/273,469, filed 05 Mar. 2001, and U.S. Provisional Application No. 60/284,616, filed 18 Apr. 2001.

FIELD OF THE INVENTION

This, invention relates to certain pyrazoles and pyrazolines, their N-oxides, agriculturally suitable salts and compositions, and methods of their use for controlling undesired vegetation.

BACKGROUND OF THE INVENTION

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Uncontrolled weed growth in such useful crops can cause significant reduction in productivity and thereby result in increased costs to the consumer. The control of undesired vegetation in noncrop areas is also important. For example, many products are commercially available for these purposes, but the need continues for new compounds that are more effective, less costly, less toxic, environmentally safer or have different modes of action.

World Patent Publication 95/33719 discloses compounds of Formula i as herbicides

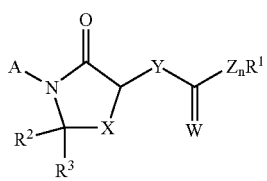

i

SUMMARY OF THE INVENTION

This invention is directed to compounds of Formula 1 including all geometric and stereoisomers, N-oxides, and agriculturally suitable salts thereof, agricultural compositions containing them and their use for controlling undesirable vegetation:

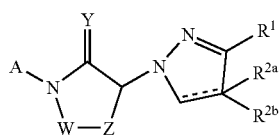

1 wherein:

A is an optionally substituted aryl or heteroaromatic ring, wherein the optional substituents are selected from halogen, cyano, $C_1$–$C_6$ alkyl, $C_1$–$C_4$ haloalkyl, $C_2$–$C_6$ alkenyl, $C_2$–$C_6$ alkynyl, $OR^8$, —$S(O)_kR^9$, —$C(O)R^{10}$, —$C(O)OR^{11}$ and —$C(O)NR^{12}R^{13}$; two substituents of the group A may combine to form a fused 5- or 6-membered saturated or partially saturated carbocyclic or heterocyclic ring, and said fused ring system is optionally substituted with one or more $R^7$;

Y is O or S;

Z is O, $S(O)_n$ or $CR^3R^4$;

W is $(CR^3R^4)_q$;

$R^1$ is H, $C_1$–$C_{12}$ alkyl, $C_1$–$C_{12}$ haloalkyl, $C_3$–$C_{12}$ cycloalkyl, $C_3$–$C_{12}$ halocycloalkyl, $C_4$–$C_{12}$ alkylcycloalkyl, $C_4$–$C_{12}$ alkylhalocycloalkyl, $C_1$–$C_{12}$ alkoxy, $C_1$–$C_{12}$ alkylthio, di-($C_1$–$C_2$ alkyl)amino, Cl, Br, I, —$C(O)R^5$, —$C(O)OR^5$, —$C(O)NR^5R^6$ or tri($C_1$–$C_4$ alkyl)silyl;

$R^{2a}$ is H, $C_1$–$C_4$ alkyl or $C_1$–$C_4$ haloalkyl; and $R^{2a}$ only exists when the carbon atom to which it is connected is a quaternary carbon center in which case the dotted line in Formula 1, together with the parallel solid line, represents a single bond;

$R^{2b}$ is H, $C_{1-4}$ alkyl, $C_1$–$C_4$ haloalkyl, $C_1$–$C_4$ alkoxy, $C_1$–$C_4$ haloalkoxy, F or Cl; or $R^1$ and $R^{2b}$ are taken together as —$C(R^3R^4)CH_2CH_2$—, —$C(R^3R^4)CH_2CH_2$—or —$(CH_2)_mO(CH_2)_t$—;

each $R^3$ and $R^4$ are independently H, $C_1$–$C_6$ alkyl or $C_1$–$C_6$ haloalkyl;

$R^5$ is $C_1$–$C_6$ alkyl, $C_{2-6}$ alkenyl, $C_3$–$C_6$ cycloalkyl, $C_3$–$C_6$ cycloalkyl or $C_1$–$C_6$ haloalkyl;

$R^6$ is H or $C_1$–$C_6$ alkyl;

each $R^7$ is independently $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, halogen, CN, $NO_2$ or hydroxy;

each $R^8$ is independently $C_1$–$C_4$ alkyl or $C_1$–$C_4$ haloalkyl;

each $R^9$ is independently $C_1$–$C_4$ alkyl or $C_1$–$C_4$ haloalkyl;

each $R^{10}$ is independently $C_1$–$C_4$ alkyl or $C_1$–$C_4$ haloalkyl;

each $R^{11}$ is independently $C_1$–$C_4$ alkyl, $C_{1-hd\,3}$ haloalkyl, $C_2$–$C_4$ alkenyl, $C_2$–$C_3$ haloalkenyl, $C_2$–$C_4$ alkynyl, $C_3$–$C_6$ cycloalkyl, $C_3$–$C_5$ halocycloalkyl, $C_3$–$C_6$ cycloalkenyl or $C_4$–$C_6$ cycloalkylalkyl;

each $R^{12}$ is independently H or $C_1$–$C_2$ alkyl;

each $R^{13}$ is independently $C_1$–$C_4$ alkyl; or $R^{12}$ and $R^{13}$ are taken together as —$(CH_2)_4$—, —$(CH_2)_5$— or —$(CH_2)_2O(CH_2)_2$—;

each k is independently 0, 1 or 2;

n is 0, 1 or 2;

q is 1 or 2;

m is 0, 1 or 2;

t is 0, 1 or 2; and m+t is 2 or 3;

provided that:

(a) each position on the aryl or heteroaromatic ring A vicinal (ortho) to the point of attachment of the aryl or heteroaromatic ring to the Formula 1 backbone is independently substituted with fluorine or not substituted;

(b) when A is a phenyl ring with a fluorine substituent meta to the point of attachment of the phenyl ring to the remainder of the Formula 1 backbone, then attached at the other meta position of the phenyl ring is a substituent other than fluorine;

(c) when A is a phenyl ring with at least one —$C(O)NR^{12}R^{13}$ substituent, then the at least one —$C(O)$ NR$^{12}$R$^{13}$ substituent is at a position other than meta to the point of attachment of the phenyl ring to the remainder of the Formula 1 backbone;

(d) when A is a phenyl ring, the position para to the point of attachment of the phenyl ring to the remainder of the Formula 1 backbone is unsubstituted or substituted by a substituent other than alkoxy;

(e) when A is a phenyl ring with a —C(O)OR$^{11}$ substituent at the position para to the point of attachment of the phenyl ring to the remainder of the Formula 1 backbone, then a substituent is attached to a position on the phenyl ring meta to the point of attachment of the phenyl ring to the remainder of the Formula 1 backbone;

(f) when A is a pyridine ring connected at the 2-position to the remainder of the Formula 1 backbone and methyl is at the 6-position of the pyridine ring, then the pyridine ring is substituted at the 4-position;

(g) when A is a pyrimidine ring connected at the 2-position to the remainder of the Formula 1 backbone, and when the 4-position of the pyrimidine ring is unsubstituted or is substituted with methyl, then the substituent at the 6-position of the pyrimidine ring is other than methyl, and when a methoxy substituent is at the 4-position of the pyrimidine ring, then the substituent at the 6-position of the pyrimidine ring is other than methoxy, (h) when A is an isothiazole ring connected at the 5-position to the remainder of the Formula 1 backbone, then the isothiazole ring is substituted with a substituent other than alkyl;

(i) when R$^1$ is a C$_3$–C$_{12}$ alkoxy group, then the alkyl moiety of the alkoxy group is branched at the carbon atom attached to the oxygen atom;

(j) when R$^1$ and R$^{2b}$ are taken together as —C(R$^3$R$^4$)CH$_2$CH$_2$—, —C(R$^3$R$^4$)CH$_2$CH$_2$CH$_2$—or —(CH$_2$)$_m$O(CH$_2$)$_t$— then Z is O or CR$^3$R$^4$; and (k) when R$^{2b}$ is connected to a quaternary carbon center, then R$^{2b}$ is H, C$_1$–C$_4$ alkyl or C$_1$–C$_4$ haloalkyl.

More particularly, this invention pertains to a compound of Formula 1, including all geometric and stereoisomers, an N-oxide or an agriculturally suitable salt thereof. This invention also relates to a herbicidal composition comprising a herbicidally effective amount of a compound of Formula 1 and at least one of a surfactant, a solid diluent or a liquid diluent. This invention further relates to a method for controlling the growth of undesired vegetation comprising contacting the vegetation or its environment with a herbicidally effective amount of a compound of Formula 1 (e.g., as a composition described herein).

DETAILS OF THE INVENTION

In the above recitations the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1–2 alkyl" indicates that one or two of the available positions for that substituent may be alkyl. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include CH$_3$OCH$_2$, IH$_3$OCH$_2$CH$_2$, CH$_3$CH$_2$OCH$_2$, CH$_3$CH$_2$CH$_2$CH$_2$OCH$_2$ and CH$_3$CH$_2$OCH$_2$CH$_2$. "Alkylthio" includes branched or straight-chain alkylthio moieties such as methylthio, ethylthio, and the different propylthio, butylthio, pentylthio and hexylthio isomers. "Cycloalkyl" includes, for example, cyclopropyl, cyclobutyl, cyclopentyl and cyclohexyl. "Saturated Carbocyclic" ring denotes a ring having a backbone consisting of carbon atoms linked to one another by single bonds; unless otherwise specified, the remaining carbon valences are occupied by hydrogen atoms.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include F$_3$C, ClCH$_2$, CF$_3$CH$_2$ and CF$_3$CCl$_2$. The terms "haloalkenyl", "haloalkynyl", "haloalkoxy", and the like, are defined analogously to the term "haloalkyl". Examples of "haloalkenyl" include (Cl)$_2$C=CHCH$_2$ and CF$_3$CH$_2$CH=CHCH$_2$. Examples of "haloalkynyl" include HC≡CCHCl, CF$_3$C≡C, CCl$_3$C≡C and FCH$_2$C≡CCH$_2$. Examples of "haloalkoxy" include CF$_3$O, CCl$_3$CH$_2$O, HCF$_2$CH$_2$CH$_2$O and CF$_3$CH$_2$O The total number of carbon atoms in a substituent group is indicated by the "C$_i$–C$_j$" prefix where i and j are numbers from 1 to 12. For example, C$_1$–C$_3$ alkylsulfonyl designates methylsulfonyl through propylsulfonyl; C$_2$ alkoxyalkyl designates CH$_3$OCH$_2$; C$_3$ alkoxy-alkyl designates, for example, CH$_3$CH(OCH$_3$), CH$_3$OCH$_2$CH$_2$ or CH$_3$CH$_2$OCH$_2$; and C$_4$ alkoxyalkyl designates the various isomers of an alkyl group substituted with an alkoxy group containing a total of four carbon atoms, examples including CH$_3$CH$_2$CH$_2$OCH$_2$ and CH$_3$CH$_2$OCH$_2$CH$_2$. In the above recitations, when a compound of Formula 1 contains a heterocyclic ring, all substituents are attached to this ring through any available carbon or nitrogen by replacement of a hydrogen on said carbon or nitrogen.

When a group contains a substituent which can be hydrogen, for example R$^3$, then, when this substituent is taken as hydrogen, it is recognized that this is equivalent to said group being unsubstituted. When a variable group is shown to be optionally attached to a position, for example (R$^{15}$)$_p$1 wherein p$^1$ may be 0, then hydrogen may be at the position even if not recited in the variable group definition. When a position on a group is said to be "not substituted" or "unsubstituted", then hydrogen atoms are attached to take up any free valency.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula 1, N-oxides and agriculturally suitable salts thereof. The compounds of the invention may be present as a mixture of stereoisomers, individual stereoisomers, or as an optically active form.

According to commonly accepted definition, the terms "aryl" and "aryl ring" denote a phenyl or benzene ring subject to optional substitution. The term "carbocyclic ring" denotes a ring wherein the atoms forming the ring backbone are selected only from carbon. The term "heteroaromatic ring" denotes a heterocyclic ring wherein each of the ring atoms is essentially in the same plane and has a p-orbital perpendicular to the ring plane, and in which (4n+2) π electrons, where n is 0 or a positive integer, are associated with the ring to comply with Hückel's Rule. The term "heterocyclic ring" denotes a ring wherein the atoms forming the ring backbone are selected from not only carbon but also heteroatoms such as oxygen, sulfur and nitrogen. For sake of illustration, heteroaromatic rings include, but are not limited to, furan, thiophene, pyrrole, pyrazole, imidazole, oxazole, thiazole, isoxazole, isothiazole, pyridine, pyridazine, pyrimidine, pyrazine and 1,3,5-triazine. The heterocyclic ring can be attached through any available carbon or nitrogen by replacement of a hydrogen on said carbon or nitrogen.

The aryl or heteroaromatic ring of radical A of Formula 1 is optionally substituted by one or more substituents selected from halogen, cyano, $C_1$–$C_6$ alkyl, $C_1$–$C_4$ haloalkyl, $C_2$–$C_6$ alkenyl, $C_2$–$C_6$ alkynyl, $OR^8$, —$S(O)_kR^9$, —$C(O)R^{10}$, —$C(O)OR^{11}$ and —$C(O)NR^{12}R^{13}$. Furthermore for the purpose of defining the scope of the invention, by removing in effect one hydrogen radical from each of two substituent groups, the groups may be combined to form a saturated or partially saturated 5 or 6-membered ring fused to the aforementioned aryl or heteroaromatic ring, and said fused ring system is optionally substituted with one or more $R^7$. For example, removing one hydrogen from each methyl of A-14 allows combination to form the fused dihydrofuran ring of A-56.

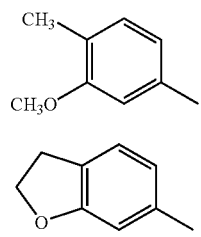

A-14

A-56

One skilled in the art will appreciate that not all nitrogen-containing heterocycles can form N-oxides, as oxidation to the oxide requires an available lone electron pair on the nitrogen atom; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–19, A. J. Boulton and A. McKillop, Eds., Pergamon Press; M. R. Grimmett and B. R. T. Keene in *Advances in Heterocyclic Chemistry*, vol. 43, pp 139–151, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Preferred for reason of better activity and/or ease of synthesis are compounds of Formula 1 above, geometric and stereoisomers thereof, N-oxides thereof, and agriculturally suitable salts thereof, wherein the dotted line in Formula 1, together with the parallel solid line, represents a double bond.

For reason of better activity and/or ease of synthesis, certain substituent groups in Formula 1 are preferred. Y is preferably O. Z is preferably O, S or $CH_2$. W is preferably $CH_2$. $R^1$ is preferably $C_{1-12}$ alkyl or $C_{3-12}$ cycloalkyl. More preferably, $R^1$ is $C_3$–$C_{12}$ alkyl, preferably branched, or $C_3$–$C_8$ cycloalkyl. Even more preferably, $R^1$ is branched $C_3$–$C_6$ alkyl or $C_4$–$C_6$ cycloalkyl. Most preferably, $R^1$ is isopropyl, tert-butyl, sec-butyl (—$CH(CH_3)(CH_2CH_3)$) or 3-pentyl (—$CH(CH_2CH_3)_2$). $R^{2a}$ is preferably H. $R^{2b}$ is preferably H or $C_1$–$C_4$ alkyl. More preferably, $R^{2b}$ is H. A is preferably substituted phenyl or 5 or 6-membered heterocyclic ring comprising 0–3 nitrogen atoms, 0–1 oxygen atoms and 0–1 sulfur atoms in said ring. More preferably, A is $A^1$, $A^2$, $A^3$, $A^4$, $A^5$, $A^6$, $A^7$ or $A^8$ as depicted:

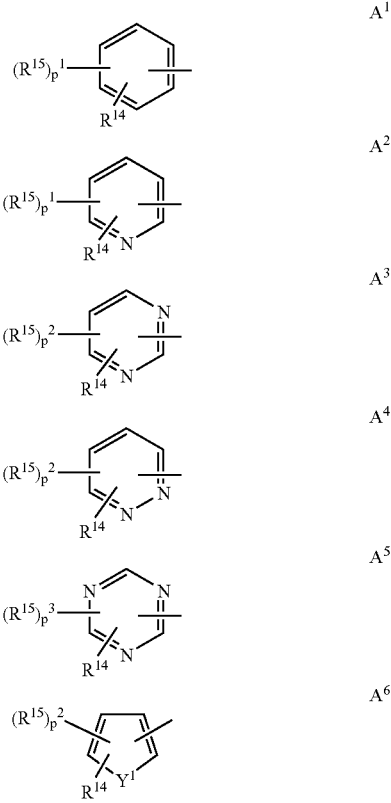

-continued

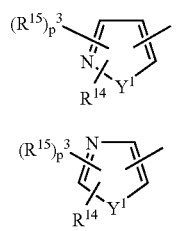

A⁷

$$A^8$$

wherein

R$^{14}$ is H, halogen, cyano, C$_1$–C$_6$ alkyl, C$_1$–C$_4$ haloalkyl, OR$^8$, —S(O)$_k$R$^9$, —C(O)R$^{10}$, —C(O)OR$^{11}$ or —C(O)NR$^{12}$R$^{13}$; such that R$^{14}$ is bound to a ring atom joined through one intervening ring atom to the ring atom linking the ring to the remainder of Formula 1;

each R$^{15}$ is independently halogen, cyano, C$_1$–C$_4$ alkyl, C$_1$–C$_4$ haloalkyl, C$_1$–C$_4$ alkoxy, C$_1$–C$_4$ alkylthio, C$_1$–C$_4$ haloalkylthio or C$_1$–C$_4$ haloalkoxy, or R$^{14}$ taken together with an adjacent R$^{15}$ is —(CH$_2$)$_3$—, —(CH$_2$)$_4$—, —O(CH$_2$)$_2$—, —O(CH$_2$)—, —S(CH2)$_2$— or —S(CH$_2$)$_3$—, each optionally substituted with 1–3 substituents selected from CH$_3$, CH$_2$CH$_3$ and F;

Y$^1$ is O, S or N—H; such that when Y$^1$ is N—H, the H of N—H may be replaced by an R$^{14}$ or R$^{15}$ substituent selected from alkyl, or the H of N—H may be replaced by the bond linking the ring to the remainder of Formula 1;

p$^1$ is 0, 1, 2 or 3;

p$^2$ is 0, 1 or 2;

p$^3$ is 0 or 1;

provided that at least one R$^{14}$ or R$^{15}$ is other than H.

Preferably, A is A$^1$, A$^2$, A$^3$, A$^4$ or A$^6$ wherein Y$^1$ is O or S. More preferably, A is A$^1$, A$^2$ or A$^6$ wherein Y$^1$ is O or S. Most preferably, A is A$^1$, A$^2$ or A$^6$ wherein Y$^1$ is S. Preferably R$^{14}$ is halogen, cyano, C$_1$–C$_6$ alkyl, C$_1$–C$_4$ haloalkyl, OR$^8$, —S(O)$_k$R$^9$, —C(O)R$^{10}$ or —C(O)OR$^{11}$; and R$^{15}$ is halogen, cyano, C$_{1-4}$ alkyl, C$_1$–C$_4$ haloalkyl, C$_1$–C$_4$ alkoxy, C$_1$–C$_4$ alkylthio, C$_1$–C$_4$ haloalkylthio or C$_1$–C$_4$ haloalkoxy, or R$^{14}$ taken together with an adjacent R$^{15}$ is —(CH$_2$)$_3$—, —(CH$_2$)$_4$—, —O(CH$_2$)$_2$—, —O(CH$_2$)$_3$—S(CH$_2$)$_2$— or —S(CH$_2$)$_3$—, each optionally substituted with 1–3 substituents selected from CH$_3$, CH$_2$CH$_3$ and F; such that the left-hand bond is connected at the R$^{14}$ position and the right-hand bond is connected at the R$^{15}$ position. More preferably, R$^{14}$ is halogen, C$_1$–C$_6$ alkyl, C$_1$–C$_4$ haloalkyl, OR$^8$, —S(O)$_k$R$^9$, —C(O)R$^{10}$ or —C(O)OR$^{11}$. Even more preferably, R$^{14}$ is Br, C$_1$–C$_6$ alkyl, CF$_2$H, CF$_3$, C$_1$–C$_4$ alkoxy, OCF$_3$, OCF$_2$H, —C(O)R$^{10}$ or —C(O)OR$^{11}$. Most preferably, R$^{14}$ is Br, C$_1$–C$_5$ alkyl, CF$_2$H, CF$_3$, C$_1$–C$_4$ alkoxy, OCF$_3$, OCF$_2$H or —C(O)OCH$_3$. Preferably, p$^1$ is 0 or 1, p$^2$ is 0 or 1 and p$^3$ is 0 or 1. More preferably, R$^{15}$ is halogen, C$_{1-2}$ alkyl or C$_1$–C$_2$ alkoxy. Even more preferably, R$^{15}$ is C$_1$–C$_6$ alkyl or halogen. Most preferably, R$^{15}$ is CH$_3$, F, Cl or Br, or p$^1$ is 0, p$^2$ is 0 and p$^3$ is 0, and when R$^{15}$ is CH$_3$, Cl or Br, it is preferably bound to a ring atom joined through two intervening ring atoms to the ring atom linking the ring to the remainder of Formula 1; for example, when A is A$^1$, R$^{15}$ being CH$_3$ is preferably in the para position. k is preferably 0. R$^{10}$ is preferably C$_1$–C$_2$ alkyl, and most preferably CH$_3$. R$^{11}$ is preferably C$_1$–C$_2$ alkyl, and most preferably CH$_3$. R$^{12}$ is preferably CH$_3$. R$^{13}$ is preferably CH$_3$.

Compounds of the invention illustrating groups preferred for reasons of better activity and/or ease of synthesis are:

Preferred A. A compound of Formula 1 above, geometric and stereoisomers thereof, N-oxides thereof, and agriculturally suitable salts thereof of, wherein the optional substituents on A are selected from halogen, C$_1$–C$_4$ alkyl, C$_1$–C$_4$ haloalkyl, C$_1$–C$_4$ alkoxy, C$_1$–C$_4$ alkylthio, C$_1$–C$_4$ haloalkylthio or C$_1$–C$_4$ haloalkoxy; two or more substituents of the group A may combine to form a fused 5 or 6-membered saturated or partially saturated carbocyclic or heterocyclic ring, and said ring system is optionally substituted with one or more R$^7$; and R$^1$ is H, C$_1$–C$_6$ alkyl, C$_1$–C$_6$ haloalkyl, C$_3$–C$_9$ cycloalkyl, C$_3$–C$_9$ halocycloalkyl, C$_3$–C$_{12}$ alkylcycloalkyl, C$_3$–C$_{12}$ alkylhalocycloalkyl, C$_1$–C$_6$ alkoxy, C$_1$–C$_6$ alkylthio, Cl, Br, I, —C(O)R$^5$, —C(O)OR$^5$, —C(O)NR$^5$R$^6$ or tialkylsilane.

Preferred B. A compound of Formula 1 above, geometric and stereoisomers thereof, N-oxides thereof, and agriculturally suitable salts thereof, wherein A is substituted phenyl or 5 or 6-membered heterocyclic ring comprising 0–3 nitrogen atoms, 0–1 oxygen atoms and 0–1 sulfur atoms in said ring.

Preferred B1. A compound of Preferred B wherein

A is A$^1$, A$^2$, A$^3$, A$^4$, A$^5$, A$^6$, A$^7$ or A$^8$;

R$^{14}$ is H, halogen, cyano, C$_1$–C$_6$ alkyl, C$_1$–C$_4$ haloalkyl, OR$^8$, —S(O)$_k$R$^9$, —C(O)R$^{10}$ or —C(O)OR$^{11}$; such that R$^{14}$ is bound to a ring atom joined through one intervening ring atom to the ring atom limiting the ring to the remainder of Formula 1;

each R$^{15}$ is independently halogen, cyano, C$_1$–C$_4$ alkyl, C$_1$–C$_4$ haloalkyl, C$_1$–C$_4$ alkoxy, C$_1$–C$_4$ alkylthio, C$_1$–C$_4$ haloalkylthio or C$_1$–C$_4$ haloalkoxy; or R$^{14}$ taken together with an adjacent R$^{15}$ is —(CH$_2$)$_3$—, —(CH$_2$)$_4$—, —O(CH$_2$)$_2$—, —O(CH$_2$)$_3$—, —S(CH$_2$)$_2$— or —S(CH$_2$)$_3$—, each optionally substituted with 1–3 substituents selected from CH$_3$, CH$_2$CH$_3$ and F;

Y$^1$ is O, S or N—H; such that when Y$^1$ is N—H, an alkyl R$^{14}$ or R$^{15}$ substituent or the linking bond may replace H of N—H;

p$^1$ is 0, 1, 2 or 3;

p$^2$ is 0, 1 or 2;

p$^3$ is 0 or 1;

provided that at least one R$^{14}$ or R$^{15}$ is other than H.

Preferred B2. A compound of Preferred B1 wherein

Y is O;

Z is O, S or CH$_2$;

W is CH$_2$;

R$^1$ is C$_1$–C$_{12}$ alkyl or C$_3$–C$_{12}$ cycloalkyl;

R$^{2a}$ is H; and

R$^{2b}$ is H or C$_1$–C$_4$ alkyl.

Preferred B3. A compound of Preferred B2 wherein the dotted line in Formula 1, together with the parallel solid line, represents a double bond; and R$^{2b}$ is H.

Preferred B4. A compound of Preferred B3 wherein

A is A$^1$, A$^2$ or A$^6$;

Y$^1$ is O or S;

R$^{14}$ is halogen, C$_1$–C$_6$ alkyl, C$_1$–C$_4$ haloalkyl, OR$^8$, —S(O)$_k$R$^9$, —C(O)R$^{10}$ or —C(O)OR$^{11}$;

R$^{15}$ is halogen, C$_1$–C$_4$ alkyl, C$_1$–C$_4$ haloalkyl, C$_1$–C$_4$ alkoxy, C$_1$–C$_4$ alkylthio, C$_1$–C$_4$ haloalkylthio or C$_1$–C$_4$ haloalkoxy;

or R$^{14}$ taken together with an adjacent R$^{15}$ is —(CH$_2$)$_3$—, —(CH$_2$)$_4$—, —O(CH$_2$)$_2$—, —O(CH$_2$)$_3$—, —S(CH$_2$)$_2$—, —S(CH$_2$)$_3$—, each optionally substituted with 1–2 CH$_3$, CH$_2$CH$_3$ or F; such that the left-hand bond is connected at the $R^{14}$ position and the right-hand bond is connected at the $R^{15}$ position;
$p^1$ is 0 or 1; and
$p^2$ is 0 or 1.

Preferred B5. A compound of Preferred B4 wherein $R^1$ is branched $C_3$–$C_8$ alkyl or $C_4$–$C_6$ cycloalkyl.

Preferred B6. A compound of Preferred B5 wherein $R^1$ is isopropyl, tert-butyl, sec-butyl or 3-pentyl.

Preferred B7. A compound of Preferred B4 wherein
Y¹ is S;
$R^{14}$ is Br, $C_1$–$C_6$ alkyl, $CF_2H$, $CF_3$, $C_1$–$C_4$ alkoxy, $OCF_3$, $OCF_2H$, —C(O)$R^{10}$ or —C(O)O$R^{11}$;
$R^{15}$ is halogen, $C_1$–$C_2$ alkyl or $C_1$–$C_2$ alkoxy;
$R^{10}$ is $C_1$–$C_2$ alkyl; and
$R^{11}$ is $C_1$–$C_2$ alkyl.

Preferred B8. A compound of Preferred B7 wherein
$R^{14}$ is Br, $C_1$–$C_5$ alkyl, $CF_2H$, $CF_3$, $C_1$–$C_4$ alkoxy, $OCF_3$, $OCF_2H$, or —C(O)OCH$_3$;

Preferred B9. A compound of Preferred B8 wherein $R^{15}$ is $C_1$–$C_2$ alkyl.

Preferred B10. A compound of Preferred B9 wherein
$p^1$ is 0 and
$p^2$ is 0.

Preferred B11. A compound of Preferred B4 wherein $R^{15}$ is $CH_3$.

Preferred B12. A compound of Preferred B11 wherein
$p^1$ is 0; and
$p^2$ is 0.

Preferred B13. A compound of Preferred B4 wherein
A is $A^1$;
$R^{14}$ is $C_1$–$C_4$ alkoxy;
$R^{15}$ is $CH_3$, F, Cl or Br and is in the para position relative to the bond connecting A to the remainder of Formula 1; and
$p^1$ is 1.

Preferred B14. A compound of Preferred B5 wherein A is selected from

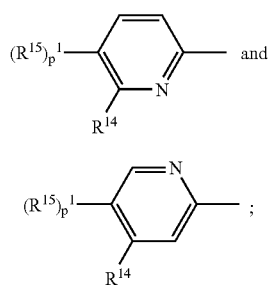

$R^{14}$ is $OCH_3$ or $OCH_2CH_3$;
$R^{15}$ is F, Cl or Br;
$p^1$ is 0 or 1; and
$R^1$ is $CH(CH_3)_2$, $CH(CH_3)(C_2H_5)$, $C(CH_3)_3$, $CH(C_2H_5)_2$ or $CH(CH_3)(CH_2CH_2CH_3)$.

Specifically preferred is a compound of Formula 1 selected from the group consisting of:
(a) 5-[3-(1,1-dimethylethyl)-1H-pyrazol-1-yl]-3-[3-(trifluoromethyl)phenyl]-4-thiazolidinone;
(b) 3-[3-(1,1-dimethylethyl)-1H-pyrazol-1-yl]-1-[3-(trifluoromethyl)phenyl)]-2-pyrrolidinone;
(c) 5-[3-(1,1-dimethylethyl)-1H-pyrazol-1-yl]-3-[3-(trifluoromethyl)phenyl]-4-oxazolidinone;
(d) 3-[3-(1,1-dimethylethyl)-1H-pyrazol-1-yl]-1-(3-methoxy-4-methylphenyl)-2-pyrrolidinone;
(e) 5-[3-(1-methylpropyl)-1H-pyrazol-1-yl]-3-[3-(trifluoromethyl)phenyl]-4-oxazolinone; and
(f) 5-[(3-(1-ethylpropyl)-1H-pyrazol-1-yl]-3-[3-(trifluoromethyl)phenyl]-4-oxazolidinone;
(g) 1-(4-chloro-3-methoxyphenyl)-3-[3-(1,1dimethylethyl)-1H-pyrazol-1-yl]-2-pyrrolidinone; and
(h) 1-(4-chloro-3-methoxyphenyl)-3-[3-(1-ethylpropyl)-1H-pyrazol-1-yl]-2-pyrrolidinone.

The preferred compositions of the present invention and the preferred methods of use are those involving the above preferred compounds. Compounds of the invention are particularly useful for selective control of weeds in maize (corn) and/or rice crops.

Compounds of the Formula 1 can be readily prepared by one skilled in the art by using the reactions and techniques described in Scheme 1 to Scheme 4 below. In cases where a substituent of the starting material is not compatible with the reaction conditions described for any of the reaction schemes, the substituent can be converted to a protected form prior to the described reaction scheme and then deprotected after the reaction using commonly accepted protection/deprotection techniques (see Green, T. W and Wuts, P. G., *Protecting Groups in Organic Transformations*, 3rd Edition, John Wiley and Sons, New York, 1999). Otherwise, alternative approaches known to one skilled in the art are available. The definitions of A, $R^1$, $R^{2a}$, $R^{2b}$, W, Y, and Z in compounds of Formulae 1–4 below are as defined in the Summary of the Invention.

As shown in Scheme 1, a compound of Formula 1 wherein Y is O can be prepared by contacting a compound of Formula 2 with 1–2 molar equivalents of a compound of Formula 3 in the presence of 1–1.5 molar equivalents of a dialkyl azodicarboxylate such as diethyl azodicarboxylate and 1–2 molar equivalents of a triarylphosphine such as triphenylphosphine.

SCHEME 1

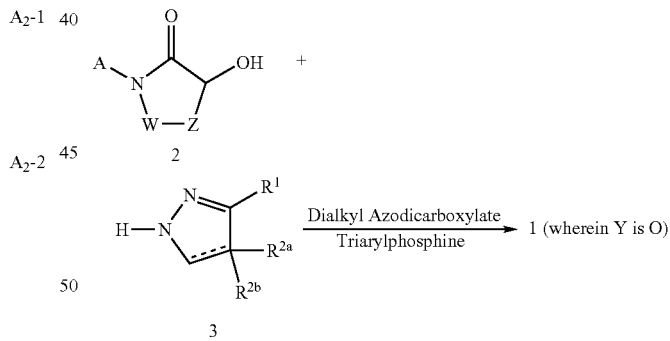

The reaction is carried out in an inert solvent such as diethyl ether, tetrahydrofuran, methylene chloride, toluene or xylene at temperatures between −20 and 110° C., and preferably from −10° C. to ambient temperatures. The reaction time ranges from 1 hour to 4 days. The compound of Formula 1 is isolated using conventional purification methods such as extraction, concentration, chromatography and crystallization.

As shown in Scheme 2, a compound of Formula 1 wherein Y is O and Z is O or S can also be prepared by contacting a compound of Formula 2 wherein Z is O or S with a mixture prepared by mixing 1–2.5 molar equivalents of a compound of Formula 3, 1–2.5 molar equivalents of thionyl chloride and 2–5 molar equivalents of diisopropylethylamine in an inert solvent such as methylene chloride, tetrahydrofuran, diethyl ether, toluene or xylene.

SCHEME 2

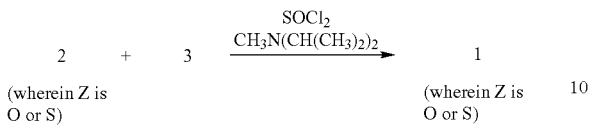

(wherein Z is O or S)    (wherein Z is O or S)

The reaction is carried out at temperatures between −20 and 110° C. and preferably from 0° C. to ambient temperature. The reaction time ranges from 1 hour to 5 days. The compound of Formula 1 is isolated using conventional purification methods.

Alternatively as shown in Scheme 3, a compound of Formula 1 wherein Y is O is prepared by contacting a compound of Formula 4 with a compound of Formula 3 in the presence of a base such as N,N-diisopropylethylamine, NaH or KOC(CH$_3$)$_3$ or an excess of the compound of Formula 3.

SCHEME 3

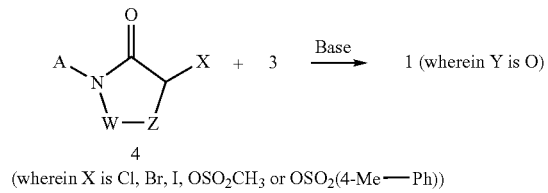

(wherein X is Cl, Br, I, OSO$_2$CH$_3$ or OSO$_2$(4-Me—Ph))

The reaction is carried out by adding 1 molar equivalent of a compound of Formula 4 to a mixture of 1–2.5 molar equivalents of a compound of Formula 3 in an inert solvent such as diethyl ether, tetrahydrofuran, methylene chloride, NN-dimethylformamide or toluene under N$_2$ at ambient temperature. When less than about 2 molar equivalents of the Formula 3 compound is used, then about 0.5–2.5 molar equivalents of an additional base such as N,N-diisopropylethylamine, NaH or KOC(CH$_3$)$_3$ is optionally included in the Formula 3 mixture before addition of the Formula 4 compound. After the addition, the reaction mixture is stirred at temperatures between about −20 to 110° C., and preferably from about −10° C. to around 90° C. for a period of time ranging from 1 hour to 4 days. The reaction mixture is then poured into an excess amount of water and the aqueous layer is extracted with ethyl acetate between one to three times. The organic layers are separated from the aqueous layers, then combined and dried over a drying agent such as MgSO$_4$ or Na$_2$SO$_4$ and subsequently concentrated. The residue is purified by conventional techniques such as column chromatography over silica gel with eluents such as solutions of ethyl acetate and hexanes in various ratios or solutions of methylene chloride and hexanes in various ratios to give the desired compounds of Formula 1 wherein Y is O.

As shown in Scheme 4, a compound of Formula 1 wherein Y is S is prepared by treating a compound of Formula 1 wherein Y is O with Lawesson's Reagent (2,4-bis(4-methoxyphenyl)-1,3-dithia-2,4-diphosphetane-2,4-disulfide) or P$_2$S$_5$ using methods or slight modification thereof taught in: *Heterocycles* 1995, 40(1), 271–8; *J. Med. Chem.* 1990, 33(10), 2697–706; *Synthesis* 1989, (5), 396–7; *J. Chem. Soc., Perkin Trans.* 1 1988, (7), 1663–8; *Tetrahedron* 1988, 44(10), 3025–36; and *J. Org. Chem.* 1988, 53(6), 1323–6.

SCHEME 4

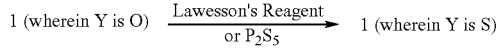

1 (wherein Y is O)  →(Lawesson's Reagent or P$_2$S$_5$)→  1 (wherein Y is S)

Compounds of Formula 2 and Formula 4 are known in the art. Useful methods for their synthesis are compiled in European Patent Publication 0200415-A1 and World Patent Publications 94/13652, 95/33719, 97/19920, 97/20838, 97/28138 and 00/21928, and references cited therein.

Compounds of Formula 3 are either commercially available or can be prepared by one skilled in the art using literature methods or with slight modification thereof. Some examples of the above-mentioned literature methods are published in: A. R. Katritzky & C. W. Rees (editors), *Comprehensive Heterocyclic Chemistry*, (1984) Vol. 5, 167–304; Arnold Weissberger (editor), *Heterocyclic Compounds*, (1967), Vol. 22, 3–278; *Chin. Chem. Lett.* 1998, 9(9), 803–804; *Synthesis* 1998, (11), 1645–1654; *Indian J. Chem., Sect. B: Org. Chem. Incl. Med. Chem.* 1995, 34B(9), 811–15; European Patent Number 546420; *J. Indian Chem. Soc.* 1991, 68(5), 281–4; *J. Heterocycl. Chem.* 1990, 27(2), 205–8; *Synth. Commun.* 1989, 19(18), 315–968; *Synthesis* 1989, (4), 320–1; *J. Chem. Soc., Perkin Trans.* 1 1987, (4), 885–97; *J. Chem. Soc., Perkin Trans.* 1 1985, (10), 2177–84; *J. Org. Chem.* 1986, 51(12), 2366–8; *J. Chem. Soc., Perkin Trans.* 1 1994, (4), 461–70; *Heterocycles* 1986, 24(2), 289–96; *Tetrahedron Lett.* 1998, 39(20), 3287–3290; *Synthesis* 1997, (3), 337–341; *J. Am. Chem. Soc.* 1993, 115(3), 1153–4; *Heterocycles* 1986, 24(4), 1075–8; *Synthesis* 1997, (10), 1140–1142; *Tetrahedron Lett.* 1996, 37(7), 1095–6; *Synth. Commun.* 1995, 25(5), 761–74; *J. Org. Chem.* 1988, 53(24), 5685–9; *Heterocycles* 1986, 24(4), 1075–8; and *Synthesis* 1985, (6–7), 690–1.

It is recognized that some reagents and reaction conditions described may not be compatible with certain functionalities present in the intermediates. In these instances, the incorporation of protection/deprotection sequences into the synthesis will aid in obtaining the desired products. The use and choice of protecting groups will be apparent to one skilled in chemical synthesis.

One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane, s=singlet, d=doublet, t=triplet, q=quartet, m=multiplet, dd=doublet of doublets, dt=doublet of triplets, br s=broad singlet.

EXAMPLE 1

Preparation of 5-[3-(1,1-dimethylethyl)-1H-pyrazol-1-yl]-3-[3-(trifluoromethyl)phenyl]-4-thiazolidinone To tetrahydrofuran (15 mL) at about −10° C. stirred under a nitrogen atmosphere were added diethyl azodicarboxylate (0.66 mL, 4.18 mmol), 5-hydroxy-3-[3-(trifluoromethyl)phenyl]-4-thiazolidinone (1 g, 3.8mmol), 3-(1,1-dimethylethyl)-1H-pyrazole (0.48 g, 3.8 mmol) and triphenylphosphine (1.2 g, 4.41 mmol). After the addition, the reaction mixture was allowed to warm up to room temperature, and stirred overnight under a nitrogen atmosphere. The reaction mixture was concentrated, and the residue taken into a small amount of methylene chloride and then filtered. The filtrate was loaded on silica gel in a medium pressure liquid chromatography column and eluted with a solution of 20% ethyl acetate and 80% hexanes followed by a solution of 33% ethyl acetate and 67% hexanes to give 0.26 g of a crude product. The crude product was further purified by medium pressure liquid chromatography (silica gel, 9% ethyl acetate/91% hexanes) to afford the title compound, a compound of this invention, as a viscous oil (130 mg).

$^1$H NMR (CDCl$_3$): δ 1.28 (s, 9H), 4.75 (d, 1H), 5.37 (d, 1H), 5.97 (s, 1H),616 (d, 1H), 745 (d, 1H), 7.46–7.8 (m, 4H).

EXAMPLE 2

Preparation of 5-[3-(1,1-dimethylethyl)-1H-pyrazol-1-yl]-3-[3-(trifluoromethyl)phenyl]-4-thiazolidinone To a stirred solution of thionyl chloride (5.3 mL, 73 mmol) in 120 mL of methylene chloride at ~10° C. was slowly added 3-(1,1-dimethylethyl)-1H-pyrazole (11.32 g, 91 mmol). The resulting solution was stirred for ~20 minutes and was then cooled further to ~0° C. To this solution was added N,N-diisopropylethylamine (26.5 mL, 152 mmol) dropwise at ~0° C. and then 5-hydroxy-3-[3-(trifluoromethyl)phenyl]4thiazolidinone (16 g, 61 mmol) portionwise at temperatures between 0° C. and 10° C. After the addition, the reaction mixture was allowed to warm up to room temperature, and stirred at room temperature for 3 days. To the reaction mixture was then added 120 mL of concentrated sodium bicarbonate aqueous solution. The methylene chloride layer was separated and the aqueous layer was extracted twice with methylene chloride (~120 mL each). The methylene chloride layers were combined, dried over MgSO$_4$ and then concentrated. The residue was loaded on silica gel in a flash chromatography column and eluted with hexanes followed by methylene chloride to give 15.74 g of a crude product. The crude product was further purified by trituration in hexanes followed by filtration to give the title compound, a compound of this invention, as a tan solid (11.8 g) melting at 66–69° C.

$^1$H NMR (CDCl$_3$): δ 1.28 (s, 9H), 4.75 (d, 1H), 5.37 (d, 1H), 5.97 (s, 1H),616 (d, 1H), 745 (d, 1H), 7.46–7.8 (m, 4H).

EXAMPLE 3

Preparation of 3-[3-(1,1-dimethylethyl)-1H-pyrazol-1-yl]-1-[3-(trifluoromethyl)phenyl]-2-pyrrolidinone To a solution of 3-(1,1-dimethylethyl)1H-pyrazole (0.22 g, 1.8 mmol) in N,N-dimethylformamide (20 mL) under nitrogen at room temperature was added 60% sodium hydride in mineral oil (90 mg, 2.16 mmol). After the addition, the mixture was stirred at room temperature for ~15 minutes, and 3-hydroxy-1-[3-(trifluoromethyl)phenyl]-2-pyrrolidinone methanesulfonate (0.5 g, 1.8 mmol) was added. The resulting reaction mixture was stirred at room temperature overnight and then poured into water (~100 mL). The aqueous layer was extracted twice with ethyl acetate (~30 mL each; brine solution was added to separate the two layers). The organic extracts were combined, dried over MgSO$_4$ and filtered. The filtrate was concentrated and the residue purified by column chromatography (silica gel, ~20% ethyl acetate/80% hexanes) to give the title compound, a compound of this invention, as a yellow solid (300 mg) melting at 76–78° C.

$^1$H NMR (CDCl$_3$): δ 1.29 (s, 9H), 2.69–2.92 (m, 2H), 3.93 (m, 1H), 4.12 (m, 1H),4.12 (m,1H),504 t, 1H), 6.16 (d, 1H), 7.4–7.55 (m, 3H), 7.89–8.00 (m, 2H).

EXAMPLE 4

Preparation of 5-[3-(1,1-dimethylethyl)-1H-pyrazol-1-yl]-3-[3-(trifluoromethyl)phenyl]-4-oxazolidinone To a solution of 5-hydroxy-3-[3-(trifluoromethyl)phenyl]-4-oxazolidinone (1 g, 4.05 mmol) in tetrahydrofuran (20 mL) under nitrogen at ~0° C., were added 3-(1,1-dimethylethyl)-1H-pyrazole (0.5 g, 4.05 mmol), triphenylphosphine (1.23 g, 4.7 mmol) and diisopropyl azodicarboxylate (0.88 mL, 4.46 mmol). After the addition, the reaction mixture was allowed to warm up slowly to room temperature and stirred at room temperature overnight. The reaction mixture was then concentrated, and the residue was purified by column chromatography (silica gel, ~20% ethylacetate/80% hexanes) to give a crude product. The crude product was further purified by column chromatography (silica gel, ~20% ethyl acetate/~80% hexanes) to give the title compound, a compound of this invention, as a white solid (14 mg) melting at 95–98° C.

$^1$H NMR (CDCl$_3$): δ 1.26 (s, 9H), 5.57 (d, 1H), 5.79 (d, 1H), 6.08 (s, 1H), 620 (d, 1H) 7.45–7.6 (m, 3H), 7.8–7.9 (m, 2H).

EXAMPLE 5

Step A: Preparation of 3-(1-ethylpropyl)-1H-pyrazole

To a stirred suspension of sodium methoxide (23.6 g, 0.437 mol) in diethyl ether (~800 mL) was added dropwise a solution of 3-ethyl-2-pentanone (49.9 g, 0.437 mol) and ethyl formate (32.4 g, 0.437 mol) in diethyl ether (~200 mL) at temperatures between 10° C. and 20° C. After the addition, the reaction mixture was allowed to warm up to room temperature, and stirred at room temperature for 2 hours. Additional diethyl ether (~800 mL) was then added. The reaction mixture was stirred at room temperature for one additional hour and then concentrated. The residue was suspended in a solution of ethanol (950 mL) and acetic acid (30 mL). To this suspension was added hydrazine monohydrate (24 mL, 0.49 mol). The reaction mixture was heated at reflux for 60 hours and was then allowed to cool slowly to room temperature. The reaction mixture was then concentrated. To the residue was added 200 mL of 1N hydrochloric acid, followed by ~75 mL of concentrated hydrochloric acid until pH ~0. The acidic aqueous solution was then washed twice with diethyl ether (~250 mL each). The pH of the aqueous solution was then adjusted to 9–10 by addition of aqueous 50% sodium hydroxide solution. The aqueous solution was then extracted twice with diethyl ether (~300 mL each). The diethyl ether extracts were combined, dried over MgSO$_4$ and concentrated to give the title compound as a pale yellow oil (41 g).

$^1$H NMR (CDCl$_3$): δ 0.84 (t, 6H), 1.5–1.8 (m, 4H), 2.53–2.65 (m, 1H), 6.06 (d, 1H).

Step B: Preparation of 5-[3-(1-ethylpropyl)-1H-pyrazol-1-yl]-3-[3-(trifluoromethyl)phenyl]-4-oxazolidinone To a stirred solution of thionyl chloride (5 mL, 68.55 mmol) in methylene chloride (100 mL) at ~10° C. was slowly added 3-(1-ethylpropyl)-1H-pyrazole (11.74 g, 84.94 mmol). The resulting solution was stirred for ~20 minutes and was then cooled to ~0° C. To this solution was added N,N-diisopropylethylamine (24.7 mL, 141.8 mmol) dropwise and then 5-hydroxy-3-[3-(trifluoromethyl)phenyl]-4-oxazolidinone (14 g, 56.64 mmol), portionwise at temperatures between 0° C. and 15° C. After the addition, the reaction mixture was allowed to warm to room temperature, and then stirred at room temperature for 2 days. To the reaction mixture was then added concentrated aqueous sodium bicarbonate solution (100 mL). The methylene chloride layer was separated, and the aqueous layer was extracted twice with methylene chloride (~100 mL each). The methylene chloride layers were combined, dried over MgSO$_4$ and then concentrated. The residue was loaded on silica gel in a column and eluted with methylene chloride to give a crude product. The crude product was further purified by trituration in hexanes followed by filtration to give the title compound, a compound of this invention, as a white solid (10.67 g) melting at 83–85° C.

$^1$H NMR (CDCl$_3$): δ 0.83 (t, 6H), 1.44–1.7 (m, 4H), 2.45–2.60 (m, 1H), 556 (m, 1H),580 (m, 1H), 6.08 (s, 1H), 6.15 (d, 1H), 7.5–7.6 (m, 3H), 7.85 (m, 2H).

EXAMPLE 6

Step A: Preparation of 3-bromo-1-(4-chloro-3-methoxyphenyl)-2-pyrrolidinone

To a stirred solution of 4-chloro-3-methoxybenzeneamine (4.7 g, 29.6 mmol) in methylene chloride (100 mL) at ~0° C. was slowly added 2,4dibromobutyryl chloride (5.1 mL, 39 mmol). After the addition, the reaction mixture was stirred for ~5 minutes and triethylamine (24.7 mL, 178 mmol) was then added. The resulting reaction mixture was allowed to warm up to room temperature and stirred at room temperature for 5 days. Water (~100 mL) was then added to the reaction mixture. The organic layer was separated, dried over MgSO$_4$ and concentrated. The residue was purified by column chromatography (silica gel, ~33% ethyl acetate/~67% hexanes) to give the title compound as a yellow solid (3.9 g) melting at 113–115° C.

$^1$H NMR (CDCl$_3$): δ 2.3–2.53 (m, 1H), 2.6–2.8 (m, 1H), 3.78–4.1 (m, 5H), 4.5–4.6 (m, 1H), 6.8 (m, 1H), 7.34 (d, 1H), 7.77 (d, 1H).

Step B: Preparation of 1-(4-chloro-3-methoxyphenyl)-3-[3-(1,1-dimethylethyl)-1H-pyrazol-1-yl]-2-pyrrolidinone To a solution of 3-(1,1-dimethylethyl)-1H-pyrazole (0.22 g, 1.8 mmol) in N,N-dimethylformamide (20 mL) under nitrogen at room temperature was added 60% sodium hydride in mineral oil (79 mg, 2.0 mmol). After the addition, the mixture was stirred at room temperature for ~15 minutes, and then 3-bromo-1-(4-chloro-3-methoxyphenyl)-2-pyrrolidinone (0.5 g, 1.6 mmol) was added. The resulting reaction mixture was stirred at room temperature overnight and then poured into water (~100 mL). The aqueous layer was extracted twice with ethyl acetate (~50 mL each). The organic extracts were combined, washed twice with water (~100 mL each), dried over MgSO$_4$ and filtered. The filtrate was concentrated. The residue was purified by medium pressure liquid chromatography (silica gel) using as eluant methylene chloride and then 10:1 (by volume) ethyl acetate-methylene chloride to give the title compound, a compound of this invention, as a solid (186 mg) melting at 128–130 ° C.

$^1$H NMR (CDCl$_3$): δ 1.29 (s, 9H), 2.7–2.98 (m, 2H), 3.84–4.17 (m, 5H), 5.04 (t,1H), 617 (d, 1H), 6.81–6.9 (m, 1H), 7.35 (d, 1H), 7.47 (d, 1H), 7.84 (d, 1H).

EXAMPLE 7

Step A: Preparation of 2-[(dimethylamino)methylene]-5,5-dimethylcyclopentanone

A mixture of N,N-dimethylformamide dimethyl acetal (67 mL, 503 mmol) and 2,2-dimethylcyclopentanone (10 g, 90 mmol) was heated at reflux for 2 days. The reaction mixture was then cooled down to room temperature and concentrated. Water (~380 mL) was added to the residue, and the resulting solution was extracted with methylene chloride. The organic layer was separated, dried over MgSO$_4$ and concentrated to give the title compound (12.5 g) as a yellow-orange oil.

$^1$H NMR (CDCl$_3$): δ 1.03 (s, 6H), 1.68 (t, 2H), 2.74 (t, 2H), 3.06 (s, 6H), 7.19 (s, 1H).

Step B: Preparation of 2,4,5,6-tetrahydro-6,6-dimethylcyclopentapyrazole

To a solution of 2-[(dimethylamino)methylene]-5,5-dimethylcyclopentanone (12.5 g, 75 mmol) in ethanol (100 mL) at room temperature was added hydrazine hydrate (4 mL, 82.3 mmol). The reaction mixture was heated at reflux overnight. It was then cooled to room temperature and concentrated. Water (700 mL) was added to the residue, and the resulting solution was extracted twice with diethyl ether (2×250 mL). The organic extracts were combined, dried over MgSO$_4$ and concentrated to give the title compound as an oil (10.5 g). $^1$H NMR indicated the oil to be ~60% pure. It was used directly for Step C.

Step C: Preparation of 3-(5,6-dihydro-4,4-dimethyl-2(4B)-cyclopentapyrazolyl)-1-[3-(trifluoromethyl)phenyl]-2-pyrrolidinone To a solution of 2,4,5,6-tetrahydro-6,6-dimethylcyclopentapyrazole (0.41 g with 60% purity, 1.8 mmol) in N,N-dimethylformamide (20 mL) under nitrogen at room temperature was added sodium hydride (60% in mineral oil, 86 mg, 2.16 mmol). The mixture was stirred at room temperature under nitrogen for ~15 minutes, and then 3-hydroxy-1-[3-(trifluoromethyl)phenyl]-2-pyrrolidinone methanesulfonate (0.5 g, 1.8 mmol) was added. The resulting reaction mixture was stirred at room temperature for 72 hours. The reaction mixture was then poured into water (~100 mL) and the aqueous layer extracted with ethyl acetate (2×30 mL; brine solution was added to separate the layers). The organic extracts were combined and concentrated to give a crude product. This crude product was further purified by column chromatography (silica gel, ~20% ethyl acetate/~80% hexanes) to give the title compound, a compound of this invention, as an oil, which on standing crystallized to provide a solid (69 mg) melting at 123–126° C.

$^1$H NMR (CDCl$_3$): δ 1.3 (s, 6H), 2.21 (t, 2H), 2.61 (t, 2H), 2.7–2.87(m, 2H), 387–4.1(m, 2H), 5.04 (t, 1H), 7.13 (s, 1H), 7.4–7.55 (m, 2H) 7.9–8.0 (m, 2H).

By the procedures described herein together with methods known in the art, the following compounds of Tables 1A to 6 can be prepared.
A-1
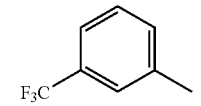
A-2
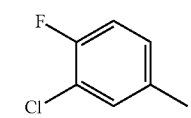
A-3
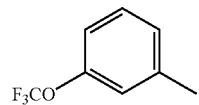
A-4
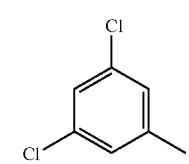
A-5
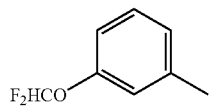
A-6
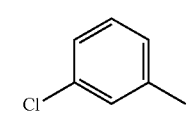
A-7
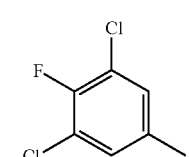
A-8
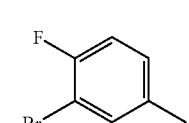
A-9
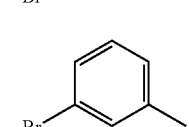
A-10
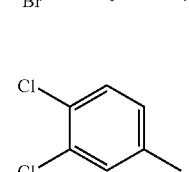
A-11
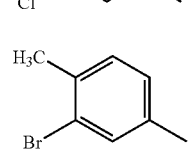
-continued
A-12
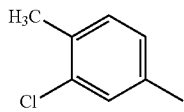
A-13
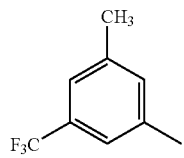
A-14
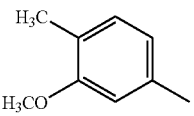
A-15
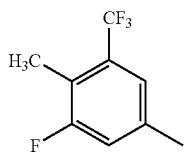
A-16
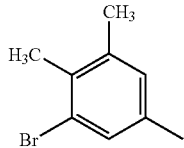
A-17
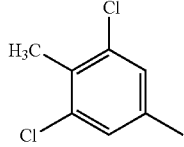
A-18
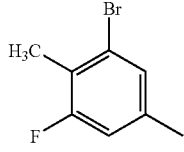
A-19
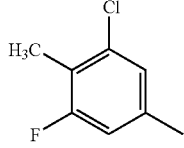
A-20
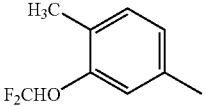
A-21
A-22
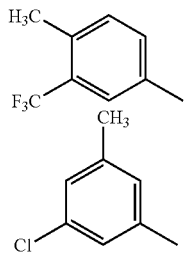

-continued
A-23 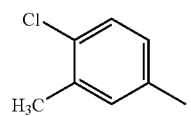
A-24 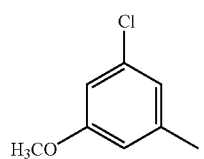
A-25 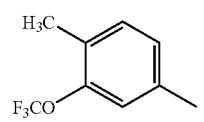
A-26 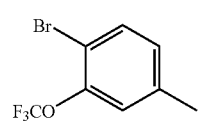
A-27 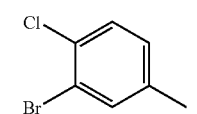
A-28 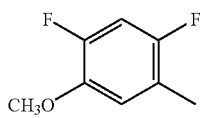
A-29 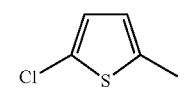
A-30 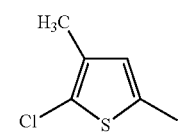
A-31 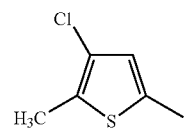
A-32 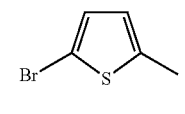
A-33 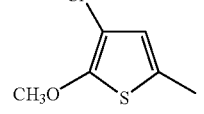
A-34 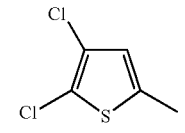
-continued
A-35 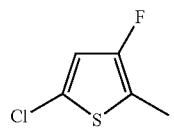
A-36 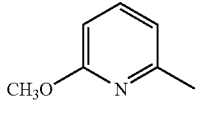
A-37 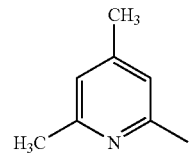
A-38 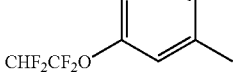
A-39 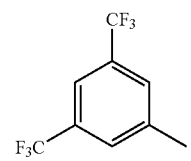
A-40 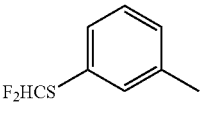
A-41 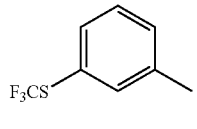
A-42 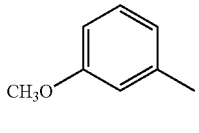
A-43 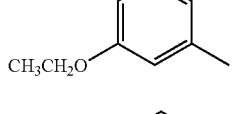
A-44 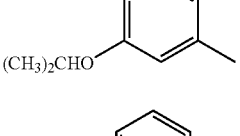
A-45 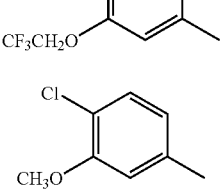
A-46

-continued
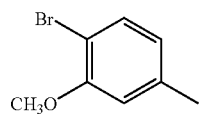 A-47
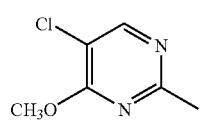 A-48
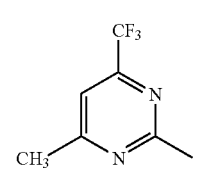 A-49
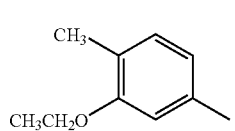 A-50
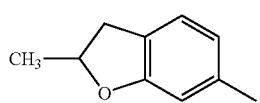 A-51
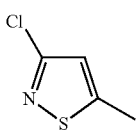 A-52
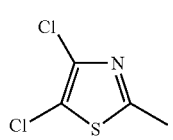 A-53
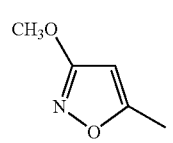 A-54
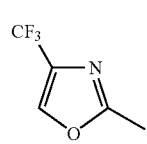 A-55
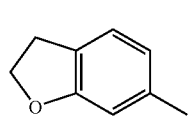 A-56
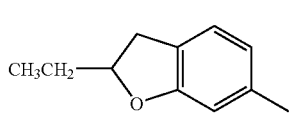 A-57
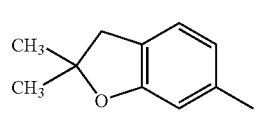 A-58
-continued
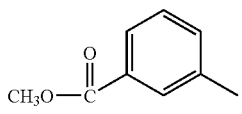 A-59
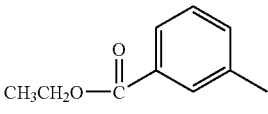 A-60
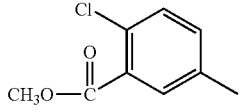 A-61
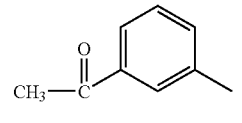 A-62
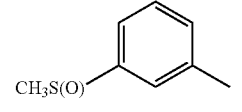 A-63
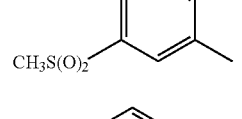 A-64
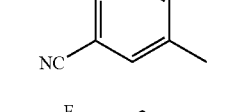 A-65
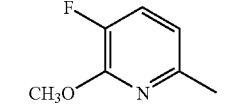 A-66
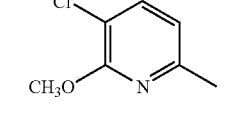 A-67
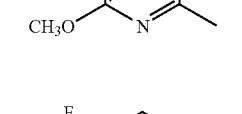 A-68
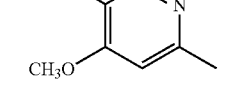 A-69
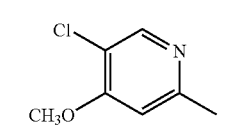 A-70

-continued
A-71 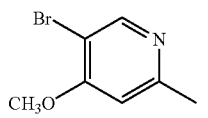
A-72 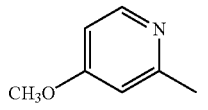
A-73 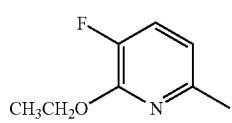
A-74 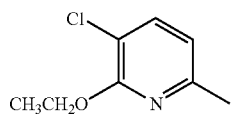
A-75 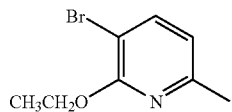
A-76 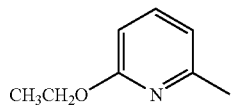
A-77 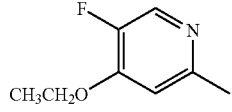
A-78 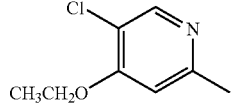
A-79 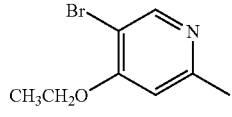
A-80 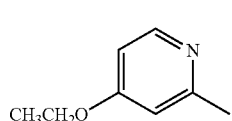
A-81 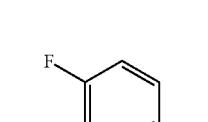
A-82 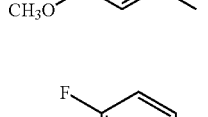
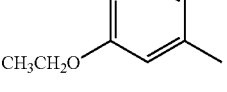
-continued
A-83 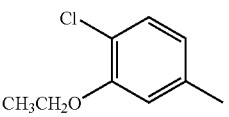
A-84 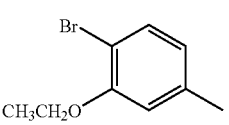
A-85 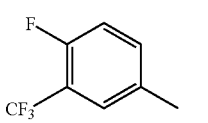
A-86 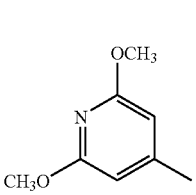
A-87 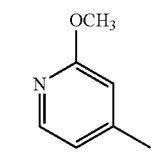
A-88 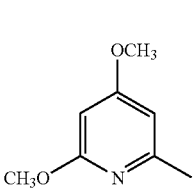
A-89 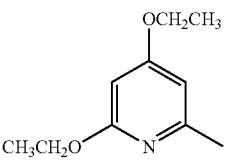
A-90 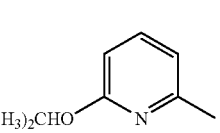
The following tables use the following well-established abbreviations: n means normal, i means iso, s means secondary, t means tertiary and c means cyclo.

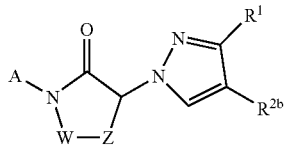

| Z | R¹ | Z | R¹ | Z | R¹ |
|---|---|---|---|---|---|
| A is A-1; W is CH$_2$; R$^{2b}$ is H | | A is A-1; W is CH$_2$; R$^{2b}$ is H | | A is A-1; W is CH$_2$; R$^{2b}$ is H | |
| S | C(CH$_3$)$_3$ | CH$_2$ | C(CH$_3$)$_3$ | O | C(CH$_3$)$_3$ |
| S | CH(CH$_3$)$_2$ | CH$_2$ | CH(CH$_3$)$_2$ | O | CH(CH$_3$)$_2$ |
| S | CH(CH$_3$)(C$_2$H$_5$) | CH$_2$ | CH(CH$_3$)(C$_2$H$_5$) | O | CH(CH$_3$)(C$_2$H$_5$) |
| S | CH(C$_2$H$_5$)$_2$ | CH$_2$ | CH(C$_2$H$_5$)$_2$ | O | CH(C$_2$H$_5$)$_2$ |
| S | c-Pr | CH$_2$ | c-Pr | O | c-Pr |
| S | 1-Me-c-Pr | CH$_2$ | 1-Me-c-Pr | O | 1-Me-c-Pr |
| S | 2-Me-c-Pr | CH$_2$ | 2-Me-c-Pr | O | 2-Me-c-Pr |
| S | 1-Me-2,2-di-Cl-c-Pr | CH$_2$ | 1-Me-2,2-di-Cl-c-Pr | O | 1-Me-2,2-di-Cl-c-Pr |
| S | c-Bu | CH$_2$ | c-Bu | O | c-Bu |
| S | 2,2-di-Cl-c-Pr | CH$_2$ | 2,2-di-Cl-c-Pr | O | 2,2-di-Cl-c-Pr |
| S | Trimethylsilyl | CH$_2$ | Trimethylsilyl | O | Trimethylsilyl |
| S | Si(CH$_3$)$_2$(t-C$_4$H$_9$) | CH$_2$ | Si(CH$_3$)$_2$(t-C$_4$H$_9$) | O | Si(CH$_3$)$_2$(t-C$_4$H$_9$) |
| S | C$_2$H$_5$ | CH$_2$ | C$_2$H$_5$ | O | C$_2$H$_5$ |
| S | CH$_3$ | CH$_2$ | CH$_3$ | O | CH$_3$ |
| S | H | CH$_2$ | H | O | H |
| S | Br | CH$_2$ | Br | O | Br |
| S | I | CH$_2$ | I | O | I |
| S | Cl | CH$_2$ | Cl | O | Cl |
| S | C(=O)CH$_3$ | CH$_2$ | C(=O)CH$_3$ | O | C(=O)CH$_3$ |
| S | C(=O)OCH$_3$ | CH$_2$ | C(=O)OCH$_3$ | O | C(=O)OCH$_3$ |
| S | C(=O)CH(CH$_3$)$_2$ | CH$_2$ | C(=O)CH(CH$_3$)$_2$ | O | C(=O)CH(CH$_3$)$_2$ |
| S | OCH$_3$ | CH$_2$ | OCH$_3$ | O | OCH$_3$ |
| S | SCH$_3$ | CH$_2$ | SCH$_3$ | O | SCH$_3$ |
| S | N(CH$_3$)$_2$ | CH$_2$ | N(CH$_3$)$_2$ | O | N(CH$_3$)$_2$ |
| S | C(=O)N(CH$_3$)$_2$ | CH$_2$ | C(=O)N(CH$_3$)$_2$ | O | C(=O)N(CH$_3$)$_2$ |
| S | C(=O)C(CH$_3$)$_3$ | CH$_2$ | C(=O)C(CH$_3$)$_3$ | O | C(=O)C(CH$_3$)$_3$ |
| S | n-C$_3$H$_7$ | CH$_2$ | n-C$_3$H$_7$ | O | n-C$_3$H$_7$ |
| S | CCl$_3$ | CH$_2$ | CCl$_3$ | O | CCl$_3$ |
| S | CHClCH$_3$ | CH$_2$ | CHClCH$_3$ | O | CHClCH$_3$ |
| S | SC$_2$H$_5$ | CH$_2$ | SC$_2$H$_5$ | O | SC$_2$H$_5$ |
| S | SCH(CH$_3$)$_2$ | CH$_2$ | SCH(CH$_3$)$_2$ | O | SCH(CH$_3$)$_2$ |
| S | SCH(CH$_3$)(C$_2$H$_5$) | CH$_2$ | SCH(CH$_3$)(C$_2$H$_5$) | O | SCH(CH$_3$)(C$_2$H$_5$) |
| S | SCF$_3$ | CH$_2$ | SCF$_3$ | O | SCF$_3$ |
| S | OCH(CH$_3$)$_2$ | CH$_2$ | OCH(CH$_3$)$_2$ | O | OCH(CH$_3$)$_2$ |
| S | OCH(CH$_3$)(C$_2$H$_5$) | CH$_2$ | OCH(CH$_3$)(C$_2$H$_5$) | O | OCH(CH$_3$)(C$_2$H$_5$) |
| S | OCH(C$_2$H$_5$)$_2$ | CH$_2$ | OCH(C$_2$H$_5$)$_2$ | O | OCH(C$_2$H$_5$)$_2$ |
| S | OCHF$_2$ | CH$_2$ | OCHF$_2$ | O | OCHF$_2$ |
| S | C(CH$_3$)$_2$C$_2$H$_5$ | CH$_2$ | C(CH$_3$)$_2$C$_2$H$_5$ | O | C(CH$_3$)$_2$C$_2$H$_5$ |
| S | CH$_2$C(CH$_3$)$_3$ | CH$_2$ | CH$_2$C(CH$_3$)$_3$ | O | CH$_2$C(CH$_3$)$_3$ |
| S | c-Pentyl | CH$_2$ | c-Pentyl | O | c-Pentyl |
| S | c-Hexyl | CH$_2$ | c-Hexyl | O | c-Hexyl |
| S | c-Octyl | CH$_2$ | c-Octyl | O | c-Octyl |
| S | CH(CH$_3$)(n-C$_3$H$_7$) | CH$_2$ | CH(CH$_3$)(n-C$_3$H$_7$) | O | CH(CH$_3$)(n-C$_3$H$_7$) |
| S | CH(C$_2$H$_5$)(n-C$_3$H$_7$) | CH$_2$ | CH(C$_2$H$_5$)(n-C$_3$H$_7$) | O | CH(C$_2$H$_5$)(n-C$_3$H$_7$) |
| S | CH(n-C$_3$H$_7$)$_2$ | CH$_2$ | CH(n-C$_3$H$_7$)$_2$ | O | CH(n-C$_3$H$_7$)$_2$ |
| S | CH(n-C$_4$H$_9$)$_2$ | CH$_2$ | CH(n-C$_4$H$_9$)$_2$ | O | CH(n-C$_4$H$_9$)$_2$ |
| S | CH(CH$_3$)(n-C$_4$H$_9$) | CH$_2$ | CH(CH$_3$)(n-C$_4$H$_9$) | O | CH(CH$_3$)(n-C$_4$H$_9$) |
| S | CH(CH$_3$)(n-C$_5$H$_{11}$) | CH$_2$ | CH(CH$_3$)(n-C$_5$H$_{11}$) | O | CH(CH$_3$)(n-C$_5$H$_{11}$) |
| S | CH(CH$_3$)(n-C$_{10}$H$_{21}$) | CH$_2$ | CH(CH$_3$)(n-C$_{10}$H$_{21}$) | O | CH(CH$_3$)(n-C$_{10}$H$_{21}$) |
| S | C(CH$_3$)(C$_2$H$_5$)$_2$ | CH$_2$ | C(CH$_3$)(C$_2$H$_5$)$_2$ | O | C(CH$_3$)(C$_2$H$_5$)$_2$ |
| S | CH$_2$CF$_3$ | CH$_2$ | CH$_2$CF$_3$ | O | CH$_2$CF$_3$ |
| S | C(CH$_3$)$_3$ | CH$_2$ | C(CH$_3$)$_3$ | O | C(CH$_3$)$_3$ |
| S | CH(CH$_3$)$_2$ | CH$_2$ | CH(CH$_3$)$_2$ | O | CH(CH$_3$)$_2$ |
| S | CH(CH$_3$)(C$_2$H$_5$) | CH$_2$ | CH(CH$_3$)(C$_2$H$_5$) | O | CH(CH$_3$)(C$_2$H$_5$) |
| S | CH(C$_2$H$_5$)$_2$ | CH$_2$ | CH(C$_2$H$_5$)$_2$ | O | CH(C$_2$H$_5$)$_2$ |
| S | c-Pr | CH$_2$ | c-Pr | O | c-Pr |
| S | 1-Me-c-Pr | CH$_2$ | 1-Me-c-Pr | O | 1-Me-c-Pr |
| S | 2-Me-c-Pr | CH$_2$ | 2-Me-c-Pr | O | 2-Me-c-Pr |
| S | 1-Me-2,2-di-Cl-c-Pr | CH$_2$ | 1-Me-2,2-di-Cl-c-Pr | O | 1-Me-2,2-di-Cl-c-Pr |
| S | c-Bu | CH$_2$ | c-Bu | O | c-Bu |
| S | 2,2-di-Cl-c-Pr | CH$_2$ | 2,2-di-Cl-c-Pr | O | 2,2-di-Cl-c-Pr |
| S | Trimethylsilyl | CH$_2$ | Trimethylsilyl | O | Trimethylsilyl |
| S | Si(CH$_3$)$_2$(t-C$_4$H$_9$) | CH$_2$ | Si(CH$_3$)$_2$(t-C$_4$H$_9$) | O | Si(CH$_3$)$_2$(t-C$_4$H$_9$) |
| S | C$_2$H$_5$ | CH$_2$ | C$_2$H$_5$ | O | C$_2$H$_5$ |
| S | CH$_3$ | CH$_2$ | CH$_3$ | O | CH$_3$ |
| S | H | CH$_2$ | H | O | H |

-continued

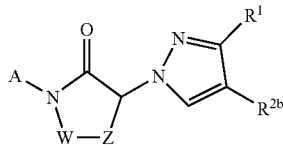

| Z | R¹ | Z | R¹ | Z | R¹ |
|---|---|---|---|---|---|
| S | Br | CH$_2$ | Br | O | Br |
| S | I | CH$_2$ | I | O | I |
| S | Cl | CH$_2$ | Cl | O | Cl |
| S | C(=O)CH$_3$ | CH$_2$ | C(=O)CH$_3$ | O | C(=O)CH$_3$ |
| S | C(=O)OCH$_3$ | CH$_2$ | C(=O)OCH$_3$ | O | C(=O)OCH$_3$ |
| S | C(=O)CH(CH$_3$)$_2$ | CH$_2$ | C(=O)CH(CH$_3$)$_2$ | O | C(=O)CH(CH$_3$)$_2$ |
| S | OCH$_3$ | CH$_2$ | OCH$_3$ | O | OCH$_3$ |
| S | SCH$_3$ | CH$_2$ | SCH$_3$ | O | SCH$_3$ |
| S | N(CH$_3$)$_2$ | CH$_2$ | N(CH$_3$)$_2$ | O | N(CH$_3$)$_2$ |
| S | C(=O)N(CH$_3$)$_2$ | CH$_2$ | C(=O)N(CH$_3$)$_2$ | O | C(=O)N(CH$_3$)$_2$ |
| S | C(=O)C(CH$_3$)$_3$ | CH$_2$ | C(=O)C(CH$_3$)$_3$ | O | C(=O)C(CH$_3$)$_3$ |
| S | n-C$_3$H$_7$ | CH$_2$ | n-C$_3$H$_7$ | O | n-C$_3$H$_7$ |
| S | CCl$_3$ | CH$_2$ | CCl$_3$ | O | CCl$_3$ |
| S | CHClCH$_3$ | CH$_2$ | CHClCH$_3$ | O | CHClCH$_3$ |
| S | SC$_2$H$_5$ | CH$_2$ | SC$_2$H$_5$ | O | SC$_2$H$_5$ |
| S | SCH(CH$_3$)$_2$ | CH$_2$ | SCH(CH$_3$)$_2$ | O | SCH(CH$_3$)$_2$ |
| S | SCH(CH$_3$)(C$_2$H$_5$) | CH$_2$ | SCH(CH$_3$)(C$_2$H$_5$) | O | SCH(CH$_3$)(C$_2$H$_5$) |
| S | SCF$_3$ | CH$_2$ | SCF$_3$ | O | SCF$_3$ |
| S | OCH(CH$_3$)$_2$ | CH$_2$ | OCH(CH$_3$)$_2$ | O | OCH(CH$_3$)$_2$ |
| S | OCH(CH$_3$)(C$_2$H$_5$) | CH$_2$ | OCH(CH$_3$)(C$_2$H$_5$) | O | OCH(CH$_3$)(C$_2$H$_5$) |
| S | OCH(C$_2$H$_5$)$_2$ | CH$_2$ | OCH(C$_2$H$_5$)$_2$ | O | OCH(C$_2$H$_5$)$_2$ |
| A is A-3; W is CH$_2$; R$^{2b}$ is H | | A is A-3; W is CH$_2$; R$^{2b}$ is H | | A is A-3; W is CH$_2$; R$^{2b}$ is H | |
| S | OCHF$_2$ | CH$_2$ | OCHF$_2$ | O | OCHF$_2$ |
| S | C(CH$_3$)$_2$C$_2$H$_5$ | CH$_2$ | C(CH$_3$)$_2$C$_2$H$_5$ | O | C(CH$_3$)$_2$C$_2$H$_5$ |
| S | CH$_2$C(CH$_3$)$_3$ | CH$_2$ | CH$_2$C(CH$_3$)$_3$ | O | CH$_2$C(CH$_3$)$_3$ |
| S | c-Pentyl | CH$_2$ | c-Pentyl | O | c-Pentyl |
| S | c-Hexyl | CH$_2$ | c-Hexyl | O | c-Hexyl |
| S | c-Octyl | CH$_2$ | c-Octyl | O | c-Octyl |
| S | CH(CH$_3$)(n-C$_3$H$_7$) | CH$_2$ | CH(CH$_3$)(n-C$_3$H$_7$) | O | CH(CH$_3$)(n-C$_3$H$_7$) |
| S | CH(C$_2$H$_5$)(n-C$_3$H$_7$) | CH$_2$ | CH(C$_2$H$_5$)(n-C$_3$H$_7$) | O | CH(C$_2$H$_5$)(n-C$_3$H$_7$) |
| S | CH(n-C$_3$H$_7$)$_2$ | CH$_2$ | CH(n-C$_3$H$_7$)$_2$ | O | CH(n-C$_3$H$_7$)$_2$ |
| S | CH(n-C$_4$H$_9$)$_2$ | CH$_2$ | CH(n-C$_4$H$_9$)$_2$ | O | CH(n-C$_4$H$_9$)$_2$ |
| S | CH(CH$_3$)(n-C$_4$H$_9$) | CH$_2$ | CH(CH$_3$)(n-C$_4$H$_9$) | O | CH(CH$_3$)(n-C$_4$H$_9$) |
| S | CH(CH$_3$)(n-C$_5$H$_{11}$) | CH$_2$ | CH(CH$_3$)(n-C$_5$H$_{11}$) | O | CH(CH$_3$)(n-C$_5$H$_{11}$) |
| S | CH(CH$_3$)(n-C$_{10}$H$_{21}$) | CH$_2$ | CH(CH$_3$)(n-C$_{10}$H$_{21}$) | O | CH(CH$_3$)(n-C$_{10}$H$_{21}$) |
| S | C(CH$_3$)(C$_2$H$_5$)$_2$ | CH$_2$ | C(CH$_3$)(C$_2$H$_5$)$_2$ | O | C(CH$_3$)(C$_2$H$_5$)$_2$ |
| S | CH$_2$CF$_3$ | CH$_2$ | CH$_2$CF$_3$ | O | CH$_2$CF$_3$ |
| A is A-5; W is CH$_2$; R$^{2b}$ is H | | A is A-5; W is CH$_2$; R$^{2b}$ is H | | A is A-5; W is CH$_2$; R$^{2b}$ is H | |
| S | C(CH$_3$)$_3$ | CH$_2$ | C(CH$_3$)$_3$ | O | C(CH$_3$)$_3$ |
| S | CH(CH$_3$)$_2$ | CH$_2$ | CH(CH$_3$)$_2$ | O | CH(CH$_3$)$_2$ |
| S | CH(CH$_3$)(C$_2$H$_5$) | CH$_2$ | CH(CH$_3$)(C$_2$H$_5$) | O | CH(CH$_3$)(C$_2$H$_5$) |
| S | CH(C$_2$H$_5$)$_2$ | CH$_2$ | CH(C$_2$H$_5$)$_2$ | O | CH(C$_2$H$_5$)$_2$ |
| S | c-Pr | CH$_2$ | c-Pr | O | c-Pr |
| S | 1-Me-c-Pr | CH$_2$ | 1-Me-c-Pr | O | 1-Me-c-Pr |
| S | 2-Me-c-Pr | CH$_2$ | 2-Me-c-Pr | O | 2-Me-c-Pr |
| S | 1-Me-2,2-di-Cl-c-Pr | CH$_2$ | 1-Me-2,2-di-Cl-c-Pr | O | 1-Me-2,2-di-Cl-c-Pr |
| S | c-Bu | CH$_2$ | c-Bu | O | c-Bu |
| S | 2,2-di-Cl-c-Pr | CH$_2$ | 2,2-di-Cl-c-Pr | O | 2,2-di-Cl-c-Pr |
| S | Trimethylsilyl | CH$_2$ | Trimethylsilyl | O | Trimethylsilyl |
| S | Si(CH$_3$)$_2$(t-C$_4$H$_9$) | CH$_2$ | Si(CH$_3$)$_2$(t-C$_4$H$_9$) | O | Si(CH$_3$)$_2$(t-C$_4$H$_9$) |
| S | C$_2$H$_5$ | CH$_2$ | C$_2$H$_5$ | O | C$_2$H$_5$ |
| S | CH$_3$ | CH$_2$ | CH$_3$ | O | CH$_3$ |
| S | H | CH$_2$ | H | O | H |
| S | Br | CH$_2$ | Br | O | Br |
| S | I | CH$_2$ | I | O | I |
| S | Cl | CH$_2$ | Cl | O | Cl |
| S | C(=O)CH$_3$ | CH$_2$ | C(=O)CH$_3$ | O | C(=O)CH$_3$ |
| S | C(=O)OCH$_3$ | CH$_2$ | C(=O)OCH$_3$ | O | C(=O)OCH$_3$ |
| S | C(=O)CH(CH$_3$)$_2$ | CH$_2$ | C(=O)CH(CH$_3$)$_2$ | O | C(=O)CH(CH$_3$)$_2$ |
| S | OCH$_3$ | CH$_2$ | OCH$_3$ | O | OCH$_3$ |
| S | SCH$_3$ | CH$_2$ | SCH$_3$ | O | SCH$_3$ |
| S | N(CH$_3$)$_2$ | CH$_2$ | N(CH$_3$)$_2$ | O | N(CH$_3$)$_2$ |
| S | C(=O)N(CH$_3$)$_2$ | CH$_2$ | C(=O)N(CH$_3$)$_2$ | O | C(=O)N(CH$_3$)$_2$ |
| S | C(=O)C(CH$_3$)$_3$ | CH$_2$ | C(=O)C(CH$_3$)$_3$ | O | C(=O)C(CH$_3$)$_3$ |
| S | n-C$_3$H$_7$ | CH$_2$ | n-C$_3$H$_7$ | O | n-C$_3$H$_7$ |
| S | CCl$_3$ | CH$_2$ | CCl$_3$ | O | CCl$_3$ |

-continued

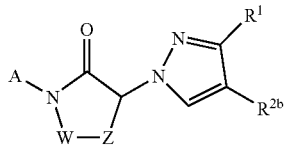

| Z | R¹ | Z | R¹ | Z | R¹ |
|---|---|---|---|---|---|
| S | CHClCH₃ | CH₂ | CHClCH₃ | O | CHClCH₃ |
| S | SC₂H₅ | CH₂ | SC₂H₅ | O | SC₂H₅ |
| S | SCH(CH₃)₂ | CH₂ | SCH(CH₃)₂ | O | SCH(CH₃)₂ |
| S | SCH(CH₃)(C₂H₅) | CH₂ | SCH(CH₃)(C₂H₅) | O | SCH(CH₃)(C₂H₅) |
| S | SCF₃ | CH₂ | SCF₃ | O | SCF₃ |
| S | OCH(CH₃)₂ | CH₂ | OCH(CH₃)₂ | O | OCH(CH₃)₂ |
| S | OCH(CH₃)(C₂H₅) | CH₂ | OCH(CH₃)(C₂H₅) | O | OCH(CH₃)(C₂H₅) |
| S | OCH(C₂H₅)₂ | CH₂ | OCH(C₂H₅)₂ | O | OCH(C₂H₅)₂ |
| S | OCHF₂ | CH₂ | OCHF₂ | O | OCHF₂ |
| S | C(CH₃)₂C₂H₅ | CH₂ | C(CH₃)₂C₂H₅ | O | C(CH₃)₂C₂H₅ |
| S | CH₂C(CH₃)₃ | CH₂ | CH₂C(CH₃)₃ | O | CH₂C(CH₃)₃ |
| S | c-Pentyl | CH₂ | c-Pentyl | O | c-Pentyl |
| S | c-Hexyl | CH₂ | c-Hexyl | O | c-Hexyl |
| S | c-Octyl | CH₂ | c-Octyl | O | c-Octyl |
| S | CH(CH₃)(n-C₃H₇) | CH₂ | CH(CH₃)(n-C₃H₇) | O | CH(CH₃)(n-C₃H₇) |
| S | CH(C₂H₅)(n-C₃H₇) | CH₂ | CH(C₂H₅)(n-C₃H₇) | O | CH(C₂H₅)(n-C₃H₇) |
| S | CH(n-C₃H₇)₂ | CH₂ | CH(n-C₃H₇)₂ | O | CH(n-C₃H₇)₂ |
| S | CH(n-C₄H₉)₂ | CH₂ | CH(n-C₄H₉)₂ | O | CH(n-C₄H₉)₂ |
| S | CH(CH₃)(n-C₄H₉) | CH₂ | CH(CH₃)(n-C₄H₉) | O | CH(CH₃)(n-C₄H₉) |
| S | CH(CH₃)(n-C₅H₁₁) | CH₂ | CH(CH₃)(n-C₅H₁₁) | O | CH(CH₃)(n-C₅H₁₁) |
| S | CH(CH₃)(n-C₁₀H₂₁) | CH₂ | CH(CH₃)(n-C₁₀H₂₁) | O | CH(CH₃)(n-C₁₀H₂₁) |
| S | C(CH₃)(C₂H₅)₂ | CH₂ | C(CH₃)(C₂H₅)₂ | O | C(CH₃)(C₂H₅)₂ |
| S | CH₂CF₃ | CH₂ | CH₂CF₃ | O | CH₂CF₃ |

A is A-14; W is CH₂; R²ᵇ is H    A is A-14; W is CH₂; R²ᵇ is H    A is A-14; W is CH₂; R²ᵇ is H

| Z | R¹ | Z | R¹ | Z | R¹ |
|---|---|---|---|---|---|
| S | C(CH₃)₃ | CH₂ | C(CH₃)₃ | O | C(CH₃)₃ |
| S | CH(CH₃)₂ | CH₂ | CH(CH₃)₂ | O | CH(CH₃)₂ |
| S | CH(CH₃)(C₂H₅) | CH₂ | CH(CH₃)(C₂H₅) | O | CH(CH₃)(C₂H₅) |
| S | CH(C₂H₅)₂ | CH₂ | CH(C₂H₅)₂ | O | CH(C₂H₅)₂ |
| S | c-Pr | CH₂ | c-Pr | O | c-Pr |
| S | 1-Me-c-Pr | CH₂ | 1-Me-c-Pr | O | 1-Me-c-Pr |
| S | 2-Me-c-Pr | CH₂ | 2-Me-c-Pr | O | 2-Me-c-Pr |
| S | 1-Me-2,2-di-Cl-c-Pr | CH₂ | 1-Me-2,2-di-Cl-c-Pr | O | 1-Me-2,2-di-Cl-c-Pr |
| S | c-Bu | CH₂ | c-Bu | O | c-Bu |
| S | 2,2-di-Cl-c-Pr | CH₂ | 2,2-di-Cl-c-Pr | O | 2,2-di-Cl-c-Pr |
| S | Trimethylsilyl | CH₂ | Trimethylsilyl | O | Trimethylsilyl |
| S | Si(CH₃)₂(t-C₄H₉) | CH₂ | Si(CH₃)₂(t-C₄H₉) | O | Si(CH₃)₂(t-C₄H₉) |
| S | C₂H₅ | CH₂ | C₂H₅ | O | C₂H₅ |
| S | CH₃ | CH₂ | CH₃ | O | CH₃ |
| S | H | CH₂ | H | O | H |
| S | Br | CH₂ | Br | O | Br |
| S | I | CH₂ | I | O | I |
| S | Cl | CH₂ | Cl | O | Cl |
| S | C(=O)CH₃ | CH₂ | C(=O)CH₃ | O | C(=O)CH₃ |
| S | C(=O)OCH₃ | CH₂ | C(=O)OCH₃ | O | C(=O)OCH₃ |
| S | C(=O)CH(CH₃)₂ | CH₂ | C(=O)CH(CH₃)₂ | O | C(=O)CH(CH₃)₂ |
| S | OCH₃ | CH₂ | OCH₃ | O | OCH₃ |
| S | SCH₃ | CH₂ | SCH₃ | O | SCH₃ |
| S | N(CH₃)₂ | CH₂ | N(CH₃)₂ | O | N(CH₃)₂ |
| S | C(=O)N(CH₃)₂ | CH₂ | C(=O)N(CH₃)₂ | O | C(=O)N(CH₃)₂ |
| S | C(=O)C(CH₃)₃ | CH₂ | C(=O)C(CH₃)₃ | O | C(=O)C(CH₃)₃ |
| S | n-C₃H₇ | CH₂ | n-C₃H₇ | O | n-C₃H₇ |
| S | CCl₃ | CH₂ | CCl₃ | O | CCl₃ |
| S | CHClCH₃ | CH₂ | CHClCH₃ | O | CHClCH₃ |
| S | SC₂H₅ | CH₂ | SC₂H₅ | O | SC₂H₅ |
| S | SCH(CH₃)₂ | CH₂ | SCH(CH₃)₂ | O | SCH(CH₃)₂ |
| S | SCH(CH₃)(C₂H₅) | CH₂ | SCH(CH₃)(C₂H₅) | O | SCH(CH₃)(C₂H₅) |
| S | SCF₃ | CH₂ | SCF₃ | O | SCF₃ |
| S | OCH(CH₃)₂ | CH₂ | OCH(CH₃)₂ | O | OCH(CH₃)₂ |
| S | OCH(CH₃)(C₂H₅) | CH₂ | OCH(CH₃)(C₂H₅) | O | OCH(CH₃)(C₂H₅) |
| S | OCH(C₂H₅)₂ | CH₂ | OCH(C₂H₅)₂ | O | OCH(C₂H₅)₂ |
| S | OCHF₂ | CH₂ | OCHF₂ | O | OCHF₂ |
| S | C(CH₃)₂C₂H₅ | CH₂ | C(CH₃)₂C₂H₅ | O | C(CH₃)₂C₂H₅ |
| S | CH₂C(CH₃)₃ | CH₂ | CH₂C(CH₃)₃ | O | CH₂C(CH₃)₃ |
| S | c-Pentyl | CH₂ | c-Pentyl | O | c-Pentyl |
| S | c-Hexyl | CH₂ | c-Hexyl | O | c-Hexyl |
| S | c-Octyl | CH₂ | c-Octyl | O | c-Octyl |
| S | CH(CH₃)(n-C₃H₇) | CH₂ | CH(CH₃)(n-C₃H₇) | O | CH(CH₃)(n-C₃H₇) |

-continued

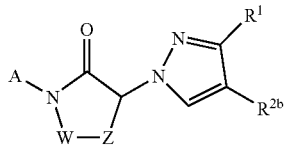

| Z | R¹ | Z | R¹ | Z | R¹ |
|---|---|---|---|---|---|
| S | CH(C₂H₅)(n-C₃H₇) | CH₂ | CH(C₂H₅)(n-C₃H₇) | O | CH(C₂H₅)(n-C₃H₇) |
| S | CH(n-C₃H₇)₂ | CH₂ | CH(n-C₃H₇)₂ | O | CH(n-C₃H₇)₂ |
| S | CH(n-C₄H₉)₂ | CH₂ | CH(n-C₄H₉)₂ | O | CH(n-C₄H₉)₂ |
| S | CH(CH₃)(n-C₄H₉) | CH₂ | CH(CH₃)(n-C₄H₉) | O | CH(CH₃)(n-C₄H₉) |
| S | CH(CH₃)(n-C₅H₁₁) | CH₂ | CH(CH₃)(n-C₅H₁₁) | O | CH(CH₃)(n-C₅H₁₁) |
| S | CH(CH₃)(n-C₁₀H₂₁) | CH₂ | CH(CH₃)(n-C₁₀H₂₁) | O | CH(CH₃)(n-C₁₀H₂₁) |
| S | C(CH₃)(C₂H₅)₂ | CH₂ | C(CH₃)(C₂H₅)₂ | O | C(CH₃)(C₂H₅)₂ |
| S | CH₂CF₃ | CH₂ | CH₂CF₃ | O | CH₂CF₃ |

A is A-29; W is CH₂; R²ᵇ is H    A is A-29; W is CH₂; R²ᵇ is H    A is A-29; W is CH₂; R²ᵇ is H

| S | C(CH₃)₃ | CH₂ | C(CH₃)₃ | O | C(CH₃)₃ |
| S | CH(CH₃)₂ | CH₂ | CH(CH₃)₂ | O | CH(CH₃)₂ |
| S | CH(CH₃)(C₂H₅) | CH₂ | CH(CH₃)(C₂H₅) | O | CH(CH₃)(C₂H₅) |
| S | CH(C₂H₅)₂ | CH₂ | CH(C₂H₅)₂ | O | CH(C₂H₅)₂ |
| S | c-Pr | CH₂ | c-Pr | O | c-Pr |
| S | 1-Me-c-Pr | CH₂ | 1-Me-c-Pr | O | 1-Me-c-Pr |
| S | 2-Me-c-Pr | CH₂ | 2-Me-c-Pr | O | 2-Me-c-Pr |
| S | 1-Me-2,2-di-Cl-c-Pr | CH₂ | 1-Me-2,2-di-Cl-c-Pr | O | 1-Me-2,2-di-Cl-c-Pr |
| S | c-Bu | CH₂ | c-Bu | O | c-Bu |
| S | 2,2-di-Cl-c-Pr | CH₂ | 2,2-di-Cl-c-Pr | O | 2,2-di-Cl-c-Pr |
| S | Trimethylsilyl | CH₂ | Trimethylsilyl | O | Trimethylsilyl |
| S | Si(CH₃)₂(t-C₄H₉) | CH₂ | Si(CH₃)₂(t-C₄H₉) | O | Si(CH₃)₂(t-C₄H₉) |
| S | C₂H₅ | CH₂ | C₂H₅ | O | C₂H₅ |
| S | CH₃ | CH₂ | CH₃ | O | CH₃ |
| S | H | CH₂ | H | O | H |
| S | Br | CH₂ | Br | O | Br |
| S | I | CH₂ | I | O | I |
| S | Cl | CH₂ | Cl | O | Cl |
| S | C(=O)CH₃ | CH₂ | C(=O)CH₃ | O | C(=O)CH₃ |
| S | C(=O)OCH₃ | CH₂ | C(=O)OCH₃ | O | C(=O)OCH₃ |
| S | C(=O)CH(CH₃)₂ | CH₂ | C(=O)CH(CH₃)₂ | O | C(=O)CH(CH₃)₂ |
| S | OCH₃ | CH₂ | OCH₃ | O | OCH₃ |
| S | SCH₃ | CH₂ | SCH₃ | O | SCH₃ |
| S | N(CH₃)₂ | CH₂ | N(CH₃)₂ | O | N(CH₃)₂ |
| S | C(=O)N(CH₃)₂ | CH₂ | C(=O)N(CH₃)₂ | O | C(=O)N(CH₃)₂ |
| S | C(=O)C(CH₃)₃ | CH₂ | C(=O)C(CH₃)₃ | O | C(=O)C(CH₃)₃ |
| S | n-C₃H₇ | CH₂ | n-C₃H₇ | O | n-C₃H₇ |
| S | CCl₃ | CH₂ | CCl₃ | O | CCl₃ |
| S | CHClCH₃ | CH₂ | CHClCH₃ | O | CHClCH₃ |
| S | SC₂H₅ | CH₂ | SC₂H₅ | O | SC₂H₅ |
| S | SCH(CH₃)₂ | CH₂ | SCH(CH₃)₂ | O | SCH(CH₃)₂ |
| S | SCH(CH₃)(C₂H₅) | CH₂ | SCH(CH₃)(C₂H₅) | O | SCH(CH₃)(C₂H₅) |
| S | SCF₃ | CH₂ | SCF₃ | O | SCF₃ |
| S | OCH(CH₃)₂ | CH₂ | OCH(CH₃)₂ | O | OCH(CH₃)₂ |
| S | OCH(CH₃)(C₂H₅) | CH₂ | OCH(CH₃)(C₂H₅) | O | OCH(CH₃)(C₂H₅) |
| S | OCH(C₂H₅)₂ | CH₂ | OCH(C₂H₅)₂ | O | OCH(C₂H₅)₂ |
| S | OCHF₂ | CH₂ | OCHF₂ | O | OCHF₂ |
| S | C(CH₃)₂C₂H₅ | CH₂ | C(CH₃)₂C₂H₅ | O | C(CH₃)₂C₂H₅ |
| S | CH₂C(CH₃)₃ | CH₂ | CH₂C(CH₃)₃ | O | CH₂C(CH₃)₃ |
| S | c-Pentyl | CH₂ | c-Pentyl | O | c-Pentyl |
| S | c-Hexyl | CH₂ | c-Hexyl | O | c-Hexyl |
| S | c-Octyl | CH₂ | c-Octyl | O | c-Octyl |
| S | CH(CH₃)(n-C₃H₇) | CH₂ | CH(CH₃)(n-C₃H₇) | O | CH(CH₃)(n-C₃H₇) |
| S | CH(C₂H₅)(n-C₃H₇) | CH₂ | CH(C₂H₅)(n-C₃H₇) | O | CH(C₂H₅)(n-C₃H₇) |
| S | CH(n-C₃H₇)₂ | CH₂ | CH(n-C₃H₇)₂ | O | CH(n-C₃H₇)₂ |
| S | CH(n-C₄H₉)₂ | CH₂ | CH(n-C₄H₉)₂ | O | CH(n-C₄H₉)₂ |
| S | CH(CH₃)(n-C₄H₉) | CH₂ | CH(CH₃)(n-C₄H₉) | O | CH(CH₃)(n-C₄H₉) |
| S | CH(CH₃)(n-C₅H₁₁) | CH₂ | CH(CH₃)(n-C₅H₁₁) | O | CH(CH₃)(n-C₅H₁₁) |
| S | CH(CH₃)(n-C₁₀H₂₁) | CH₂ | CH(CH₃)(n-C₁₀H₂₁) | O | CH(CH₃)(n-C₁₀H₂₁) |
| S | C(CH₃)(C₂H₅)₂ | CH₂ | C(CH₃)(C₂H₅)₂ | O | C(CH₃)(C₂H₅)₂ |
| S | CH₂CF₃ | CH₂ | CH₂CF₃ | O | CH₂CF₃ |

A is A-46; W is CH₂; R²ᵇ is H    A is A-46; W is CH₂; R²ᵇ is H    A is A-46; W is CH₂; R²ᵇ is H

| S | C(CH₃)₃ | CH₂ | C(CH₃)₃ | O | C(CH₃)₃ |
| S | CH(CH₃)₂ | CH₂ | CH(CH₃)₂ | O | CH(CH₃)₂ |
| S | CH(CH₃)(C₂H₅) | CH₂ | CH(CH₃)(C₂H₅) | O | CH(CH₃)(C₂H₅) |
| S | CH(C₂H₅)₂ | CH₂ | CH(C₂H₅)₂ | O | CH(C₂H₅)₂ |
| S | c-Pr | CH₂ | c-Pr | O | c-Pr |

-continued

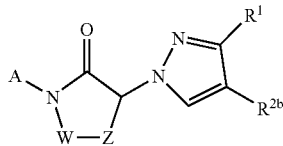

| Z | R¹ | Z | R¹ | Z | R¹ |
|---|---|---|---|---|---|
| S | 1-Me-c-Pr | CH₂ | 1-Me-c-Pr | O | 1-Me-c-Pr |
| S | 2-Me-c-Pr | CH₂ | 2-Me-c-Pr | O | 2-Me-c-Pr |
| S | 1-Me-2,2-di-Cl-c-Pr | CH₂ | 1-Me-2,2-di-Cl-c-Pr | O | 1-Me-2,2-di-Cl-c-Pr |
| S | c-Bu | CH₂ | c-Bu | O | c-Bu |
| S | 2,2-di-Cl-c-Pr | CH₂ | 2,2-di-Cl-c-Pr | O | 2,2-di-Cl-c-Pr |
| S | Trimethylsilyl | CH₂ | Trimethylsilyl | O | Trimethylsilyl |
| S | Si(CH₃)₂(t-C₄H₉) | CH₂ | Si(CH₃)₂(t-C₄H₉) | O | Si(CH₃)₂(t-C₄H₉) |
| S | C₂H₅ | CH₂ | C₂H₅ | O | C₂H₅ |
| S | CH₃ | CH₂ | CH₃ | O | CH₃ |
| S | H | CH₂ | H | O | H |
| S | Br | CH₂ | Br | O | Br |
| S | I | CH₂ | I | O | I |
| S | Cl | CH₂ | Cl | O | Cl |
| S | C(=O)CH₃ | CH₂ | C(=O)CH₃ | O | C(=O)CH₃ |
| S | C(=O)OCH₃ | CH₂ | C(=O)OCH₃ | O | C(=O)OCH₃ |
| S | C(=O)CH(CH₃)₂ | CH₂ | C(=O)CH(CH₃)₂ | O | C(=O)CH(CH₃)₂ |
| S | OCH₃ | CH₂ | OCH₃ | O | OCH₃ |
| S | SCH₃ | CH₂ | SCH₃ | O | SCH₃ |
| S | N(CH₃)₂ | CH₂ | N(CH₃)₂ | O | N(CH₃)₂ |
| S | C(=O)N(CH₃)₂ | CH₂ | C(=O)N(CH₃)₂ | O | C(=O)N(CH₃)₂ |
| S | C(=O)C(CH₃)₃ | CH₂ | C(=O)C(CH₃)₃ | O | C(=O)C(CH₃)₃ |
| S | n-C₃H₇ | CH₂ | n-C₃H₇ | O | n-C₃H₇ |
| S | CCl₃ | CH₂ | CCl₃ | O | CCl₃ |
| S | CHClCH₃ | CH₂ | CHClCH₃ | O | CHClCH₃ |
| S | SC₂H₅ | CH₂ | SC₂H₅ | O | SC₂H₅ |
| S | SCH(CH₃)₂ | CH₂ | SCH(CH₃)₂ | O | SCH(CH₃)₂ |
| S | SCH(CH₃)(C₂H₅) | CH₂ | SCH(CH₃)(C₂H₅) | O | SCH(CH₃)(C₂H₅) |
| S | SCF₃ | CH₂ | SCF₃ | O | SCF₃ |
| S | OCH(CH₃)₂ | CH₂ | OCH(CH₃)₂ | O | OCH(CH₃)₂ |
| S | OCH(CH₃)(C₂H₅) | CH₂ | OCH(CH₃)(C₂H₅) | O | OCH(CH₃)(C₂H₅) |
| S | OCH(C₂H₅)₂ | CH₂ | OCH(C₂H₅)₂ | O | OCH(C₂H₅)₂ |
| S | OCHF₂ | CH₂ | OCHF₂ | O | OCHF₂ |
| S | C(CH₃)₂C₂H₅ | CH₂ | C(CH₃)₂C₂H₅ | O | C(CH₃)₂C₂H₅ |
| S | CH₂C(CH₃)₃ | CH₂ | CH₂C(CH₃)₃ | O | CH₂C(CH₃)₃ |
| S | c-Pentyl | CH₂ | c-Pentyl | O | c-Pentyl |
| S | c-Hexyl | CH₂ | c-Hexyl | O | c-Hexyl |
| S | c-Octyl | CH₂ | c-Octyl | O | c-Octyl |
| S | CH(CH₃)(n-C₃H₇) | CH₂ | CH(CH₃)(n-C₃H₇) | O | CH(CH₃)(n-C₃H₇) |
| S | CH(C₂H₅)(n-C₃H₇) | CH₂ | CH(C₂H₅)(n-C₃H₇) | O | CH(C₂H₅)(n-C₃H₇) |
| S | CH(n-C₃H₇)₂ | CH₂ | CH(n-C₃H₇)₂ | O | CH(n-C₃H₇)₂ |
| S | CH(n-C₄H₉)₂ | CH₂ | CH(n-C₄H₉)₂ | O | CH(n-C₄H₉)₂ |
| S | CH(CH₃)(n-C₄H₉) | CH₂ | CH(CH₃)(n-C₄H₉) | O | CH(CH₃)(n-C₄H₉) |
| S | CH(CH₃)(n-C₅H₁₁) | CH₂ | CH(CH₃)(n-C₅H₁₁) | O | CH(CH₃)(n-C₅H₁₁) |
| S | CH(CH₃)(n-C₁₀H₂₁) | CH₂ | CH(CH₃)(n-C₁₀H₂₁) | O | CH(CH₃)(n-C₁₀H₂₁) |
| S | C(CH₃)(C₂H₅)₂ | CH₂ | C(CH₃)(C₂H₅)₂ | O | C(CH₃)(C₂H₅)₂ |
| S | CH₂CF₃ | CH₂ | CH₂CF₃ | O | CH₂CF₃ |
| | A is A-59; W is CH₂; R²ᵇ is H    A is A-59; W is CH₂; R²ᵇ is H    A is A-59; W is CH₂; R²ᵇ is H |
| S | C(CH₃)₃ | CH₂ | C(CH₃)₃ | O | C(CH₃)₃ |
| S | CH(CH₃)₂ | CH₂ | CH(CH₃)₂ | O | CH(CH₃)₂ |
| S | CH(CH₃)(C₂H₅) | CH₂ | CH(CH₃)(C₂H₅) | O | CH(CH₃)(C₂H₅) |
| S | CH(C₂H₅)₂ | CH₂ | CH(C₂H₅)₂ | O | CH(C₂H₅)₂ |
| S | c-Pr | CH₂ | c-Pr | O | c-Pr |
| S | 1-Me-c-Pr | CH₂ | 1-Me-c-Pr | O | 1-Me-c-Pr |
| S | 2-Me-c-Pr | CH₂ | 2-Me-c-Pr | O | 2-Me-c-Pr |
| S | 1-Me-2,2-di-Cl-c-Pr | CH₂ | 1-Me-2,2-di-Cl-c-Pr | O | 1-Me-2,2-di-Cl-c-Pr |
| S | c-Bu | CH₂ | c-Bu | O | c-Bu |
| S | 2,2-di-Cl-c-Pr | CH₂ | 2,2-di-Cl-c-Pr | O | 2,2-di-Cl-c-Pr |
| S | Trimethylsilyl | CH₂ | Trimethylsilyl | O | Trimethylsilyl |
| S | Si(CH₃)₂(t-C₄H₉) | CH₂ | Si(CH₃)₂(t-C₄H₉) | O | Si(CH₃)₂(t-C₄H₉) |
| S | C₂H₅ | CH₂ | C₂H₅ | O | C₂H₅ |
| S | CH₃ | CH₂ | CH₃ | O | CH₃ |
| S | H | CH₂ | H | O | H |
| S | Br | CH₂ | Br | O | Br |
| S | I | CH₂ | I | O | I |
| S | Cl | CH₂ | Cl | O | Cl |
| S | C(=O)CH₃ | CH₂ | C(=O)CH₃ | O | C(=O)CH₃ |
| S | C(=O)OCH₃ | CH₂ | C(=O)OCH₃ | O | C(=O)OCH₃ |

-continued

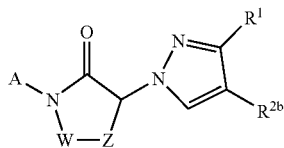

| Z | R¹ | Z | R¹ | Z | R¹ |
|---|---|---|---|---|---|
| S | C(=O)CH(CH$_3$)$_2$ | CH$_2$ | C(=O)CH(CH$_3$)$_2$ | O | C(=O)CH(CH$_3$)$_2$ |
| S | OCH$_3$ | CH$_2$ | OCH$_3$ | O | OCH$_3$ |
| S | SCH$_3$ | CH$_2$ | SCH$_3$ | O | SCH$_3$ |
| S | N(CH$_3$)$_2$ | CH$_2$ | N(CH$_3$)$_2$ | O | N(CH$_3$)$_2$ |
| S | C(=O)N(CH$_3$)$_2$ | CH$_2$ | C(=O)N(CH$_3$)$_2$ | O | C(=O)N(CH$_3$)$_2$ |
| S | C(=O)C(CH$_3$)$_3$ | CH$_2$ | C(=O)C(CH$_3$)$_3$ | O | C(=O)C(CH$_3$)$_3$ |
| S | n-C$_3$H$_7$ | CH$_2$ | n-C$_3$H$_7$ | O | n-C$_3$H$_7$ |
| S | CCl$_3$ | CH$_2$ | CCl$_3$ | O | CCl$_3$ |
| S | CHClCH$_3$ | CH$_2$ | CHClCH$_3$ | O | CHClCH$_3$ |
| S | SC$_2$H$_5$ | CH$_2$ | SC$_2$H$_5$ | O | SC$_2$H$_5$ |
| S | SCH(CH$_3$)$_2$ | CH$_2$ | SCH(CH$_3$)$_2$ | O | SCH(CH$_3$)$_2$ |
| S | SCH(CH$_3$)(C$_2$H$_5$) | CH$_2$ | SCH(CH$_3$)(C$_2$H$_5$) | O | SCH(CH$_3$)(C$_2$H$_5$) |
| S | SCF$_3$ | CH$_2$ | SCF$_3$ | O | SCF$_3$ |
| S | OCH(CH$_3$)$_2$ | CH$_2$ | OCH(CH$_3$)$_2$ | O | OCH(CH$_3$)$_2$ |
| S | OCH(CH$_3$)(C$_2$H$_5$) | CH$_2$ | OCH(CH$_3$)(C$_2$H$_5$) | O | OCH(CH$_3$)(C$_2$H$_5$) |
| S | OCH(C$_2$H$_5$)$_2$ | CH$_2$ | OCH(C$_2$H$_5$)$_2$ | O | OCH(C$_2$H$_5$)$_2$ |
| S | OCHF$_2$ | CH$_2$ | OCHF$_2$ | O | OCHF$_2$ |
| S | C(CH$_3$)$_2$C$_2$H$_5$ | CH$_2$ | C(CH$_3$)$_2$C$_2$H$_5$ | O | C(CH$_3$)$_2$C$_2$H$_5$ |
| S | CH$_2$C(CH$_3$)$_3$ | CH$_2$ | CH$_2$C(CH$_3$)$_3$ | O | CH$_2$C(CH$_3$)$_3$ |
| S | c-Pentyl | CH$_2$ | c-Pentyl | O | c-Pentyl |
| S | c-Hexyl | CH$_2$ | c-Hexyl | O | c-Hexyl |
| S | c-Octyl | CH$_2$ | c-Octyl | O | c-Octyl |
| S | CH(CH$_3$)(n-C$_3$H$_7$) | CH$_2$ | CH(CH$_3$)(n-C$_3$H$_7$) | O | CH(CH$_3$)(n-C$_3$H$_7$) |
| S | CH(C$_2$H$_5$)(n-C$_3$H$_7$) | CH$_2$ | CH(C$_2$H$_5$)(n-C$_3$H$_7$) | O | CH(C$_2$H$_5$)(n-C$_3$H$_7$) |
| S | CH(n-C$_3$H$_7$)$_2$ | CH$_2$ | CH(n-C$_3$H$_7$)$_2$ | O | CH(n-C$_3$H$_7$)$_2$ |
| S | CH(n-C$_4$H$_9$)$_2$ | CH$_2$ | CH(n-C$_4$H$_9$)$_2$ | O | CH(n-C$_4$H$_9$)$_2$ |
| S | CH(CH$_3$)(n-C$_4$H$_9$) | CH$_2$ | CH(CH$_3$)(n-C$_4$H$_9$) | O | CH(CH$_3$)(n-C$_4$H$_9$) |
| S | CH(CH$_3$)(n-C$_5$H$_{11}$) | CH$_2$ | CH(CH$_3$)(n-C$_5$H$_{11}$) | O | CH(CH$_3$)(n-C$_5$H$_{11}$) |
| S | CH(CH$_3$)(n-C$_{10}$H$_{21}$) | CH$_2$ | CH(CH$_3$)(n-C$_{10}$H$_{21}$) | O | CH(CH$_3$)(n-C$_{10}$H$_{21}$) |
| S | C(CH$_3$)(C$_2$H$_5$)$_2$ | CH$_2$ | C(CH$_3$)(C$_2$H$_5$)$_2$ | O | C(CH$_3$)(C$_2$H$_5$)$_2$ |
| S | CH$_2$CF$_3$ | CH$_2$ | CH$_2$CF$_3$ | O | CH$_2$CF$_3$ |

TABLE 1B

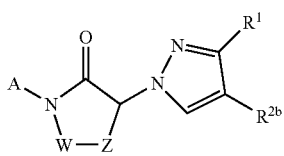

| W | Z | R¹ | R$^{2b}$ | W | Z | R¹ | R$^{2b}$ |
|---|---|---|---|---|---|---|---|
| | | A is A-1 | | | | A is A-1 | |
| CH$_2$ | S(O) | C(CH$_3$)$_3$ | H | CH$_2$ | CH$_2$ | c-Pr | CH$_3$ |
| CH$_2$ | S(O) | CH(CH$_3$)$_2$ | H | CH$_2$ | CH$_2$ | 1-Me-c-Pr | CH$_3$ |
| CH$_2$ | S(O) | CH(CH$_3$)(C$_2$H$_5$) | H | CH$_2$ | CH$_2$ | c-Bu | CH$_3$ |
| CH$_2$ | S(O) | CH(C$_2$H$_5$)$_2$ | H | CH$_2$ | O | C(CH$_3$)$_3$ | CH$_3$ |
| CH$_2$ | S(O) | c-Pr | H | CH$_2$ | O | CH(CH$_3$)$_2$ | CH$_3$ |
| CH$_2$ | S(O) | 1-Me-c-Pr | H | CH$_2$ | O | CH(CH$_3$)(C$_2$H$_5$) | CH$_3$ |
| CH$_2$ | S(O) | c-Bu | H | CH$_2$ | O | c-Pr | CH$_3$ |
| CH$_2$ | S(O) | 1-Me-2,2-di-Cl-c-Pr | H | CH$_2$ | O | 1-Me-c-Pr | CH$_3$ |
| CH$_2$ | S | C(CH$_3$)$_3$ | CH$_3$ | CH$_2$ | O | c-Pentyl | CH$_3$ |
| CH$_2$ | S | CH(CH$_3$)$_2$ | CH$_3$ | CH$_2$ | O | 1-Me-2,2-di-Cl-c-Pr | CH$_3$ |
| CH$_2$ | S | CH(CH$_3$)(C$_2$H$_5$) | CH$_3$ | CH(CH$_3$) | CH$_2$ | C(CH$_3$)$_3$ | H |
| CH$_2$ | S | c-Pr | CH$_3$ | CH(CH$_3$) | CH$_2$ | CH(CH$_3$)$_2$ | H |
| CH$_2$ | S | 1-Me-c-Pr | CH$_3$ | CH(CH$_3$) | CH$_2$ | CH(CH$_3$)(C$_2$H$_5$) | H |
| CH$_2$ | S | c-Bu | CH$_3$ | CH(CH$_3$) | CH$_2$ | CH(C$_2$H$_5$)$_2$ | H |
| CH$_2$ | CH$_2$ | C(CH$_3$)$_3$ | CH$_3$ | CH(CH$_3$) | CH$_2$ | c-Pr | H |
| CH$_2$ | CH$_2$ | CH(CH$_3$)$_2$ | CH$_3$ | CH(CH$_3$) | CH$_2$ | c-Bu | H |
| CH$_2$ | CH$_2$ | CH(CH$_3$)(C$_2$H$_5$) | CH$_3$ | CH$_2$ | CH$_2$ | CH(CH$_3$)(n-C$_{10}$H$_{21}$) | CH$_3$ |

TABLE 1B-continued

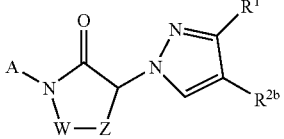

| W | Z | R¹ | R²ᵇ | W | Z | R¹ | R²ᵇ |
|---|---|---|---|---|---|---|---|
| \multicolumn{4}{c}{A is A-5} | | | A is A-5 | | |
| CH₂ | S(O) | C(CH₃)₃ | H | CH₂ | CH₂ | c-Pr | CH₃ |
| CH₂ | S(O) | CH(CH₃)₂ | H | CH₂ | CH₂ | 1-Me-c-Pr | CH₃ |
| CH₂ | S(O) | CH(CH₃)(C₂H₅) | H | CH₂ | CH₂ | c-Bu | CH₃ |
| CH₂ | S(O) | CH(C₂H₅)₂ | H | CH₂ | O | C(CH₃)₃ | CH₃ |
| CH₂ | S(O) | c-Pr | H | CH₂ | O | CH(CH₃)₂ | CH₃ |
| CH₂ | S(O) | 1-Me-c-Pr | H | CH₂ | O | CH(CH₃)(C₂H₅) | CH₃ |
| CH₂ | S(O) | c-Bu | H | CH₂ | O | c-Pr | CH₃ |
| CH₂ | S(O) | 1-Me-2,2-di-Cl-c-Pr | H | CH₂ | O | 1-Me-c-Pr | CH₃ |
| CH₂ | S | C(CH₃)₃ | CH₃ | CH₂ | O | c-Pentyl | CH₃ |
| CH₂ | S | CH(CH₃)₂ | CH₃ | CH₂ | O | 1-Me-2,2-di-Cl-c-Pr | CH₃ |
| CH₂ | S | CH(CH₃)(C₂H₅) | CH₃ | CH(CH₃) | CH₂ | C(CH₃)₃ | H |
| CH₂ | S | c-Pr | CH₃ | CH(CH₃) | CH₂ | CH(CH₃)₂ | H |
| CH₂ | S | 1-Me-c-Pr | CH₃ | CH(CH₃) | CH₂ | CH(CH₃)(C₂H₅) | H |
| CH₂ | S | c-Bu | CH₃ | CH(CH₃) | CH₂ | CH(C₂H₅)₂ | H |
| CH₂ | CH₂ | C(CH₃)₃ | CH₃ | CH(CH₃) | CH₂ | c-Pr | H |
| CH₂ | CH₂ | CH(CH₃)₂ | CH₃ | CH(CH₃) | CH₂ | c-Bu | H |
| CH₂ | CH₂ | CH(CH₃)(C₂H₅) | CH₃ | CH₂ | CH₂ | CH(CH₃)(n-C₁₀H₂₁) | CH₃ |

TABLE 1C

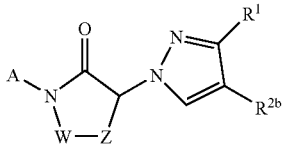

| Z | R¹ | Z | R¹ | Z | R¹ |
|---|---|---|---|---|---|
| A is A-6; W is CH₂; R²ᵇ is H | | A is A-6; W is CH₂; R²ᵇ is H | | A is A-6; W is CH₂; R²ᵇ is H | |
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |
| A is A-8; W is CH₂; R²ᵇ is H | | A is A-8; W is CH₂; R²ᵇ is H | | A is A-8; W is CH₂; R²ᵇ is H | |
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |
| A is A-9; W is CH₂; R²ᵇ is H | | A is A-9; W is CH₂; R²ᵇ is H | | A is A-9; W is CH₂; R²ᵇ is H | |
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |

TABLE 1C-continued

| Z | R¹ | Z | R¹ | Z | R¹ |
|---|---|---|---|---|---|
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-12; W is CH₂; R²ᵇ is H   A is A-12; W is CH₂; R²ᵇ is H   A is A-12; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-20; W is CH₂; R²ᵇ is H   A is A-20; W is CH₂; R²ᵇ is H   A is A-20; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-21; W is CH₂; R²ᵇ is H   A is A-21; W is CH₂; R²ᵇ is H   A is A-21; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-32; W is CH₂; R²ᵇ is H   A is A-32; W is CH₂; R²ᵇ is H   A is A-32; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |

TABLE 1C-continued

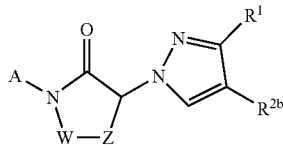

| Z | R¹ | Z | R¹ | Z | R¹ |
|---|---|---|---|---|---|
| S | c-Hexyl | CH$_2$ | c-Pentyl | O | N(CH$_3$)$_2$ |
| S | N(CH$_3$)$_2$ | CH$_2$ | c-Hexyl | CH$_2$ | N(CH$_3$)$_2$ |
| S | SCH$_3$ | O | C(CH$_3$)$_3$ | CH$_2$ | CH(CH$_3$)(n-C$_{10}$H$_{21}$) |

A is A-34; W is CH$_2$; R$^{2b}$ is H   A is A-34; W is CH$_2$; R$^{2b}$ is H   A is A-34; W is CH$_2$; R$^{2b}$ is H

| Z | R¹ | Z | R¹ | Z | R¹ |
|---|---|---|---|---|---|
| S | C(CH$_3$)$_3$ | S | SCH(CH$_3$)$_2$ | O | CH(CH$_3$)$_2$ |
| S | CH(CH$_3$)$_2$ | CH$_2$ | C(CH$_3$)$_3$ | O | CH(CH$_3$)(C$_2$H$_5$) |
| S | CH(CH$_3$)(C$_2$H$_5$) | CH$_2$ | CH(CH$_3$)$_2$ | O | CH(CH$_3$)(CH$_2$)$_2$CH$_3$ |
| S | CH(CH$_3$)(CH$_2$)$_2$CH$_3$ | CH$_2$ | CH(CH$_3$)(C$_2$H$_5$) | O | CH(C$_2$H$_5$)$_2$ |
| S | CH(C$_2$H$_5$)$_2$ | CH$_2$ | CH(CH$_3$)(CH$_2$)$_2$CH$_3$ | O | c-Pr |
| S | c-Pr | CH$_2$ | CH(C$_2$H$_5$)$_2$ | O | 1-Me-c-Pr |
| S | 1-Me-c-Pr | CH$_2$ | c-Pr | O | c-Bu |
| S | c-Bu | CH$_2$ | 1-Me-c-Pr | O | 1-Me-2,2-di-Cl-c-Pr |
| S | 1-Me-2,2-di-Cl-c-Pr | CH$_2$ | c-Bu | O | c-Pentyl |
| S | c-Pentyl | CH$_2$ | 1-Me-2,2-di-Cl-c-Pr | O | c-Hexyl |
| S | c-Hexyl | CH$_2$ | c-Pentyl | O | N(CH$_3$)$_2$ |
| S | N(CH$_3$)$_2$ | CH$_2$ | c-Hexyl | CH$_2$ | N(CH$_3$)$_2$ |
| S | SCH$_3$ | O | C(CH$_3$)$_3$ | CH$_2$ | CH(CH$_3$)(n-C$_{10}$H$_{21}$) |

A is A-36; W is CH$_2$; R$^{2b}$ is H   A is A-36; W is CH$_2$; R$^{2b}$ is H   A is A-36; W is CH$_2$; R$^{2b}$ is H

| Z | R¹ | Z | R¹ | Z | R¹ |
|---|---|---|---|---|---|
| S | C(CH$_3$)$_3$ | S | SCH(CH$_3$)$_2$ | O | CH(CH$_3$)$_2$ |
| S | CH(CH$_3$)$_2$ | CH$_2$ | C(CH$_3$)$_3$ | O | CH(CH$_3$)(C$_2$H$_5$) |
| S | CH(CH$_3$)(C$_2$H$_5$) | CH$_2$ | CH(CH$_3$)$_2$ | O | CH(CH$_3$)(CH$_2$)$_2$CH$_3$ |
| S | CH(CH$_3$)(CH$_2$)$_2$CH$_3$ | CH$_2$ | CH(CH$_3$)(C$_2$H$_5$) | O | CH(C$_2$H$_5$)$_2$ |
| S | CH(C$_2$H$_5$)$_2$ | CH$_2$ | CH(CH$_3$)(CH$_2$)$_2$CH$_3$ | O | c-Pr |
| S | c-Pr | CH$_2$ | CH(C$_2$H$_5$)$_2$ | O | 1-Me-c-Pr |
| S | 1-Me-c-Pr | CH$_2$ | c-Pr | O | c-Bu |
| S | c-Bu | CH$_2$ | 1-Me-c-Pr | O | 1-Me-2,2-di-Cl-c-Pr |
| S | 1-Me-2,2-di-Cl-c-Pr | CH$_2$ | c-Bu | O | c-Pentyl |
| S | c-Pentyl | CH$_2$ | 1-Me-2,2-di-Cl-c-Pr | O | c-Hexyl |
| S | c-Hexyl | CH$_2$ | c-Pentyl | O | N(CH$_3$)$_2$ |
| S | N(CH$_3$)$_2$ | CH$_2$ | c-Hexyl | CH$_2$ | N(CH$_3$)$_2$ |
| S | SCH$_3$ | O | C(CH$_3$)$_3$ | CH$_2$ | CH(CH$_3$)(n-C$_{10}$H$_{21}$) |

A is A-43; W is CH$_2$; R$^{2b}$ is H   A is A-43; W is CH$_2$; R$^{2b}$ is H   A is A-43; W is CH$_2$; R$^{2b}$ is H

| Z | R¹ | Z | R¹ | Z | R¹ |
|---|---|---|---|---|---|
| S | C(CH$_3$)$_3$ | S | SCH(CH$_3$)$_2$ | O | CH(CH$_3$)$_2$ |
| S | CH(CH$_3$)$_2$ | CH$_2$ | C(CH$_3$)$_3$ | O | CH(CH$_3$)(C$_2$H$_5$) |
| S | CH(CH$_3$)(C$_2$H$_5$) | CH$_2$ | CH(CH$_3$)$_2$ | O | CH(CH$_3$)(CH$_2$)$_2$CH$_3$ |
| S | CH(CH$_3$)(CH$_2$)$_2$CH$_3$ | CH$_2$ | CH(CH$_3$)(C$_2$H$_5$) | O | CH(C$_2$H$_5$)$_2$ |
| S | CH(C$_2$H$_5$)$_2$ | CH$_2$ | CH(CH$_3$)(CH$_2$)$_2$CH$_3$ | O | c-Pr |
| S | c-Pr | CH$_2$ | CH(C$_2$H$_5$)$_2$ | O | 1-Me-c-Pr |
| S | 1-Me-c-Pr | CH$_2$ | c-Pr | O | c-Bu |
| S | c-Bu | CH$_2$ | 1-Me-c-Pr | O | 1-Me-2,2-di-Cl-c-Pr |
| S | 1-Me-2,2-di-Cl-c-Pr | CH$_2$ | c-Bu | O | c-Pentyl |
| S | c-Pentyl | CH$_2$ | 1-Me-2,2-di-Cl-c-Pr | O | c-Hexyl |
| S | c-Hexyl | CH$_2$ | c-Pentyl | O | N(CH$_3$)$_2$ |
| S | N(CH$_3$)$_2$ | CH$_2$ | c-Hexyl | CH$_2$ | N(CH$_3$)$_2$ |
| S | SCH$_3$ | O | C(CH$_3$)$_3$ | CH$_2$ | CH(CH$_3$)(n-C$_{10}$H$_{21}$) |

A is A-47; W is CH$_2$; R$^{2b}$ is H   A is A-47; W is CH$_2$; R$^{2b}$ is H   A is A-47; W is CH$_2$; R$^{2b}$ is H

| Z | R¹ | Z | R¹ | Z | R¹ |
|---|---|---|---|---|---|
| S | C(CH$_3$)$_3$ | S | SCH(CH$_3$)$_2$ | O | CH(CH$_3$)$_2$ |
| S | CH(CH$_3$)$_2$ | CH$_2$ | C(CH$_3$)$_3$ | O | CH(CH$_3$)(C$_2$H$_5$) |
| S | CH(CH$_3$)(C$_2$H$_5$) | CH$_2$ | CH(CH$_3$)$_2$ | O | CH(CH$_3$)(CH$_2$)$_2$CH$_3$ |
| S | CH(CH$_3$)(CH$_2$)$_2$CH$_3$ | CH$_2$ | CH(CH$_3$)(C$_2$H$_5$) | O | CH(C$_2$H$_5$)$_2$ |
| S | CH(C$_2$H$_5$)$_2$ | CH$_2$ | CH(CH$_3$)(CH$_2$)$_2$CH$_3$ | O | c-Pr |
| S | c-Pr | CH$_2$ | CH(C$_2$H$_5$)$_2$ | O | 1-Me-c-Pr |
| S | 1-Me-c-Pr | CH$_2$ | c-Pr | O | c-Bu |
| S | c-Bu | CH$_2$ | 1-Me-c-Pr | O | 1-Me-2,2-di-Cl-c-Pr |
| S | 1-Me-2,2-di-Cl-c-Pr | CH$_2$ | c-Bu | O | c-Pentyl |
| S | c-Pentyl | CH$_2$ | 1-Me-2,2-di-Cl-c-Pr | O | c-Hexyl |
| S | c-Hexyl | CH$_2$ | c-Pentyl | O | N(CH$_3$)$_2$ |
| S | N(CH$_3$)$_2$ | CH$_2$ | c-Hexyl | CH$_2$ | N(CH$_3$)$_2$ |
| S | SCH$_3$ | O | C(CH$_3$)$_3$ | CH$_2$ | CH(CH$_3$)(n-C$_{10}$H$_{21}$) |

A is A-60; W is CH$_2$; R$^{2b}$ is H   A is A-60; W is CH$_2$; R$^{2b}$ is H   A is A-60; W is CH$_2$; R$^{2b}$ is H

| Z | R¹ | Z | R¹ | Z | R¹ |
|---|---|---|---|---|---|
| S | C(CH$_3$)$_3$ | S | SCH(CH$_3$)$_2$ | O | CH(CH$_3$)$_2$ |
| S | CH(CH$_3$)$_2$ | CH$_2$ | C(CH$_3$)$_3$ | O | CH(CH$_3$)(C$_2$H$_5$) |
| S | CH(CH$_3$)(C$_2$H$_5$) | CH$_2$ | CH(CH$_3$)$_2$ | O | CH(CH$_3$)(CH$_2$)$_2$CH$_3$ |

TABLE 1C-continued

[Structure: pyrazolidinone with A-N, W-Z ring, attached to pyrazole bearing R¹ and R²ᵇ]

| Z | R¹ | Z | R¹ | Z | R¹ |
|---|---|---|---|---|---|
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-62; W is CH₂; R²ᵇ is H    A is A-62; W is CH₂; R²ᵇ is H    A is A-62; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-66; W is CH₂; R²ᵇ is H    A is A-66; W is CH₂; R²ᵇ is H    A is A-66; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-67; W is CH₂; R²ᵇ is H    A is A-67; W is CH₂; R²ᵇ is H    A is A-67; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-68; W is CH₂; R²ᵇ is H    A is A-68; W is CH₂; R²ᵇ is H    A is A-68; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |

TABLE 1C-continued

[Structure: pyrazolone ring with A-N, W-Z, and pyrazole substituents R¹, R²ᵇ]

| Z | R¹ | Z | R¹ | Z | R¹ |
|---|---|---|---|---|---|
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-69; W is CH₂; R²ᵇ is H   A is A-69; W is CH₂; R²ᵇ is H   A is A-69; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-70; W is CH₂; R²ᵇ is H   A is A-70; W is CH₂; R²ᵇ is H   A is A-70; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-71; W is CH₂; R²ᵇ is H   A is A-71; W is CH₂; R²ᵇ is H   A is A-71; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-72; W is CH₂; R²ᵇ is H   A is A-72; W is CH₂; R²ᵇ is H   A is A-72; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-73; W is CH₂; R²ᵇ is H   A is A-73; W is CH₂; R²ᵇ is H   A is A-73; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |

TABLE 1C-continued

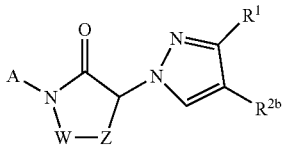

| Z | R¹ | Z | R¹ | Z | R¹ |
|---|---|---|---|---|---|
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-74; W is CH₂; R²ᵇ is H   A is A-74; W is CH₂; R²ᵇ is H   A is A-74; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-75; W is CH₂; R²ᵇ is H   A is A-75; W is CH₂; R²ᵇ is H   A is A-75; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-76; W is CH₂; R²ᵇ is H   A is A-76; W is CH₂; R²ᵇ is H   A is A-76; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-77; W is CH₂; R²ᵇ is H   A is A-77; W is CH₂; R²ᵇ is H   A is A-77; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |

TABLE 1C-continued

| Z | R¹ | Z | R¹ | Z | R¹ |
|---|---|---|---|---|---|
| S | N(CH$_3$)$_2$ | CH$_2$ | c-Hexyl | CH$_2$ | N(CH$_3$)$_2$ |
| S | SCH$_3$ | O | C(CH$_3$)$_3$ | CH$_2$ | CH(CH$_3$)(n-C$_{10}$H$_{21}$) |

A is A-78; W is CH$_2$; R$^{2b}$ is H    A is A-78; W is CH$_2$; R$^{2b}$ is H    A is A-78; W is CH$_2$; R$^{2b}$ is H

| Z | R¹ | Z | R¹ | Z | R¹ |
|---|---|---|---|---|---|
| S | C(CH$_3$)$_3$ | S | SCH(CH$_3$)$_2$ | O | CH(CH$_3$)$_2$ |
| S | CH(CH$_3$)$_2$ | CH$_2$ | C(CH$_3$)$_3$ | O | CH(CH$_3$)(C$_2$H$_5$) |
| S | CH(CH$_3$)(C$_2$H$_5$) | CH$_2$ | CH(CH$_3$)$_2$ | O | CH(CH$_3$)(CH$_2$)$_2$CH$_3$ |
| S | CH(CH$_3$)(CH$_2$)$_2$CH$_3$ | CH$_2$ | CH(CH$_3$)(C$_2$H$_5$) | O | CH(C$_2$H$_5$)$_2$ |
| S | CH(C$_2$H$_5$)$_2$ | CH$_2$ | CH(CH$_3$)(CH$_2$)$_2$CH$_3$ | O | c-Pr |
| S | c-Pr | CH$_2$ | CH(C$_2$H$_5$)$_2$ | O | 1-Me-c-Pr |
| S | 1-Me-c-Pr | CH$_2$ | c-Pr | O | c-Bu |
| S | c-Bu | CH$_2$ | 1-Me-c-Pr | O | 1-Me-2,2-di-Cl-c-Pr |
| S | 1-Me-2,2-di-Cl-c-Pr | CH$_2$ | c-Bu | O | c-Pentyl |
| S | c-Pentyl | CH$_2$ | 1-Me-2,2-di-Cl-c-Pr | O | c-Hexyl |
| S | c-Hexyl | CH$_2$ | c-Pentyl | O | N(CH$_3$)$_2$ |
| S | N(CH$_3$)$_2$ | CH$_2$ | c-Hexyl | CH$_2$ | N(CH$_3$)$_2$ |
| S | SCH$_3$ | O | C(CH$_3$)$_3$ | CH$_2$ | CH(CH$_3$)(n-C$_{10}$H$_{21}$) |

A is A-79; W is CH$_2$; R$^{2b}$ is H    A is A-79; W is CH$_2$; R$^{2b}$ is H    A is A-79; W is CH$_2$; R$^{2b}$ is H

| Z | R¹ | Z | R¹ | Z | R¹ |
|---|---|---|---|---|---|
| S | C(CH$_3$)$_3$ | S | SCH(CH$_3$)$_2$ | O | CH(CH$_3$)$_2$ |
| S | CH(CH$_3$)$_2$ | CH$_2$ | C(CH$_3$)$_3$ | O | CH(CH$_3$)(C$_2$H$_5$) |
| S | CH(CH$_3$)(C$_2$H$_5$) | CH$_2$ | CH(CH$_3$)$_2$ | O | CH(CH$_3$)(CH$_2$)$_2$CH$_3$ |
| S | CH(CH$_3$)(CH$_2$)$_2$CH$_3$ | CH$_2$ | CH(CH$_3$)(C$_2$H$_5$) | O | CH(C$_2$H$_5$)$_2$ |
| S | CH(C$_2$H$_5$)$_2$ | CH$_2$ | CH(CH$_3$)(CH$_2$)$_2$CH$_3$ | O | c-Pr |
| S | c-Pr | CH$_2$ | CH(C$_2$H$_5$)$_2$ | O | 1-Me-c-Pr |
| S | 1-Me-c-Pr | CH$_2$ | c-Pr | O | c-Bu |
| S | c-Bu | CH$_2$ | 1-Me-c-Pr | O | 1-Me-2,2-di-Cl-c-Pr |
| S | 1-Me-2,2-di-Cl-c-Pr | CH$_2$ | c-Bu | O | c-Pentyl |
| S | c-Pentyl | CH$_2$ | 1-Me-2,2-di-Cl-c-Pr | O | c-Hexyl |
| S | c-Hexyl | CH$_2$ | c-Pentyl | O | N(CH$_3$)$_2$ |
| S | N(CH$_3$)$_2$ | CH$_2$ | c-Hexyl | CH$_2$ | N(CH$_3$)$_2$ |
| S | SCH$_3$ | O | C(CH$_3$)$_3$ | CH$_2$ | CH(CH$_3$)(n-C$_{10}$H$_{21}$) |

A is A-80; W is CH$_2$; R$^{2b}$ is H    A is A-80; W is CH$_2$; R$^{2b}$ is H    A is A-80; W is CH$_2$; R$^{2b}$ is H

| Z | R¹ | Z | R¹ | Z | R¹ |
|---|---|---|---|---|---|
| S | C(CH$_3$)$_3$ | S | SCH(CH$_3$)$_2$ | O | CH(CH$_3$)$_2$ |
| S | CH(CH$_3$)$_2$ | CH$_2$ | C(CH$_3$)$_3$ | O | CH(CH$_3$)(C$_2$H$_5$) |
| S | CH(CH$_3$)(C$_2$H$_5$) | CH$_2$ | CH(CH$_3$)$_2$ | O | CH(CH$_3$)(CH$_2$)$_2$CH$_3$ |
| S | CH(CH$_3$)(CH$_2$)$_2$CH$_3$ | CH$_2$ | CH(CH$_3$)(C$_2$H$_5$) | O | CH(C$_2$H$_5$)$_2$ |
| S | CH(C$_2$H$_5$)$_2$ | CH$_2$ | CH(CH$_3$)(CH$_2$)$_2$CH$_3$ | O | c-Pr |
| S | c-Pr | CH$_2$ | CH(C$_2$H$_5$)$_2$ | O | 1-Me-c-Pr |
| S | 1-Me-c-Pr | CH$_2$ | c-Pr | O | c-Bu |
| S | c-Bu | CH$_2$ | 1-Me-c-Pr | O | 1-Me-2,2-di-Cl-c-Pr |
| S | 1-Me-2,2-di-Cl-c-Pr | CH$_2$ | c-Bu | O | c-Pentyl |
| S | c-Pentyl | CH$_2$ | 1-Me-2,2-di-Cl-c-Pr | O | c-Hexyl |
| S | c-Hexyl | CH$_2$ | c-Pentyl | O | N(CH$_3$)$_2$ |
| S | N(CH$_3$)$_2$ | CH$_2$ | c-Hexyl | CH$_2$ | N(CH$_3$)$_2$ |
| S | SCH$_3$ | O | C(CH$_3$)$_3$ | CH$_2$ | CH(CH$_3$)(n-C$_{10}$H$_{21}$) |

A is A-81; W is CH$_2$; R$^{2b}$ is H    A is A-81; W is CH$_2$; R$^{2b}$ is H    A is A-81; W is CH$_2$; R$^{2b}$ is H

| Z | R¹ | Z | R¹ | Z | R¹ |
|---|---|---|---|---|---|
| S | C(CH$_3$)$_3$ | S | SCH(CH$_3$)$_2$ | O | CH(CH$_3$)$_2$ |
| S | CH(CH$_3$)$_2$ | CH$_2$ | C(CH$_3$)$_3$ | O | CH(CH$_3$)(C$_2$H$_5$) |
| S | CH(CH$_3$)(C$_2$H$_5$) | CH$_2$ | CH(CH$_3$)$_2$ | O | CH(CH$_3$)(CH$_2$)$_2$CH$_3$ |
| S | CH(CH$_3$)(CH$_2$)$_2$CH$_3$ | CH$_2$ | CH(CH$_3$)(C$_2$H$_5$) | O | CH(C$_2$H$_5$)$_2$ |
| S | CH(C$_2$H$_5$)$_2$ | CH$_2$ | CH(CH$_3$)(CH$_2$)$_2$CH$_3$ | O | c-Pr |
| S | c-Pr | CH$_2$ | CH(C$_2$H$_5$)$_2$ | O | 1-Me-c-Pr |
| S | 1-Me-c-Pr | CH$_2$ | c-Pr | O | c-Bu |
| S | c-Bu | CH$_2$ | 1-Me-c-Pr | O | 1-Me-2,2-di-Cl-c-Pr |
| S | 1-Me-2,2-di-Cl-c-Pr | CH$_2$ | c-Bu | O | c-Pentyl |
| S | c-Pentyl | CH$_2$ | 1-Me-2,2-di-Cl-c-Pr | O | c-Hexyl |
| S | c-Hexyl | CH$_2$ | c-Pentyl | O | N(CH$_3$)$_2$ |
| S | N(CH$_3$)$_2$ | CH$_2$ | c-Hexyl | CH$_2$ | N(CH$_3$)$_2$ |
| S | SCH$_3$ | O | C(CH$_3$)$_3$ | CH$_2$ | CH(CH$_3$)(n-C$_{10}$H$_{21}$) |

A is A-82; W is CH$_2$; R$^{2b}$ is H    A is A-82; W is CH$_2$; R$^{2b}$ is H    A is A-82; W is CH$_2$; R$^{2b}$ is H

| Z | R¹ | Z | R¹ | Z | R¹ |
|---|---|---|---|---|---|
| S | C(CH$_3$)$_3$ | S | SCH(CH$_3$)$_2$ | O | CH(CH$_3$)$_2$ |
| S | CH(CH$_3$)$_2$ | CH$_2$ | C(CH$_3$)$_3$ | O | CH(CH$_3$)(C$_2$H$_5$) |
| S | CH(CH$_3$)(C$_2$H$_5$) | CH$_2$ | CH(CH$_3$)$_2$ | O | CH(CH$_3$)(CH$_2$)$_2$CH$_3$ |
| S | CH(CH$_3$)(CH$_2$)$_2$CH$_3$ | CH$_2$ | CH(CH$_3$)(C$_2$H$_5$) | O | CH(C$_2$H$_5$)$_2$ |

TABLE 1C-continued

| Z | R¹ | Z | R¹ | Z | R¹ |
|---|---|---|---|---|---|
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-83; W is CH₂; R²ᵇ is H   A is A-83; W is CH₂; R²ᵇ is H   A is A-83; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-84; W is CH₂; R²ᵇ is H   A is A-84; W is CH₂; R²ᵇ is H   A is A-84; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂CH₃ | O | c-Pr |
| S | c-Pr | CH₂ | CH(C₂H₅)₂ | O | 1-Me-c-Pr |
| S | 1-Me-c-Pr | CH₂ | c-Pr | O | c-Bu |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

A is A-85; W is CH₂; R²ᵇ is H   A is A-85; W is CH₂; R²ᵇ is H   A is A-85; W is CH₂; R²ᵇ is H

| Z | R¹ | Z | R¹ | Z | R¹ |
|---|---|---|---|---|---|
| S | C(CH₃)₃ | S | SCH(CH₃)₂ | O | CH(CH₃)₂ |
| S | CH(CH₃)₂ | CH₂ | C(CH₃)₃ | O | CH(CH₃)(C₂H₅) |
| S | CH(CH₃)(C₂H₅) | CH₂ | CH(CH₃)₂ | O | CH(CH₃)(CH₂)₂CH₃ |
| S | CH(CH₃)(CH₂)₂CH₃ | CH₂ | CH(CH₃)(C₂H₅) | O | CH(C₂H₅)₂ |
| S | CH(C₂H₅)₂ | CH₂ | CH(CH₃)(CH₂)₂OH₃ | O | c-Pr |
| S | c-Pr | CH₂ | CH(C₂H₅)₂ | O | 1-Me-c-Pr |
| S | 1-Me-c-Pr | CH₂ | c-Pr | O | c-N |
| S | c-Bu | CH₂ | 1-Me-c-Pr | O | 1-Me-2,2-di-Cl-c-Pr |
| S | 1-Me-2,2-di-Cl-c-Pr | CH₂ | c-Bu | O | c-Pentyl |
| S | c-Pentyl | CH₂ | 1-Me-2,2-di-Cl-c-Pr | O | c-Hexyl |
| S | c-Hexyl | CH₂ | c-Pentyl | O | N(CH₃)₂ |
| S | N(CH₃)₂ | CH₂ | c-Hexyl | CH₂ | N(CH₃)₂ |
| S | SCH₃ | O | C(CH₃)₃ | CH₂ | CH(CH₃)(n-C₁₀H₂₁) |

TABLE 1D

W is CH₂; R²ᵇ is H

| A | Z | R¹ | A | Z | R¹ | A | Z | R¹ | A | Z | R¹ |
|---|---|---|---|---|---|---|---|---|---|---|---|
| A-2 | S | C(CH₃)₃ | A-4 | CH₂ | CH(CH₃)(C₂H₅) | A-22 | CH₂ | CH(CH₃)₂ | A-19 | CH₂ | CH(CH₃)₂ |
| A-2 | S | CH(CH₃)₂ | A-4 | CH₂ | c-Pr | A-22 | CH₂ | CH(CH₃)(C₂H₅) | A-19 | CH₂ | CH(CH₃)(C₂H₅) |
| A-2 | S | CH(CH₃)(C₂H₅) | A-4 | O | C(CH₃)₃ | A-22 | CH₂ | c-Pr | A-19 | CH₂ | c-Pr |
| A-2 | S | c-Pr | A-4 | O | CH(CH₃)₂ | A-22 | O | C(CH₃)₃ | A-19 | O | C(CH₃)₃ |
| A-2 | CH₂ | C(CH₃)₃ | A-4 | O | CH(CH₃)(C₂H₅) | A-22 | O | CH(CH₃)₂ | A-19 | O | CH(CH₃)₂ |
| A-2 | CH₂ | CH(CH₃)₂ | A-4 | O | c-Pr | A-22 | O | CH(CH₃)(C₂H₅) | A-19 | O | CH(CH₃)(C₂H₅) |
| A-2 | CH₂ | CH(CH₃)(C₂H₅) | A-7 | S | C(CH₃)₃ | A-22 | O | c-Pr | A-19 | O | c-Pr |
| A-2 | CH₂ | c-Pr | A-7 | S | CH(CH₃)₂ | A-23 | S | C(CH₃)₃ | A-23 | CH₂ | CH(CH₃)(C₂H₅) |
| A-2 | O | C(CH₃)₃ | A-7 | S | CH(CH₃)(C₂H₅) | A-23 | S | CH(CH₃)₂ | A-23 | CH₂ | c-Pr |
| A-2 | O | CH(CH₃)₂ | A-7 | S | c-Pr | A-23 | S | CH(CH₃)(C₂H₅) | A-23 | O | C(CH₃)₃ |
| A-2 | O | CH(CH₃)(C₂H₅) | A-7 | CH₂ | C(CH₃)₃ | A-23 | S | c-Pr | A-23 | O | CH(CH₃)₂ |
| A-2 | O | c-Pr | A-7 | CH₂ | CH(CH₃)₂ | A-23 | CH₂ | C(CH₃)₃ | A-23 | O | CH(CH₃)(C₂H₅) |
| A-4 | S | C(CH₃)₃ | A-7 | CH₂ | CH(CH₃)(C₂H₅) | A-23 | CH₂ | CH(CH₃)₂ | A-23 | O | c-Pr |
| A-4 | S | CH(CH₃)₂ | A-7 | CH₂ | c-Pr | A-25 | S | C(CH₃)₃ | A-24 | S | C(CH₃)₃ |
| A-4 | S | CH(CH₃)(C₂H₅) | A-7 | O | C(CH₃)₃ | A-25 | S | CH(CH₃)₂ | A-24 | S | CH(CH₃)₂ |
| A-4 | S | c-Pr | A-7 | O | CH(CH₃)₂ | A-25 | S | CH(CH₃)(C₂H₅) | A-24 | S | CH(CH₃)(C₂H₅) |
| A-4 | CH₂ | C(CH₃)₃ | A-7 | O | CH(CH₃)(C₂H₅) | A-25 | S | c-Pr | A-24 | S | c-Pr |
| A-4 | CH₂ | CH(CH₃)₂ | A-7 | O | c-Pr | A-25 | CH₂ | C(CH₃)₃ | A-24 | CH₂ | C(CH₃)₃ |
| A-10 | S | C(CH₃)₃ | A-11 | CH₂ | CH(CH₃)(C₂H₅) | A-25 | CH₂ | CH(CH₃)₂ | A-24 | CH₂ | CH(CH₃)₂ |
| A-10 | S | CH(CH₃)₂ | A-11 | CH₂ | c-Pr | A-25 | CH₂ | CH(CH₃)(C₂H₅) | A-24 | CH₂ | CH(CH₃)(C₂H₅) |
| A-10 | S | CH(CH₃)(C₂H₅) | A-11 | O | C(CH₃)₃ | A-25 | CH₂ | c-Pr | A-24 | CH₂ | c-Pr |
| A-10 | S | c-Pr | A-11 | O | CH(CH₃)₂ | A-25 | O | C(CH₃)₃ | A-24 | O | C(CH₃)₃ |
| A-10 | CH₂ | C(CH₃)₃ | A-11 | O | CH(CH₃)(C₂H₅) | A-25 | O | CH(CH₃)₂ | A-24 | O | CH(CH₃)₂ |
| A-10 | CH₂ | CH(CH₃)₂ | A-11 | O | c-Pr | A-25 | O | CH(CH₃)(C₂H₅) | A-24 | O | CH(CH₃)(C₂H₅) |
| A-10 | CH₂ | CH(CH₃)(C₂H₅) | A-13 | S | C(CH₃)₃ | A-25 | O | c-Pr | A-24 | O | c-Pr |
| A-10 | CH₂ | c-Pr | A-13 | S | CH(CH₃)₂ | A-26 | S | C(CH₃)₃ | A-26 | CH₂ | CH(CH₃)(C₂H₅) |
| A-10 | O | C(CH₃)₃ | A-13 | S | CH(CH₃)(C₂H₅) | A-26 | S | CH(CH₃)₂ | A-26 | CH₂ | c-Pr |
| A-10 | O | CH(CH₃)₂ | A-13 | S | c-Pr | A-26 | S | CH(CH₃)(C₂H₅) | A-26 | O | C(CH₃)₃ |
| A-10 | O | CH(CH₃)(C₂H₅) | A-13 | CH₂ | C(CH₃)₃ | A-26 | S | c-Pr | A-26 | O | CH(CH₃)₂ |
| A-10 | O | c-Pr | A-13 | CH₂ | CH(CH₃)₂ | A-26 | CH₂ | C(CH₃)₃ | A-26 | O | CH(CH₃)(C₂H₅) |
| A-11 | S | C(CH₃)₃ | A-13 | CH₂ | CH(CH₃)(C₂H₅) | A-26 | CH₂ | CH(CH₃)₂ | A-26 | O | c-Pr |
| A-11 | S | CH(CH₃)₂ | A-13 | CH₂ | c-Pr | A-28 | S | C(CH₃)₃ | A-27 | S | C(CH₃)₃ |
| A-11 | S | CH(CH₃)(C₂H₅) | A-13 | O | C(CH₃)₃ | A-28 | S | CH(CH₃)₂ | A-27 | S | CH(CH₃)₂ |
| A-11 | S | c-Pr | A-13 | O | CH(CH₃)₂ | A-28 | S | CH(CH₃)(C₂H₅) | A-27 | S | CH(CH₃)(C₂H₅) |
| A-11 | CH₂ | C(CH₃)₃ | A-13 | O | CH(CH₃)(C₂H₅) | A-28 | S | c-Pr | A-27 | S | c-Pr |
| A-11 | CH₂ | CH(CH₃)₂ | A-13 | O | c-Pr | A-28 | CH₂ | C(CH₃)₃ | A-27 | CH₂ | C(CH₃)₃ |
| A-15 | S | C(CH₃)₃ | A-15 | CH₂ | C(CH₃)₃ | A-28 | CH₂ | CH(CH₃)₂ | A-27 | CH₂ | CH(CH₃)₂ |
| A-15 | S | CH(CH₃)₂ | A-15 | CH₂ | c-Pr | A-28 | CH₂ | CH(CH₃)(C₂H₅) | A-27 | CH₂ | CH(CH₃)(C₂H₅) |
| A-15 | S | CH(CH₃)(C₂H₅) | A-15 | O | C(CH₃)₃ | A-28 | CH₂ | c-Pr | A-27 | CH₂ | c-Pr |
| A-15 | S | c-Pr | A-15 | O | CH(CH₃)₂ | A-28 | O | C(CH₃)₃ | A-27 | O | C(CH₃)₃ |
| A-15 | CH₂ | C(CH₃)₃ | A-15 | O | CH(CH₃)(C₂H₅) | A-28 | O | CH(CH₃)₂ | A-27 | O | CH(CH₃)₂ |
| A-15 | CH₂ | CH(CH₃)₂ | A-15 | O | c-Pr | A-28 | O | CH(CH₃)(C₂H₅) | A-27 | O | CH(CH₃)(C₂H₅) |
| A-17 | S | C(CH₃)₃ | A-16 | S | C(CH₃)₃ | A-28 | O | c-Pr | A-27 | O | c-Pr |
| A-17 | S | CH(CH₃)₂ | A-16 | S | CH(CH₃)₂ | A-30 | S | C(CH₃)₃ | A-30 | CH₂ | CH(CH₃)(C₂H₅) |
| A-17 | S | CH(CH₃)(C₂H₅) | A-16 | S | CH(CH₃)(C₂H₅) | A-30 | S | CH(CH₃)₂ | A-30 | CH₂ | c-Pr |
| A-17 | S | c-Pr | A-16 | S | c-Pr | A-30 | S | CH(CH₃)(C₂H₅) | A-30 | O | C(CH₃)₃ |
| A-17 | CH₂ | C(CH₃)₃ | A-16 | CH₂ | C(CH₃)₃ | A-30 | S | c-Pr | A-30 | O | CH(CH₃)₂ |
| A-17 | CH₂ | CH(CH₃)₂ | A-16 | CH₂ | CH(CH₃)₂ | A-30 | CH₂ | C(CH₃)₃ | A-30 | O | CH(CH₃)(C₂H₅) |
| A-17 | CH₂ | CH(CH₃)(C₂H₅) | A-16 | CH₂ | CH(CH₃)(C₂H₅) | A-30 | CH₂ | CH(CH₃)₂ | A-30 | O | c-Pr |
| A-17 | CH₂ | c-Pr | A-16 | CH₂ | c-Pr | A-33 | S | C(CH₃)₃ | A-31 | S | C(CH₃)₃ |
| A-17 | O | C(CH₃)₃ | A-16 | O | C(CH₃)₃ | A-33 | S | CH(CH₃)₂ | A-31 | S | CH(CH₃)₂ |
| A-17 | O | CH(CH₃)₂ | A-16 | O | CH(CH₃)₂ | A-33 | S | CH(CH₃)(C₂H₅) | A-31 | S | CH(CH₃)(C₂H₅) |
| A-17 | O | CH(CH₃)(C₂H₅) | A-16 | O | CH(CH₃)(C₂H₅) | A-33 | S | c-Pr | A-31 | S | c-Pr |
| A-17 | O | c-Pr | A-16 | O | c-Pr | A-33 | CH₂ | C(CH₃)₃ | A-31 | CH₂ | C(CH₃)₃ |
| A-18 | S | C(CH₃)₃ | A-18 | CH₂ | CH(CH₃)(C₂H₅) | A-33 | CH₂ | CH(CH₃)₂ | A-31 | CH₂ | CH(CH₃)₂ |
| A-18 | S | CH(CH₃)₂ | A-18 | CH₂ | c-Pr | A-33 | CH₂ | CH(CH₃)(C₂H₅) | A-31 | CH₂ | CH(CH₃)(C₂H₅) |
| A-18 | S | CH(CH₃)(C₂H₅) | A-18 | O | C(CH₃)₃ | A-33 | CH₂ | c-Pr | A-31 | CH₂ | c-Pr |
| A-18 | S | c-Pr | A-18 | O | CH(CH₃)₂ | A-33 | O | C(CH₃)₃ | A-31 | O | C(CH₃)₃ |
| A-18 | CH₂ | C(CH₃)₃ | A-18 | O | CH(CH₃)(C₂H₅) | A-33 | O | CH(CH₃)₂ | A-31 | O | CH(CH₃)₂ |
| A-18 | CH₂ | CH(CH₃)₂ | A-18 | O | c-Pr | A-33 | O | CH(CH₃)(C₂H₅) | A-31 | O | CH(CH₃)(C₂H₅) |
| A-22 | S | C(CH₃)₃ | A-19 | S | C(CH₃)₃ | A-33 | O | c-Pr | A-31 | O | c-Pr |
| A-22 | S | CH(CH₃)₂ | A-19 | S | CH(CH₃)₂ | A-35 | S | C(CH₃)₃ | A-35 | CH₂ | CH(CH₃)(C₂H₅) |
| A-22 | S | CH(CH₃)(C₂H₅) | A-19 | S | CH(CH₃)(C₂H₅) | A-35 | S | CH(CH₃)₂ | A-35 | CH₂ | c-Pr |
| A-22 | S | c-Pr | A-19 | S | c-Pr | A-35 | S | CH(CH₃)(C₂H₅) | A-35 | O | C(CH₃)₃ |
| A-22 | CH₂ | C(CH₃)₃ | A-19 | CH₂ | C(CH₃)₃ | A-35 | S | c-Pr | A-35 | O | CH(CH₃)₂ |

TABLE 1D-continued

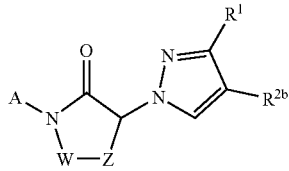
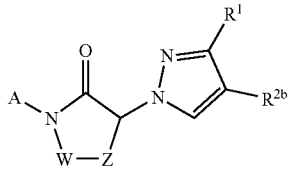

W is CH$_2$; R$^{2b}$ is H

| A | Z | R$^1$ | A | Z | R$^1$ | A | Z | R$^1$ | A | Z | R$^1$ |
|---|---|---|---|---|---|---|---|---|---|---|---|
| A-35 | CH$_2$ | C(CH$_3$)$_3$ | A-35 | O | CH(CH$_3$)(C$_2$H$_5$) | A-50 | S | c-Pr | A-50 | O | CH(CH$_3$)$_2$ |
| A-35 | CH$_2$ | CH(CH$_3$)$_2$ | A-35 | O | c-Pr | A-50 | CH$_2$ | C(CH$_3$)$_3$ | A-50 | O | CH(CH$_3$)(C$_2$H$_5$) |
| A-37 | S | C(CH$_3$)$_3$ | A-37 | S | C(CH$_3$)$_3$ | A-50 | CH$_2$ | CH(CH$_3$)$_2$ | A-50 | O | c-Pr |
| A-38 | S | CH(CH$_3$)$_2$ | A-37 | S | CH(CH$_3$)$_2$ | A-51 | S | C(CH$_3$)$_3$ | A-51 | CH$_2$ | CH(CH$_3$)(C$_2$H$_5$) |
| A-38 | S | CH(CH$_3$)(C$_2$H$_5$) | A-37 | S | CH(CH$_3$)(C$_2$H$_5$) | A-51 | S | CH(CH$_3$)$_2$ | A-51 | CH$_2$ | c-Pr |
| A-38 | S | c-Pr | A-37 | S | c-Pr | A-51 | S | CH(CH$_3$)(C$_2$H$_5$) | A-51 | O | C(CH$_3$)$_3$ |
| A-38 | CH$_2$ | C(CH$_3$)$_3$ | A-37 | CH$_2$ | C(CH$_3$)$_3$ | A-51 | S | c-Pr | A-51 | O | CH(CH$_3$)$_2$ |
| A-38 | CH$_2$ | CH(CH$_3$)$_2$ | A-37 | CH$_2$ | CH(CH$_3$)$_2$ | A-51 | CH$_2$ | C(CH$_3$)$_3$ | A-51 | O | CH(CH$_3$)(C$_2$H$_5$) |
| A-38 | CH$_2$ | CH(CH$_3$)(C$_2$H$_5$) | A-37 | CH$_2$ | CH(CH$_3$)(C$_2$H$_5$) | A-51 | CH$_2$ | CH(CH$_3$)$_2$ | A-51 | O | c-Pr |
| A-38 | CH$_2$ | c-Pr | A-37 | CH$_2$ | c-Pr | A-52 | S | C(CH$_3$)$_3$ | A-52 | CH$_2$ | CH(CH$_3$)(C$_2$H$_5$) |
| A-38 | O | C(CH$_3$)$_3$ | A-37 | O | C(CH$_3$)$_3$ | A-52 | S | CH(CH$_3$)$_2$ | A-52 | CH$_2$ | c-Pr |
| A-38 | O | CH(CH$_3$)$_2$ | A-37 | O | CH(CH$_3$)$_2$ | A-52 | S | CH(CH$_3$)(C$_2$H$_5$) | A-52 | O | C(CH$_3$)$_3$ |
| A-38 | O | CH(CH$_3$)(C$_2$H$_5$) | A-37 | O | CH(CH$_3$)(C$_2$H$_5$) | A-52 | S | c-Pr | A-52 | O | CH(CH$_3$)$_2$ |
| A-38 | O | c-Pr | A-37 | O | c-Pr | A-52 | CH$_2$ | C(CH$_3$)$_3$ | A-52 | O | CH(CH$_3$)(C$_2$H$_5$) |
| A-39 | S | C(CH$_3$)$_3$ | A-39 | CH$_2$ | CH(CH$_3$)(C$_2$H$_5$) | A-52 | CH$_2$ | CH(CH$_3$)$_2$ | A-52 | O | c-Pr |
| A-39 | S | CH(CH$_3$)$_2$ | A-39 | CH$_2$ | c-Pr | A-53 | S | C(CH$_3$)$_3$ | A-53 | CH$_2$ | CH(CH$_3$)(C$_2$H$_5$) |
| A-39 | S | CH(CH$_3$)(C$_2$H$_5$) | A-39 | O | C(CH$_3$)$_3$ | A-53 | S | CH(CH$_3$)$_2$ | A-53 | CH$_2$ | c-Pr |
| A-39 | S | c-Pr | A-39 | O | CH(CH$_3$)$_2$ | A-53 | S | CH(CH$_3$)(C$_2$H$_5$) | A-53 | O | C(CH$_3$)$_3$ |
| A-39 | CH$_2$ | C(CH$_3$)$_3$ | A-39 | O | CH(CH$_3$)(C$_2$H$_5$) | A-53 | S | c-Pr | A-53 | O | CH(CH$_3$)$_2$ |
| A-39 | CH$_2$ | CH(CH$_3$)$_2$ | A-39 | O | c-Pr | A-53 | CH$_2$ | C(CH$_3$)$_3$ | A-53 | O | CH(CH$_3$)(C$_2$H$_5$) |
| A-40 | CH$_2$ | CH(CH$_3$)(C$_2$H$_5$) | A-40 | S | C(CH$_3$)$_3$ | A-53 | CH$_2$ | CH(CH$_3$)$_2$ | A-53 | O | c-Pr |
| A-40 | CH$_2$ | c-Pr | A-40 | S | CH(CH$_3$)$_2$ | A-54 | S | C(CH$_3$)$_3$ | A-54 | CH$_2$ | CH(CH$_3$)(C$_2$H$_5$) |
| A-40 | O | C(CH$_3$)$_3$ | A-40 | S | c-Pr | A-54 | S | CH(CH$_3$)$_2$ | A-54 | CH$_2$ | c-Pr |
| A-40 | O | CH(CH$_3$)$_2$ | A-40 | CH$_2$ | C(CH$_3$)$_3$ | A-54 | S | CH(CH$_3$)(C$_2$H$_5$) | A-54 | O | C(CH$_3$)$_3$ |
| A-40 | O | CH(CH$_3$)(C$_2$H$_5$) | A-40 | CH$_2$ | CH(CH$_3$)$_2$ | A-54 | S | c-Pr | A-54 | O | CH(CH$_3$)$_2$ |
| A-40 | O | c-Pr | A-40 | CH$_2$ | CH(CH$_3$)(C$_2$H$_5$) | A-54 | CH$_2$ | C(CH$_3$)$_3$ | A-54 | O | CH(CH$_3$)(C$_2$H$_5$) |
| A-41 | S | C(CH$_3$)$_3$ | A-41 | CH$_2$ | CH(CH$_3$)(C$_2$H$_5$) | A-54 | CH$_2$ | CH(CH$_3$)$_2$ | A-54 | O | c-Pr |
| A-41 | S | CH(CH$_3$)$_2$ | A-41 | CH$_2$ | c-Pr | A-55 | S | C(CH$_3$)$_3$ | A-55 | CH$_2$ | CH(CH$_3$)(C$_2$H$_5$) |
| A-41 | S | CH(CH$_3$)(C$_2$H$_5$) | A-41 | O | C(CH$_3$)$_3$ | A-55 | S | CH(CH$_3$)$_2$ | A-55 | CH$_2$ | c-Pr |
| A-41 | S | c-Pr | A-41 | O | CH(CH$_3$)$_2$ | A-55 | S | CH(CH$_3$)(C$_2$H$_5$) | A-55 | O | C(CH$_3$)$_3$ |
| A-41 | CH$_2$ | C(CH$_3$)$_3$ | A-41 | O | CH(CH$_3$)(C$_2$H$_5$) | A-55 | S | c-Pr | A-55 | O | CH(CH$_3$)$_2$ |
| A-41 | CH$_2$ | CH(CH$_3$)$_2$ | A-41 | O | c-Pr | A-55 | CH$_2$ | C(CH$_3$)$_3$ | A-55 | O | CH(CH$_3$)(C$_2$H$_5$) |
| A-42 | S | C(CH$_3$)$_3$ | A-42 | CH$_2$ | CH(CH$_3$)(C$_2$H$_5$) | A-55 | CH$_2$ | CH(CH$_3$)$_2$ | A-55 | O | c-Pr |
| A-42 | S | CH(CH$_3$)$_2$ | A-42 | CH$_2$ | c-Pr | A-56 | S | C(CH$_3$)$_3$ | A-56 | CH$_2$ | CH(CH$_3$)(C$_2$H$_5$) |
| A-42 | S | CH(CH$_3$)(C$_2$H$_5$) | A-42 | O | C(CH$_3$)$_3$ | A-56 | S | CH(CH$_3$)$_2$ | A-56 | CH$_2$ | c-Pr |
| A-42 | S | c-Pr | A-42 | O | CH(CH$_3$)$_2$ | A-56 | S | CH(CH$_3$)(C$_2$H$_5$) | A-56 | O | C(CH$_3$)$_3$ |
| A-42 | CH$_2$ | C(CH$_3$)$_3$ | A-42 | O | CH(CH$_3$)(C$_2$H$_5$) | A-56 | S | c-Pr | A-56 | O | CH(CH$_3$)$_2$ |
| A-42 | CH$_2$ | CH(CH$_3$)$_2$ | A-42 | O | c-Pr | A-56 | CH$_2$ | C(CH$_3$)$_3$ | A-56 | O | CH(CH$_3$)(C$_2$H$_5$) |
| A-44 | S | C(CH$_3$)$_3$ | A-44 | CH$_2$ | CH(CH$_3$)(C$_2$H$_5$) | A-56 | CH$_2$ | CH(CH$_3$)$_2$ | A-56 | O | c-Pr |
| A-44 | S | CH(CH$_3$)$_2$ | A-44 | CH$_2$ | c-Pr | A-57 | S | C(CH$_3$)$_3$ | A-57 | CH$_2$ | CH(CH$_3$)(C$_2$H$_5$) |
| A-44 | S | CH(CH$_3$)(C$_2$H$_5$) | A-44 | O | C(CH$_3$)$_3$ | A-57 | S | CH(CH$_3$)$_2$ | A-57 | CH$_2$ | c-Pr |
| A-44 | S | c-Pr | A-44 | O | CH(CH$_3$)$_2$ | A-57 | S | CH(CH$_3$)(C$_2$H$_5$) | A-57 | O | C(CH$_3$)$_3$ |
| A-44 | CH$_2$ | C(CH$_3$)$_3$ | A-44 | O | CH(CH$_3$)(C$_2$H$_5$) | A-57 | S | c-Pr | A-57 | O | CH(CH$_3$)$_2$ |
| A-44 | CH$_2$ | CH(CH$_3$)$_2$ | A-44 | O | c-Pr | A-57 | CH$_2$ | C(CH$_3$)$_3$ | A-57 | O | CH(CH$_3$)(C$_2$H$_5$) |
| A-45 | S | C(CH$_3$)$_3$ | A-45 | CH$_2$ | CH(CH$_3$)(C$_2$H$_5$) | A-57 | CH$_2$ | CH(CH$_3$)$_2$ | A-57 | O | c-Pr |
| A-45 | S | CH(CH$_3$)$_2$ | A-45 | CH$_2$ | c-Pr | A-58 | S | C(CH$_3$)$_3$ | A-58 | CH$_2$ | CH(CH$_3$)(C$_2$H$_5$) |
| A-45 | S | CH(CH$_3$)(C$_2$H$_5$) | A-45 | O | C(CH$_3$)$_3$ | A-58 | S | CH(CH$_3$)$_2$ | A-58 | CH$_2$ | c-Pr |
| A-45 | S | c-Pr | A-45 | O | CH(CH$_3$)$_2$ | A-58 | S | CH(CH$_3$)(C$_2$H$_5$) | A-58 | O | C(CH$_3$)$_3$ |
| A-45 | CH$_2$ | C(CH$_3$)$_3$ | A-45 | O | CH(CH$_3$)(C$_2$H$_5$) | A-58 | S | c-Pr | A-58 | O | CH(CH$_3$)$_2$ |
| A-45 | CH$_2$ | CH(CH$_3$)$_2$ | A-45 | O | c-Pr | A-58 | CH$_2$ | C(CH$_3$)$_3$ | A-58 | O | CH(CH$_3$)(C$_2$H$_5$) |
| A-48 | S | C(CH$_3$)$_3$ | A-48 | CH$_2$ | CH(CH$_3$)(C$_2$H$_5$) | A-58 | CH$_2$ | CH(CH$_3$)$_2$ | A-58 | O | c-Pr |
| A-48 | S | CH(CH$_3$)$_2$ | A-48 | CH$_2$ | c-Pr | A-61 | S | C(CH$_3$)$_3$ | A-61 | CH$_2$ | CH(CH$_3$)(C$_2$H$_5$) |
| A-48 | S | CH(CH$_3$)(C$_2$H$_5$) | A-48 | O | C(CH$_3$)$_3$ | A-61 | S | CH(CH$_3$)$_2$ | A-61 | CH$_2$ | c-Pr |
| A-48 | S | c-Pr | A-48 | O | CH(CH$_3$)$_2$ | A-61 | S | CH(CH$_3$)(C$_2$H$_5$) | A-61 | O | C(CH$_3$)$_3$ |
| A-48 | CH$_2$ | C(CH$_3$)$_3$ | A-48 | O | CH(CH$_3$)(C$_2$H$_5$) | A-61 | S | c-Pr | A-61 | O | CH(CH$_3$)$_2$ |
| A-48 | CH$_2$ | CH(CH$_3$)$_2$ | A-48 | O | c-Pr | A-61 | CH$_2$ | C(CH$_3$)$_3$ | A-61 | O | CH(CH$_3$)(C$_2$H$_5$) |
| A-49 | S | C(CH$_3$)$_3$ | A-49 | CH$_2$ | CH(CH$_3$)(C$_2$H$_5$) | A-61 | CH$_2$ | CH(CH$_3$)$_2$ | A-61 | O | c-Pr |
| A-49 | S | CH(CH$_3$)$_2$ | A-49 | CH$_2$ | c-Pr | A-63 | S | C(CH$_3$)$_3$ | A-63 | CH$_2$ | CH(CH$_3$)(C$_2$H$_5$) |
| A-49 | S | CH(CH$_3$)(C$_2$H$_5$) | A-49 | O | C(CH$_3$)$_3$ | A-63 | S | CH(CH$_3$)$_2$ | A-63 | CH$_2$ | c-Pr |
| A-49 | S | c-Pr | A-49 | O | CH(CH$_3$)$_2$ | A-63 | S | CH(CH$_3$)(C$_2$H$_5$) | A-63 | O | C(CH$_3$)$_3$ |
| A-49 | CH$_2$ | C(CH$_3$)$_3$ | A-49 | O | CH(CH$_3$)(C$_2$H$_5$) | A-63 | S | c-Pr | A-63 | O | CH(CH$_3$)$_2$ |
| A-49 | CH$_2$ | CH(CH$_3$)$_2$ | A-49 | O | c-Pr | A-63 | CH$_2$ | C(CH$_3$)$_3$ | A-63 | O | CH(CH$_3$)(C$_2$H$_5$) |
| A-50 | S | C(CH$_3$)$_3$ | A-50 | CH$_2$ | CH(CH$_3$)(C$_2$H$_5$) | A-63 | CH$_2$ | CH(CH$_3$)$_2$ | A-63 | O | c-Pr |
| A-50 | S | CH(CH$_3$)$_2$ | A-50 | CH$_2$ | c-Pr | A-64 | S | C(CH$_3$)$_3$ | A-64 | CH$_2$ | CH(CH$_3$)(C$_2$H$_5$) |
| A-50 | S | CH(CH$_3$)(C$_2$H$_5$) | A-50 | O | C(CH$_3$)$_3$ | A-64 | S | CH(CH$_3$)$_2$ | A-64 | CH$_2$ | c-Pr |

TABLE 1D-continued

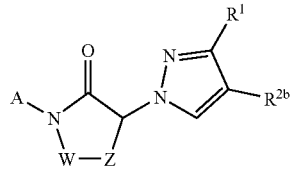

| A | Z | R¹ | A | Z | R¹ |
|---|---|---|---|---|---|
| | W is CH$_2$; R$^{2b}$ is H | | | W is CH$_2$; R$^{2b}$ is H | |
| A-64 | S | CH(CH$_3$)(C$_2$H$_5$) | A-64 | O | C(CH$_3$)$_3$ |
| A-64 | S | c-Pr | A-64 | O | CH(CH$_3$)$_2$ |
| A-64 | CH$_2$ | C(CH$_3$)$_3$ | A-64 | O | CH(CH$_3$)(C$_2$H$_5$) |
| A-64 | CH$_2$ | CH(CH$_3$)$_2$ | A-64 | O | c-Pr |
| A-65 | S | C(CH$_3$)$_3$ | A-65 | CH$_2$ | CH(CH$_3$)(C$_2$H$_5$) |
| A-65 | S | CH(CH$_3$)$_2$ | A-65 | CH$_2$ | c-Pr |
| A-65 | S | CH(CH$_3$)(C$_2$H$_5$) | A-65 | O | C(CH$_3$)$_3$ |
| A-65 | S | c-Pr | A-65 | O | CH(CH$_3$)$_2$ |
| A-65 | CH$_2$ | C(CH$_3$)$_3$ | A-65 | O | CH(CH$_3$)(C$_2$H$_5$) |
| A-65 | CH$_2$ | CH(CH$_3$)$_2$ | A-65 | O | c-Pr |
| A-86 | S | C(CH$_3$)$_3$ | A-86 | CH$_2$ | CH(CH$_3$)(C$_2$H$_5$) |
| A-86 | S | CH(CH$_3$)$_2$ | A-86 | CH$_2$ | c-Pr |
| A-86 | S | CH(CH$_3$)(C$_2$H$_5$) | A-86 | O | C(CH$_3$)$_3$ |
| A-86 | S | c-Pr | A-86 | O | CH(CH$_3$)$_2$ |
| A-86 | CH$_2$ | C(CH$_3$)$_3$ | A-86 | O | CH(CH$_3$)(C$_2$H$_5$) |
| A-86 | CH$_2$ | CH(CH$_3$)$_2$ | A-86 | O | c-Pr |
| A-87 | S | C(CH$_3$)$_3$ | A-87 | CH$_2$ | CH(CH$_3$)(C$_2$H$_5$) |
| A-87 | S | CH(CH$_3$)$_2$ | A-87 | CH$_2$ | c-Pr |
| A-87 | S | CH(CH$_3$)(C$_2$H$_5$) | A-87 | O | C(CH$_3$)$_3$ |
| A-87 | S | c-Pr | A-87 | O | CH(CH$_3$)$_2$ |
| A-87 | CH$_2$ | C(CH$_3$)$_3$ | A-87 | O | CH(CH$_3$)(C$_2$H$_5$) |
| A-87 | CH$_2$ | CH(CH$_3$)$_2$ | A-87 | O | c-Pr |
| A-88 | S | C(CH$_3$)$_3$ | A-88 | CH$_2$ | CH(CH$_3$)(C$_2$H$_5$) |
| A-88 | S | CH(CH$_3$)$_2$ | A-88 | CH$_2$ | c-Pr |
| A-88 | S | CH(CH$_3$)(C$_2$H$_5$) | A-88 | O | C(CH$_3$)$_3$ |
| A-88 | S | c-Pr | A-88 | O | CH(CH$_3$)$_2$ |
| A-88 | CH$_2$ | C(CH$_3$)$_3$ | A-88 | O | CH(CH$_3$)(C$_2$H$_5$) |
| A-88 | CH$_2$ | CH(CH$_3$)$_2$ | A-88 | O | c-Pr |
| A-89 | S | C(CH$_3$)$_3$ | A-89 | CH$_2$ | CH(CH$_3$)(C$_2$H$_5$) |
| A-89 | S | CH(CH$_3$)$_2$ | A-89 | CH$_2$ | c-Pr |
| A-89 | S | CH(CH$_3$)(C$_2$H$_5$) | A-89 | O | C(CH$_3$)$_3$ |
| A-89 | S | c-Pr | A-89 | O | CH(CH$_3$)$_2$ |
| A-89 | CH$_2$ | C(CH$_3$)$_3$ | A-89 | O | CH(CH$_3$)(C$_2$H$_5$) |
| A-89 | CH$_2$ | CH(CH$_3$)$_2$ | A-89 | O | c-Pr |
| A-90 | S | C(CH$_3$)$_3$ | A-90 | CH$_2$ | CH(CH$_3$)(C$_2$H$_5$) |
| A-90 | S | CH(CH$_3$)$_2$ | A-90 | CH$_2$ | c-Pr |
| A-90 | S | CH(CH$_3$)(C$_2$H$_5$) | A-90 | O | C(CH$_3$)$_3$ |
| A-90 | S | c-Pr | A-90 | O | CH(CH$_3$)$_2$ |
| A-90 | CH$_2$ | C(CH$_3$)$_3$ | A-90 | O | CH(CH$_3$)(C$_2$H$_5$) |
| A-90 | CH$_2$ | CH(CH$_3$)$_2$ | A-90 | O | c-Pr |

TABLE 1E

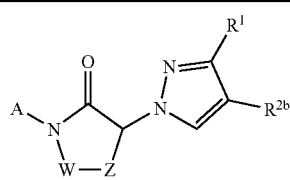

| A | W | Z | R¹ | R$^{2b}$ |
|---|---|---|---|---|
| A-1 | C(CH$_3$)$_2$ | S | C(CH$_3$)$_3$ | H |
| A-1 | C(CH$_3$)$_2$ | S | CH(CH$_3$)$_2$ | H |
| A-1 | C(CH$_3$)$_2$ | S | CH(CH$_3$)(C$_2$H$_5$) | H |
| A-1 | C(CH$_3$)$_2$ | S | c-Pr | H |
| A-1 | C(CH$_3$)$_2$ | CH$_2$ | C(CH$_3$)$_3$ | H |
| A-1 | C(CH$_3$)$_2$ | CH$_2$ | CH(CH$_3$)$_2$ | H |
| A-1 | C(CH$_3$)$_2$ | CH$_2$ | CH(CH$_3$)(C$_2$H$_5$) | H |
| A-1 | C(CH$_3$)$_2$ | CH$_2$ | c-Pr | H |
| A-1 | C(CH$_3$)$_2$ | O | C(CH$_3$)$_3$ | H |

TABLE 1E-continued

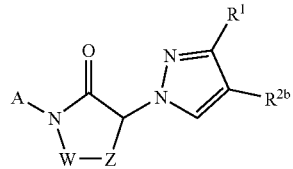

| A | W | Z | R¹ | R$^{2b}$ |
|---|---|---|---|---|
| A-1 | C(CH$_3$)$_2$ | O | CH(CH$_3$)$_2$ | H |
| A-1 | C(CH$_3$)$_2$ | O | CH(CH$_3$)(C$_2$H$_5$) | H |
| A-1 | C(CH$_3$)$_2$ | O | c-Pr | H |
| A-5 | C(CH$_3$)$_2$ | S | C(CH$_3$)$_3$ | H |
| A-5 | C(CH$_3$)$_2$ | S | CH(CH$_3$)$_2$ | H |
| A-5 | C(CH$_3$)$_2$ | S | CH(CH$_3$)(C$_2$H$_5$) | H |
| A-5 | C(CH$_3$)$_2$ | S | c-Pr | H |
| A-5 | C(CH$_3$)$_2$ | CH$_2$ | C(CH$_3$)$_3$ | H |
| A-5 | C(CH$_3$)$_2$ | CH$_2$ | CH(CH$_3$)$_2$ | H |
| A-5 | C(CH$_3$)$_2$ | CH$_2$ | CH(CH$_3$)(C$_2$H$_5$) | H |
| A-5 | C(CH$_3$)$_2$ | CH$_2$ | c-Pr | H |
| A-5 | C(CH$_3$)$_2$ | O | C(CH$_3$)$_3$ | H |
| A-5 | C(CH$_3$)$_2$ | O | CH(CH$_3$)$_2$ | H |
| A-5 | C(CH$_3$)$_2$ | O | CH(CH$_3$)(C$_2$H$_5$) | H |
| A-5 | C(CH$_3$)$_2$ | O | c-Pr | H |
| A-1 | C(CH$_3$)$_2$ | S | C(CH$_3$)$_3$ | CH$_3$ |
| A-1 | C(CH$_3$)$_2$ | S | CH(CH$_3$)$_2$ | CH$_3$ |
| A-1 | C(CH$_3$)$_2$ | S | CH(CH$_3$)(C$_2$H$_5$) | CH$_3$ |
| A-1 | C(CH$_3$)$_2$ | S | c-Pr | CH$_3$ |
| A-1 | C(CH$_3$)$_2$ | CH$_2$ | C(CH$_3$)$_3$ | CH$_3$ |
| A-1 | C(CH$_3$)$_2$ | CH$_2$ | CH(CH$_3$)$_2$ | CH$_3$ |
| A-1 | C(CH$_3$)$_2$ | CH$_2$ | CH(CH$_3$)(C$_2$H$_5$) | CH$_3$ |
| A-1 | C(CH$_3$)$_2$ | CH$_2$ | c-Pr | CH$_3$ |
| A-1 | C(CH$_3$)$_2$ | O | C(CH$_3$)$_3$ | CH$_3$ |
| A-1 | C(CH$_3$)$_2$ | O | CH(CH$_3$)$_2$ | CH$_3$ |
| A-1 | C(CH$_3$)$_2$ | O | CH(CH$_3$)(C$_2$H$_5$) | CH$_3$ |
| A-1 | C(CH$_3$)$_2$ | O | c-Pr | CH$_3$ |
| A-1 | CH(CH$_3$) | S | C(CH$_3$)$_3$ | H |
| A-1 | CH(CH$_3$) | S | CH(CH$_3$)$_2$ | H |
| A-1 | CH(CH$_3$) | S | CH(CH$_3$)(C$_2$H$_5$) | H |
| A-1 | CH(CH$_3$) | S | CH(C$_2$H$_5$)$_2$ | H |
| A-1 | CH(CH$_3$) | S | c-Pr | H |
| A-1 | CH(CH$_3$) | S | 1-Me-c-Pr | H |
| A-1 | CH(CH$_3$) | S | c-Bu | H |
| A-1 | CH(CH$_3$) | S | 1-Me-2,2-di-Cl-c-Pr | H |
| A-1 | CH(CH$_3$) | S | c-Pentyl | H |
| A-1 | CH(CH$_3$) | S | c-Hexyl | H |
| A-1 | CH(CH$_3$) | S | N(CH$_3$)$_2$ | H |
| A-1 | CH(CH$_3$) | S | SCH$_3$ | H |
| A-1 | CH(CH$_3$) | S | SCH(CH$_3$)$_2$ | H |
| A-1 | CH(CH$_3$) | CH$_2$ | C(CH$_3$)$_3$ | CH$_3$ |
| A-1 | CH(CH$_3$) | CH$_2$ | CH(CH$_3$)$_2$ | CH$_3$ |
| A-1 | CH(CH$_3$) | CH$_2$ | CH(CH$_3$)(C$_2$H$_5$) | CH$_3$ |
| A-1 | CH(CH$_3$) | CH$_2$ | CH(C$_2$H$_5$)$_2$ | CH$_3$ |
| A-1 | CH(CH$_3$) | CH$_2$ | c-Pr | CH$_3$ |
| A-1 | CH(CH$_3$) | CH$_2$ | 1-Me-c-Pr | CH$_3$ |
| A-1 | CH(CH$_3$) | CH$_2$ | c-Bu | CH$_3$ |
| A-1 | CH(CH$_3$) | CH$_2$ | 1-Me-2,2-di-Cl-c-Pr | CH$_3$ |
| A-1 | CH(CH$_3$) | CH$_2$ | c-Pentyl | CH$_3$ |
| A-1 | CH(CH$_3$) | CH$_2$ | c-Hexyl | CH$_3$ |
| A-1 | CH(CH$_3$) | O | C(CH$_3$)$_3$ | H |
| A-1 | CH(CH$_3$) | O | CH(CH$_3$)$_2$ | H |
| A-1 | CH(CH$_3$) | O | CH(CH$_3$)(C$_2$H$_5$) | H |
| A-1 | CH(CH$_3$) | O | CH(C$_2$H$_5$)$_2$ | H |
| A-1 | CH(CH$_3$) | O | c-Pr | H |
| A-1 | CH(CH$_3$) | O | 1-Me-c-Pr | H |
| A-1 | CH(CH$_3$) | O | c-Bu | H |
| A-1 | CH(CH$_3$) | O | 1-Me-2,2-di-Cl-c-Pr | H |
| A-1 | CH(CH$_3$) | O | c-Pentyl | H |
| A-1 | CH(CH$_3$) | O | c-Hexyl | H |
| A-1 | CH(CH$_3$) | O | N(CH$_3$)$_2$ | H |
| A-1 | CH(CH$_3$) | CH$_2$ | N(CH$_3$)$_2$ | H |
| A-5 | CH(CH$_3$) | S | C(CH$_3$)$_3$ | H |
| A-5 | CH(CH$_3$) | S | CH(CH$_3$)$_2$ | H |
| A-5 | CH(CH$_3$) | S | CH(CH$_3$)(C$_2$H$_5$) | H |
| A-5 | CH(CH$_3$) | S | CH(C$_2$H$_5$)$_2$ | H |
| A-5 | CH(CH$_3$) | S | c-Pr | H |

TABLE 1E-continued

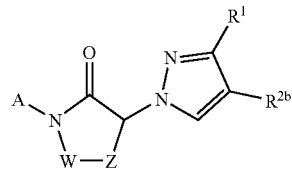

| A | W | Z | R¹ | R²ᵇ |
|---|---|---|----|-----|
| A-5 | CH(CH₃) | S | 1-Me-c-Pr | H |
| A-5 | CH(CH₃) | S | c-Bu | H |
| A-5 | CH(CH₃) | S | 1-Me-2,2-di-Cl-c-Pr | H |
| A-5 | CH(CH₃) | S | c-Pentyl | H |
| A-5 | CH(CH₃) | S | c-Hexyl | H |
| A-5 | CH(CH₃) | S | N(CH₃)₂ | H |
| A-5 | CH(CH₃) | S | SCH₃ | H |
| A-5 | CH(CH₃) | S | SCH(CH₃)₂ | H |
| A-5 | CH(CH₃) | CH₂ | C(CH₃)₃ | CH₃ |
| A-5 | CH(CH₃) | CH₂ | CH(CH₃)₂ | CH₃ |
| A-5 | CH(CH₃) | CH₂ | CH(CH₃)(C₂H₅) | CH₃ |
| A-5 | CH(CH₃) | CH₂ | CH(C₂H₅)₂ | CH₃ |
| A-5 | CH(CH₃) | CH₂ | c-Pr | CH₃ |
| A-5 | CH(CH₃) | CH₂ | 1-Me-c-Pr | CH₃ |
| A-5 | CH(CH₃) | CH₂ | c-Bu | CH₃ |
| A-5 | CH(CH₃) | CH₂ | 1-Me-2,2-di-Cl-c-Pr | CH₃ |
| A-5 | CH(CH₃) | CH₂ | c-Pentyl | CH₃ |
| A-5 | CH(CH₃) | CH₂ | c-Hexyl | CH₃ |
| A-5 | CH(CH₃) | O | C(CH₃)₃ | H |
| A-5 | CH(CH₃) | O | CH(CH₃)₂ | H |
| A-5 | CH(CH₃) | O | CH(CH₃)(C₂H₅) | H |
| A-5 | CH(CH₃) | O | CH(C₂H₅)₂ | H |
| A-5 | CH(CH₃) | O | c-Pr | H |
| A-5 | CH(CH₃) | O | 1-Me-c-Pr | H |
| A-5 | CH(CH₃) | O | c-Bu | H |
| A-5 | CH(CH₃) | O | 1-Me-2,2-di-Cl-c-Pr | H |
| A-5 | CH(CH₃) | O | c-Pentyl | H |
| A-5 | CH(CH₃) | O | c-Hexyl | H |
| A-5 | CH(CH₃) | O | N(CH₃)₂ | H |
| A-5 | CH(CH₃) | CH₂ | N(CH₃)₂ | H |
| A-29 | CH(CH₃) | S | C(CH₃)₃ | H |
| A-29 | CH(CH₃) | S | CH(CH₃)₂ | H |
| A-29 | CH(CH₃) | S | CH(CH₃)(C₂H₅) | H |
| A-29 | CH(CH₃) | S | CH(C₂H₅)₂ | H |
| A-29 | CH(CH₃) | S | c-Pr | H |
| A-29 | CH(CH₃) | S | 1-Me-c-Pr | H |
| A-29 | CH(CH₃) | S | c-Bu | H |
| A-29 | CH(CH₃) | S | 1-Me-2,2-di-Cl-c-Pr | H |
| A-29 | CH(CH₃) | S | c-Pentyl | H |
| A-29 | CH(CH₃) | S | c-Hexyl | H |
| A-29 | CH(CH₃) | S | N(CH₃)₂ | H |
| A-29 | CH(CH₃) | S | SCH₃ | H |
| A-29 | CH(CH₃) | S | SCH(CH₃)₂ | H |
| A-29 | CH(CH₃) | CH₂ | C(CH₃)₃ | H |
| A-29 | CH(CH₃) | CH₂ | CH(CH₃)₂ | H |
| A-29 | CH(CH₃) | CH₂ | CH(CH₃)(C₂H₅) | H |
| A-29 | CH(CH₃) | CH₂ | CH(C₂H₅)₂ | H |
| A-29 | CH(CH₃) | CH₂ | c-Pr | H |
| A-29 | CH(CH₃) | CH₂ | 1-Me-c-Pr | H |
| A-29 | CH(CH₃) | CH₂ | c-Bu | H |
| A-29 | CH(CH₃) | CH₂ | 1-Me-2,2-di-Cl-c-Pr | H |
| A-29 | CH(CH₃) | CH₂ | c-Pentyl | H |
| A-29 | CH(CH₃) | CH₂ | c-Hexyl | H |
| A-29 | CH(CH₃) | O | C(CH₃)₃ | H |
| A-29 | CH(CH₃) | O | CH(CH₃)₂ | H |
| A-29 | CH(CH₃) | O | CH(CH₃)(C₂H₅) | H |
| A-29 | CH(CH₃) | O | CH(C₂H₅)₂ | H |
| A-29 | CH(CH₃) | O | c-Pr | H |
| A-29 | CH(CH₃) | O | 1-Me-c-Pr | H |
| A-29 | CH(CH₃) | O | c-Bu | H |
| A-29 | CH(CH₃) | O | 1-Me-2,2-di-Cl-c-Pr | H |
| A-29 | CH(CH₃) | O | c-Pentyl | H |
| A-29 | CH(CH₃) | O | c-Hexyl | H |
| A-29 | CH(CH₃) | O | N(CH₃)₂ | H |
| A-29 | CH(CH₃) | CH₂ | N(CH₃)₂ | H |
| A-1 | CH₂CH₂ | S | C(CH₃)₃ | H |
| A-1 | CH₂CH₂ | S | CH(CH₃)₂ | H |

TABLE 1E-continued

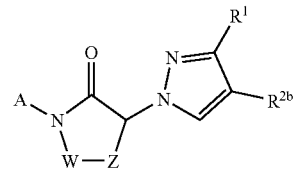

| A | W | Z | R¹ | R²ᵇ |
|---|---|---|----|-----|
| A-1 | CH₂CH₂ | S | CH(CH₃)(C₂H₅) | H |
| A-1 | CH₂CH₂ | S | c-Pr | H |
| A-1 | CH₂CH₂ | CH₂ | C(CH₃)₃ | H |
| A-1 | CH₂CH₂ | CH₂ | CH(CH₃)₂ | H |
| A-1 | CH₂CH₂ | CH₂ | CH(CH₃)(C₂H₅) | H |
| A-1 | CH₂CH₂ | CH₂ | c-Pr | H |
| A-1 | CH₂CH₂ | O | C(CH₃)₃ | H |
| A-1 | CH₂CH₂ | O | CH(CH₃)₂ | H |
| A-1 | CH₂CH₂ | O | CH(CH₃)(C₂H₅) | H |
| A-1 | CH₂CH₂ | O | c-Pr | H |
| A-5 | CH₂CH₂ | S | C(CH₃)₃ | H |
| A-5 | CH₂CH₂ | S | CH(CH₃)₂ | H |
| A-5 | CH₂CH₂ | S | CH(CH₃)(C₂H₅) | H |
| A-5 | CH₂CH₂ | S | c-Pr | H |
| A-5 | CH₂CH₂ | CH₂ | C(CH₃)₃ | H |
| A-5 | CH₂CH₂ | CH₂ | CH(CH₃)₂ | H |
| A-5 | CH₂CH₂ | CH₂ | CH(CH₃)(C₂H₅) | H |
| A-5 | CH₂CH₂ | CH₂ | c-Pr | H |
| A-5 | CH₂CH₂ | O | C(CH₃)₃ | H |
| A-5 | CH₂CH₂ | O | CH(CH₃)₂ | H |
| A-5 | CH₂CH₂ | O | CH(CH₃)(C₂H₅) | H |
| A-5 | CH₂CH₂ | O | c-Pr | H |
| A-29 | CH₂CH₂ | S | C(CH₃)₃ | H |
| A-29 | CH₂CH₂ | S | CH(CH₃)₂ | H |
| A-29 | CH₂CH₂ | S | CH(CH₃)(C₂H₅) | H |
| A-29 | CH₂CH₂ | S | c-Pr | H |
| A-29 | CH₂CH₂ | CH₂ | C(CH₃)₃ | H |
| A-29 | CH₂CH₂ | CH₂ | CH(CH₃)₂ | H |
| A-29 | CH₂CH₂ | CH₂ | CH(CH₃)(C₂H₅) | H |
| A-29 | CH₂CH₂ | CH₂ | c-Pr | H |
| A-29 | CH₂CH₂ | O | C(CH₃)₃ | H |
| A-29 | CH₂CH₂ | O | CH(CH₃)₂ | H |
| A-29 | CH₂CH₂ | O | CH(CH₃)(C₂H₅) | H |
| A-29 | CH₂CH₂ | O | c-Pr | H |
| A-1 | CH₂ | CH₂ | c-Pr | Cl |
| A-1 | CH₂ | CH₂ | CH(CH₃)₂ | Cl |
| A-1 | CH₂ | CH₂ | CH(CH₃)(C₂H₅) | Cl |

TABLE 2

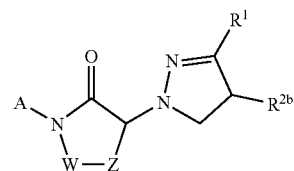

| Z | R¹ |
|---|----|
| *A is A-1; W is CH₂; R²ᵇ is H* | |
| S | C(CH₃)₃ |
| S | CH(CH₃)₂ |
| S | CH(CH₃)(C₂H₅) |
| S | CH(C₂H₅)₂ |
| S | c-Pr |
| S | 1-Me-c-Pr |
| S | c-Bu |
| S | 1-Me-2,2-di-Cl-c-Pr |
| S | c-Pentyl |
| S | c-Hexyl |
| S | N(CH₃)₂ |
| S | SCH₃ |

TABLE 2-continued

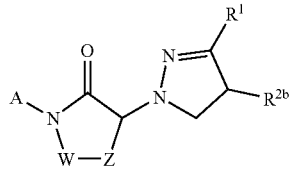

| Z | R¹ |
|---|---|
| S | SCH(CH₃)₂ |
| CH₂ | C(CH₃)₃ |
| CH₂ | CH(CH₃)₂ |
| CH₂ | CH(CH₃)(C₂H₅) |
| CH₂ | CH(C₂H₅)₂ |
| CH₂ | c-Pr |
| CH₂ | 1-Me-c-Pr |
| CH₂ | c-Bu |
| CH₂ | 1-Me-2,2-di-Cl-c-Pr |
| CH₂ | c-Pentyl |
| CH₂ | N(CH₃)₂ |
| O | C(CH₃)₃ |
| O | CH(CH₃)₂ |
| O | CH(CH₃)(C₂H₅) |
| O | CH(C₂H₅)₂ |
| O | c-Pr |
| O | 1-Me-c-Pr |
| O | c-Bu |
| O | 1-Me-2,2-di-Cl-c-Pr |
| O | c-Pentyl |
| O | c-Hexyl |
| O | N(CH₃)₂ |
| CH₂ | N(CH₃)₂ |

A is A-5; W is CH₂; R²ᵇ is H

| Z | R¹ |
|---|---|
| S | C(CH₃)₃ |
| S | CH(CH₃)₂ |
| S | CH(CH₃)(C₂H₅) |
| S | CH(C₂H₅)₂ |
| S | c-Pr |
| S | 1-Me-c-Pr |
| S | c-Bu |
| S | 1-Me-2,2-di-Cl-c-Pr |
| S | c-Pentyl |
| S | c-Hexyl |
| S | N(CH₃)₂ |
| S | SCH₃ |
| S | SCH(CH₃)₂ |
| CH₂ | C(CH₃)₃ |
| CH₂ | CH(CH₃)₂ |
| CH₂ | CH(CH₃)(C₂H₅) |
| CH₂ | CH(C₂H₅)₂ |
| CH₂ | c-Pr |
| CH₂ | 1-Me-c-Pr |
| CH₂ | c-Bu |
| CH₂ | 1-Me-2,2-di-Cl-c-Pr |
| CH₂ | c-Pentyl |
| CH₂ | c-Hexyl |
| O | C(CH₃)₃ |
| O | CH(CH₃)₂ |
| O | CH(CH₃)(C₂H₅) |
| O | CH(C₂H₅)₂ |
| O | c-Pr |
| O | 1-Me-c-Pr |
| O | c-Bu |
| O | 1-Me-2,2-di-Cl-c-Pr |
| O | c-Pentyl |
| O | c-Hexyl |
| O | N(CH₃)₂ |
| CH₂ | N(CH₃)₂ |
| CH₂ | CH(CH₃)(n-C₁₀H₂₁) |

A is A-29; W is CH₂; R²ᵇ is H

| Z | R¹ |
|---|---|
| S | C(CH₃)₃ |
| S | CH(CH₃)₂ |
| S | CH(CH₃)(C₂H₅) |
| S | CH(C₂H₅)₂ |

TABLE 2-continued

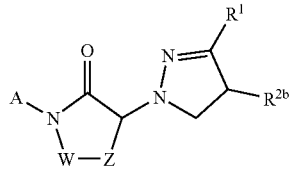

| Z | R¹ |
|---|---|
| S | c-Pr |
| S | 1-Me-c-Pr |
| S | c-Bu |
| S | 1-Me-2,2-di-Cl-c-Pr |
| S | c-Pentyl |
| S | c-Hexyl |
| S | N(CH₃)₂ |
| S | SCH₃ |
| S | SCH(CH₃)₂ |
| CH₂ | C(CH₃)₃ |
| CH₂ | CH(CH₃)₂ |
| CH₂ | CH(CH₃)(C₂H₅) |
| CH₂ | CH(C₂H₅)₂ |
| CH₂ | c-Pr |
| CH₂ | 1-Me-c-Pr |
| CH₂ | c-Bu |
| CH₂ | 1-Me-2,2-di-Cl-c-Pr |
| CH₂ | c-Pentyl |
| CH₂ | c-Hexyl |
| O | C(CH₃)₃ |
| O | CH(CH₃)₂ |
| O | CH(CH₃)(C₂H₅) |
| O | CH(C₂H₅)₂ |
| O | c-Pr |
| O | 1-Me-c-Pr |
| O | c-Bu |
| O | 1-Me-2,2-di-Cl-c-Pr |
| O | c-Pentyl |
| O | c-Hexyl |
| O | N(CH₃)₂ |
| CH₂ | N(CH₃)₂ |
| CH₂ | CH(CH₃)(n-C₁₀H₂₁) |

TABLE 3

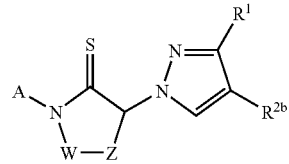

W is CH₂; R²ᵇ is H

| A | Z | R¹ |
|---|---|---|
| A-1 | S | C(CH₃)₃ |
| A-1 | S | CH(CH₃)₂ |
| A-1 | S | CH(CH₃)(C₂H₅) |
| A-1 | S | c-Pr |
| A-1 | CH₂ | C(CH₃)₃ |
| A-1 | CH₂ | CH(CH₃)₂ |
| A-1 | CH₂ | CH(CH₃)(C₂H₅) |
| A-1 | CH₂ | c-Pr |
| A-1 | O | C(CH₃)₃ |
| A-1 | O | CH(CH₃)₂ |
| A-1 | O | CH(CH₃)(C₂H₅) |
| A-1 | O | c-Pr |
| A-5 | S | C(CH₃)₃ |
| A-5 | S | CH(CH₃)₂ |
| A-5 | S | CH(CH₃)(C₂H₅) |
| A-5 | S | c-Pr |
| A-5 | CH₂ | C(CH₃)₃ |

TABLE 3-continued

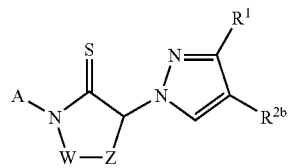

W is $CH_2$; $R^{2b}$ is H

| A | Z | $R^1$ |
|---|---|---|
| A-5 | $CH_2$ | $CH(CH_3)_2$ |
| A-5 | $CH_2$ | $CH(CH_3)(C_2H_5)$ |
| A-5 | $CH_2$ | c-Pr |
| A-5 | O | $C(CH_3)_3$ |
| A-5 | O | $CH(CH_3)_2$ |
| A-5 | O | $CH(CH_3)(C_2H_5)$ |
| A-5 | O | c-Pr |
| A-29 | S | $C(CH_3)_3$ |
| A-29 | S | $CH(CH_3)_2$ |
| A-29 | S | $CH(CH_3)(C_2H_5)$ |
| A-29 | S | c-Pr |
| A-29 | $CH_2$ | $C(CH_3)_3$ |
| A-29 | $CH_2$ | $CH(CH_3)_2$ |
| A-29 | $CH_2$ | $CH(CH_3)(C_2H_5)$ |
| A-29 | $CH_2$ | c-Pr |
| A-29 | O | $C(CH_3)_3$ |
| A-29 | O | $CH(CH_3)_2$ |
| A-29 | O | $CH(CH_3)(C_2H_5)$ |
| A-29 | O | c-Pr |

TABLE 4

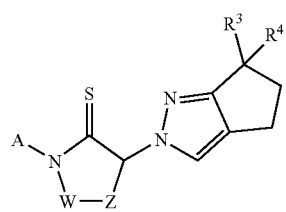

| A | W | Z | $R^3$ | $R^4$ | A | W | Z | $R^3$ | $R^4$ |
|---|---|---|---|---|---|---|---|---|---|
| A-1 | $CH_2$ | S | $CH_3$ | $CH_3$ | A-29 | $CH_2$ | $CH_2$ | $CH_3$ | $CH_3$ |
| A-1 | $CH_2$ | $CH_2$ | $CH_3$ | $CH_3$ | A-29 | $CH_2$ | O | $CH_3$ | $CH_3$ |
| A-1 | $CH_2$ | O | $CH_3$ | $CH_3$ | A-29 | $CH_2$ | S | $CH_3$ | H |
| A-1 | $CH_2$ | S | $CH_3$ | H | A-29 | $CH_2$ | $CH_2$ | $CH_3$ | H |
| A-1 | $CH_2$ | $CH_2$ | $CH_3$ | H | A-29 | $CH_2$ | O | $CH_3$ | H |
| A-1 | $CH_2$ | O | $CH_3$ | H | A-1 | $CH_2$ | S | H | H |
| A-5 | $CH_2$ | S | $CH_3$ | $CH_3$ | A-1 | $CH_2$ | $CH_2$ | H | H |
| A-5 | $CH_2$ | $CH_2$ | $CH_3$ | $CH_3$ | A-1 | $CH_2$ | O | H | H |
| A-5 | $CH_2$ | O | $CH_3$ | $CH_3$ | A-5 | $CH_2$ | S | H | H |
| A-5 | $CH_2$ | S | $CH_3$ | H | A-5 | $CH_2$ | $CH_2$ | H | H |
| A-5 | $CH_2$ | $CH_2$ | $CH_3$ | H | A-5 | $CH_2$ | O | H | H |
| A-5 | $CH_2$ | O | $CH_3$ | H | A-29 | $CH_2$ | S | H | H |
| A-29 | $CH_2$ | S | $CH_3$ | $CH_3$ | A-29 | $CH_2$ | $CH_2$ | H | H |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrolidone, ethylene glycol, polypropylene glycol, propylene carbonate, dibasic esters, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy4-methyl-2-pentanone, and alcohols such as methanol, cyclohexanol, decanol, benzyl and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling, see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and World Patent Publication 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120–133. See also U.S. Pat. No. 3,235,361, Col. 6, line 16 through Col. 7, line 19 and Examples 101; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A1–A5 below.

Example A

High Strength Concentrate

| | |
|---|---|
| Compound 1 | 98.5% |
| silica aerogel | 0.5% |
| synthetic amorphous fine silica | 1.0%. |

Example B

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| Compound 1 | 10.0% |
| attapulgite granules (low volatile matter, 0.71/0.30 mm; U.S.S. No. 25–50 sieves) | 90.0%. |

Example D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example E

Granule

| | |
|---|---|
| Compound 117 | 10.0% |
| attapulgite granules (low volatile matter, 0.71/0.30 mm; U.S.S. No. 25–50 sieves) | 90.0%. |

Test results indicate that the compounds of the present invention are highly active preemergent and postemergent herbicides or plant growth regulators. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to about 20 kg/ha with a preferred range of about 0.004 to about 1.0 kg/ha One skilled in the art can easily determine the herbicidally effective amount necessary for the desired level of weed control.

Compounds of this invention, properly formulated for application onto agricultural land or crops, are especially useful for prevention of weed growth in cultivated rice crops such as flooded paddy rice or dryland seeded or upland rice. These general groupings of rice crop cultivation methods include transplanted (i.e. transplanted into a flooded field (paddy)), water-seeded (i.e. seeded onto a flooded field so the seeds are positioned at or near the soil surface), broadcast dry-seeded (i.e. seeded onto the surface of the soil (typically prepared by cultivation) of a dry field, which is then flooded), and dry soil planted (i.e. seeded into the soil (so that the soil covers the seeds) of a dry field) with flood (i.e. the field is subsequently flooded) or without flood (i.e. the field is not subsequently flooded, and the rice crop relies instead on natural rainfall or non-flood irrigation).

The formulated compounds of the invention can be applied (i.e. contacted to the weeds or their environment) using a variety of methods, timings, or their combination(s), which allow the user to choose that which is most appropriate for the particular rice culture. The compounds can be applied: to soil or flood waters before transplants or seed are planted; at time of transplanting or seed planting; after transplanting or seed planting; after seed planting but before crop and/or weeds emerge; or after planting and the crop and/or weeds have emerged. The compounds can be applied, for example, as a treatment spray mixture, mixed with solid fertilizer or alone, or included in irrigation water. Applications to the soil can be enhanced by shallow mixing of the compounds into the soil with tillage equipment. The compound(s), alone or in mixture, can be applied directly to flood waters of the paddy as a liquid spray, suspension concentrate, or prepared granule or dispersible solid. The compounds can be applied over the top of the rice crop to emerged weed foliage and flood waters, or as a granule that can be broadcast-distributed onto the soil surface or into the flood, or they can incorporated in the soil before planting.

Applications of the compounds of the invention can be timed to coincide with specific stages of weed and/or crop growth dependent upon the rice culture practiced. The compounds can be applied to soil or flood waters: before crops are planted, at time of planting, after the crop is planted but before emergence, or after the crop emerges.

The compounds can be applied to the paddy by various means including, but not limited to: introduction or injection at the water source; manual or mechanical-equipment aided distribution from within or upon the levees; and dispersal or delivery by boat, airplane or helicopter.

Compounds of this invention, properly formulated for application onto agricultural land or crops, are also especially useful for prevention of weed growth in nonflooded crops such as maize when applied to the soil before weeds emerge or shortly after their emergence, either before or after the crop emerges. Applications to the soil can be made before, during, or after planting, and can be enhanced by shallow mixing of the compounds into the soil with tillage equipment. The formulated compounds can be applied to the soil, for example, as a treatment spray mixture, mixed with solid fertilizer or included in irrigation water.

Compounds of this invention can be used alone or in combination with other commercial herbicides, insecticides and fungicides, and other agricultural chemicals such as fertilizers. Compounds of this invention can also be used in combination with commercial herbicide safeners such as benoxacor, dichlormid and furilazole to increase safety to certain crops. Mixtures of the compounds of the invention with other herbicides can broaden the spectrum of activity against additional weed species, and suppress the proliferation of any resistant biotypes. A mixture of one or more of the following herbicides with a compound of this invention may be particularly useful for weed control: acetochlor, acifluorfen and its sodium salt, aclonifen, acrolein (2-propenal), alachlor, alloxydim, ametr, amicarbazone, amidosulfuron, amitrole, ammonium sulfamate, anilofos, asulam, atrazine, azafenidin, azimsulfuron, beflubutamid, benazolin, benazolin-ethyl, benfluralin, benfuresate, bensulfuron-methyl, bensulide, bentazone, benzobicyclon, benzofenap, bifenox, bilanafos, bispyribac and its sodium salt, bromacil, bromobutide, bromoxynil, bromoxynil octanoate, butachlor, butafenacil, butamifos, butralin, butroxydim butylate, cafenstrole, caloxydim (QAS 620H), carbetamide, carfentrazone-ethyl, chlomethoxyfen, chloramben, chlorbromuron, chlorflurenol-methyl, chloridazon, chlorimuron-ethyl, chlornitrofen, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, clopyralid, clopyralid-olamine, cloransulam-methyl, cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichilorprop, diclofop-methyl, diclosulam, difenzoquat metilsulfate, diflufenican, diflufenzopyr, dimefuron, dimepiperate, dimethachlor, dimethametryn, dimethenamid, dimethipin, dimethylarsinic acid and its sodium salt, dinitra ine, dinoterb, diphenamid, diquat dibromide, dithiopyr, diuron, DNOC, endothal, EPTC, esprocarb, ethalfluralin, ethametsulfuron-methyl, ethofumesate, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, fluchloralin, flufenacet, flumetsulam, flumiclorac-pentyl, flumioxazin, fluometuron, fluoroglycofen-ethyl, flupoxam, flupyrsulfuron-methyl and its sodium salt, fluridone, flurochloridone, fluroxypyr, flurtamone, fluthiacet-methyl, fomesafen, foramnsulfuron, fosamine-ammonium, glufosinate, glufosinate-ammonium, glyphosate, glyphosate-isopropylammonium, glyphosate-sesquisodium, glyphosate-trinmesium, halosulfuron-methyl, haloxyfop-etotyl, haloxyfop-methyl, hexazinone, imazamethabenz-methyl, imazamox, imazapic, imazapyr, imazaquin, iazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, lactofen, lenacil, linuron, maleic hydrazide, MCPA and its dimethyammonium, potassium and sodium salts, MCPA-isoctyl, MCPB and its sodium salt, MCPB-ethyl, mecoprop, mecoprop-P, mefenacet, mefluidide, mesosulfuron-methyl, mesotrione, metam-sodium, metamitron, metazachlor, methabenzthiazuron, methylarsonic acid and its calcium, monoammonium, monosodium and disodium salts, methyldymron, methyl [[[1-[5-[2-chloro4-(trifluoromethyl)phenoxy]-2-nitrophenyl]-2-methoxyethylidene]-amino]oxy]acetate (AKH-7088), methyl 5-[[[[(4,6 dimethyl-2-pyrimidinyl)amino]carbonyl]-amino]sulfonyl]-1-(2-pyridinyl)-1H-pyrazole-4-carboxylate (NC-330), metobenzuron, metobromuron, metolachlor, S-metholachlor, metosulam, metoxuron, metribuzin, metsulfuron-methyl, molinate, monolinuron, naproanilide, napropamide, naptalam, neburon, nicosulfuron, norflurazon, orbencarb, oryzalin, oxadiargyl, oxadiazon, oxasulfuron, oxaziclomefone, oxyfluorfen, paraquat dichloride, pebulate, pendimethalin, pentanochlor, pentoxazone, perfluidone, phenmedipham, picloram, picloram-potassium, picolinafen, piperofos, pretilachlor, primisulfuron-methyl, prodiamine, profoxydim (BAS625H, 2-[1-[[2-(4-cblorophenoxy)propoxy]imino]butyl]-3-hydroxy-5-(tetrahydro-2H-thiopyran-3-yl)-2-cyclohexen-1-one), prometon, prometryn, propachlor, propanil, propaquizafop, propazine, propham, propisochlor, propyzamide, prosulfocarb, prosulfuron, pyraflufen-ethyl, pyrazolynate, pyrazoxyfen, pyrazosulfuron-ethyl, pyribenzoxim, pyributicarb, pyridate, pynminobac-methyl, pyrithiobac, pyrithiobac-sodium, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tepraloxydim, terbacil, terbumeton, terbuthylazine, terbutryn, thenylchlor, thiafluamide (BAY 11390), thiazopyr, thifeonmethyl, thiobencarb, tiocarbazil, tralkoxydim, tri-allate, triasulfuron, triaziflam, tribenuron-methyl, triclopyr, triclopyr-butotyl, tdclopyr-triethylammonium, tridiphane, trietazine, trifloxysulfuron, trifluralin, triusulfuron-methyl, tritosulfuron and vernolate.

Especially useful herbicide mixture partners for the compounds of the invention in rice crops are the sulfonylurea herbicides azimsfuron, bensulfiron-methyl, metsulfuron-methyl, chlorimuron-ethyl, cinosulfuron, cyclosulfamuron, halosulfuron-methyl, imazosulfuron and pyrazosulfuron-ethyl, and the nonsulfonylurea herbicides bispyribac-sodium, carfentrazone-ethyl, molinate, propanil, quinchlorac, thiobencarb and triclopyr. Other herbicides useful in combination with the compounds of the invention for control of undesired vegetation in rice crops include, but are not limited to, anilofos, benfuresate, benzofenap, bispyribac-sodium, bromobutid, cafenstrole, copper(II) sulfate, cyhalofop-butyl, dimepiperate, epoprodan, etobenzanid, fenoxaprop-ethyl, fentrazamide, indanofan, mefenacet, pretilachlor, profoxydim, pyrazolate, pyributicarb and thenylchlor.

To achieve complete knockdown and residual weed control in maize crops, mixtures of the Formula 1 compounds of this invention with the following herbicides may be especially useful: acetochlor, atrazine, dicamba, dimethenamid, foramsulfuron, flufenacet, flumetsulam, glyphosate, isoxaflutole, mesotrione, metolachlor, metribuzin, nicosulfuron, rimsulfuron, simazine and sulcotrione.

Combination of these companion herbicides with the novel herbicidal compounds of the invention may provide reduction of injury (i.e. safening) on crops and greater control of weeds than expected from additive effects (i.e. synergism). Daimuron and quinoclamine are examples of companion herbicides safening the novel compounds of the invention on crops and also providing greater than expected control of certain weeds. Particularly preferred are mixtures of Index Table A Compound 1 with daimuron and mixtures of Index Table A Compound 1 with quinoclamine.

The following Tests demonstrate the control efficacy of the compounds of this invention against specific weeds. The weed control afforded by the compounds is not limited, however, to these species. See Index Tables A1 to B for compound descriptions. The abbreviation "Ex." stands for "Example" and is followed by a number indicating in which example the compound is prepared.

INDEX TABLE A1*

| Cmpd. No. | $(R)_p$ | Y | Z | $R^1$ | $R^{2b}$ | m.p. (° C.) |
|---|---|---|---|---|---|---|
| 1 (Ex. 1, 2) | 3-$CF_3$ | O | S | t-$C_4H_9$ | H | 66–69* |
| 2 | 3-$CF_3$ | O | S | trimethylsilyl | H | oil* |
| 3 (Ex. 3) | 3-$CF_3$ | O | $CH_2$ | t-$C_4H_9$ | H | 76–78 |
| 4 | 3-$CF_3$ | O | $CH_2$ | trimethylsilyl | H | 93–95 |
| 5 | 3-$CF_3$ | O | $CH_2$ | $CH(C_2H_5)_2$ | H | oil* |
| 6 | 3-$CF_3$ | O | $CH_2$ | $CH(CH_3)_2$ | H | oil* |
| 7 | 3-$CF_3$ | O | $CH_2$ | $CH(CH_3)(C_2H_5)$ | H | oil* |
| 8 | 3-$CF_3$ | O | $CH_2$ | cyclopropyl | H | oil* |
| 9 (Ex. 4) | 3-$CF_3$ | O | O | t-$C_4H_9$ | H | 95–98 |
| 10 (Ex. 7) | 3-$CF_3$ | O | $CH_2$ | $C(CH_3)_2CH_2CH_2$ | | 123–26 |
| 11 | 3-$CF_3$ | O | $CH_2$ | $CH(CH_3)CH_2CH_2$ | | 91–92 |
| 12 | 3-$CF_3$ | O | $CH_2$ | cyclopropyl | Cl | 90–92 |
| 13 | 3-$CF_3$ | O | $CH_2$ | $CH(CH_3)(C_2H_5)$ | Cl | oil* |
| 14 | 3-$CF_3$ | O | $CH_2$ | t-$C_4H_9$ | Cl | 97–101 |
| 15 | 3-$CF_3$ | O | $CH_2$ | H | H | 86–88 |
| 16 | 3-$CF_3$ | O | $CH_2$ | $CH_3$ | H | oil* |
| 17 | 3-$CF_3$ | O | $CH_2$ | $CH(CH_3)_2$ | $CH_3$ | 65–68 |
| 18 | 3-$CF_3$ | O | S | H | H | oil* |
| 19 | 3-$CF_3$ | O | S | $CH_3$ | H | 93–95 |
| 20 | 3-$CF_3$ | O | S | $CH(CH_3)(C_2H_5)$ | H | oil* |
| 21 | 3-$CF_3$ | O | S | $CH(C_2H_5)_2$ | H | oil* |
| 22 | 3-$CF_3$ | S | $CH_2$ | t-$C_4H_9$ | H | 82–85 |
| 23 | 3-$CF_3$ | O | S | $CH(CH_3)_2$ | H | oil* |
| 24 | 3-$CF_3$ | O | O | $CH(CH_3)(C_2H_5)$ | H | 59–61 |
| 25 (Ex. 5) | 3-$CF_3$ | O | S | $CH(C_2H_5)_2$ | H | 83–85 |
| 26 | 3-$CF_3$ | O | S | cyclopropyl | H | oil* |
| 27 | 3-$CF_3$ | O | O | $CH(CH_3)_2$ | H | oil* |
| 28 | 3-$CF_3$ | O | O | cyclopropyl | H | oil* |

INDEX TABLE A1*-continued

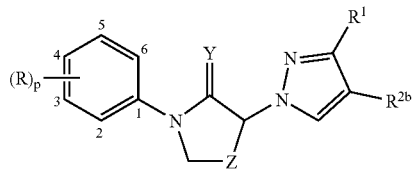

| Cmpd. No. | (R)p | Y | Z | R¹ | R²b | m.p. (° C.) |
|---|---|---|---|---|---|---|
| 29 | 3-CF$_3$ | O | S(O) | t-C$_4$H$_9$ | H | 156–159 |
| 30 | 3-OCF$_3$ | O | S | t-C$_4$H$_9$ | H | oil* |
| 31 | 3-OCF$_3$ | O | S | CH(CH$_3$)$_2$ | H | oil* |
| 32 | 3-OCF$_3$ | O | S | CH(CH$_3$)(C$_2$H$_5$) | H | oil* |
| 33 | 3-Br | O | CH$_2$ | t-C$_4$H$_9$ | H | oil* |
| 34 | 3,4-Cl | O | CH$_2$ | t-C$_4$H$_9$ | H | oil* |
| 35 | 3-Br-4-CH$_3$ | O | CH$_2$ | t-C$_4$H$_9$ | H | oil* |
| 36 | 3-OCF$_2$H | O | S | t-C$_4$H$_9$ | H | oil* |
| 37 | 3-CF$_3$ | O | S | cyclobutyl | H | oil* |
| 38 | 3-OCF$_3$ | O | S | cyclobutyl | H | oil* |
| 39 | 3-CF$_3$ | O | O | cyclobutyl | H | 88–90 |
| 40 | 3-OCF$_3$ | O | S | CH(CH$_3$)(C$_2$H$_5$) | H | oil* |
| 41 | 3-Cl-4-CH$_3$ | O | CH$_2$ | t-C$_4$H$_9$ | H | oil* |
| 42 | 3-OCH$_3$-4-CH$_3$ | O | CH$_2$ | t-C$_4$H$_9$ | H | 122–124 |
| 43 | 3-Cl | O | CH$_2$ | t-C$_4$H$_9$ | H | oil* |
| 44 | 3-OCF$_2$H | O | S | CH(CH$_3$)$_2$ | H | oil* |
| 45 | 3-OCF$_2$H | O | S | cyclobutyl | H | oil* |
| 46 | 3-Cl-4-F | O | CH$_2$ | t-C$_4$H$_9$ | H | oil* |
| 47 | 3-CF$_3$-4-CH$_3$ | O | CH$_2$ | t-C$_4$H$_9$ | H | oil* |
| 48 | 3-OCF$_2$CF$_2$H | O | CH$_2$ | t-C$_4$H$_9$ | H | oil* |
| 49 | 3-OCF$_3$ | O | CH$_2$ | t-C$_4$H$_9$ | H | oil* |
| 50 | 3-OCF$_3$ | O | S | cyclohexyl | H | oil* |
| 51 | 3-CF$_3$ | O | O | cyclohexyl | H | 91–94 |
| 52 | 3-CF$_3$ | O | S | cyclohexyl | H | oil* |
| 53 | 3-CH$_3$-4-Cl | O | CH$_2$ | t-C$_4$H$_9$ | H | oil* |
| 54 | 3,5-di-CF$_3$ | O | CH$_2$ | t-C$_4$H$_9$ | H | oil |
| 55 | 3,5-di-Cl | O | CH$_2$ | t-C$_4$H$_9$ | H | oil* |
| 56 | 3-Br-4-Cl | O | CH$_2$ | t-C$_4$H$_9$ | H | oil* |
| 57 | 3-OCH$_3$ | O | CH$_2$ | t-C$_4$H$_9$ | H | 97–99 |
| 58 | 3-CF$_3$ | O | CH$_2$ | OCH(CH$_3$)(C$_2$H$_5$) | H | oil* |
| 59 | 3-CF$_3$ | O | CH$_2$ | OCH(CH$_3$)$_2$ | H | oil* |
| 60 | 3-CF$_3$ | O | CH$_2$ | OCH$_3$ | H | oil* |
| 61 | 3-CF$_3$ | O | CH$_2$ | OCH$_2$CH$_3$ | H | oil* |
| 62 | 3-CF$_3$ | O | O | 1-methylcyclopropyl | H | 65–67 |
| 63 | 3-OCF$_3$ | O | S | 1-methylcyclopropyl | H | 53–55 |
| 64 | 3-CF$_3$ | O | S | 1-methyloyclopropyl | H | 50–54 |
| 65 | 3-OCF$_3$ | O | O | CH(CH$_3$)$_2$ | H | 55–58 |
| 66 | 3-OCF$_3$ | O | O | t-C$_4$H$_9$ | H | 42–43 |
| 67 | 3-OCF$_3$ | O | O | CH(CH$_3$)(C$_2$H$_5$) | H | 45–49 |
| 68 | 3-OCF$_3$ | O | O | CH(C$_2$H$_5$)$_2$ | H | 35–37 |
| 69 | 3-OCF$_3$ | O | O | 1-methylcyclopropyl | H | 59–62 |
| 70 | 3-OCH(CH$_3$)$_2$ | O | CH$_2$ | t-C$_4$H$_9$ | H | 80–84 |
| 71 | 3,5-di-OCH$_3$ | O | CH$_2$ | t-C$_4$H$_9$ | H | oil* |
| 72 | 3-CO$_2$C$_2$H$_5$ | O | CH$_2$ | t-C$_4$H$_9$ | H | oil* |
| 73 | 3-CO$_2$CH$_3$ | O | CH$_2$ | t-C$_4$H$_9$ | H | oil* |
| 74 | 3,5-di-Cl-4-CH$_3$ | O | CH$_2$ | t-C$_4$H$_9$ | H | oil* |
| 75 | 3-Br-4-F | O | CH$_2$ | t-C$_4$H$_9$ | H | oil* |
| 76 | 3-OCF$_2$H | O | CH$_2$ | t-C$_4$H$_9$ | H | oil* |
| 77 | 3,4-di-CH$_3$-5-Br | O | CH$_2$ | t-C$_4$H$_9$ | H | oil |
| 78 | 3-Br-4-CH$_3$-5-F | O | CH$_2$ | t-C$_4$H$_9$ | H | oil |
| 79 | 3-OCF$_2$H-4-CH$_3$ | O | CH$_2$ | t-C$_4$H$_9$ | H | oil* |
| 80 | 3-OCH$_3$-4-CH$_3$ | O | CH$_2$ | CH(CH$_3$)(C$_2$H$_5$) | H | 65–68 |
| 81 | 3-OCH$_3$-4-CH$_3$ | O | CH$_2$ | CH(C$_2$H$_5$)$_2$ | H | 55–57 |
| 82 | 3-OCH(CH$_3$)$_2$ | O | CH$_2$ | CH(CH$_3$)$_2$ | H | 50–53 |
| 83 | 3-OCH(CH$_3$)$_2$ | O | CH$_2$ | CH(CH$_3$)(C$_2$H$_5$) | H | oil* |
| 84 | 3-OCH(CH$_3$)$_2$ | O | CH$_2$ | CH(C$_2$H$_5$)$_2$ | H | oil* |
| 85 | 3-OCH$_3$-4-CH$_3$ | O | CH$_2$ | CH(CH$_3$)$_2$ | H | 89–91 |
| 86 | 3-SCH$_3$ | O | CH$_2$ | t-C$_4$H$_9$ | H | 65–69 |
| 87 | 3-OCH$_3$ | O | CH$_2$ | t-C$_4$H$_9$ | H | oil* |
| 88 | 3-I | O | CH$_2$ | t-C$_4$H$_9$ | H | 112–114 |
| 89 | 3-CF$_3$ | O | O | CH(CH$_3$)(CH$_2$)$_2$CH$_3$ | H | oil* |
| 90 | 3-OCF$_3$ | O | S | CH(CH$_3$)(CH$_2$)$_2$CH$_3$ | H | oil* |
| 91 | 3-OCF$_3$ | O | O | CH(CH$_3$)(CH$_2$)$_2$CH$_3$ | H | oil* |
| 92 | 3-CF$_3$ | O | S | CH(CH$_3$)(CH$_2$)$_2$CH$_3$ | H | oil* |

INDEX TABLE A1*-continued

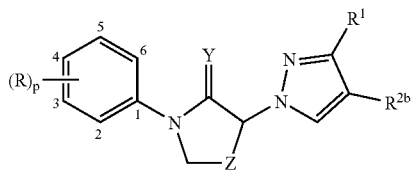

| Cmpd. No. | $(R)_p$ | Y | Z | $R^1$ | $R^{2b}$ | m.p. (° C.) |
|---|---|---|---|---|---|---|
| 93 | 3-SCF$_3$ | O | CH$_2$ | t-C$_4$H$_9$ | H | 56–57 |
| 94 | 3-OC(O)CF$_3$ | O | CH$_2$ | t-C$_4$H$_9$ | H | 201–203 |
| 95 | 3-OCH$_3$ | O | CH$_2$ | CH(CH$_3$)(C$_2$H$_5$) | H | oil* |
| 96 | 3-OCH$_3$ | O | CH$_2$ | CH(C$_2$H$_5$)$_2$ | H | oil* |
| 97 | 3-OCF$_3$ | O | O | CH(CH$_3$)(CH$_2$)$_3$CH$_3$ | H | oil* |
| 98 | 3-CF$_3$ | O | O | CH(CH$_3$)(CH$_2$)$_3$CH$_3$ | H | oil* |
| 99 | 3-OCH$_3$ | O | CH$_2$ | CH(CH$_3$)(CH$_2$)$_2$CH$_3$ | H | oil* |
| 100 | 3-CF$_3$ | O | CH$_2$ | CH(CH$_3$)(CH$_2$)$_2$CH$_3$ | H | oil* |
| 101 | 3-S(O)CF$_3$ | O | CH$_2$ | t-C$_4$H$_9$ | H | oil* |
| 102 | 3-S(O)$_2$CH$_3$ | O | CH$_2$ | t-C$_4$H$_9$ | H | 134–136 |
| 103 | 3-CF$_3$ | O | S | CH(CH$_3$)(CH$_2$)$_3$CH$_3$ | H | oil* |
| 104 | 3-CN | O | CH$_2$ | t-C$_4$H$_9$ | H | 160–164 |
| 105 | 3,4-CH$_2$CH$_2$CH$_2$ | O | CH$_2$ | t-C$_4$H$_9$ | H | 108–110 |
| 106 | 3-OC$_2$H$_5$-4-CH$_3$ | O | CH$_2$ | t-C$_4$H$_9$ | H | oil* |
| 107 | 3-O(CH$_2$)$_2$CH$_3$-4-CH$_3$ | O | CH$_2$ | t-C$_4$H$_9$ | H | oil* |
| 108 | 3-O(CH$_2$)$_2$I-4-CH$_3$ | O | CH$_2$ | t-C$_4$H$_9$ | H | oil* |
| 109 | 3-O(CH$_2$)$_2$Cl-4-CH$_3$ | O | CH$_2$ | t-C$_4$H$_9$ | H | oil* |
| 110 | 3-OCH(CH$_3$)$_2$-4-CH$_3$ | O | CH$_2$ | t-C$_4$H$_9$ | H | oil* |
| 111 | 3-CH(CH$_3$)$_2$ | O | CH$_2$ | t-C$_4$H$_9$ | H | 108–110 |
| 112 | 3-CH$_3$ | O | CH$_2$ | t-C$_4$H$_9$ | H | 118–119 |
| 113 | 3-OCF$_3$ | O | O | CH((CH$_2$)$_3$CH$_3$)$_2$ | H | oil* |
| 114 | 3-CF$_3$ | O | O | CH((CH$_2$)$_3$CH$_3$)$_2$ | H | 52–54 |
| 115 | 3-OCF$_3$ | O | S | CH((CH$_2$)$_3$CH$_3$)$_2$ | H | 64–65 |
| 116 | 3-CF$_3$ | O | S | CH((CH$_2$)$_3$CH$_3$)$_2$ | H | 54–55 |
| 117 (Ex. 6) | 3-OCH$_3$-4-Cl | O | CH$_2$ | t-C$_4$H$_9$ | H | 128–130 |
| 118 | 3-OCH$_3$-4-Cl | O | CH$_2$ | CH(C$_2$H$_5$)$_2$ | H | oil* |
| 119 | 3-OCH$_3$-4-Cl | O | CH$_2$ | CH(CH$_3$)(C$_2$H$_5$) | H | 71–74 |
| 120 | 3-OCH$_3$-4-Cl | O | CH$_2$ | CH(CH$_3$)$_2$ | H | 93–95 |
| 121 | 3-OCH$_3$-4-Cl | O | CH$_2$ | CH(CH$_3$)(CH$_2$)$_2$CH$_3$ | H | 85–88 |
| 122 | 3-I-4-CH$_3$ | O | CH$_2$ | t-C$_4$H$_9$ | H | oil* |
| 123 | 3-CO$_2$(CH$_2$)$_2$CH$_3$ | O | CH$_2$ | t-C$_4$H$_9$ | H | oil* |
| 124 | 3-CO$_2$CH(CH$_3$)$_2$ | O | CH$_2$ | t-C$_4$H$_9$ | H | oil* |
| 125 | 3-OC$_2$H$_5$ | O | CH$_2$ | CH(C$_2$H$_5$)$_2$ | H | 81–82 |
| 126 | 3-OC$_2$H$_5$ | O | CH$_2$ | CH(CH$_3$)(C$_2$H$_5$) | H | 71–72 |
| 127 | 3-OCH(CH$_3$)(C$_2$H$_5$) | O | CH$_2$ | t-C$_4$H$_9$ | H | 50–51 |
| 128 | 3-OC$_2$H$_5$ | O | CH$_2$ | CH(CH$_3$)$_2$ | H | 78–79 |
| 129 | 3-OC$_2$H$_5$ | O | CH$_2$ | CH(CH$_3$)(CH$_2$)$_2$CH$_3$ | H | 70–71 |
| 130 | 3-OC$_2$H$_5$ | O | CH$_2$ | t-C$_4$H$_9$ | H | 125–126 |
| 131 | 3-OCF$_2$H | O | O | CH(C$_2$H$_5$)$_2$ | H | oil* |
| 132 | 3-OCF$_2$H | O | O | CH(CH$_3$)(CH$_2$)$_2$CH$_3$ | H | oil* |
| 133 | 3-OCF$_2$H | O | O | t-C$_4$H$_9$ | H | 74–75 |
| 134 | 3-OCF$_2$H | O | O | CH(CH$_3$)(C$_2$H$_5$) | H | oil* |
| 140 | 3-OCH$_3$-4-Br | O | CH$_2$ | CH(CH$_3$)$_2$ | H | 100–105 |
| 141 | 3-OCH$_3$-4-Br | O | CH$_2$ | t-C$_4$H$_9$ | H | 135–137 |
| 142 | 3-OCH$_3$-4-Br | O | CH$_2$ | CH(CH$_3$)(C$_2$H$_5$) | H | oil* |
| 143 | 3-OCH$_3$-4-Br | O | CH$_2$ | CH(C$_2$H$_5$)$_2$ | H | oil* |
| 144 | 3-CF$_3$-4-F | O | CH$_2$ | CH(C$_2$H$_5$)$_2$ | H | oil* |
| 145 | 3-CF$_3$-4-F | O | CH$_2$ | CH(CH$_3$)(C$_2$H$_5$) | H | oil* |
| 146 | 3-CF$_3$-4-F | O | CH$_2$ | t-C$_4$H$_9$ | H | oil* |

*see Index Table B for $^1$H NMR data.

INDEX TABLE A2*

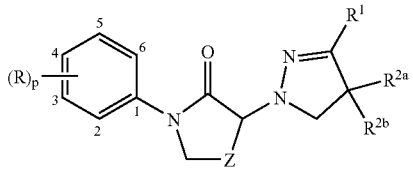

| Cmpd. No. | (R)$_p$ | Z | R$^1$ | R$^{2a}$ | R$^{2b}$ | m.p. (° C.) |
|---|---|---|---|---|---|---|
| 135 | 3-CF$_3$ | CH$_2$ | t-C$_4$H$_9$ | H | H | oil |

*see Index Table B for $^1$H NMR data.

INDEX TABLE A3*

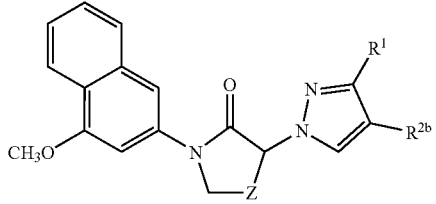

| Cmpd. No. | Z | R$^1$ | R$^{2b}$ | m.p. (° C.) |
|---|---|---|---|---|
| 136 | CH$_2$ | t-C$_4$H$_9$ | H | oil* |

*see Index Table B for $^1$H NMR data.

INDEX TABLE A4

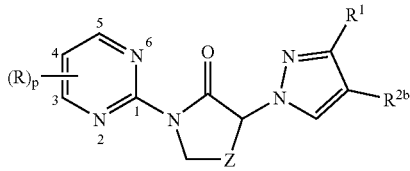

| Cmpd. No. | (R)$_p$ | Z | R$^1$ | R$^{2b}$ | m.p. (° C.) |
|---|---|---|---|---|---|
| 137 | 4-CH$_3$-6-OCH$_3$ | CH$_2$ | t-C$_4$H$_9$ | H | 120–122 |

INDEX TABLE A5*

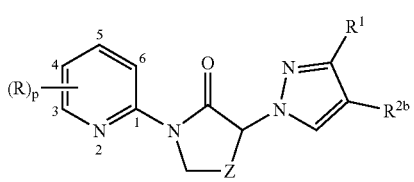

| Cmpd. No. | (R)$_p$ | Z | R$^1$ | R$^{2b}$ | m.p. (° C.) |
|---|---|---|---|---|---|
| 138 | 4,6-di-CH$_3$ | CH$_2$ | t-C$_4$H$_9$ | H | oil* |
| 139 | 4-CH$_3$ | CH$_2$ | t-C$_4$H$_9$ | H | oil* |

*see Index Table B for $^1$H NMR data.

INDEX TABLE B

| Cmpd. No. | $^1$H NMR Data$^a$ |
|---|---|
| 1 | δ 1.28 (s, 9H), 4.75 (d, 1H), 5.37 (d, 1H), 5.97 (s, 1H), 6.16 (d, 1H), 7.45 (d, 1H), 7.46–7.8 (m, 4H). |
| 2 | δ 0.26 (s, 9H), 4.78 (d, 1H), 5.35 (d, 1H), 6.13 (s, 1H), 6.41 (d, 1H), 7.43–7.8 (m, 5H). |
| 5 | δ 0.83 (t, 6H), 1.44–1.8 (m, 4H), 2.44–2.6 (m, 1H), 2.65–2.98 (m, 2H), 3.9–4.18 (m, 2H), 5.06 (t, 1H), 6.08 (d, 1H), 7.4–7.56 (m, 3H), 7.9–8 (m, 2H). |
| 6 | δ 1.25 (d, 6H), 2.7–3.1 (m, 3H), 3.9–4.2 (m, 2H), 5.05 (t, 1H), 6.17 (d, 1H), 7.4–7.55 (m, 3H), 7.95–8 (m, 2H). |
| 7 | δ 0.87 (t, 3H), 1.2 (d, 3H), 1.5–1.74 (m, 2H), 2.7–2.98 (m, 3H), 3.95–4 (m, 1H), 4.03–4.14 (m, 1H), 5.05 (t, 1H), 6.11 (d, 1h), 7.4–7.55 (m, 3H), 7.95–8 (m, 2H). |
| 8 | δ 0.64–0.74 (m, 2H), 0.8–0.95 (m, 2H), 1.87–2 (m, 1H), 2.64–3 (m, 2H), 3.87–4.2 (m, 2H), 5 (t, 1H), 5.93 (d, 1H), 7.4–7.55 ( m, 3H), 7.87–8 (m, 2H). |
| 13 | δ 0.9 (m, 3H), 1.3 (m, 3H), 1.8 (m, 2H), 2.8 (m, 3H), 3.9 (m, 1H), 4.1 (m, 1H), 5.0 (t, 1H), 7.4–7.6 (m, 3H), 7.9 (m, 2H). |
| 16 | δ 2.3 (s, 3H), 2.7–3.0 (m, 2H), 3.9–4.1 (m, 2H), 5.0 (t, 1H), 6.1 (s, 1H), 7.4–7.5 (m, 3H), 7.9 (m, 1H), 8.0 (s, 1H). |
| 18 | δ 4.8 (m, 1H), 5.4 (m, 1H), 6.1 (s, 1H), 6.3 (m, 1H), 7.5–7.7 (m, 4H), 7.8–7.9 (m, 2H). |
| 20 | δ 0.9 (m, 3H), 1.3 (m, 3H), 1.6 (m, 2H), 2.8 (m, 1H), 4.8 (m, 1H), 5.3 (m, 1H), 6.0 (s, 1H), 6.1 (s, 1H), 7.5–7.6 (m, 3H), 7.7–7.8 (m, 2H). |
| 21 | δ 0.8 (m, 6H), 1.6 (m, 4H), 2.5 (m, 1H), 4.8 (m, 1H), 5.3 (m, 1H), 6.0 (s, 1H), 6.1 (s, 1H), 7.5–7.6 (m, 3H), 7.7–7.8 (m, 2H). |
| 23 | δ 1.2 (d, 6H), 3.0 (m, 1H), 4.8 (m, 1H), 5.7 (m, 1H), 6.0 (s, 1H), 6.1 (s, 1H), 7.5–7.6 (m, 3H), 7.7–7.8 (m, 2H). |
| 26 | δ 0.7 (m, 2H), 0.9 (m, 2H), 1.9 (m, 1H), 4.8 (d, 1H), 5.3 (d, 1H), 5.9 (s, 1H), 6.0 (s, 1H), 7.5 (m, 3H), 7.7–7.8 (m, 2H). |
| 27 | δ 1.2 (d, 6H), 2.9 (m, 1H), 5.6 (s, 1H), 5.8 (m, 1H), 6.1 (s, 1H), 6.2 (m, 1H), 7.5 (m, 3H), 7.9 (m, 2H). |
| 28 | δ 0.7 (m, 2H), 0.9 (m, 2H), 1.9 (m, 1H), 5.6 (m, 1H), 5.8 (m, 1H), 5.9 (m, 1H), 6.1 (m, 1H), 7.5 (m, 3H), 7.9 (m, 2H). |

INDEX TABLE B-continued

| Cmpd. No. | ¹H NMR Data[a] |
|---|---|
| 30 | δ 1.28 (s, 9H), 4.73 (d, 1H), 5.37 (d, 1H), 5.96 (s, 1H), 6.17 (d, 1H), 7.15–7.2 (m, 1H), 7.4–7.5 (m, 4H). |
| 31 | δ 1.24 (d, 6H), 2.9–3.1 (m, 1H), 4.78 (d, 1H), 5.35 (d, 1H), 6.0 (s, 1H), 6.15 (d, 1H), 7.15–7.2 (m, 1H), 7.4–7.6 (m, 4H). |
| 32 | δ 0.87 (t, 3H), 1.22 (d, 3H), 2.5–2.7 (m, 2H), 2.7–2.9 (m, 1H), 4.78 (d, 1H), 5.35 (d, 1H), 6.0 (s, 1H), 6.1 (d, 1H), 7.15–7.2 (m, 1H), 7.4–7.6 (m, 4H). |
| 33 | δ 1.3 (s, 9H), 2.6–2.9 (m, 2H), 3.8 (m, 1H), 4.0 (m, 1H), 5.0 (t, 1H), 6.1 (s, 1H), 7.2–7.3 (m, 2H), |
| 34 | δ 1.3 (s, 9H), 2.6–2.9 (m, 2H), 3.8 (m, 1H), 4.0 (m, 1H), 5.0 (t, 1H), 6.2 (s, 1H), 7.4 (m, 2H), 7.5 (m, 1H), 7.8 (s, 1H). |
| 35 | δ 1.3 (s, 9H), 2.4 (s, 3H), 2.6–2.9 (m, 2H), 3.7 (m, 1H), 4.0 (m, 1H), 5.0 (t, 1H), 6.2 (m, 1H), 7.2 |
| 36 | δ 1.28 (s, 9H), 4.73 (d, 1H), 5.35 (d, 1H), 5.96 (s, 1H), 6.16 (d, 1H), 6.57 (t, 1H), 7.04 (d, 1H), 7.3–7.5 (m, 4H). |
| 37 | δ 1.8–2.4 (m, 6H), 3.58 (m, 1H), 4.79 (d, 1H), 5.38 (d, 1H), 6.02 (s, 1H), 6.20 (d, 1H), 7.48–7.6 (m, 3H:), 7.7–7.9 (m, 2H). |
| 38 | δ 1.8–2.4 (m, 6H), 3.55 (m, 1H), 4.76 (d, 1H), 5.35 (d, 1H), 6.01 (s, 1H), 6.20 (d, 1H), 7.16 (m, 1H), 7.4–7.55 (m, 4H). |
| 40 | δ 0.88 (t, 3H), 1.22 (d, 3H), 1.5–1.7 (m, 2H), 2.78 (m, 1H), 4.78 (d, 1H), 5.3 (d, 1H), 6 (s, 1H), 6.11 (d, 1H), 6.53 (t, 1H), 7.05 (d, 1H), 7.3–7.5 (m, 4H). |
| 41 | δ 1.3 (s, 9H), 2.4 (s, 3H), 2.6–2.9 (m, 2H), 3.4 (m, 1H), 4.1 (m, 1H), 5.0 (t, 1H), 5.2 (s, 1H), 7.2 (m, 1H), 7.5 (m, 2H), 7.7 (m, 1H). |
| 43 | δ 1.3 (s, 9H), 2.6–2.9 (m, 2H), 3.8 (m, 1H), 4.0 (m, 1H), 5.0 (t, 1H), 6.2 (m, 1H), 7.2 (m, 1H), 7.3 (m, 1H), 7.4 (m, 1H), 7.6 (m, 1H), 7.8 (m, 1H). |
| 44 | δ 1.24 (d, 6H), 2.98 (m, 1H), 4.75 (d, 1H), 5.33 (d, 1H), 6.04 (s, 1H), 6.14 (d, 1H), 6.55 (t, 1H), 7.05 (d, 1H), 7.34–7.5 (m, 4H). |
| 45 | δ 1.8–2.4 (m, 6H), 3.58 (m, 1H), 4.76 (d, 1H), 5.32 (d, 1H), 6.02 (s, 1H), 6.20 (d, 1H), 6.54 (t, 1H), 7.05 (d, 1H), 7.35–7.5 (m, 4H). |
| 46 | δ 1.3 (s, 9H), 2.6–2.8 (m, 2H), 3.9–4.1 (m, 2H), 5.3 (t, 1H), 6.2 (m, 1H), 7.3 (t, 1H), 7.6 (m, 2H), 8.0 (m, 1H). |
| 47 | δ 1.3 (s, 9H), 2.5 (s, 3H), 2.6–2.8 (m, 2H), 3.9–4.1 (m, 2H), 5.3 (t, 1H), 6.2 (m, 1H), 7.4 (m, 1H), 7.6 (m, 1H), 7.8 (m, 1H), 8.1 (m, 1H). |
| 48 | δ 1.3 (s, 9H), 2.6–2.7 (m, 2H), 3.9–4.1 (m, 2H), 5.3 (t, 1H), 6.2 (m, 1H), 7.1 (m, 1H), 7.5 (m, 1H), 7.6 (m, 2H), 7.9 (m, 1H). |
| 49 | δ 1.3 (s, 9H), 2.5–2.7 (m, 2H), 3.8–4.1 (m, 2H), 5.3 (t, 1H), 6.2 (m, 1H), 7.1 (m, 1H), 7.4 (m, 1H), 7.6 (m, 2H), 7.9 (m, 1H). |
| 50 | δ 1.2 2.05 (m, 10H), 2.6–2.7 (m, 1H), 4.76 (d, 1H), 5.32 (d, 1H), 6.0 (s, 1H), 6.12 (d, 1H), 7.1–7.2 (m, 1H), 7.4–7.55 (m, 4H). |
| 52 | δ 1.2–2.1 (m, 10H), 2.6–2.75 (m, 1H), 4.78 (d, 1H), 5.35 (d, 1H), 6.0 (s, 1H), 6.12 (d, 1H), 7.47 (d, 1H), 7.5–7.6 (m, 2H), 7.7–7.9 (m, 2H). |
| 53 | δ 1.3 (s, 9H), 2.4 (s, 3H), 2.6–2.8 (m, 2H), 3.9–4.1 (m, 2H), 5.3 (t, 1H), 6.2 (m, 1H), 7.4 (m, 1H), 7.5 (m, 1H), 7.6 (m, 1H), 7.7 (m, 1H). |
| 54 | δ 1.3 (s, 9H), 2.6–2.8 (m, 2H), 3.9–4.2 (m, 2H), 5.3 (t, 1H), 6.2 (m, 1H), 7.6 (m, 1H), 8.4 (m, 1H). |
| 55 | δ 1.3 (s, 9H), 2.6–2.8 (m, 2H), 3.9–4.1 (m, 2H), 5.3 (t, 1H), 6.2 (m, 1H), 7.3 (m, 1H), 7.6 (s, 1H), 7.8 (m, 2H). |
| 56 | δ 1.3 (s, 9H), 2.7–2.9 (m, 2H), 3.9 (m, 1H), 4.0 (m, 1H), 5.0 (t, 1H), 8.2 (m, 1H), 7.4 (m, 2H), 7.6 (m, 1H), 8.0 (m, 1H). |
| 58 | δ 0.9 (m, 3H), 1.3 (m, 5H), 2.7 (m, 1H), 2.9 (m, 1H), 3.9 (m, 1H), 4.1 (m, 1H), 4.4 (m, 1H), 4.9 (t, 1H), 5.7 (s, 1H), 7.5 (m, 3H), 7.9 (m, 2H). |
| 59 | δ 1.3 (m, 6H), 2.7 (m, 1H), 2.9 (m, 1H), 3.9 (m, 1H), 4.1 (m, 1H), 4.6 (m, 1H), 4.8 (t, 1H), 5.7 (s, 1H), 7.5 (m, 3H), 7.9 (m, 2H). |
| 60 | δ 2.7 (m, 1H), 2.9 (m, 1H), 3.8 (s, 3H), 3.9 (m, 1H), 4.1 (m, 1H), 4.9 (t, 1H), 5.7 (s, 1H), 7.5 (m, 3H), 7.9 (m, 2H). |
| 61 | δ 1.4 (t, 3H), 2.7 (m, 1H), 2.9 (m, 1H), 3.9 (m, 1H), 4.1 (m, 3H), 4.9 (t, 1H), 5.7 (s, 1H), 7.5 (m, 3H), 7.9 (m, 2H). |
| 71 | δ 1.29 (s, 9H), 2.62–2.90 (m, 2H), 3.79–3.90 (m, 7H), 4.0–4.08 (m, 1H), 5.03 (t, 1H), 6.15 (d, 1H), 6.31 (t, 1H), 6.93 (d, 2H), 7.47 (d, 1H). |
| 72 | δ 1.3–1.4 (m, 12H), 2.8 (m, 2H), 3.9 (m, 1H), 4.1 (m, 1H), 4.4 (m, 2H), 6.1 (m, 2H), 7.5 (m, 2H), 7.9 (m, 1H), 8.1 (m, 2H). |
| 73 | δ 1.3 (s, 9H), 2.8 (m, 2H), 3.9 (m, 4H), 4.1 (m, 1H), 5.0 (t, 1H), 6.1 (m, 1H), 7.5 (m, 2H), 7.8 (m, 1H), 8.1 (m, 2H). |
| 74 | δ 1.3 (s, 9H), 2.4 (s, 3H), 2.7–2.9 (m, 2H), 3.8 (m, 1H), 4.0 (m, 1H), 5.0 (t, 1H), 6.2 (m, 1H), 7.5 (m, 1H), 7.7 (m, 2H). |
| 75 | δ 1.3 (s, 9H), 2.6–2.9 (m, 2H), 3.7 (m, 1H), 4.0 (m, 1H), 5.0 (t, 1H), 6.2 (m, 1H), 7.1 (m, 1H), 7.4 (m, 1H), 7.6 (m, 1H), 7.9 (m, 1H). |
| 76 | δ 1.3 (s, 9H), 2.6–2.9 (m, 2H), 3.8 (m, 1H), 4.0 (m, 1H), 5.0 (t, 1H), 6.1 (m, 1H), 6.9 (m, 1H), 7.4 (m, 1H), 7.5 (m, 3H), 7.6 (m, 1H). |
| 77 | δ 1.3 (s, 9H), 2.3 (s, 6H), 2.6–2.9 (m, 2H), 3.8 (m, 1H), 4.0 (m, 1H), 5.0 (t, 1H), 6.2 (m, 1H), 7.5 (m, 2H), 7.7 (m, 1H). |
| 78 | δ 1.3 (s, 9H), 2.3 (s, 3H), 2.7–2.9 (m, 2H), 3.8 (m, 1H), 4.0 (m, 1H), 5.0 (t, 1H), 6.2 (m, 1H), 7.4 (m, 1H), 7.5 (m, 1H), 7.7 (m, 1H). |
| 79 | δ 1.3 (s, 9H), 2.3 (s, 3H), 2.6–2.9 (m, 2H), 3.8 (m, 1H), 4.0 (m, 1H), 5.0 (t, 1H), 6.1 (m, 1H), 7.2–7.3 (m, 3H), 7.4 (m, 1H), 7.7 (m, 1H). |
| 83 | δ 0.88 (t, 3H), 1.23 (d, 3H), 1.33 (d, 6H), 1.5–1.7 (m, 2H), 2.65–2.9 (m, 3H), 3.84–3.97 (m, 1H), 3.98–4.1 (m, 1H), 4.5–4.65 (m, 1H), 5.03 (t, 1H), 6.1 (d, 1H), 6.74 (m, 1H), 7.1–7.55 (m, 4H). |
| 84 | δ 0.83 (t, 6H), 1.33 (d, 6H), 1.5–1.8 (m, 4H), 2.45–2.6 (m, 1H), 2.65–2.9 (m, 2H), 3.8–4.1 (m, 2H), 4.5–4.65 (m, 1H), 5.03 (t, 1H), 6.07 (d, 1H), 6.74 (m, 1H), 7.1–7.55 (m, 4H). |

INDEX TABLE B-continued

| Cmpd. No. | ¹H NMR Data[a] |
|---|---|
| 87 | δ 1.29 (s, 9H), 2.62 (s, 3H), 2.65–2.92 (m, 2H), 3.84–4.15 (m, 2H), 5.05 (t, 1H), 6.17 (bs, 1H), 7.43–7.53 (m, 2H), 7.78 (d, 1H), 8.02 (d, 1H) 8.2 (s, 1H). |
| 88 | δ 1.29 (s, 9H), 2.62–2.90 (m, 2H), 3.80–3.90 (m, 1H), 3.98–4.10 (m, 1H), 5.0 (t, 1H), 6.15 (d, 1H), 7.11 (t, 1H), 7.46 (d, 1H), 7.5 (d, 1H) 7.67 (d, 1H). |
| 89 | δ 0.85 (t, 3H), 1.17–1.65 (m, 7H), 2.78–2.9 (m, 1H), 5.58 (d, 1H), 5.8 (d, 1H), 6.07 (s, 1H), 6.15 (d, 1H), 7.5–7.6 (m, 3H), 7.82–7.92 (m, 2H). |
| 90 | δ 0.87 (t, 3H), 1.17–1.65 (m, 7H), 2.78–2.9 (m, 1H), 4.75 (d, 1H), 5.32 (d, 1H), 6.0 (s, 1H), 6.11 (d, 1H), 7.1 (m, 1H), 7.4–7.57 (m, 4H). |
| 91 | δ 0.86 (t, 3H), 1.17–1.65 (m, 7H), 2.78–2.9 (m, 1H), 5.55 (bs, 1H), 5.77 (bs, 1H), 6.05 (s, 1H), 6.15 (d, 1H), 7.14 (d, 1H), 7.4–7.55 (m, 3H), 7.64 (s, 1H). |
| 92 | δ 0.87 (t, 3H), 1.19–1.7 (m, 7H), 2.78–2.97 (m, 1H), 4.8 (m, 1H), 5.35 (d, 1H), 6.0 (d, 1H), 6.11 (d, 1H), 7.45–7.6 (m, 3H), 7.7–7.9 (m, 2H). |
| 95 | δ 0.88 (t, 3H), 1.23 (d, 3H), 1.47–1.74 (m, 2H), 2.64–2.9 (m, 3H), 3.8–4.1 (m, 5H), 5.04 (t, 1H), 6.11 (d, 1H), 6.75 (dd, 1H), 7.15 (dd, 1H), 7.28 (t, 1H), 7.44–7.54 (m, 2H). |
| 96 | δ 0.83 (t, 6H), 1.47–1.78 (m, 4H), 2.47–2.6 (m, 1H), 2.65–2.9 (m, 2H), 3.81–4.1 (m, 5H), 5.04 (t, 1H), 6.07 (d, 1H), 6.75 (dd, 1H), 7.16 (dd, 1H), 7.28 (t, 1H), 7.42–7.54 (m, 2H). |
| 97 | δ 0.8 (m, 3H), 1.2–1.4 (m, 9H), 2.8 (m, 1H), 5.6 (m, 1H), 5.8 (m, 1H), 6.1 (m, 1H), 6.2 (m, 1H), 7.1 (m, 1H), 7.5 (m, 3H), 7.6 (m, 1H). |
| 98 | δ 0.9 (m, 3H), 1.2–1.4 (m, 9H), 3.8 (m, 1H), 5.6 (m, 1H), 5.8 (m, 1H), 6.1 (m, 1H), 6.2 (m, 1H), 7.5–7.6 (m, 3H), 7.8–7.9 (m, 2H). |
| 99 | δ 0.8 (t, 3H), 1.2–1.6 (m, 5H), 2.6–2.9 (m, 3H), 3.8 (s, 3H), 3.9 (m, 1H), 4.01 (m, 1H), 5.0 (t, 1H), 6.1 (m, 1H), 6.7 (m, 1H), 7.1 (m, 1H), 7.3 (m, 1H) 7.5 (m, 2H). |
| 100 | δ 0.9 (m, 3H), 1.2–1.7 (m, 7H), 2.7–3.0 (m, 3H), 3.9 (m, 1H), 4.1 (m, 1H), 5.0 (t, 1H), 6.1 (m, 1H), 7.4–7.6 (m, 3H), 7.8–8.0 (m, 2H). |
| 101 | δ 1.3 (s, 9H), 2.7–2.9 (m, 2H), 3.9 (m, 1H), 4.1 (m, 1H), 5.0 (t, 1H), 6.1 (m, 1H), 7.5 (m, 1H), 7.6 (m, 2H), 8.1 (m, 2H). |
| 103 | δ 0.9 (m, 3H), 1.2–1.7 (m, 7H), 2.9 (m, 1H), 4.8 (m, 1H), 5.3 (m, 1H), 6.0 (m, 1H), 6.1 (s, 1H), 7.5–7.6 (m, 3H), 7.7–7.9 (m, 2H). |
| 106 | δ 1.3 (s, 9H), 1.4 (t, 3H), 2.2 (s, 3H), 2.6–2.8 (m, 2H), 3.8 (m, 1H), 3.9–4.1 (m, 3H), 5.0 (t, 1H), 6.2 (m, 1H), 6.7 (m, 1H), 7.1 (m, 1H), 7.4 (m, 1H), 7.6 (m, 1H). |
| 107 | δ 1.0 (t, 3H), 1.3 (s, 9H), 1.8 (m, 2H), 2.2 (s, 3H), 2.6–2.8 (m, 2H), 3.8–4.1 (m, 4H), 5.0 (t, 1H), 6.2 (m, 1H), 6.8 (m, 1H), 7.1 (m, 1H), 7.5 (m, 1H), 7.6 (m, 1H). |
| 108 | δ 1.3 (s, 9H), 2.2 (s, 3H), 2.6–2.8 (m, 2H), 3.4 (m, 2H), 3.9 (m, 1H), 4.0 (m, 1H), 4.2 (t, 2H), 5.0 (t, 1H), 6.2 (m, 1H), 6.8 (m, 1H), 7.2 (m, 1H), 7.5 (m, 1H), 7.6 (m, 1H). |
| 109 | δ 1.3 (s, 9H), 2.2 (s, 3H), 2.7–2.9 (m, 2H), 3.9 (m, 3H), 4.1 (m, 1H), 4.3 (m, 2H), 5.1 (t, 1H), 6.2 (m, 1H), 6.9 (m, 1H), 7.2 (m, 1H), 7.5 (m, 1H), 7.7 (m, 1H). |
| 110 | δ 1.3 (m, 15H), 2.2 (s, 3H), 2.7 (m, 2H), 3.8 (m, 1H), 4.0 (m, 1H), 4.5 (m, 1H), 5.0. (t, 1H), 6.2 (m, 1H), 6.8 (m, 1H), 7.2 (m, 1H), 7.4 (m, 1H), 7.6 (m, 1H). |
| 113 | δ 0.8 (m, 6H), 1.1–1.4 (m, 8H), 1.5–1.7 (m, 4H), 2.7 (m, 1H), 5.5 (s, 1H), 5.8 (m, 1H), 6.1 (d, 2H), 7.1 (m, 1H), 7.5 (m, 3H), 7.6 (m, 1H). |
| 118 | δ 0.8 (m, 6H), 1.5–1.8 (m, 4H), 2.5 (m, 1H), 2.7–2.9 (m, 2H), 3.8–4.1 (m, 5H), 5.0 (t, 1H), 6.1 (m, 1H), 6.8 (m, 1H), 7.4 (m, 1H), 7.5 (m, 1H), 7.9 (m, 1H). |
| 122 | δ 1.29 (s, 9H), 2.41 (s, 3H), 2.69–2.85 (m, 2H), 3.78–3.90 (m, 1H), 3.98–4.19 (m, 1H), 4.0 (t, 1H), 6.15 (d, 1H), 7.22 (d, 1H), 7.47 (d, 1H) 7.6 (dd, 1H); 8.10 (d, 1H). |
| 123 | δ 1.0 (t, 3H), 1.3 (s, 9H), 1.8 (m, 2H), 2.8 (m, 2H), 3.9 (m, 1H), 4.1 (m, 1H), 4.3 (t, 2H), 5.0 (t, 1H), 6.2 (s, 1H), 7.5 (m, 2H), 7.9 (m, 1H), 8.1 (m, 2H). |
| 124 | δ 1.3 (s, 9H), 1.4 (d, 6H), 2.8 (m, 2H), 3.9 (m, 1H), 4.1 (m, 1H), 5.0 (t, 1H), 5.2 (m, 1H), 6.1. (s, 1H), 7.5 (m, 2H), 7.9 (m, 1H), 8.1 (m, 2H). |
| 131 | δ 0.8 (m, 6H), 1.5–1.7 (m, 4H), 2.5 (m, 1H), 5.5 (m, 1H), 5.8 (m, 1H), 6.1 (d, 2H), 7.0 (m, 1H), 7.4 (m, 3H), 7.5 (m, 2H). |
| 132 | δ 0.8 (m, 3H), 1.2–1.4 (m, 7H), 2.8 (m, 1H), 5.5 (m, 1H), 5.8 (m, 1H), 6.1 (m, 1H), 6.2 (m, 1H), 7.0 (m, 1H), 7.4 (m, 3H), 7.5 (m, 2H). |
| 134 | δ 0.8 (t, 3H), 1.2 (d, 3H), 1.5–1.7 (m, 2H), 2.7 (q, 1H), 5.5 (m, 1H), 5.7 (m, 1H), 6.1 (s, 1H), 6.2 (m, 1H), 7.0 (m, 1H), 7.4–7.6 (m, 5H). |
| 135 | δ 1.29 (s, 9H), 2.18–2.28 (m, 2H), 2.64–2.9 (m, 2H), 3.75–4 (m, 4H), 4.97 (t, 1H), 7.4–7.55 (m, 2H), 7.8–8 (m, 2H). |
| 136 | δ 1.3 (s, 9H), 3.8 (m, 2H), 3.7 (m, 1H), 4.0 (m, 4H), 5.1 (t, 1H), 6.2 (m, 1H), 7.2 (m, 1H), 7.4 (m, 2H), 7.7 (m, 2H), 8.2 (m, 1H). |
| 138 | δ 1.3 (s, 9H), 2.3 (s, 3H), 2.4 (s, 3H), 2.5–2.7 (m, 2H), 3.9 (m, 1H), 43 (m, 1H), 5.3 (t, 1H), 6.2 (s, 1H), 6.8 (s, 1H), 7.6 (s, 1H), 7.9 (s, 1H). |
| 139 | δ 1.3 (s, 9H), 2.4 (s, 3H), 2.6–2.8 (m, 2H), 4.0 (m, 1H), 4.3 (m, 1H), 5.3 (m, 1H), 6.2 (m, 1H), 7.0 (m, 1H), 7.6 (m, 1H), 8.2–8.3 (m, 2H). |
| 142 | δ 0.87 (t, 3H), 1.24 (d, 3H), 1.4–1.8 (m, 2H), 2.6–3.0 (m, 3H), 3.8–4.1 (m, 5H), 5.03 (t, 1H), 6.14 (m, 1H), 6.78 (m, 1H), 7.5 (m, 2H), 7.81 (m, 1H). |
| 143 | δ 0.83 (t, 6H), 1.4–1.8 (m, 4H), 2.5–2.97 (m, 3H), 3.8–4.1 (m, 5H), 5.03 (t, 1H), 6.1 (m, 1H), 6.79 (m, 1H), 7.5 (m, 2H), 7.81 (m, 1H). |
| 144 | δ 0.82 (t, 6H), 1.5–1.75 (m, 4H), 2.55 (m, 1H), 2.7–2.97 (m, 2H), 3.93 (m, 1H), 4.05 (m, 1H), 5.03 (t, 1H), 6.08 (d, 1h), 7.21 (d, 1H), 7.51 (d, 1H), 7.88–7.98 (m, 2H). |
| 145 | δ 0.87 (t, 3H), 1.22 (d, 3H), 1.4–1.74 (m, 2H), 2.7–3.0 (m, 3H), 3.93 (m, 1H), 4.05 (m, 1H), 5.03 (t, 1H), 6.11 (d, 1H), 7.2 (d, 1H), 7.5 (m, 1H), 7.9–7.98 (m, 2H). |
| 146 | δ 1.28 (s, 9H), 2.65–2.95 (m, 2H), 3.8–4.18 (m, 2H), 5.03 (t, 1H), 6.16 (d, 1H), 7.2 (m, 1H), 7.46 (d, 1H), 7.8–8.0 (m, 7H). |

[a]¹H NMR data are in ppm downfield from tetramethylsilane. Couplings are designated by (s)-singlet, (d)-doublet, (t)-triplet, (q)-quartet, (m)-multiplet, (dd)-doublet of doublets, (dt)-doublet of triplets, (br s)-broad singlet.

Test A

Seeds of barnyardgrass (*Echinochloa crus-galli*), crabgrass (*Digitaria* spp.), giant foxtail (*Setaria viridis*), morning glory (*Ipomoea* spp.), redroot pigweed (*Amaranthus retroflexus*) and velvetleaf (*Abutilon theophrasti*) were planted into a sandy loam soil and treated preemergence by soil drench with test chemicals formulated in a non-phytotoxic solvent mixture which included a surfactant. At the same time, these crop and weed species were also treated postemergence sprayed to runoff with test chemicals formulated in the same manner.

Plants ranged in height from two to eighteen cm and were in the one- to two-leaf stage for the postemergence treatment. Treated plants and untreated controls were maintained in a greenhouse for approximately eleven days, after which time all treated plants were compared to untreated controls and visually evaluated for injury. Plant response ratings, summarized in Table A, are based on a 0 to 10 scale where 0 is no effect and 10 is complete control. A dash (-) response means no test results.

TABLE A

Postemergence

| | Rate 2000 g/ha COMPOUND | | | | | | | | | | | | | | | | | Rate 1000 g/ha COMPOUND |
|---|---|---|---|---|---|---|---|---|---|---|---|---|---|---|---|---|---|---|
| | 1 | 4 | 5 | 6 | 7 | 9 | 10 | 11 | 12 | 13 | 14 | 15 | 16 | 26 | 27 | 28 | 88 | 3 |
| Barnyardgrass | 90 | 0 | 90 | 90 | 90 | 90 | 10 | 40 | 0 | 0 | 0 | 10 | 10 | 90 | 80 | 60 | 80 | 10 |
| Crabgrass | 10 | 0 | 10 | 20 | 20 | 10 | 10 | 10 | 0 | 0 | 0 | 10 | 20 | 20 | 60 | 40 | 40 | 0 |
| Giant foxtail | 30 | 0 | 20 | 90 | 100 | 100 | 10 | 50 | 0 | 0 | 0 | 10 | 30 | 100 | 90 | 90 | 90 | 10 |
| Morningglory | 90 | 0 | 10 | 10 | 10 | 10 | 20 | 10 | 0 | 0 | 0 | 20 | 20 | 50 | 20 | 20 | 30 | 10 |
| Pigweed | 90 | 30 | 80 | 70 | 80 | 80 | 100 | 90 | 0 | 70 | 20 | 0 | 0 | 80 | 80 | 80 | 100 | 10 |
| Velvetleaf | 30 | 0 | 40 | 0 | 30 | 40 | 50 | 0 | 0 | 0 | 0 | 10 | 20 | 10 | 20 | 50 | 0 | 0 |

| | Rate 500 g/ha COMPOUND | | | | | | | | | | | | | | | | | Rate 250 g/ha COMPOUND |
|---|---|---|---|---|---|---|---|---|---|---|---|---|---|---|---|---|---|---|
| | 1 | 4 | 5 | 6 | 7 | 9 | 10 | 11 | 12 | 13 | 14 | 15 | 16 | 26 | 27 | 28 | 88 | 3 |
| Barnyardgrass | 60 | 0 | 90 | 90 | 90 | 80 | 20 | 20 | 0 | 0 | 0 | 10 | 0 | 90 | 70 | 60 | 30 | 20 |
| Crabgrass | 10 | 0 | 10 | 10 | 10 | 20 | 10 | 0 | 0 | 0 | 0 | 10 | 10 | 30 | 20 | 20 | 20 | 0 |
| Giant foxtail | 30 | 0 | 20 | 60 | 80 | 30 | 10 | 0 | 0 | 0 | 0 | 10 | 0 | 50 | 50 | 80 | 40 | 0 |
| Morningglory | 90 | 0 | 10 | 0 | 10 | 10 | 10 | 10 | 0 | 0 | 0 | 30 | 20 | 20 | 0 | 10 | 10 | 10 |
| Pigweed | 20 | 20 | 10 | 40 | 10 | 20 | 20 | 70 | 0 | 20 | 0 | 0 | 0 | 40 | 20 | 20 | 80 | 60 |
| Velvetleaf | 10 | 0 | 0 | 0 | 30 | 0 | 0 | 0 | 0 | 0 | 0 | 0 | 0 | 10 | 0 | 0 | 0 | 0 |

Preemergence

| | Rate 2000 g/ha COMPOUND | | | | | | | | | | | | | | | |
|---|---|---|---|---|---|---|---|---|---|---|---|---|---|---|---|---|
| | 1 | 4 | 5 | 6 | 7 | 9 | 10 | 11 | 12 | 13 | 14 | 15 | 16 | 26 | 27 | 28 |
| Barnyardgrass | 100 | 80 | 100 | 100 | 100 | 100 | 100 | 100 | 0 | 10 | 0 | 10 | 70 | 100 | 100 | 100 |
| Crabgrass | 100 | 70 | 100 | 100 | 100 | 100 | 100 | 100 | 60 | 80 | 0 | 100 | 100 | 100 | 90 | 100 |
| Giant foxtail | 100 | 100 | 100 | 100 | 100 | 100 | 100 | 100 | 30 | 90 | 0 | 100 | 90 | 100 | 100 | 100 |
| Morningglory | 80 | 0 | 0 | 0 | 10 | 0 | 20 | 0 | 0 | 20 | 0 | 0 | 20 | 30 | 20 | 0 |
| Pigweed | 100 | 80 | 100 | 100 | 100 | 100 | 100 | 100 | 40 | 100 | 70 | 100 | 100 | 100 | 100 | 100 |
| Velvetleaf | 70 | 0 | 30 | 20 | 0 | 10 | 10 | 20 | 0 | 0 | 0 | 100 | 100 | 40 | 10 | 10 |

| | Rate 2000 g/ha COMPOUND | Rate 1000 g/ha COMPOUND | Rate 500 g/ha COMPOUND | | | | | | | | | | | |
|---|---|---|---|---|---|---|---|---|---|---|---|---|---|---|
| | 88 | 3 | 1 | 4 | 5 | 6 | 7 | 9 | 10 | 11 | 12 | 13 | 14 | 15 |
| Barnyardgrass | 100 | 100 | 90 | 10 | 100 | 100 | 100 | 100 | 100 | 100 | 0 | 0 | 0 | 10 |
| Crabgrass | 100 | 100 | 90 | 50 | 100 | 100 | 100 | 90 | 90 | 100 | 0 | 0 | 0 | 80 |
| Giant foxtail | 100 | 100 | 90 | 10 | 100 | 100 | 100 | 100 | 90 | 100 | 0 | 20 | 0 | 50 |
| Morningglory | 30 | 0 | 10 | 0 | 0 | 0 | 0 | 0 | 0 | 0 | 0 | 0 | 0 | 0 |
| Pigweed | 100 | 100 | 100 | 70 | 100 | 100 | 100 | 100 | 100 | 100 | 0 | 80 | 40 | 30 |
| Velvetleaf | 30 | 0 | 10 | 0 | 20 | 20 | 20 | 20 | 20 | 0 | 0 | 0 | 0 | 30 |

| | Rate 500 g/ha COMPOUND | | | | | Rate 250 g/ha COMPOUND |
|---|---|---|---|---|---|---|
| | 16 | 26 | 27 | 28 | 88 | 3 |
| Barnyardgrass | 10 | 100 | 100 | 100 | 40 | 100 |
| Crabgrass | 100 | 100 | 100 | 90 | 80 | 100 |
| Giant foxtail | 80 | 100 | 100 | 100 | 70 | 100 |
| Morningglory | 0 | 0 | 0 | 0 | 0 | 0 |
| Pigweed | 80 | 100 | 100 | 100 | 100 | 100 |
| Velvetleaf | 10 | 50 | 20 | 10 | 0 | 0 |

Test B

Seeds selected from barnyardgrass (*Echinochloa crus-galli*), Surinam grass (*Brachiaria decumbens*), cocklebur (*Xanthium strumarium*), corn (*Zea mays*), crabgrass (*Digitaria sanguinalis*), giant foxtail (*Setaria faberii*), lambsquarters (*Chenopodium album*), morning glory (*Ipomoea hederacea*), pigweed (*Amaranthus retroflexus*), rice (*Oryza saliva*) and velvetleaf (*Abutilon theophrasti*) were planted and treated preemergence with test chemicals formulated in a non-phytotoxic solvent mixture which included a surfactant.

At the same time, plants selected from these crop and weed species and also blackgrass (*Alopecurus myosuroides*), wheat (*Triticum aestivum*) and wild oat (*Avena fatua*) were treated with postemergence applications of test chemicals formulated in the same manner. Plants ranged in height from 2 to 18 cm (1- to 4-leaf stage) for postemergence treatments. Plant species in the flooded paddy test consisted of rice (*Oryza saliva*), smallflower flatsedge (*Cyperus difformis*), duck salad (*Heteranthera limosa*) and barnyardgrass (*Echinochloa crus-galli*) grown to the 2-leaf stage for testing. Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

Postemergence

Rate 500 g/ha COMPOUND

| | 1 | 2 | 3 | 4 | 5 | 6 | 7 | 8 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|
| Barnyardgrass | 50 | 0 | 70 | 0 | 90 | 60 | 100 | 0 | 0 | 0 | 0 | 0 | 0 | 0 | 0 | 0 | 0 | 0 | 100 | 100 | 80 | 90 | 100 |
| Blackgrass | 0 | 0 | 0 | 0 | 0 | 0 | 0 | 0 | 0 | 0 | 0 | 0 | 0 | 30 | 0 | 0 | 0 | 0 | 0 | 0 | 0 | 20 | 0 |
| Surinam grass | 0 | 0 | 20 | 0 | 0 | 0 | 20 | 0 | 0 | 0 | 0 | 0 | 0 | 0 | 0 | 0 | 0 | 10 | 0 | 0 | 20 | 20 | 50 |
| Cocklebur | 80 | 60 | 30 | 0 | 20 | 0 | 0 | 10 | 0 | 0 | 0 | 0 | 0 | 0 | 0 | 0 | 20 | 20 | 90 | 80 | 20 | 80 | 40 |
| Corn | 60 | 0 | 0 | 0 | 20 | 0 | 0 | 0 | 0 | 0 | 0 | 0 | 0 | 0 | 0 | 0 | 0 | 0 | 20 | 0 | 0 | 50 | 50 |
| Crabgrass | 40 | 0 | 40 | 0 | 50 | 30 | 70 | 0 | 0 | 0 | 0 | 60 | 70 | 50 | 60 | 0 | 0 | 20 | 80 | 70 | 40 | 40 | 90 |
| Foxtail, Giant | 60 | 0 | 30 | 0 | 70 | 0 | 70 | 0 | 0 | 0 | 0 | 0 | 30 | 30 | 30 | 0 | 0 | 0 | 90 | 60 | 0 | 80 | 80 |
| Lambsquarters | 100 | 80 | 100 | 80 | 90 | 60 | 80 | 50 | 0 | 0 | 0 | 0 | 0 | 0 | 0 | 80 | 70 | 70 | 90 | 100 | 90 | 100 | 100 |
| Morningglory | 100 | 0 | 30 | 0 | 10 | 0 | 70 | 0 | 0 | 0 | 0 | 70 | 80 | 0 | 0 | 0 | 10 | 30 | 60 | 80 | 30 | 80 | 40 |
| Pigweed | 100 | 100 | 90 | 50 | 80 | 90 | 80 | 10 | 0 | 0 | 0 | — | — | — | — | 0 | 0 | 0 | 90 | 90 | 90 | 100 | 100 |
| Velvetleaf | 60 | 0 | 0 | 40 | 10 | 20 | 50 | 0 | 0 | 0 | 0 | 0 | 0 | 0 | 0 | 0 | 20 | 20 | 20 | 60 | 30 | 30 | 0 |
| Wheat | 30 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild Oat | 0 | 0 | 0 | 0 | 0 | 0 | 0 | 0 | 0 | 0 | 0 | 20 | 0 | 50 | 50 | 0 | 0 | 0 | 0 | 0 | 0 | 0 | 0 |

Rate 500 g/ha COMPOUND

| | 25 | 26 | 27 | 28 | 29 | 30 | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|---|---|---|---|---|---|
| Barnyardgrass | 100 | 80 | 60 | 60 | 0 | 100 | 100 | 90 | 0 | 0 | 40 | 100 | 100 | 100 | 100 | 100 | 70 | 100 | 70 | 100 | 100 |
| Blackgrass | 0 | 0 | 0 | 0 | 0 | 20 | 0 | 0 | 0 | 0 | 0 | 0 | 0 | 0 | 0 | 0 | 0 | 50 | 0 | 0 | 0 |
| Surinam grass | 40 | 20 | 20 | 0 | 0 | 20 | 0 | 10 | 0 | 0 | 50 | 0 | 0 | 0 | 0 | 0 | 0 | 0 | 0 | 0 | 0 |
| Cocklebur | 70 | 60 | 30 | 0 | 0 | 70 | 70 | 60 | 10 | 0 | 40 | 60 | 30 | 80 | 0 | 50 | 0 | 60 | 0 | 70 | 40 |
| Corn | 60 | 70 | 10 | 0 | 0 | 0 | 0 | 0 | 0 | 0 | 0 | 70 | 20 | 0 | 10 | 50 | 0 | 40 | 0 | 20 | 0 |
| Crabgrass | 90 | 20 | 40 | 30 | 50 | 100 | 40 | 100 | 0 | 0 | 0 | 100 | 100 | 100 | 70 | 90 | 40 | 80 | 50 | 40 | 0 |
| Foxtail, Giant | 80 | 50 | 30 | 30 | 0 | 80 | 20 | 60 | 20 | 0 | 0 | 90 | 80 | 80 | 0 | 90 | 0 | 70 | 0 | 60 | 0 |
| Lambsquarters | 100 | 80 | 90 | 70 | 20 | 90 | 80 | 90 | 80 | 100 | 80 | 100 | 90 | 90 | 90 | 90 | 60 | 100 | 80 | 60 | 0 |
| Morningglory | 100 | 10 | 50 | 0 | 0 | 90 | 30 | 20 | 10 | 0 | 20 | 40 | 40 | 20 | 0 | 20 | 20 | 100 | 0 | 0 | 0 |
| Pigweed | 100 | 60 | 60 | 30 | 30 | 100 | 60 | 60 | 80 | 90 | 90 | 100 | 90 | 80 | 90 | 80 | 80 | 100 | 80 | 0 | 0 |
| Velvetleaf | 20 | 20 | 0 | 0 | 20 | 0 | 0 | 0 | 0 | 0 | 0 | 60 | 0 | 70 | 0 | 0 | 0 | 80 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild Oat | 0 | 0 | 0 | 0 | 0 | 0 | 0 | 0 | 0 | 0 | 0 | 20 | 0 | 0 | 0 | 0 | 0 | 40 | 0 | 0 | 0 |

Rate 500 g/ha COMPOUND

| | 46 | 47 | 48 | 49 | 50 | 51 | 52 | 53 | 54 | 55 | 56 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|---|---|---|---|---|---|---|---|---|---|
| Barnyardgrass | 0 | 0 | 0 | 80 | 90 | 0 | 0 | 0 | 0 | 0 | 0 | 0 | 0 | 0 | 0 | 0 | 60 | 50 | 100 | 100 | 100 | 100 | 90 | 0 | 0 | 70 |
| Blackgrass | 0 | 0 | 0 | 60 | 0 | 0 | 0 | 0 | 0 | 0 | 0 | 0 | 0 | 0 | 0 | 0 | 0 | 0 | 0 | 0 | 0 | 0 | 70 | 0 | 0 | 0 |
| Surinam grass | 0 | 0 | 0 | 90 | 0 | 0 | 0 | 0 | 0 | 0 | 0 | 0 | 0 | 0 | 0 | 0 | 40 | 40 | 30 | 30 | 30 | 0 | 0 | 30 | 0 | 0 |
| Cocklebur | 0 | 0 | 0 | 30 | 50 | 0 | 0 | 0 | 20 | 10 | 0 | 0 | 0 | 0 | 0 | 0 | 50 | 70 | 30 | 20 | 60 | 80 | 20 | 0 | 20 | 90 |
| Corn | 0 | 0 | 0 | 0 | 0 | 0 | 20 | 10 | 0 | 0 | 0 | 0 | 0 | 0 | 0 | 0 | 0 | 20 | 0 | 0 | 0 | 0 | 0 | 0 | 0 | 0 |
| Crabgrass | 0 | 0 | 0 | 40 | 50 | 20 | 0 | 0 | 0 | 0 | 0 | 0 | 0 | 0 | 0 | 0 | 60 | 50 | 100 | 100 | 100 | 100 | 30 | 0 | 30 | 30 |
| Foxtail, Giant | 0 | 0 | 0 | 0 | 50 | 0 | 0 | 0 | 0 | 0 | 0 | 0 | 0 | 0 | 0 | 0 | 50 | 30 | 0 | 60 | 40 | 40 | 0 | 0 | 20 | 50 |
| Lambsquarters | 70 | 90 | 80 | 50 | 80 | 90 | 0 | 80 | 30 | 0 | 90 | 0 | 0 | 0 | 0 | 60 | 80 | 80 | 70 | 90 | 100 | 100 | 80 | 0 | 50 | 0 |
| Morningglory | 0 | 30 | 0 | 0 | 0 | 0 | 0 | 10 | 20 | 30 | 10 | 0 | 0 | 0 | 0 | 40 | 60 | 0 | 0 | 0 | 0 | 0 | 0 | 30 | 20 | 50 |
| Pigweed | 0 | 50 | 0 | 30 | 0 | 80 | 0 | 90 | 0 | 0 | 90 | 0 | 0 | 0 | 0 | 40 | 70 | 70 | 0 | 0 | 0 | 0 | 0 | 0 | 60 | 60 |
| Velvetleaf | 0 | 0 | 0 | 40 | 0 | 0 | 0 | 0 | 0 | 0 | 0 | 0 | 0 | 0 | 0 | 0 | 50 | 30 | 0 | 20 | 20 | 20 | 0 | 0 | 20 | 60 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild Oat | 0 | 0 | 0 | 30 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

Rate 500 g/ha COMPOUND

| | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|---|---|---|---|
| Barnyardgrass | 90 | 0 | 0 | 90 | 0 | 0 | 0 | 10 | 0 | 0 | 0 | 80 | 50 | 0 | 30 | 90 | 80 | 80 | 90 | 70 | 0 | 0 | 30 | 90 |
| Blackgrass | 0 | 0 | 0 | 0 | 0 | 0 | 0 | 0 | 0 | 0 | 0 | 0 | 20 | 0 | 0 | 0 | 0 | 0 | 0 | 0 | 0 | 0 | 0 | 0 |
| Surinam grass | 0 | 0 | 0 | 10 | 0 | 0 | 0 | 0 | 10 | 0 | 0 | 10 | 0 | 0 | 0 | 0 | 0 | 30 | 10 | 10 | 0 | 0 | 0 | 0 |
| Cocklebur | 90 | 0 | 0 | 20 | 20 | 20 | 30 | 80 | 100 | 20 | 10 | 20 | 100 | 0 | 0 | 30 | 30 | 60 | 80 | 80 | 50 | 0 | 20 | 20 |
| Corn | 40 | 0 | 0 | 0 | 0 | 0 | 0 | 0 | 10 | 0 | 0 | 0 | 30 | 0 | 0 | 10 | 0 | 10 | 10 | 10 | 0 | 0 | 0 | 0 |
| Crabgrass | 50 | 0 | 0 | 40 | 0 | 0 | 0 | 40 | 30 | 10 | 0 | 10 | 50 | 0 | 0 | 0 | 60 | 50 | 90 | 50 | 0 | 0 | 20 | 70 |
| Foxtail, Giant | 50 | 0 | 0 | 30 | 0 | 0 | 0 | 0 | 0 | 0 | 0 | 10 | 20 | 0 | 0 | 60 | 70 | 40 | 40 | 30 | 0 | 0 | 0 | 40 |
| Lambsquarters | 70 | 0 | 80 | 40 | 20 | 10 | 10 | 90 | 90 | 70 | 60 | 60 | 90 | 50 | 50 | 100 | 100 | 100 | 100 | 90 | 80 | 20 | 90 | 90 |
| Morningglory | 20 | 0 | 60 | 20 | 0 | 0 | 40 | 90 | 100 | 10 | 10 | 30 | 80 | 0 | 0 | 70 | 40 | 70 | 80 | 50 | 10 | 0 | 20 | 50 |
| Pigweed | 90 | 90 | 90 | 80 | 80 | 80 | 70 | 80 | 90 | 10 | 10 | 70 | 90 | 0 | 40 | 100 | 90 | 90 | 90 | 60 | 20 | 10 | 60 | 90 |
| Velvetleaf | 70 | 0 | 50 | 0 | 0 | 0 | 0 | 70 | 90 | 0 | 0 | 10 | 50 | 0 | 0 | 40 | 0 | 40 | 30 | 20 | 10 | 0 | 0 | 10 |
| Wheat | 0 | 0 | 0 | 0 | 0 | 0 | 0 | 0 | 0 | 0 | 0 | 0 | 0 | 0 | 0 | 30 | 0 | 0 | 0 | 0 | 0 | 0 | 0 | 0 |
| Wild Oat | 0 | 0 | 0 | 0 | 0 | 0 | 0 | 0 | 0 | 0 | 0 | 10 | 20 | 0 | 0 | 0 | 0 | 20 | 0 | 0 | 0 | 0 | 0 | 0 |

Rate 500 g/ha COMPOUND

| | 98 | 99 | 100 | 101 | 102 | 103 | 104 | 105 | 106 | 107 | 108 | 109 | 110 | 111 | 112 | 113 | 114 | 115 | 116 |
|---|---|---|---|---|---|---|---|---|---|---|---|---|---|---|---|---|---|---|---|
| Barnyardgrass | 0 | 0 | 0 | 0 | 0 | 0 | 0 | 0 | 0 | 0 | 0 | 0 | 0 | 0 | 20 | 0 | 20 | 0 | 20 |
| Blackgrass | 0 | 0 | 0 | 0 | 0 | 0 | 0 | 0 | 0 | 0 | 0 | 0 | 0 | 20 | 0 | 0 | 0 | 0 | 60 |
| Surinam grass | 0 | 0 | 0 | 0 | 0 | 0 | 0 | 0 | 0 | 0 | 20 | 0 | 0 | 40 | 100 | 0 | 30 | 100 | 20 |
| Cocklebur | — | — | — | — | — | — | — | — | 90 | 100 | 40 | 90 | 30 | 0 | 0 | 70 | 60 | 70 | 50 |
| Corn | 0 | 0 | 0 | 0 | 0 | 0 | 0 | 0 | 0 | 0 | 0 | 0 | 0 | 0 | 0 | 0 | 0 | 20 | 20 |
| Crabgrass | 20 | 0 | 0 | 0 | 0 | 0 | 0 | 0 | 0 | 0 | 0 | 0 | 0 | 30 | 30 | 40 | 30 | 30 | 40 |
| Foxtail, Giant | 20 | 0 | 0 | 0 | 0 | 0 | 0 | 0 | 0 | 0 | 0 | 0 | 0 | 0 | 0 | 20 | 0 | 0 | 0 |
| Lambsquarters | 80 | 70 | 80 | 0 | 0 | 50 | 0 | 0 | 100 | 100 | 80 | 90 | 90 | 20 | 30 | 100 | 100 | 0 | 90 |
| Morningglory | 0 | 0 | 0 | 0 | 0 | 0 | 0 | 0 | 100 | 70 | 70 | 100 | 60 | 0 | 50 | 30 | 60 | 0 | 30 |
| Pigweed | 100 | 0 | 0 | 0 | 0 | 0 | 0 | 0 | 90 | 90 | 40 | 90 | 70 | 0 | 80 | 100 | 100 | 60 | 70 |
| Velvetleaf | 20 | 0 | 0 | 0 | 0 | 0 | 0 | 0 | 80 | 70 | 60 | 80 | 70 | 0 | 0 | 0 | 0 | 0 | 30 |
| Wheat | 0 | 0 | 0 | 0 | 0 | 0 | 0 | 0 | 0 | 0 | 0 | 0 | 0 | 20 | 40 | 30 | 30 | 50 | 20 |
| Wild Oat | 0 | 0 | 0 | 0 | 0 | 0 | 0 | 0 | 0 | 0 | 0 | 0 | 0 | 60 | 60 | 40 | 50 | 60 | 50 |

Rate 500 g/ha COMPOUND

| | 117 | 118 | 119 | 120 | 121 | 122 | 123 | 124 | 126 | 127 | 128 | 129 | 130 | 131 | 132 | 133 | 134 | 136 |
|---|---|---|---|---|---|---|---|---|---|---|---|---|---|---|---|---|---|---|
| Barnyardgrass | 90 | 90 | 100 | 60 | 90 | 0 | 0 | 0 | 80 | 0 | 80 | 60 | 90 | 100 | 30 | 100 | 100 | 0 |
| Blackgrass | 0 | 0 | 0 | 0 | 0 | — | 0 | — | 0 | 0 | 0 | 0 | 20 | 0 | 0 | 0 | 0 | 0 |
| Surinam grass | 40 | 40 | 50 | 40 | 40 | 0 | 0 | 0 | 0 | 0 | 100 | 0 | 40 | 30 | 0 | 40 | 60 | 0 |
| Cocklebur | 100 | 100 | 100 | 100 | 100 | 90 | 80 | 90 | 70 | 60 | 50 | 30 | 50 | 70 | 0 | 30 | 30 | 0 |
| Corn | 0 | 20 | 0 | 20 | 30 | 0 | 0 | 0 | 0 | 0 | 0 | 0 | 0 | 20 | 0 | 0 | 20 | 0 |
| Crabgrass | 40 | 40 | 100 | 70 | 60 | 0 | 0 | 0 | 0 | 0 | 60 | 0 | 30 | 90 | 90 | 80 | 90 | 0 |
| Foxtail, Giant | 20 | 0 | 0 | 50 | 0 | 0 | 0 | 0 | 60 | 0 | 60 | 0 | 40 | 50 | 0 | 50 | 60 | 0 |
| Lambsquarters | 100 | 100 | 100 | 90 | 90 | 100 | 20 | 40 | 100 | 50 | 0 | 100 | 100 | 100 | 80 | 100 | 100 | 0 |
| Morningglory | 100 | 60 | 80 | 90 | 70 | 100 | 0 | 30 | 50 | 0 | 0 | 0 | 80 | 80 | 0 | 30 | 40 | 0 |
| Pigweed | 100 | 70 | 80 | 80 | 90 | 70 | 0 | 30 | 100 | 0 | 100 | 60 | 100 | 90 | 30 | 100 | 80 | 0 |
| Velvetleaf | 70 | 70 | 60 | 50 | 30 | 0 | 0 | 20 | 0 | 0 | 0 | 0 | 30 | 30 | 0 | 30 | 10 | 0 |
| Wheat | 30 | 20 | 40 | 20 | 50 | 0 | 0 | 0 | 0 | 0 | 0 | 0 | 0 | 0 | 0 | 10 | 0 | 0 |
| Wild Oat | 70 | 60 | 50 | 60 | 50 | 0 | 0 | 0 | 0 | 0 | 0 | 0 | 0 | 30 | 0 | 0 | 0 | 0 |

| | Rate 500 g/ha COMPOUND | | | | | | | | | | Rate 250 g/ha COMPOUND | | | | Rate 125 g/ha COMPOUND | | | | | | | |
|---|---|---|---|---|---|---|---|---|---|---|---|---|---|---|---|---|---|---|---|---|---|---|
| | 137 | 138 | 139 | 140 | 141 | 142 | 143 | 144 | 145 | 146 | 9 | 10 | 109 | 125 | 1 | 2 | 3 | 4 | 5 | 6 | 7 | 8 |
| Barnyard-grass | 0 | 0 | 0 | 80 | 80 | 60 | 70 | 0 | 90 | 90 | 60 | 0 | 0 | 80 | 0 | 0 | 0 | 0 | 50 | 0 | 20 | 0 |
| Blackgrass | 0 | 0 | 0 | 0 | 40 | 0 | 0 | 0 | 0 | 0 | 0 | 0 | 0 | 0 | 0 | 0 | 0 | 0 | 0 | 0 | 0 | 0 |
| Surinam grass | 0 | 0 | 0 | 0 | 0 | 0 | 0 | 0 | 0 | 0 | 0 | 0 | 0 | 20 | 0 | 0 | 0 | 0 | 0 | 0 | 0 | 0 |
| Cocklebur | 0 | 0 | 0 | 90 | 100 | 90 | 100 | 30 | 0 | 0 | 20 | 0 | 70 | 70 | 60 | 20 | 0 | 0 | 20 | 0 | 0 | 0 |
| Corn | 0 | 0 | 0 | 0 | 0 | 30 | 0 | 0 | 0 | 0 | 0 | 0 | 0 | 0 | 0 | 0 | 0 | 0 | 10 | 0 | 0 | 0 |
| Crabgrass | 0 | 0 | 0 | 80 | 40 | 60 | 80 | 40 | 0 | 60 | 0 | 0 | 0 | 0 | 0 | 0 | 0 | 0 | 50 | 0 | 0 | 0 |
| Foxtail, Giant | 90 | 0 | 0 | 70 | 50 | 90 | 80 | 40 | 40 | 70 | 0 | 0 | 20 | 0 | 30 | 0 | 0 | 0 | 20 | 0 | 0 | 0 |
| Lambs-quarters | 0 | 0 | 0 | 100 | 100 | 100 | 100 | 100 | 100 | 100 | 80 | 100 | 90 | 100 | 90 | 80 | 80 | 50 | 80 | 0 | 30 | 30 |
| Morning-glory | 0 | 30 | 0 | 100 | 70 | 100 | 100 | 30 | 0 | 0 | 10 | 0 | 100 | 100 | 50 | — | 0 | 0 | 0 | 0 | 0 | 0 |
| Pigweed | 0 | 30 | 0 | 90 | 100 | 80 | 90 | 100 | 80 | 70 | 80 | 0 | 60 | 70 | 90 | 0 | 70 | 20 | 10 | 0 | 20 | 0 |
| Velvetleaf | 0 | 0 | 0 | 60 | 70 | 70 | 70 | 0 | 30 | 0 | 0 | 0 | 0 | 80 | 0 | 50 | 0 | 20 | 0 | 0 | 0 | 0 |

TABLE B-continued

| | | | | | | | | | | | | | | | | | | | | | | | |
|---|---|---|---|---|---|---|---|---|---|---|---|---|---|---|---|---|---|---|---|---|---|---|---|
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild Oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Rate 125 g/ha
COMPOUND

| | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|---|---|---|---|---|---|---|
| Barnyardgrass | 0 | 0 | 0 | 0 | 0 | 0 | 0 | 0 | 0 | 0 | 0 | 60 | 90 | 0 | 20 | 70 | 100 | 0 | 20 | 0 | 0 | 100 | 100 | 80 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Surinam grass | 0 | 0 | 0 | 0 | 0 | 0 | 0 | 0 | 0 | 0 | 0 | 0 | 0 | 200 | 20 | 0 | 0 | 20 | 0 | 0 | 0 | 0 | 0 | 0 | 0 | 0 |
| Cocklebur | 0 | 0 | 0 | 0 | 0 | 0 | 0 | 0 | 0 | 0 | 20 | 80 | 70 | 20 | 40 | 20 | 60 | 50 | 0 | 0 | 0 | 70 | 60 | 60 | 0 | 0 |
| Corn | 0 | 0 | 0 | 0 | 0 | 0 | 0 | 0 | 0 | 0 | 0 | 0 | 0 | 0 | 20 | 0 | 0 | 0 | 0 | 0 | 0 | 0 | 0 | 0 | 0 | 0 |
| Crabgrass | 0 | 0 | 0 | 60 | 50 | 20 | 0 | 0 | 0 | 0 | 20 | 30 | 40 | 20 | 60 | 60 | 0 | 20 | 20 | 0 | 50 | 0 | 80 | 0 | 0 |
| Foxtail, Giant | 0 | 0 | 0 | 0 | 20 | 0 | 0 | 0 | 0 | 0 | 50 | 20 | 0 | 20 | 20 | 20 | 20 | 0 | 0 | 0 | 10 | 0 | 0 | 0 | 0 |
| Lambsquarters | 0 | 0 | 0 | 0 | 0 | 0 | 0 | 80 | 60 | 10 | 90 | 100 | 90 | 80 | 90 | 100 | 80 | 50 | 60 | 0 | 90 | 70 | 80 | 70 | 90 |
| Morningglory | 0 | 0 | 0 | 0 | 30 | 0 | 0 | 0 | 10 | 20 | 60 | 70 | 30 | 20 | 0 | 90 | 0 | 0 | 0 | 0 | 40 | 10 | 20 | 0 | 0 |
| Pigweed | 0 | 0 | 0 | — | — | — | — | 0 | 0 | 0 | 90 | 70 | 80 | 70 | 80 | 70 | 0 | 40 | 30 | 30 | 100 | 20 | 40 | 70 | 90 |
| Velvetleaf | 0 | 0 | 0 | 0 | 0 | 0 | 0 | 0 | 0 | 10 | 10 | 20 | 20 | 20 | 0 | 0 | 20 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild Oat | 0 | 0 | 0 | 20 | 0 | 0 | 0 | 0 | 0 | 0 | 0 | 0 | 0 | 0 | 0 | 0 | 0 | 0 | 0 | 0 | 0 | 0 | 0 | 0 | 0 |

Rate 125 g/ha
COMPOUND

| | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 58 | 59 | 60 | 61 | 62 |
|---|---|---|---|---|---|---|---|---|---|---|---|---|---|---|---|---|---|---|---|---|---|---|---|---|---|---|---|
| Barnyardgrass | 0 | 90 | 80 | 100 | 0 | 90 | 0 | 60 | 0 | 40 | 30 | 0 | 0 | 0 | 0 | 0 | 0 | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Surinam grass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cocklebur | 40 | 20 | 10 | 40 | 0 | 30 | 0 | 40 | 0 | 20 | 20 | 0 | 0 | 0 | 0 | 0 | 0 | 0 | 0 | 0 | 10 | 0 | 0 | 0 | 0 | 0 | 0 |
| Corn | 0 | 0 | 0 | 0 | 0 | 0 | — | 0 | 0 | 0 | 0 | 0 | 0 | 0 | 0 | 0 | 0 | 20 | 0 | 0 | 0 | 0 | 0 | 0 | 0 | 0 | 0 |
| Crabgrass | 0 | 80 | 0 | 60 | 0 | 60 | 0 | 50 | 0 | 0 | 0 | 0 | 0 | 0 | 0 | 30 | 0 | 0 | 0 | 0 | 0 | 0 | 0 | 0 | 0 | 0 | 0 |
| Foxtail, Giant | 0 | 60 | 60 | 30 | 0 | 70 | 0 | 50 | 0 | 0 | 0 | 0 | 0 | 0 | 0 | 0 | 0 | 0 | 0 | 0 | 0 | 0 | 0 | 0 | 0 | 0 | 0 |
| Lambsquarters | 0 | 90 | 0 | 80 | 70 | 70 | 0 | 70 | 50 | 20 | 0 | 0 | 70 | 0 | 30 | 70 | 80 | 0 | 40 | 0 | 0 | 80 | 0 | 0 | 0 | 0 | 0 |
| Morningglory | 0 | 30 | 20 | 10 | 0 | 10 | 0 | 60 | 0 | 0 | 0 | 0 | 0 | 0 | 0 | 0 | 0 | 0 | 0 | 0 | 0 | 0 | 0 | 0 | 0 | 0 | 0 |
| Pigweed | 90 | 90 | 20 | 60 | 60 | 40 | 0 | 80 | 50 | 0 | 0 | 50 | 0 | 30 | 0 | 0 | 0 | 80 | 0 | 0 | 90 | 0 | 0 | 0 | 0 | 0 | 0 |
| Velvetleaf | 0 | 0 | 0 | 0 | 0 | 0 | 0 | 50 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild Oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Rate 125 g/ha
COMPOUND

| | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|
| Barnyardgrass | 0 | 0 | 0 | 100 | 90 | 90 | 0 | 0 | 0 | 30 | 30 | 0 | 0 | 0 | 0 | 0 | 0 | 0 | 0 | 0 | 0 | 0 | 0 | 0 | 0 | 0 |
| Blackgrass | 0 | 0 | 0 | 0 | 0 | 0 | 70 | 0 | 0 | 0 | 0 | 0 | 0 | 0 | 0 | 0 | 0 | 0 | 0 | 0 | 0 | 0 | 0 | 0 | 0 | 0 |
| Surinam grass | 0 | 0 | 20 | 0 | 30 | 20 | 0 | 0 | 0 | 0 | 0 | 0 | 0 | 0 | 0 | 0 | 0 | 0 | 0 | 0 | 0 | 0 | 0 | 0 | 0 | 0 |
| Cocklebur | 0 | 70 | 20 | 0 | 0 | 50 | 0 | 0 | 0 | 80 | 20 | 0 | 0 | 0 | 0 | 30 | 70 | 90 | 0 | 10 | 10 | 40 | 0 | 0 | 0 | 20 |
| Corn | 0 | 0 | 0 | 0 | 0 | 0 | 0 | 0 | 0 | 0 | 30 | 0 | 0 | 0 | 0 | 0 | 0 | 0 | 10 | 0 | 0 | 0 | 0 | 0 | 0 | 0 |
| Crabgrass | 0 | 0 | 0 | 30 | 50 | 90 | 0 | 0 | 0 | 0 | 0 | 0 | 0 | 0 | 0 | 0 | 0 | 0 | 0 | 0 | 0 | 0 | 20 | 0 | 0 | 0 |
| Foxtail, Giant | 0 | 0 | 0 | 0 | 20 | 20 | 0 | 0 | 0 | 0 | 20 | 0 | 0 | 0 | 0 | 0 | 0 | 0 | 0 | 0 | 0 | 0 | 0 | 0 | 0 | 20 |
| Lambsquarters | 60 | 70 | 60 | 90 | 90 | 100 | 80 | 0 | 0 | 0 | 0 | 0 | 70 | 0 | 0 | 0 | 0 | 10 | 20 | 20 | 10 | 50 | 30 | 0 | 0 | 100 |
| Morningglory | 0 | 0 | 0 | 0 | 0 | 0 | 0 | 30 | 20 | 20 | 20 | 0 | 20 | 0 | 0 | 0 | 30 | 40 | 80 | 0 | 10 | 0 | 0 | 0 | 0 | 20 |
| Pigweed | 50 | 40 | 0 | 0 | 0 | 0 | 0 | 0 | 0 | 30 | 20 | 20 | 80 | 50 | 30 | 70 | 70 | 70 | 70 | 0 | 0 | 60 | 60 | 0 | 0 | 90 |
| Velvetleaf | 0 | 0 | 0 | 20 | 0 | 0 | 0 | 0 | 0 | 0 | 30 | 50 | 0 | 0 | 0 | 0 | 0 | 0 | 40 | 80 | 0 | 0 | 20 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild Oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Rate 125 g/ha
COMPOUND

| | 89 | 90 | 91 | 92 | 93 | 94 | 95 | 96 | 97 | 98 | 99 | 100 | 101 | 102 | 103 | 104 | 105 | 106 | 107 | 108 | 109 | 110 |
|---|---|---|---|---|---|---|---|---|---|---|---|---|---|---|---|---|---|---|---|---|---|---|
| Barnyardgrass | 0 | 20 | 50 | 0 | 0 | 0 | 0 | 0 | 0 | 0 | 0 | 0 | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Surinam grass | 0 | 0 | 10 | 0 | 0 | 0 | 0 | 0 | 0 | 0 | 0 | 0 | 0 | 0 | 0 | 0 | 0 | 0 | 0 | 0 | 0 | 0 |
| Cocklebur | 0 | 20 | 20 | 20 | 30 | 0 | 0 | 10 | — | — | — | — | — | — | — | — | — | 90 | 70 | 20 | 40 | 30 |
| Corn | 30 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 20 | 40 | 10 | 0 | 0 | 20 | 0 | 0 | 0 | 0 | 0 | 0 | 0 | 0 | 0 | 0 | 0 | 0 | 0 | 0 | 0 |
| Foxtail, Giant | 90 | 0 | 0 | 0 | 0 | 0 | 0 | 0 | 0 | 0 | 0 | 0 | 0 | 0 | 0 | 0 | 0 | 0 | 0 | 0 | 0 | 0 |
| Lambsquarters | 0 | 90 | 90 | 80 | 80 | 0 | 80 | 80 | 80 | 30 | 0 | 20 | 0 | 0 | 0 | 0 | 0 | 100 | 90 | 30 | 90 | 100 |
| Morningglory | 60 | 40 | 0 | 50 | 10 | 0 | 10 | 0 | 0 | 0 | 0 | 0 | 0 | 0 | 0 | 0 | 0 | 90 | 50 | 0 | 100 | 30 |

TABLE B-continued

| | | | | | | | | | | | | | | | | | | | | | |
|---|---|---|---|---|---|---|---|---|---|---|---|---|---|---|---|---|---|---|---|---|---|
| Pigweed | 0 | 60 | 80 | 20 | 0 | 0 | 20 | 90 | 0 | 80 | 0 | 0 | 0 | 0 | 0 | 0 | 0 | 60 | 20 | 0 | 70 | 90 |
| Velvetleaf | 0 | 10 | 0 | 0 | 10 | 0 | 0 | 0 | 0 | 0 | 0 | 0 | 0 | 0 | 0 | 0 | 0 | 50 | 0 | 0 | 50 | 50 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild Oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Rate 125 g/ha
COMPOUND

| | 111 | 112 | 113 | 114 | 115 | 116 | 117 | 118 | 119 | 120 | 121 | 122 | 123 | 124 | 126 | 127 | 128 | 129 |
|---|---|---|---|---|---|---|---|---|---|---|---|---|---|---|---|---|---|---|
| Barnyardgrass | 0 | 0 | 0 | 0 | 0 | 0 | 40 | 0 | 30 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 | — | — | 0 | 0 | 0 | 0 | 0 |
| Surinam grass | 0 | 0 | 0 | 30 | 20 | 0 | 30 | 30 | 20 | 20 | 30 | 0 | 0 | 0 | 0 | 0 | 70 | 0 |
| Cocklebur | 0 | 0 | 0 | 50 | 20 | 30 | 90 | 60 | 90 | 90 | 70 | 30 | 30 | 20 | 0 | 0 | 0 | 0 |
| Corn | 0 | 0 | 0 | 0 | 20 | 20 | 0 | 20 | 0 | 0 | 20 | 0 | 0 | 0 | 0 | 0 | 0 | 0 |
| Crabgrass | 0 | 30 | 40 | 20 | 20 | 20 | 30 | 40 | 40 | 30 | 30 | — | 0 | 0 | 0 | 0 | 0 | 0 |
| Foxtail, Giant | 0 | 0 | 0 | 0 | 0 | 0 | 0 | 0 | 0 | 0 | 0 | 0 | 0 | 0 | 0 | 0 | 0 | 0 |
| Lambsquarters | 0 | 30 | 30 | 90 | 0 | 70 | 90 | 90 | 90 | 60 | 80 | 90 | 0 | 20 | 100 | 30 | 0 | 100 |
| Morningglory | 0 | 20 | 0 | 30 | 0 | 30 | 70 | 40 | 30 | 50 | 50 | 20 | 0 | 0 | 0 | 0 | 0 | 0 |
| Pigweed | 0 | 60 | 100 | 90 | 50 | 50 | 80 | 70 | 60 | 60 | 50 | 30 | 0 | 0 | 30 | 0 | 0 | 0 |
| Velvetleaf | 0 | 0 | 0 | 0 | 0 | 20 | 70 | 40 | 30 | 20 | 30 | 0 | 0 | 0 | 0 | 0 | 0 | 0 |
| Wheat | 20 | 40 | 30 | 20 | 40 | 20 | 30 | 20 | 20 | 10 | 50 | 0 | 0 | 0 | 0 | 0 | 0 | 0 |
| Wild Oat | 0 | 30 | 40 | 30 | 30 | 30 | 40 | 30 | 0 | 30 | 30 | 0 | 0 | 0 | 0 | 0 | 0 | 0 |

| | Rate 125 g/ha COMPOUND | | | | | | | | | | | | | | | | Rate 62 g/ha COMPOUND | | |
|---|---|---|---|---|---|---|---|---|---|---|---|---|---|---|---|---|---|---|---|
| | 130 | 131 | 132 | 133 | 134 | 136 | 137 | 138 | 139 | 140 | 141 | 142 | 143 | 144 | 145 | 146 | 9 | 109 | 125 |
| Barnyardgrass | 0 | 80 | 0 | 80 | 90 | 0 | 0 | 0 | 0 | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 |
| Surinam grass | 0 | 0 | 0 | 0 | 20 | 0 | 0 | 0 | 0 | 0 | 0 | 0 | 0 | 0 | 0 | 0 | 0 | 0 | 0 |
| Cocklebur | 20 | 30 | 0 | 10 | 30 | 0 | 0 | 0 | 0 | 60 | 40 | 60 | 0 | 0 | 0 | 0 | 10 | 60 | 30 |
| Corn | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 40 | 20 | 0 | 0 | 0 | 0 | 20 | 20 | 40 | 0 | 0 | 0 | 0 | 0 | 0 | 0 |
| Foxtail, Giant | 0 | 20 | 0 | 0 | 30 | 0 | 0 | 0 | 0 | 0 | 30 | 30 | 30 | 20 | 0 | 0 | 0 | 0 | 0 |
| Lambsquarters | 90 | 90 | 70 | 100 | 100 | 0 | 0 | 0 | 0 | 70 | 90 | 70 | 80 | 100 | 80 | 80 | 70 | 80 | 100 |
| Morningglory | 70 | 20 | 0 | 0 | 10 | 0 | 0 | 10 | 0 | 0 | 0 | 70 | 30 | 0 | 0 | 0 | 0 | 90 | 50 |
| Pigweed | 80 | 80 | 0 | 80 | 60 | 0 | 0 | 0 | 0 | 60 | 80 | 60 | 70 | 50 | 0 | 0 | 70 | 50 | 30 |
| Velvetleaf | 0 | 0 | 0 | 0 | 0 | 0 | 0 | 0 | 0 | 0 | 50 | 40 | 50 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 |
| Wild Oat | 0 | 20 | 0 | 0 | 0 | 0 | 0 | 0 | 0 | 0 | 0 | 0 | 0 | 0 | 0 | 0 | 0 | 0 | 0 |

Preemergence

Rate 500 g/ha
COMPOUND

| | 1 | 2 | 3 | 4 | 5 | 6 | 7 | 8 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|
| Barnyardgrass | 100 | 0 | 100 | 0 | 100 | 100 | 100 | 70 | 0 | 0 | 0 | 0 | 0 | 0 | 0 | 0 | 0 | 0 | 100 | 100 | 80 | 100 |
| Surinam grass | 0 | 0 | 70 | 0 | 20 | 30 | 20 | 70 | 0 | 0 | 0 | 0 | 0 | 20 | 0 | 0 | 0 | 20 | 0 | 20 | 50 | 20 |
| Cocklebur | 40 | 0 | 0 | 0 | 0 | 0 | 0 | 0 | 0 | 0 | 0 | 0 | 0 | 0 | 0 | 0 | 0 | 0 | 0 | 0 | 0 | 20 |
| Corn | 20 | 0 | 30 | 0 | 0 | 0 | 0 | 0 | 0 | 0 | 0 | 0 | 0 | 0 | 0 | 0 | 0 | 0 | 0 | 0 | 0 | 0 |
| Crabgrass | 100 | 0 | 100 | 0 | 100 | 100 | 100 | 100 | 0 | 0 | 0 | 0 | 0 | 0 | 0 | 0 | 0 | 0 | — | 100 | 100 | 100 |
| Foxtail, Giant | 100 | 0 | 80 | 0 | 100 | 100 | 100 | 90 | 0 | 0 | 0 | 0 | 0 | 0 | 0 | 0 | 0 | 0 | 100 | 100 | 100 | 50 |
| Lambsquarters | 100 | 90 | 100 | 0 | 100 | 100 | 100 | 100 | 0 | 0 | 0 | 0 | 0 | 60 | 0 | 0 | — | 60 | — | — | 100 | 100 |
| Morningglory | 40 | 0 | 0 | 0 | 0 | 0 | 0 | 0 | 0 | 0 | 0 | 0 | 0 | 30 | 0 | 0 | 0 | 0 | 0 | 100 | 0 | 60 |
| Pigweed | 100 | 80 | 100 | 0 | 100 | 100 | 100 | 100 | 0 | 0 | 0 | 0 | 0 | 0 | 0 | 0 | 0 | 0 | 100 | 90 | 100 | 100 |
| Rice | — | — | — | — | 0 | 0 | 20 | 0 | 0 | 0 | 0 | 0 | 0 | 0 | 0 | 0 | 0 | 0 | 0 | 0 | 0 | 30 |
| Velvetleaf | 30 | 0 | 0 | 0 | 0 | 0 | 0 | 0 | 0 | 0 | 0 | 0 | 70 | 20 | 0 | — | 0 | 0 | 0 | 0 | 0 | 0 |

Rate 500 g/ha
COMPOUND

| | 24 | 25 | 26 | 27 | 28 | 29 | 30 | 31 | 32 | 33 | 34 | 35 | 36 | 37 | 38 | 39 | 40 | 41 |
|---|---|---|---|---|---|---|---|---|---|---|---|---|---|---|---|---|---|---|
| Barnyardgrass | 100 | 100 | 100 | 100 | 100 | 20 | 100 | 100 | 100 | 80 | 60 | 60 | 100 | 100 | 100 | 100 | 100 | 100 |
| Surinam grass | 80 | 80 | 70 | 0 | 70 | 0 | 60 | 70 | 60 | 60 | 20 | 0 | 100 | 0 | 60 | 20 | 90 | 0 |
| Cocklebur | 0 | 0 | 0 | 0 | 100 | 0 | 90 | 0 | 0 | — | 0 | 0 | 0 | — | 0 | 0 | 0 | 0 |
| Corn | 20 | 0 | 70 | 0 | 0 | 0 | 0 | 0 | 0 | 0 | 0 | 0 | 0 | 0 | 0 | 0 | 60 | 0 |
| Crabgrass | 100 | 100 | 100 | 90 | 100 | 0 | 100 | 100 | 100 | 100 | — | 100 | 100 | 100 | 100 | 100 | 100 | 0 |
| Foxtail, Giant | 100 | 100 | 100 | 90 | 100 | 0 | 100 | 90 | 100 | 80 | 70 | 0 | 100 | 100 | 100 | 100 | 100 | 60 |
| Lambsquarters | 100 | 100 | 100 | 100 | 100 | 100 | 100 | 100 | 100 | 100 | 100 | 100 | 100 | 100 | 100 | 100 | 100 | 100 |
| Morningglory | 0 | 90 | 0 | 0 | 0 | 0 | 30 | 90 | 0 | 0 | 0 | 0 | 0 | 0 | 0 | 0 | 60 | 0 |
| Pigweed | 100 | 100 | 100 | 100 | 100 | 70 | 100 | 100 | 100 | 100 | 100 | 100 | 100 | 100 | 100 | 100 | 100 | 100 |
| Rice | 0 | 0 | 80 | 40 | 40 | 0 | 0 | 0 | 0 | 0 | 0 | 0 | 90 | 0 | 10 | 0 | 100 | 0 |
| Velvetleaf | 0 | 0 | 0 | 0 | 0 | 20 | 40 | 0 | 0 | 0 | 100 | 0 | 0 | 0 | 0 | 0 | 0 | 0 |

TABLE B-continued

| | Rate 500 g/ha COMPOUND | | | | | | | | | | | | | | | | | | |
|---|---|---|---|---|---|---|---|---|---|---|---|---|---|---|---|---|---|---|---|
| | 42 | 43 | 44 | 45 | 46 | 47 | 48 | 49 | 50 | 51 | 52 | 53 | 54 | 55 | 56 | 58 | 59 | 60 | 61 | 62 |
| Barnyardgrass | 100 | 100 | 100 | 100 | 80 | 0 | 0 | 100 | 90 | 80 | 100 | 90 | 0 | 0 | 50 | 70 | 90 | 0 | 0 | 90 |
| Surinam grass | 100 | 20 | 100 | 80 | 0 | 0 | 0 | 0 | 30 | 20 | 0 | 0 | 0 | 0 | 30 | 0 | 80 | 0 | 0 | 0 |
| Cocklebur | 70 | 0 | — | 0 | 0 | 0 | 0 | 0 | 0 | 0 | 0 | 0 | 0 | — | — | 0 | 0 | 0 | 0 | 0 |
| Corn | 20 | 0 | 20 | 0 | 0 | 0 | 0 | 0 | 0 | 0 | 20 | 0 | 0 | 0 | 0 | 0 | 0 | 0 | 0 | 0 |
| Crabgrass | 100 | 90 | 100 | 100 | 0 | 0 | 80 | 0 | 100 | 100 | 100 | 0 | 0 | 0 | 100 | 80 | 90 | 0 | 0 | 90 |
| Foxtail, Giant | 100 | 100 | 100 | 100 | 0 | 0 | 0 | 90 | 100 | 50 | 100 | 0 | 0 | 0 | 90 | 70 | 70 | 0 | 0 | 80 |
| Lambsquarters | 100 | 100 | 100 | 100 | 100 | 100 | 100 | 100 | 90 | 100 | 100 | 100 | 0 | 0 | 100 | 0 | 100 | 0 | — | 100 |
| Morningglory | 100 | 0 | 0 | 0 | — | 0 | 0 | 30 | 0 | 0 | 0 | 0 | 0 | 0 | 0 | 0 | 0 | 0 | 0 | 0 |
| Pigweed | 100 | 100 | 100 | 100 | 100 | 100 | 0 | 100 | 0 | 100 | 30 | 100 | 0 | 0 | 100 | 0 | 0 | 100 | 0 | 100 |
| Rice | 100 | 70 | 100 | 60 | 0 | 20 | 0 | 20 | 0 | 0 | 0 | 0 | 0 | 0 | 0 | 0 | 50 | 0 | 0 | 30 |
| Velvetleaf | 90 | 0 | 0 | 0 | 0 | 0 | 0 | 0 | 100 | 0 | 0 | 0 | 0 | 0 | 0 | 0 | 0 | 0 | 0 | 0 |

| | Rate 500 g/ha COMPOUND | | | | | | | | | | | | | | | | | |
|---|---|---|---|---|---|---|---|---|---|---|---|---|---|---|---|---|---|---|
| | 63 | 64 | 65 | 66 | 67 | 68 | 69 | 70 | 71 | 72 | 73 | 74 | 75 | 76 | 77 | 78 | 79 | 80 |
| Barnyardgrass | 90 | 90 | 100 | 100 | 100 | 100 | 40 | — | 90 | 100 | 100 | 90 | 100 | 100 | 100 | 90 | 100 | 100 |
| Surinam grass | 30 | 60 | 20 | 20 | 50 | 0 | 20 | 0 | 40 | 70 | 90 | 20 | 100 | 100 | 40 | 0 | 90 | 90 |
| Cocklebur | 0 | 10 | 20 | 0 | 0 | 0 | 20 | 0 | 0 | 60 | 90 | 0 | 70 | 0 | 0 | 0 | 0 | 0 |
| Corn | 0 | 20 | 0 | 0 | 20 | 20 | 0 | — | 20 | 0 | 30 | 0 | 20 | 70 | 0 | 0 | 0 | 20 |
| Crabgrass | 100 | 100 | 70 | 40 | 80 | 20 | 0 | 100 | 100 | 100 | 100 | 70 | 100 | 100 | 90 | 30 | 100 | 100 |
| Foxtail, Giant | 90 | 90 | 70 | 40 | 40 | 20 | 0 | 100 | 100 | 100 | 100 | 60 | 100 | 100 | 0 | 10 | 60 | 100 |
| Lambsquarters | 100 | 100 | 100 | 100 | 100 | 100 | 100 | 100 | 100 | 100 | 100 | 100 | 100 | 100 | 100 | 100 | 100 | 100 |
| Morningglory | 0 | 10 | 0 | 20 | 0 | 0 | 0 | 80 | 0 | 90 | 100 | 0 | 0 | 100 | 0 | 0 | 100 | 100 |
| Pigweed | 100 | 100 | 100 | 100 | 100 | 100 | 90 | 100 | 100 | 100 | 100 | 90 | 100 | 100 | 100 | 100 | 100 | 100 |
| Rice | 0 | 0 | 20 | 20 | 40 | 30 | 0 | 30 | 40 | 0 | 40 | 0 | 70 | 90 | 0 | 0 | 90 | 90 |
| Velvetleaf | 0 | 0 | 20 | 20 | 0 | 0 | 0 | 0 | 30 | 90 | 100 | 0 | 70 | 0 | 0 | 0 | 90 | 70 |

| | Rate 500 g/ha COMPOUND | | | | | | | | | | | | | | | | | |
|---|---|---|---|---|---|---|---|---|---|---|---|---|---|---|---|---|---|---|
| | 81 | 82 | 83 | 84 | 85 | 86 | 87 | 88 | 89 | 90 | 91 | 92 | 93 | 94 | 95 | 96 | 98 | 99 |
| Barnyardgrass | 100 | 100 | 100 | 100 | 100 | 100 | 100 | 100 | 100 | 100 | 100 | 100 | 100 | 0 | 100 | 100 | 90 | 100 |
| Surinam grass | 100 | 100 | 90 | 100 | 90 | 60 | 100 | 100 | 100 | 80 | 80 | 70 | 70 | 0 | 90 | 80 | 0 | 20 |
| Cocklebur | 90 | 0 | 0 | 0 | 90 | 0 | 0 | 0 | 0 | 0 | 0 | 0 | 0 | 0 | 60 | 30 | 0 | 0 |
| Corn | 30 | 20 | 20 | 20 | 30 | 20 | 60 | 20 | 0 | 20 | 30 | 0 | 0 | 0 | 50 | 20 | 0 | 30 |
| Crabgrass | 100 | 100 | 100 | 100 | 100 | 100 | 100 | 100 | 100 | 100 | 100 | 100 | 100 | 30 | 100 | 100 | 100 | 100 |
| Foxtail, Giant | 100 | 100 | 100 | 100 | 100 | 100 | 100 | 100 | 100 | 100 | 100 | 100 | 90 | 0 | 100 | 100 | 90 | 100 |
| Lambsquarters | 100 | 100 | 100 | — | 100 | 100 | 100 | 100 | 100 | 100 | 100 | 100 | 100 | 100 | 100 | 100 | 100 | 100 |
| Morningglory | 100 | 0 | — | 0 | 100 | 0 | 0 | 0 | 0 | 0 | 0 | 0 | 0 | 0 | 60 | 80 | 0 | 0 |
| Pigweed | 100 | 100 | 100 | 100 | 100 | 100 | 100 | 100 | 100 | 100 | 100 | 100 | 80 | 0 | 100 | 100 | 40 | 100 |
| Rice | 90 | 100 | 100 | 100 | 100 | 0 | 100 | 100 | 10 | 0 | 0 | 0 | 0 | 20 | 100 | 100 | 30 | 20 |
| Velvetleaf | 80 | 0 | 0 | 0 | 100 | 0 | 0 | 0 | 0 | 0 | 0 | 0 | 0 | 70 | 50 | 50 | 0 | 0 |

| | Rate 500 g/ha COMPOUND | | | | | | | | | | | | | | | | | |
|---|---|---|---|---|---|---|---|---|---|---|---|---|---|---|---|---|---|---|
| | 100 | 101 | 102 | 103 | 104 | 105 | 106 | 107 | 108 | 109 | 110 | 111 | 112 | 113 | 114 | 115 | 116 | 117 |
| Barnyardgrass | 100 | 100 | 0 | 0 | 0 | 0 | 100 | 30 | 0 | 100 | 0 | 100 | 100 | 0 | 0 | 0 | 0 | 100 |
| Surinam grass | 20 | 80 | 0 | 0 | 0 | 0 | 100 | 70 | 30 | 100 | 40 | 0 | 30 | 0 | 0 | 0 | 0 | 100 |
| Cocklebur | 0 | 0 | 0 | 0 | 0 | 0 | 100 | 20 | 0 | 0 | 0 | 70 | 0 | 0 | 0 | 0 | 0 | 100 |
| Corn | 20 | 70 | 0 | 0 | 0 | 0 | 30 | 0 | 0 | 0 | 0 | 30 | 30 | 0 | 30 | 0 | 0 | 30 |
| Crabgrass | 100 | 100 | 90 | 60 | 0 | 30 | 100 | 100 | 0 | 100 | 100 | 100 | 100 | 0 | 0 | 0 | 0 | 100 |
| Foxtail, Giant | 70 | 100 | 0 | 0 | 0 | 20 | 60 | 40 | 20 | 50 | 50 | 0 | 100 | 0 | 100 | 0 | 0 | 100 |
| Lambsquarters | 100 | 100 | 0 | 100 | 100 | 100 | 100 | 100 | 100 | 100 | 100 | 100 | 100 | 0 | 100 | 0 | 100 | 100 |
| Morningglory | 0 | 0 | 0 | 0 | 0 | 0 | 100 | 100 | 0 | 0 | 0 | 0 | 30 | 0 | 30 | 0 | 0 | 100 |
| Pigweed | 100 | 100 | 0 | 0 | 100 | 100 | 100 | 100 | 60 | 100 | 100 | 100 | 100 | 0 | 100 | 0 | 100 | 100 |
| Rice | 20 | — | 0 | 0 | 0 | 0 | 100 | 0 | 0 | 0 | 0 | 0 | 100 | 0 | 0 | 0 | 0 | 70 |
| Velvetleaf | 0 | 0 | 0 | 0 | 0 | 0 | 100 | 100 | 0 | 70 | 80 | 0 | 0 | 0 | 0 | 0 | 0 | 100 |

| | Rate 500 g/ha COMPOUND | | | | | | | | | | | | | | | | | |
|---|---|---|---|---|---|---|---|---|---|---|---|---|---|---|---|---|---|---|
| | 118 | 119 | 120 | 121 | 122 | 123 | 124 | 126 | 127 | 128 | 129 | 130 | 131 | 132 | 133 | 134 | 136 | 137 | 138 |
| Barnyardgrass | 100 | 100 | 100 | 100 | 100 | 0 | 100 | 100 | 100 | 100 | 100 | 100 | 100 | 100 | 100 | 100 | 0 | 40 | 100 |
| Surinam grass | 90 | 100 | 100 | 40 | 70 | 0 | 40 | 100 | 70 | 100 | 100 | 100 | 100 | 100 | 100 | 100 | 0 | 50 | 100 |
| Cocklebur | 0 | 30 | 40 | 30 | 0 | 0 | 0 | 70 | 0 | 60 | 0 | 50 | 30 | 30 | 0 | 0 | 0 | 80 | 100 |
| Corn | 30 | 40 | 50 | 50 | 0 | 0 | 0 | 50 | 0 | 60 | 30 | 70 | 50 | 0 | 90 | 90 | 0 | 0 | 20 |

TABLE B-continued

| | | | | | | | | | | | | | | | | | | |
|---|---|---|---|---|---|---|---|---|---|---|---|---|---|---|---|---|---|---|
| Crabgrass | 100 | 100 | 100 | 100 | 100 | 60 | 100 | 100 | 100 | 100 | 100 | 100 | 100 | 100 | 100 | 100 | 70 | 80 | 100 |
| Foxtail, Giant | 100 | 100 | 100 | 100 | 30 | 0 | 100 | 100 | 100 | 100 | 100 | 100 | 100 | 100 | 100 | 100 | 0 | 0 | 100 |
| Lambsquarters | 100 | 100 | 100 | 100 | 100 | 60 | 100 | 100 | 100 | 100 | 100 | 100 | 100 | 100 | 100 | 100 | 100 | 0 | 100 |
| Morningglory | 100 | 70 | 100 | 30 | 0 | 0 | 60 | 100 | 0 | 90 | 0 | 100 | 90 | 0 | 0 | 0 | 0 | 0 | 100 |
| Pigweed | 100 | 100 | 100 | 100 | 100 | 70 | 100 | 100 | 100 | 100 | 100 | 100 | 100 | 100 | 100 | 100 | 60 | 0 | 100 |
| Rice | 0 | 20 | 30 | 0 | 0 | 0 | 0 | 100 | 50 | 100 | 50 | 100 | 100 | 50 | 100 | 100 | 0 | 70 | 100 |
| Velvetleaf | 90 | 70 | 40 | 20 | 0 | 0 | 0 | 60 | 0 | 50 | 0 | 50 | 40 | 30 | — | 0 | 0 | 80 | 0 |

| | Rate 500 g/ha COMPOUND | | | | | | | | Rate 250 g/ha COMPOUND | | | | Rate 125 g/ha COMPOUND | | | | | | |
|---|---|---|---|---|---|---|---|---|---|---|---|---|---|---|---|---|---|---|---|
| | 139 | 140 | 141 | 142 | 143 | 144 | 145 | 146 | 9 | 10 | 109 | 125 | 1 | 2 | 3 | 4 | 5 | 6 | 7 |
| Barnyardgrass | 0 | 100 | 100 | 100 | 100 | 100 | 100 | 100 | 60 | 100 | 50 | 100 | 50 | 0 | 80 | 0 | 60 | 100 | 100 |
| Surinam grass | 0 | 100 | 100 | 100 | 90 | 70 | 60 | 100 | 70 | 30 | 90 | 100 | 0 | 0 | 40 | 0 | 0 | 0 | 0 |
| Cocklebur | 0 | 60 | 100 | 60 | 30 | 0 | 0 | 100 | 0 | 0 | 0 | 50 | 0 | 0 | 0 | 0 | 0 | 0 | 0 |
| Corn | 0 | 20 | 20 | 20 | 20 | 20 | 0 | 0 | 0 | 30 | 0 | 40 | 0 | 0 | 0 | 0 | 0 | 0 | 0 |
| Crabgrass | 0 | 100 | 100 | 100 | 100 | 100 | 100 | 100 | 100 | 100 | 100 | 100 | 0 | 0 | 70 | 0 | 90 | 70 | 70 |
| Foxtail, Giant | 0 | 100 | 100 | 100 | 100 | 100 | 100 | 100 | 90 | 100 | 100 | 100 | 50 | 0 | 40 | 0 | 80 | 20 | 70 |
| Lambsquarters | 100 | 100 | 100 | 100 | 100 | 100 | 100 | 100 | 100 | 100 | 100 | 100 | 100 | 80 | 100 | 0 | 100 | 100 | 100 |
| Morningglory | 0 | 100 | 100 | 50 | 70 | 0 | 0 | 40 | 0 | 0 | 0 | 80 | 20 | 0 | 0 | 0 | 0 | 0 | 0 |
| Pigweed | 100 | 100 | 100 | 100 | 100 | 100 | 100 | 100 | 100 | 100 | 100 | 100 | 100 | 20 | 100 | 0 | 80 | 100 | 100 |
| Rice | 0 | 40 | 50 | 40 | 30 | 0 | 80 | 0 | 0 | 0 | 0 | 100 | — | — | — | — | 0 | 0 | 0 |
| Velvetleaf | 0 | 80 | 100 | 90 | 80 | 0 | 0 | 20 | 0 | 0 | 60 | 40 | 0 | 0 | 0 | 0 | 0 | 0 | 0 |

| | Rate 125 g/ha COMPOUND | | | | | | | | | | | | | | | | | | |
|---|---|---|---|---|---|---|---|---|---|---|---|---|---|---|---|---|---|---|---|
| | 8 | 10 | 11 | 12 | 13 | 14 | 15 | 16 | 17 | 18 | 19 | 20 | 21 | 22 | 23 | 24 | 25 | 26 | 27 |
| Barnyardgrass | 0 | 0 | 0 | 0 | 0 | 0 | 0 | 0 | 0 | 0 | 0 | 0 | 60 | 0 | 0 | 20 | 100 | 100 | 30 |
| Surinam grass | 20 | 0 | 0 | 0 | 0 | 0 | 0 | 0 | 0 | 0 | 0 | 0 | 20 | 30 | 0 | 20 | 80 | 40 | 0 |
| Cocklebur | 0 | 0 | 0 | 0 | 0 | 0 | 0 | 0 | — | 0 | 0 | — | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 10 | 0 |
| Crabgrass | 30 | 0 | 0 | 0 | 0 | 0 | 0 | 0 | 0 | 0 | 0 | 0 | 100 | 0 | 70 | 100 | 100 | 100 | 0 |
| Foxtail, Giant | 40 | 0 | 0 | 0 | 0 | 0 | 0 | 0 | 0 | 0 | 0 | 70 | 70 | 30 | 50 | 90 | 100 | 100 | 0 |
| Lambsquarters | 0 | 0 | 0 | 0 | 0 | 0 | 0 | 0 | — | 0 | 0 | — | — | 100 | 100 | 100 | 100 | 100 | 100 |
| Morningglory | 0 | 0 | 0 | 0 | 0 | 0 | 0 | 0 | — | 0 | 0 | 0 | 90 | 0 | 0 | 0 | 0 | 0 | 0 |
| Pigweed | 20 | 0 | 0 | 0 | 0 | 0 | 0 | 0 | 0 | 0 | 0 | 0 | 90 | 100 | 100 | 100 | 100 | 100 | 100 |
| Rice | 0 | 0 | 0 | 0 | 0 | 0 | 0 | 0 | 0 | 0 | 0 | 0 | 0 | 0 | 0 | 0 | 0 | 40 | 0 |
| Velvetleaf | 0 | 0 | 0 | 0 | 0 | 0 | 50 | 0 | — | — | 0 | 0 | 0 | 0 | 0 | 0 | 0 | 0 | 0 |

| | Rate 125 g/ha COMPOUND | | | | | | | | | | | | | | | | | | |
|---|---|---|---|---|---|---|---|---|---|---|---|---|---|---|---|---|---|---|---|
| | 28 | 29 | 30 | 31 | 32 | 33 | 34 | 35 | 36 | 37 | 38 | 39 | 40 | 41 | 42 | 43 | 44 | 45 | |
| Barnyardgrass | 50 | 0 | 40 | 100 | 80 | 30 | 0 | 0 | 100 | 0 | 70 | 50 | 100 | 40 | 100 | 60 | 80 | 80 | |
| Surinam grass | 0 | 0 | 40 | 30 | 40 | 30 | 0 | 0 | 70 | 0 | 0 | 20 | 60 | 0 | 90 | 0 | 0 | 70 | |
| Cocklebur | 0 | 0 | 0 | 0 | — | 0 | 0 | 0 | 0 | 0 | — | 0 | 0 | 0 | 0 | — | 0 | 0 | |
| Corn | 0 | 0 | 0 | 0 | 0 | 0 | 0 | 0 | 0 | 0 | 0 | 0 | 0 | 0 | 20 | 0 | 0 | 0 | |
| Crabgrass | 20 | 0 | 20 | 100 | 60 | 0 | 100 | 0 | 100 | 0 | 0 | 0 | 100 | 0 | 100 | 0 | 0 | 30 | |
| Foxtail, Giant | 20 | 0 | 70 | 30 | 70 | 20 | 0 | 0 | 100 | 40 | 0 | 30 | 70 | 0 | 100 | 0 | 10 | 100 | |
| Lambsquarters | 100 | 0 | 100 | 100 | 100 | 90 | 20 | 0 | 100 | 100 | 100 | 100 | 100 | 100 | 100 | 100 | 100 | 100 | |
| Morningglory | 0 | 0 | 0 | 0 | 0 | 0 | 0 | 0 | 0 | 0 | 0 | 0 | 0 | 0 | 80 | 0 | 0 | 0 | |
| Pigweed | 100 | 0 | 100 | 100 | 100 | 100 | 30 | — | 100 | 100 | 100 | 100 | 100 | 100 | 100 | 100 | 100 | 0 | |
| Rice | 0 | 0 | 0 | 0 | 0 | 0 | 0 | 0 | 90 | 0 | 0 | 0 | 40 | 0 | 90 | 0 | 30 | 60 | |
| Velvetleaf | 0 | 0 | 0 | 0 | 0 | 0 | 0 | 0 | 0 | 0 | 0 | 0 | 0 | 0 | 70 | 0 | 0 | 0 | |

| | Rate 125 g/ha COMPOUND | | | | | | | | | | | | | | | | | | |
|---|---|---|---|---|---|---|---|---|---|---|---|---|---|---|---|---|---|---|---|
| | 46 | 47 | 48 | 49 | 50 | 51 | 52 | 53 | 54 | 55 | 56 | 58 | 59 | 60 | 61 | 62 | 63 | 64 | |
| Barnyardgrass | 0 | 0 | 0 | 100 | 0 | 80 | 0 | 0 | 0 | 0 | 0 | 0 | 0 | 0 | 0 | 0 | 50 | 50 | |
| Surinam grass | 0 | 0 | 0 | 0 | 0 | 0 | 0 | 0 | 0 | 0 | 30 | 0 | 60 | 0 | 0 | 0 | 0 | 30 | |
| Cocklebur | 0 | 0 | 0 | 0 | 0 | 0 | 0 | — | 0 | 0 | 0 | 0 | 0 | 0 | 0 | 0 | 0 | 0 | |
| Corn | 0 | 0 | 0 | 0 | 0 | 0 | 0 | 0 | 0 | 0 | 0 | 0 | 0 | 0 | 0 | 0 | 0 | 0 | |
| Crabgrass | 0 | 0 | 0 | 0 | 100 | 100 | 100 | 0 | 0 | 0 | 30 | 0 | 20 | — | 0 | 0 | 0 | 40 | |
| Foxtail, Giant | 0 | 0 | 0 | 0 | 20 | 0 | 90 | 0 | 0 | 0 | 50 | 0 | 0 | 0 | 0 | 0 | 50 | 0 | |
| Lambsquarters | 100 | 0 | 100 | 100 | 0 | 100 | 100 | 100 | 0 | 100 | 0 | 100 | 0 | 0 | — | 100 | 100 | 100 | |
| Morningglory | 0 | 0 | 0 | 0 | 0 | 0 | 0 | 0 | 0 | 0 | 0 | 0 | 0 | 0 | 0 | 0 | 0 | 0 | |
| Pigweed | 100 | 100 | 0 | 100 | 0 | 0 | 0 | 100 | 0 | — | 100 | 0 | 0 | 0 | 0 | 100 | 100 | 100 | |
| Rice | 0 | 0 | 0 | 0 | 0 | 0 | 0 | 0 | 0 | 0 | 0 | 0 | 0 | 0 | 0 | 0 | 0 | 0 | |
| Velvetleaf | 0 | 0 | 0 | 0 | 100 | 0 | — | 0 | 0 | 0 | 0 | 0 | — | 0 | 0 | 0 | 0 | 0 | |

TABLE B-continued

| | Rate 125 g/ha COMPOUND | | | | | | | | | | | | | | | | | |
|---|---|---|---|---|---|---|---|---|---|---|---|---|---|---|---|---|---|---|
| | 65 | 66 | 67 | 68 | 69 | 70 | 71 | 72 | 73 | 74 | 75 | 76 | 77 | 78 | 79 | 80 | 81 | 82 |
| Barnyardgrass | 90 | 100 | 60 | 100 | 20 | — | 10 | 100 | 100 | 30 | 100 | 100 | 20 | 0 | 70 | 0 | 100 | 100 |
| Surinam grass | 0 | 20 | 20 | 0 | 20 | 0 | 40 | 0 | 50 | 0 | 60 | 80 | 0 | 0 | 70 | 80 | 90 | 90 |
| Cocklebur | 0 | — | 0 | 0 | 0 | 0 | 0 | 0 | 0 | 0 | 30 | 0 | 0 | 0 | 0 | 0 | 0 | 0 |
| Corn | 0 | 0 | 0 | 0 | 0 | — | 0 | 0 | 0 | 0 | 0 | 0 | 0 | 0 | 0 | 0 | 0 | 0 |
| Crabgrass | 20 | 0 | 20 | — | 0 | 90 | 50 | 100 | 100 | 20 | 100 | 100 | 60 | 0 | 100 | 100 | 100 | 100 |
| Foxtail, Giant | 20 | 20 | 40 | — | 0 | 90 | 90 | 100 | 100 | 0 | 100 | 100 | 0 | 0 | 0 | 100 | 100 | 100 |
| Lambsquarters | 100 | 100 | 100 | 100 | 90 | 100 | 100 | 100 | 100 | 100 | 100 | 100 | 90 | 100 | 100 | 100 | 100 | 100 |
| Morningglory | 0 | — | 0 | 0 | 0 | 20 | 0 | 0 | 0 | 0 | 0 | 0 | 0 | 0 | 0 | 60 | 30 | 0 |
| Pigweed | 100 | 100 | 100 | 100 | 60 | 100 | 100 | 100 | 100 | 80 | 100 | 100 | 90 | 80 | 100 | 100 | 100 | 100 |
| Rice | 0 | 0 | 40 | 0 | 0 | 30 | 20 | 0 | 30 | 0 | 50 | 70 | 0 | 0 | 50 | 60 | 50 | 70 |
| Velvetleaf | 0 | 0 | 0 | 0 | 0 | 0 | 0 | 0 | 90 | 0 | 50 | 0 | 0 | 0 | 0 | 0 | 70 | 0 |

| | Rate 125 g/ha COMPOUND | | | | | | | | | | | | | | | | | |
|---|---|---|---|---|---|---|---|---|---|---|---|---|---|---|---|---|---|---|
| | 83 | 84 | 85 | 86 | 87 | 88 | 89 | 90 | 91 | 92 | 93 | 94 | 95 | 96 | 97 | 98 | 99 | 100 |
| Barnyardgrass | 100 | 100 | 100 | 0 | 100 | 100 | 80 | 50 | 100 | 30 | 0 | 0 | 90 | 100 | 30 | 0 | 0 | 0 |
| Surinam grass | 70 | 80 | 60 | 0 | 80 | 70 | 60 | 20 | 70 | 0 | 0 | 0 | 60 | 50 | 0 | 0 | 0 | 0 |
| Cocklebur | 0 | 0 | 40 | 0 | 0 | 0 | 0 | 0 | 0 | 0 | 0 | 0 | 0 | 20 | 0 | 0 | 0 | 0 |
| Corn | 20 | 0 | 20 | 0 | 30 | 20 | 0 | 0 | 0 | 0 | 0 | 0 | 20 | 0 | 0 | 0 | 0 | 0 |
| Crabgrass | 100 | 100 | 100 | 0 | 100 | 100 | 90 | 90 | 100 | 50 | 20 | 0 | 100 | 100 | 20 | 0 | 0 | 0 |
| Foxtail, Giant | 100 | 100 | 80 | 80 | 100 | 100 | 90 | 80 | 90 | 50 | 20 | 0 | 100 | 100 | 20 | 0 | 0 | 0 |
| Lambsquarters | 100 | — | 100 | 100 | 100 | 100 | 100 | 100 | 100 | 100 | 60 | 0 | 100 | 100 | 20 | 60 | 100 | 100 |
| Morningglory | 0 | 0 | 90 | 0 | 0 | 0 | 0 | 0 | 0 | 0 | 0 | 0 | 0 | 0 | 0 | 0 | 0 | 0 |
| Pigweed | 100 | 100 | 100 | 100 | 100 | 100 | 90 | 80 | 90 | 80 | 0 | 0 | 100 | 100 | 0 | 0 | 0 | 70 |
| Rice | 20 | 0 | 100 | 0 | 70 | 0 | 0 | 0 | 0 | 0 | 0 | 0 | 90 | 70 | 0 | 0 | 0 | 0 |
| Velvetleaf | 0 | 0 | 20 | 0 | 0 | 0 | 0 | 0 | 0 | 0 | 0 | 0 | 0 | 0 | 0 | 0 | 0 | 0 |

| | Rate 125 g/ha COMPOUND | | | | | | | | | | | | | | | | | |
|---|---|---|---|---|---|---|---|---|---|---|---|---|---|---|---|---|---|---|
| | 101 | 102 | 103 | 104 | 105 | 106 | 107 | 108 | 109 | 110 | 111 | 112 | 113 | 114 | 115 | 116 | 117 | 118 |
| Barnyardgrass | 30 | 0 | 0 | 0 | 0 | 90 | 0 | 0 | 30 | 30 | 0 | 90 | 0 | 0 | 0 | 0 | 100 | 100 |
| Surinam grass | 0 | 0 | 0 | 0 | 0 | 100 | 0 | 0 | 50 | 0 | 0 | 10 | 0 | 0 | 0 | 0 | 100 | 0 |
| Cocklebur | 0 | 0 | 0 | 0 | 0 | 30 | 0 | 0 | 0 | 0 | 0 | 0 | 0 | 0 | 0 | 0 | 70 | 0 |
| Corn | 0 | 0 | 0 | 0 | 0 | 30 | 0 | 0 | 0 | 0 | 0 | 0 | 0 | 20 | 0 | 0 | 20 | 30 |
| Crabgrass | 90 | 0 | 0 | 0 | 0 | 100 | 0 | 0 | 100 | 100 | 70 | 100 | 0 | 0 | 0 | 0 | 100 | 100 |
| Foxtail, Giant | 0 | 0 | 0 | 0 | 0 | 40 | 0 | 0 | 0 | 0 | 0 | 100 | 0 | 0 | 0 | 0 | 100 | 40 |
| Lambsquarters | 100 | 0 | 100 | 100 | 60 | 100 | 100 | 100 | 100 | 0 | 30 | 100 | 0 | 30 | 0 | 0 | 100 | 100 |
| Morningglory | 0 | 0 | 0 | 0 | 0 | 100 | 0 | 0 | 0 | 0 | 0 | 30 | 0 | 0 | 0 | 0 | 80 | 40 |
| Pigweed | 40 | 0 | 0 | 70 | 0 | 100 | 80 | 20 | 100 | 100 | 0 | 100 | 0 | 30 | 0 | 0 | 100 | 100 |
| Rice | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 40 | 20 |

| | Rate 125 g/ha COMPOUND | | | | | | | | | | | | | | | | | |
|---|---|---|---|---|---|---|---|---|---|---|---|---|---|---|---|---|---|---|
| | 119 | 120 | 121 | 122 | 123 | 124 | 126 | 127 | 128 | 129 | 130 | 131 | 132 | 133 | 134 | 136 | 137 | 138 |
| Barnyardgrass | 100 | 100 | 40 | 0 | 0 | 70 | 100 | 0 | 100 | 100 | 100 | 100 | 100 | 100 | 100 | 0 | 0 | 0 |
| Surinam grass | 100 | 40 | 0 | 50 | 0 | 0 | 100 | 0 | 100 | 90 | 100 | 100 | 80 | 100 | 90 | 0 | 0 | 70 |
| Cocklebur | 30 | 20 | 10 | 0 | 0 | 0 | 50 | 0 | 0 | 0 | 0 | 0 | 0 | 0 | 0 | 0 | 0 | 0 |
| Corn | 0 | 20 | 20 | 0 | 0 | 0 | 30 | 0 | 30 | 20 | 50 | 40 | 0 | 0 | 20 | 0 | 0 | 0 |
| Crabgrass | 100 | 100 | 10 | 100 | 0 | 30 | 100 | 100 | 100 | 100 | 100 | 100 | 100 | 100 | 100 | 0 | 0 | 100 |
| Foxtail, Giant | 100 | 100 | 0 | 20 | 0 | 50 | 100 | 70 | 100 | 100 | 100 | 100 | 100 | 100 | 100 | 0 | 0 | 80 |
| Lambsquarters | 100 | 100 | 100 | 100 | 0 | 100 | 100 | 90 | 100 | 100 | 100 | 100 | 100 | 100 | 100 | 100 | 0 | 100 |
| Morningglory | 50 | 70 | 20 | 0 | 0 | 0 | 70 | 0 | 70 | 0 | 50 | 0 | 0 | 0 | 0 | 0 | 0 | 90 |
| Pigweed | 100 | 100 | 100 | 100 | 0 | 80 | 100 | 0 | 100 | 100 | 100 | 100 | 70 | 100 | 100 | 0 | 0 | 100 |
| Rice | 10 | 20 | 0 | 0 | 0 | 0 | 70 | 0 | 100 | 30 | 100 | 70 | 0 | 90 | 100 | 0 | 30 | 0 |
| Velvetleaf | 30 | 20 | 10 | 0 | 0 | 0 | 0 | 0 | 0 | 0 | 0 | 0 | 0 | 0 | 0 | 0 | 0 | 0 |

| | Rate 125 g/ha COMPOUND | | | | | | | | Rate 62 g/ha COMPOUND | | | |
|---|---|---|---|---|---|---|---|---|---|---|---|---|
| | 139 | 140 | 141 | 142 | 143 | 144 | 145 | 146 | 9 | 10 | 109 | 125 |
| Barnyardgrass | 0 | 100 | 100 | 100 | 100 | 80 | 70 | 90 | 0 | 0 | 0 | 100 |
| Surinam grass | 0 | 100 | 100 | 100 | 80 | 0 | 0 | 40 | 0 | 20 | 20 | 70 |
| Cocklebur | — | 20 | 70 | 0 | 0 | 0 | 0 | 0 | 0 | — | 0 | 0 |
| Corn | 0 | 0 | 0 | 0 | 0 | 0 | 0 | 0 | 0 | 0 | 0 | 20 |
| Crabgrass | 0 | 100 | 100 | 100 | 100 | 100 | 100 | 100 | 0 | 100 | 100 | 100 |
| Foxtail, Giant | 0 | 100 | 100 | 100 | 100 | 100 | 100 | 100 | 30 | 80 | 20 | 100 |

TABLE B-continued

|  | Lambsquarters | 100 | 100 | 100 | 100 | 100 | 100 | 100 | 100 | 90 | 100 | 100 | 100 |
|---|---|---|---|---|---|---|---|---|---|---|---|---|---|
|  | Morningglory | 0 | 0 | 90 | 20 | 20 | 0 | 0 | 0 | 0 | 0 | 0 | 50 |
|  | Pigweed | 0 | 100 | 100 | 100 | 100 | 100 | 100 | 100 | 80 | 90 | 100 | 100 |
|  | Rice | 0 | 20 | 30 | 20 | 0 | 0 | 0 | 0 | 0 | 0 | 0 | 50 |
|  | Velvetleaf | 0 | 60 | 70 | 20 | 60 | 0 | 0 | 0 | 0 | 0 | 0 | 0 |

Flooded Paddy

Rate 1000 g/ha
COMPOUND

|  | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|
| Barnyardgrass | 100 | 100 | 70 | 100 | 100 | 100 | 100 | 100 | 100 | 60 | 0 | 0 | 0 | 0 | 0 | 80 | 0 | 60 | 100 | 100 | 100 |
| Ducksalad | 90 | 100 | 50 | 100 | 100 | 100 | 80 | 100 | 100 | 90 | 0 | 0 | 0 | 0 | 0 | 60 | 0 | 80 | 100 | 100 | 100 |
| Rice | 40 | 90 | 0 | 50 | 90 | 90 | 90 | 100 | 60 | 40 | 0 | 0 | 0 | 0 | 0 | 40 | 0 | 0 | 100 | 90 | 90 |
| Flatsedge | 90 | 100 | 90 | 100 | 100 | 100 | 100 | 100 | 100 | 100 | 30 | 0 | 0 | 0 | 0 | 90 | 0 | 90 | 100 | 100 | 100 |

Rate 1000 g/ha
COMPOUND

|  | 23 | 24 | 25 | 26 | 27 | 28 | 29 | 30 | 31 | 32 | 33 | 34 | 35 | 41 | 42 | 46 | 47 | 50 | 51 |
|---|---|---|---|---|---|---|---|---|---|---|---|---|---|---|---|---|---|---|---|
| Barnyardgrass | 0 | 100 | 100 | 0 | 90 | 100 | 0 | 100 | 100 | 100 | 0 | 100 | 60 | 70 | 100 | 100 | 70 | 100 | 100 |
| Ducksalad | 100 | 100 | 100 | 0 | 100 | 100 | 0 | 100 | 100 | 100 | 0 | 100 | 0 | 70 | 100 | 70 | 20 | 100 | 100 |
| Rice | 0 | 90 | 90 | 0 | 50 | 50 | 0 | 90 | 90 | 100 | 0 | 30 | 0 | 40 | 100 | 90 | 70 | 60 | 30 |
| Flatsedge | 0 | 100 | 100 | 0 | 100 | 100 | 30 | 100 | 100 | 100 | 0 | 100 | 100 | 100 | 100 | — | 100 | 100 | 100 |

Rate 1000 g/ha
COMPOUND

|  | 52 | 53 | 54 | 55 | 56 | 57 | 58 | 59 | 60 | 61 | 93 | 94 | 138 | 139 |
|---|---|---|---|---|---|---|---|---|---|---|---|---|---|---|
| Barnyardgrass | 100 | 100 | 80 | 100 | 80 | 100 | 90 | 100 | 0 | 0 | 100 | 0 | 100 | 20 |
| Ducksalad | 100 | 30 | 30 | 80 | 20 | 100 | 70 | 70 | 50 | 30 | 100 | 0 | 90 | 0 |
| Rice | 50 | 20 | 0 | 0 | 0 | 90 | 20 | 20 | 0 | 0 | 50 | 0 | 90 | 0 |
| Flatsedge | 100 | 90 | 90 | 100 | 90 | 100 | 80 | 90 | 0 | 20 | 100 | 0 | 90 | 70 |

Test C

Seeds of plant species selected from bermudagrass (*Cynodon dactylon*), Surinam grass (*Brachiaria decumbens*), cocklebur (*Xanthium strumarium*), corn (*Zea mays*), crabgrass (*Digitaria sanguinalis*), woolly cupgrass (*Eriochloa villosa*), giant foxtail (*Setaria faberii*), goosegrass (*Eleusine indica*), johnsongrass (*Sorghum halepense*), kochia (*Kochia scoparia*), lambsquarters (*Chenopodium album*), morningglory (*Ipomoea hederacea*), yellow nutsedge (*Cyperus esculentus*), pigweed (*Amaranthus retroflexus*), common ragweed (*Ambrosia elatior*), soybean (*Glycine max*) and velvetleaf (*Abutilon theophrasti*) were planted and treated preemergence with test chemicals formulated in a non-phytotoxic solvent mixture which included a surfactant.

At the same time, plants selected from these crop and weed species and also winter barley (*Hordeum vulgare*), blackgrass (*Alopecurus myosuroides*), canary grass (*Phalaris minor*), chickweed (*Stellaria media*), downy brome (*Bromus tectorum*), green foxtail (*Setaria viridis*), Italian ryegrass (*Lolium multiflorum*), wheat (*Triticum aestivum*), wild oat (*Avena fatua*) and windgrass (*Apera spica-venti*) were treated with postemergence applications of some of the test chemicals formulated in the same manner. Plants ranged in height from 2 to 18 cm (1- to 4-leaf stage) for postemergence treatments. Plant species in the flooded paddy test consisted of rice (*Oryza saliva*), smallflower flatsedge (*Cyperus difformis*), duck salad (*Heteranthera limosa*) and barnyardgrass (*Echinochloa crus-galli*) grown to the 2-leaf stage for testing. Treated plants and controls were maintained in a greenhouse for 12 to 14 days, after which time all species were compared to controls and visually evaluated. Plant response ratings, summarized in Table C, are based on a scale of 0 to 100 where 0 is no effect and 100 is complete control. A dash (-) response means no test result.

TABLE C

Postemergence

Rate 500 g/ha
COMPOUND

|  | 25 | 30 | 38 | 40 | 68 | 69 | 80 | 85 | 91 | 107 | 117 | 119 | 120 | 121 | 122 | 131 | 140 | 141 | 142 |
|---|---|---|---|---|---|---|---|---|---|---|---|---|---|---|---|---|---|---|---|
| Barley, Winter | — | — | — | — | — | 10 | — | — | — | — | 20 | — | — | — | — | — | — | — | — |
| Bermudagrass | 90 | 90 | 70 | 70 | 40 | — | 20 | 90 | 60 | 0 | 95 | 0 | 70 | 0 | 0 | 90 | 90 | 100 | 80 |
| Blackgrass | — | — | — | — | — | 20 | — | — | — | — | 40 | — | — | — | — | — | — | — | — |
| Surinam grass | 0 | 60 | 0 | 0 | 0 | — | 0 | 60 | 30 | 0 | 15 | 20 | 0 | 0 | 0 | 40 | — | 60 | 30 |
| Downy Brome | — | — | — | — | — | 0 | — | — | — | — | 40 | — | — | — | — | — | — | — | — |

TABLE C-continued

| Weed | | | | | | | | | | | | | | | | | | | |
|---|---|---|---|---|---|---|---|---|---|---|---|---|---|---|---|---|---|---|---|
| Canarygrass | — | — | — | — | — | 0 | — | — | — | — | 20 | — | — | — | — | — | — | — | — |
| Chickweed | 90 | 90 | 0 | 0 | 80 | — | 60 | 100 | 90 | 100 | — | — | — | — | — | — | — | 100 | — |
| Cocklebur | 60 | 50 | 20 | 0 | 50 | — | 40 | 90 | 20 | 80 | 100 | — | 90 | 40 | 70 | 30 | 100 | 100 | 90 |
| Corn | 30 | 40 | 0 | 0 | 0 | — | 0 | 60 | 0 | 0 | 10 | 50 | 50 | 40 | 0 | 30 | 0 | 0 | 20 |
| Crabgrass | 90 | 90 | 30 | 0 | 60 | — | 30 | 70 | 60 | 20 | 10 | 60 | 90 | 60 | 0 | 90 | 70 | 70 | 70 |
| Cupgrass, Woolly | 70 | 80 | 0 | 0 | 30 | — | 0 | 70 | 40 | 0 | 45 | 20 | 0 | 60 | 20 | 80 | 70 | 70 | 70 |
| Foxtail, Giant | 90 | 80 | 0 | 0 | 0 | — | 20 | 70 | 40 | 0 | 60 | 80 | 70 | 60 | 40 | 80 | 90 | — | 90 |
| Foxtail, Green | — | — | — | — | — | 60 | — | — | — | — | 50 | — | — | — | — | — | — | — | — |
| Goosegrass | 60 | 40 | 0 | 20 | 0 | — | 0 | 60 | 40 | 0 | 100 | 30 | 60 | 50 | 0 | 80 | — | 70 | 70 |
| Johnsongrass | 90 | 90 | 30 | 30 | 20 | — | 0 | 70 | 70 | 0 | 0 | 0 | 0 | 0 | 0 | 30 | 50 | 40 | 30 |
| Kochia | 70 | 90 | 70 | 70 | 70 | — | 50 | 90 | 90 | 85 | 90 | 90 | 90 | 90 | 100 | 90 | 90 | 90 | 90 |
| Lambsquarters | 100 | 90 | 70 | 70 | 100 | — | 90 | 100 | 100 | 100 | 100 | 100 | 100 | 100 | 100 | 100 | 100 | 100 | 100 |
| Morningglory | 100 | 40 | 20 | 0 | 70 | — | 100 | 90 | 90 | 100 | 100 | — | 100 | 100 | 100 | 100 | 100 | 100 | 100 |
| Nutsedge | 0 | 0 | 0 | 20 | 0 | — | 20 | 90 | 20 | 0 | 0 | 0 | 50 | 0 | 0 | 0 | — | 0 | 20 |
| Pigweed | 100 | 100 | 0 | 50 | 100 | — | 70 | 100 | 100 | 90 | 100 | — | 90 | 90 | 100 | 100 | 80 | 100 | 90 |
| Ragweed, Common | 40 | — | 40 | 40 | 30 | — | 80 | 90 | 40 | 50 | 90 | — | — | — | — | — | 90 | 90 | 100 |
| Ryegrass | — | — | — | — | — | 30 | — | — | — | — | 60 | — | — | — | — | — | — | — | — |
| Soybean | 30 | 0 | 0 | 0 | 20 | — | 90 | 70 | 0 | 25 | 90 | 90 | 60 | 70 | 60 | 50 | 90 | 100 | 90 |
| Velvetleaf | 50 | 60 | 0 | 20 | 30 | — | 20 | 40 | 0 | 80 | 60 | 20 | 0 | 40 | 20 | 30 | 70 | 80 | 80 |
| Wheat | — | — | — | — | — | 0 | — | — | — | — | 20 | — | — | — | — | — | — | — | — |
| Wild Oat | — | — | — | — | — | 20 | — | — | — | — | 30 | — | — | — | — | — | — | — | — |
| Windgrass | — | — | — | — | — | 20 | — | — | — | — | 60 | — | — | — | — | — | — | — | — |

| | Rate 500 g/ha COMPOUND | Rate 250 g/ha COMPOUND | | | | | | | | | | | | | | | | | |
|---|---|---|---|---|---|---|---|---|---|---|---|---|---|---|---|---|---|---|---|
| | 143 | 20 | 25 | 30 | 36 | 37 | 38 | 40 | 68 | 69 | 80 | 81 | 85 | 91 | 106 | 107 | 109 | 117 | 119 | 120 |
| Barley, Winter | — | — | — | — | — | — | — | — | 0 | — | — | — | — | — | — | — | 0 | — | — | — |
| Bermudagrass | 80 | 90 | 90 | 80 | 70 | 0 | 30 | 60 | 20 | — | 0 | 0 | 80 | 40 | 20 | 0 | 20 | 50 | 0 | 0 |
| Blackgrass | — | — | — | — | — | — | — | — | 0 | — | — | — | — | — | — | — | 20 | — | — |
| Surinam grass | 70 | 0 | 0 | 0 | 0 | 0 | 0 | 0 | 0 | — | 0 | 0 | 20 | 30 | 0 | 0 | 0 | 0 | 0 | 0 |
| Downy Brome | — | — | — | — | — | — | — | — | 0 | — | — | — | — | — | — | — | — | — | — | — |
| Canarygrass | — | — | — | — | — | — | — | — | 0 | — | — | — | — | — | — | — | 20 | — | — |
| Chickweed | — | 70 | 80 | 70 | 50 | 0 | 0 | 0 | 70 | — | 30 | 60 | 100 | 80 | — | 100 | — | — | — | — |
| Cocklebur | 90 | 60 | 60 | 30 | 0 | 0 | 0 | 0 | 0 | — | 30 | 50 | 90 | 0 | 90 | 30 | — | 85 | 70 | 80 |
| Corn | 30 | 0 | 20 | 30 | 20 | 0 | 0 | 20 | 0 | — | 0 | 0 | 50 | 0 | 20 | 0 | — | 0 | 20 | 30 |
| Crabgrass | 70 | 0 | 70 | 30 | 30 | 0 | 0 | 0 | 0 | — | 0 | 0 | 40 | 30 | 0 | 0 | 0 | 10 | 30 | 40 |
| Cupgrass, Woolly | 70 | 0 | 60 | 40 | 0 | 0 | 0 | 0 | 0 | — | 0 | 0 | 60 | 40 | 40 | 0 | 0 | 40 | 0 | 0 |
| Foxtail, Giant | 90 | 70 | 80 | 30 | 20 | 0 | 0 | 0 | 0 | — | 0 | 0 | 40 | 40 | 10 | 0 | 0 | 30 | 0 | 0 |
| Foxtail, Green | — | — | — | — | — | — | — | — | 30 | — | — | — | — | — | — | — | 30 | — | — |
| Goosegrass | 70 | 40 | 60 | 30 | 0 | 0 | 0 | 0 | 0 | — | 0 | 20 | 20 | 30 | 10 | 0 | 10 | 70 | 0 | 0 |
| Johnsongrass | 30 | 80 | 50 | 0 | 0 | 0 | 0 | 20 | 0 | — | 0 | 0 | 40 | 30 | 0 | 0 | 0 | 0 | 0 | 0 |
| Kochia | 90 | 70 | 70 | 70 | 80 | 70 | 70 | 60 | 70 | — | 30 | 70 | 80 | 90 | 100 | 80 | 90 | 85 | 90 | 90 |
| Lambsquarters | 100 | 80 | 100 | 90 | 70 | 50 | 70 | 50 | 80 | — | — | 80 | 100 | 100 | 100 | 100 | 100 | 95 | 90 | 90 |
| Morningglory | 100 | 20 | 80 | 40 | 20 | 0 | 0 | 0 | 60 | — | 60 | 80 | 80 | 60 | 100 | 100 | — | 100 | 100 | 90 |
| Nutsedge | 0 | 0 | 0 | 0 | 30 | 0 | 0 | 0 | 0 | — | 20 | 0 | — | 0 | 0 | 0 | — | 0 | 0 | 0 |
| Pigweed | 90 | 80 | 100 | 90 | 60 | 0 | 0 | 50 | 70 | — | — | 60 | 90 | 90 | 80 | 55 | 70 | 90 | 90 | 60 |
| Ragweed, Common | 90 | 30 | 30 | — | 30 | 0 | 40 | 30 | 0 | — | 50 | 0 | 20 | 0 | — | — | — | 30 | — | — |
| Ryegrass | — | — | — | — | — | — | — | — | 0 | — | — | — | — | — | — | — | — | — | — | — |
| Soybean | 100 | 20 | 30 | 0 | 0 | 0 | 0 | 0 | 0 | — | 70 | 90 | 70 | 0 | 80 | 20 | 70 | 85 | 80 | 60 |
| Velvetleaf | 90 | 30 | 50 | 50 | 30 | 0 | 0 | 0 | 0 | — | 20 | 20 | 40 | 0 | 70 | 50 | — | 35 | 10 | 0 |
| Wheat | — | — | — | — | — | — | — | — | 0 | — | — | — | — | — | — | — | 10 | — | — |
| Wild Oat | — | — | — | — | — | — | — | — | 0 | — | — | — | — | — | — | — | 30 | — | — |
| Windgrass | — | — | — | — | — | — | — | — | 0 | — | — | — | — | — | — | — | 40 | — | — |

| | Rate 250 g/ha COMPOUND | | | | | | | Rate 125 g/ha COMPOUND | | | | | | | | | | | | | | |
|---|---|---|---|---|---|---|---|---|---|---|---|---|---|---|---|---|---|---|---|---|---|---|
| | 121 | 122 | 131 | 140 | 141 | 142 | 143 | 20 | 21 | 25 | 30 | 36 | 37 | 38 | 40 | 68 | 69 | 80 | 81 | 85 | 91 | 106 |
| Barley, Winter | — | — | — | — | — | — | — | — | — | — | — | — | — | — | — | — | 0 | — | — | — | — | — |
| Bermudagrass | 0 | 0 | 90 | 70 | 60 | 60 | 70 | 90 | 50 | 70 | 80 | 0 | 0 | 0 | 20 | 0 | — | 0 | 0 | 0 | 20 | 0 |
| Blackgrass | — | — | — | — | — | — | — | — | — | — | — | — | — | — | — | — | 0 | — | — | — | — | — |
| Surinam grass | 0 | 0 | 40 | 90 | 60 | 30 | 50 | 0 | 0 | 0 | 0 | 0 | 0 | 0 | 0 | 0 | — | 0 | 0 | 20 | 20 | 0 |
| Downy Brome | — | — | — | — | — | — | — | — | — | — | — | — | — | — | — | — | 0 | — | — | — | — | — |
| Canarygrass | — | — | — | — | — | — | — | — | — | — | — | — | — | — | — | — | 0 | — | — | — | — | — |
| Chickweed | — | — | — | — | 100 | — | — | 50 | 50 | 70 | 60 | 0 | 0 | 0 | 0 | 40 | — | 20 | 20 | 70 | 80 | — |
| Cocklebur | 20 | 40 | 30 | 80 | 70 | 90 | 90 | — | 30 | 60 | 30 | 0 | 0 | 0 | 0 | 0 | — | 30 | 20 | 70 | 0 | 80 |
| Corn | 0 | 0 | 20 | 0 | 0 | 0 | 0 | 0 | 0 | 0 | 20 | 0 | 0 | 0 | 0 | 0 | — | 0 | 0 | 50 | 0 | 0 |
| Crabgrass | 40 | 0 | 80 | 70 | 60 | 70 | 70 | 0 | 0 | 30 | 30 | 0 | 0 | 0 | 0 | 0 | — | 0 | 0 | 30 | 20 | 0 |
| Cupgrass, Woolly | 30 | 20 | 70 | 70 | 50 | 50 | 60 | 0 | 0 | 40 | 30 | 0 | 0 | 0 | 0 | 0 | — | 0 | 0 | 30 | 20 | 30 |
| Foxtail, Giant | 20 | 0 | 50 | 90 | 80 | 90 | 80 | 0 | 0 | 30 | 0 | 0 | 0 | 0 | 0 | 0 | — | 0 | 0 | 20 | 20 | 0 |
| Foxtail, Green | — | — | — | — | — | — | — | — | — | — | — | — | — | — | — | — | 30 | — | — | — | — | — |
| Goosegrass | 20 | 0 | 70 | 80 | 50 | 50 | 60 | 20 | 0 | 20 | 0 | 0 | 0 | 0 | 0 | 0 | — | 0 | 0 | 10 | 20 | 0 |
| Johnsongrass | 0 | 0 | — | 50 | 30 | 30 | 30 | 0 | 50 | 20 | 0 | 0 | 0 | 0 | 0 | 0 | — | 0 | 40 | 20 | 0 |
| Kochia | 70 | 100 | 80 | 90 | 80 | 90 | 90 | 70 | 40 | 70 | 70 | 70 | 20 | 60 | 50 | 70 | — | 0 | 50 | 60 | 70 | 90 |
| Lambsquarters | 100 | 100 | 100 | 90 | — | 100 | 90 | 70 | 80 | 90 | 90 | 70 | 20 | 30 | 40 | 80 | — | — | — | 90 | 100 | 80 |
| Morningglory | 70 | 90 | 80 | 100 | — | 100 | 100 | 20 | 60 | — | 0 | 0 | 0 | 0 | 0 | 60 | — | 60 | 80 | 80 | 0 | 90 |

TABLE C-continued

| | | | | | | | | | | | | | | | | | | | | | |
|---|---|---|---|---|---|---|---|---|---|---|---|---|---|---|---|---|---|---|---|---|---|
| Nutsedge | 0 | 0 | 0 | 20 | 0 | 0 | 0 | 0 | 0 | 0 | 0 | 0 | 0 | 0 | 0 | — | 20 | 0 | — | 0 | 0 |
| Pigweed | 70 | 100 | 90 | 80 | 70 | 90 | 70 | 70 | 70 | 90 | 80 | 60 | 0 | 0 | 0 | 70 | — | 40 | 0 | 70 | 70 | 80 |
| Ragweed, Common | — | — | — | 90 | 80 | 90 | 90 | 30 | 50 | 0 | — | 0 | 0 | 0 | 0 | 0 | — | 0 | 0 | 20 | 0 | 90 |
| Ryegrass | — | — | — | — | — | — | — | — | — | — | — | — | — | — | — | — | 0 | — | — | — | — | — |
| Soybean | 60 | 50 | 30 | 90 | 100 | 90 | 100 | 20 | 30 | 20 | 0 | 0 | 0 | 0 | 0 | 0 | — | 60 | 70 | 60 | 0 | 70 |
| Velvetleaf | 20 | 0 | 20 | 70 | 50 | 80 | 80 | 30 | 30 | 40 | 30 | 0 | 0 | 0 | 0 | 0 | — | 20 | 20 | 40 | 0 | 60 |
| Wheat | — | — | — | — | — | — | — | — | — | — | — | — | — | — | — | — | 0 | — | — | — | — | — |
| Wild Oat | — | — | — | — | — | — | — | — | — | — | — | — | — | — | — | — | 0 | — | — | — | — | — |
| Windgrass | — | — | — | — | — | — | — | — | — | — | — | — | — | — | — | — | 0 | — | — | — | — | — |

| | Rate 125 g/ha COMPOUND | | | | | | | | | | | | Rate 62 g/ha COMPOUND | | | | | |
|---|---|---|---|---|---|---|---|---|---|---|---|---|---|---|---|---|---|---|
| | 107 | 109 | 117 | 119 | 120 | 121 | 122 | 131 | 140 | 141 | 142 | 143 | 20 | 21 | 25 | 30 | 36 | 37 |
| Barley, Winter | — | — | 0 | — | — | — | — | — | — | — | — | — | — | — | — | — | — | — |
| Bermudagrass | 0 | 10 | 50 | 0 | 0 | 0 | 0 | 60 | 40 | 60 | 40 | 40 | 60 | 50 | 60 | 70 | 0 | 0 |
| Blackgrass | — | — | 0 | — | — | — | — | — | — | — | — | — | — | — | — | — | — | — |
| Surinam grass | 0 | 0 | 0 | 0 | 0 | 0 | 0 | — | 30 | 40 | 30 | 20 | 0 | 0 | 0 | 0 | 0 | — |
| Downy Brome | — | — | 40 | — | — | — | — | — | — | — | — | — | — | — | — | — | — | — |
| Canarygrass | — | — | 0 | — | — | — | — | — | — | — | — | — | — | — | — | — | — | — |
| Chickweed | 100 | — | — | — | — | — | — | — | 100 | 100 | 100 | 100 | 50 | 50 | 60 | 50 | 0 | 0 |
| Cocklebur | 30 | 60 | 80 | 70 | 30 | 0 | 20 | 0 | 70 | — | 60 | 40 | 30 | 20 | 40 | 20 | 0 | — |
| Corn | 0 | 40 | 0 | 20 | 30 | 0 | 0 | 10 | 0 | 0 | 0 | 0 | 0 | 0 | 0 | 0 | 0 | 0 |
| Crabgrass | 0 | 0 | 0 | 30 | 0 | 40 | 0 | 80 | 70 | 60 | 70 | 40 | 0 | 0 | 20 | 0 | 0 | 0 |
| Cupgrass, Woolly | 0 | 0 | 30 | 0 | 0 | 0 | 20 | 60 | 60 | 50 | 50 | 40 | 0 | 0 | 40 | 0 | 0 | 0 |
| Foxtail, Giant | 0 | 0 | 0 | 0 | 0 | 0 | 0 | 40 | 80 | — | — | 80 | 0 | 0 | 20 | 0 | 0 | 0 |
| Foxtail, Green | — | — | 20 | — | — | — | — | — | — | — | — | — | — | — | — | — | — | — |
| Goosegrass | 0 | 10 | 40 | 0 | 0 | 20 | 0 | 60 | 40 | 40 | 30 | 60 | 0 | 0 | 0 | 0 | 0 | 0 |
| Johnsongrass | 0 | 0 | 0 | 0 | 0 | 0 | 0 | 20 | 30 | 30 | 30 | 10 | 0 | 30 | 0 | 0 | 0 | 0 |
| Kochia | 80 | 90 | 85 | 70 | 80 | 70 | 90 | 80 | 90 | 80 | 90 | 80 | 70 | 40 | 50 | 50 | 60 | 0 |
| Lambsquarters | 100 | 100 | 80 | 90 | 90 | 90 | 100 | 100 | 90 | 100 | 90 | 90 | 70 | 80 | 80 | 80 | 60 | 20 |
| Morningglory | 100 | 100 | 100 | 90 | 80 | 70 | 40 | 70 | 90 | 90 | 100 | 100 | 0 | 50 | 50 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 |
| Pigweed | 50 | 70 | 75 | 70 | 0 | 70 | 60 | 70 | 80 | 70 | 80 | 70 | 60 | 70 | 80 | 80 | 30 | 0 |
| Ragweed, Common | — | 90 | — | — | — | — | — | — | 80 | 80 | 70 | 70 | 0 | 20 | 0 | — | 0 | 0 |
| Ryegrass | — | — | 20 | — | — | — | — | — | — | — | — | — | — | — | — | — | — | — |
| Soybean | 10 | 70 | 70 | 40 | 50 | 60 | 40 | 30 | 80 | 90 | 90 | 70 | 0 | 30 | 0 | 0 | 0 | 0 |
| Velvetleaf | 40 | 70 | 35 | 0 | 0 | 0 | 0 | 20 | 20 | 50 | 70 | 40 | 20 | 30 | 30 | 30 | 0 | 0 |
| Wheat | — | — | 10 | — | — | — | — | — | — | — | — | — | — | — | — | — | — | — |
| Wild Oat | — | — | 30 | — | — | — | — | — | — | — | — | — | — | — | — | — | — | — |
| Windgrass | — | — | 30 | — | — | — | — | — | — | — | — | — | — | — | — | — | — | — |

| | Rate 62 g/ha COMPOUND | | | | | | | | | | | | | | | | | |
|---|---|---|---|---|---|---|---|---|---|---|---|---|---|---|---|---|---|---|
| | 38 | 40 | 68 | 69 | 80 | 81 | 85 | 91 | 106 | 107 | 109 | 117 | 119 | 120 | 121 | 122 | 131 | 140 |
| Barley, Winter | — | — | — | 0 | — | — | — | — | — | — | — | 0 | — | — | — | — | — | — |
| Bermudagrass | 0 | 0 | 0 | — | 0 | 0 | 0 | 20 | 0 | 0 | 0 | 0 | 0 | 0 | 0 | 0 | 20 | 30 |
| Blackgrass | — | — | — | 0 | — | — | — | — | — | — | — | 0 | — | — | — | — | — | — |
| Surinam grass | 0 | 0 | 0 | — | 0 | 0 | 0 | 20 | 0 | 0 | 0 | 0 | 0 | 0 | 0 | 0 | 0 | 30 |
| Downy Brome | — | — | — | 0 | — | — | — | — | — | — | — | 20 | — | — | — | — | — | — |
| Canarygrass | — | — | — | 0 | — | — | — | — | — | — | — | 0 | — | — | — | — | — | — |
| Chickweed | 0 | 0 | 30 | — | 20 | 20 | 20 | 70 | — | 50 | — | — | — | — | — | — | — | 90 |
| Cocklebur | 0 | 0 | 0 | — | 20 | 0 | 40 | 0 | 30 | 0 | 40 | 0 | 50 | 0 | 0 | 20 | 0 | 40 |
| Corn | 0 | 0 | 0 | — | 0 | 0 | 50 | 0 | 0 | 0 | 0 | 0 | 20 | 30 | 0 | 0 | 0 | 0 |
| Crabgrass | 0 | 0 | 0 | — | 0 | 0 | 30 | 20 | 0 | 0 | 0 | 0 | 30 | 0 | 0 | 0 | — | 40 |
| Cupgrass, Woolly | 0 | 0 | 0 | — | 0 | 0 | 30 | 20 | 10 | 0 | 0 | 0 | 0 | 0 | 0 | 0 | 10 | 40 |
| Foxtail, Giant | 0 | 0 | 0 | — | 0 | 0 | 20 | 20 | 0 | 0 | 0 | 0 | 0 | 0 | 0 | 0 | 20 | — |
| Foxtail, Green | — | — | — | 0 | — | — | — | — | — | — | — | 10 | — | — | — | — | — | — |
| Goosegrass | 0 | 0 | 0 | — | 0 | 0 | 10 | 20 | 0 | 0 | 0 | 10 | 0 | 0 | 0 | 0 | 40 | 20 |
| Johnsongrass | 0 | 0 | 0 | — | 0 | 0 | 30 | 20 | 0 | 0 | 0 | 0 | 0 | 0 | 0 | 0 | 0 | 30 |
| Kochia | 60 | 20 | 50 | — | 0 | 50 | 40 | 70 | 70 | 70 | 80 | 80 | 60 | 50 | 70 | 90 | 60 | 40 |
| Lambsquarters | 30 | 20 | 60 | — | 10 | 60 | 70 | 100 | 80 | 50 | 70 | 75 | 90 | 50 | 90 | 100 | 100 | 80 |
| Morningglory | 0 | 0 | 50 | — | 50 | 60 | 60 | 0 | 90 | 60 | 100 | 100 | 80 | 0 | 50 | 20 | — | 60 |
| Nutsedge | 0 | 0 | 0 | — | 0 | 0 | 10 | 0 | 0 | 0 | 0 | 0 | 0 | 0 | 0 | 0 | 0 | 0 |
| Pigweed | 0 | 0 | 60 | — | 20 | 0 | 60 | 70 | 70 | 50 | 70 | 60 | 40 | 0 | 20 | 40 | 20 | 30 |
| Ragweed, Common | 0 | 0 | 0 | — | 0 | 0 | 0 | 0 | — | 0 | — | — | — | — | — | — | — | 50 |
| Ryegrass | — | — | — | 0 | — | — | — | — | — | — | — | 10 | — | — | — | — | — | — |
| Soybean | 0 | 0 | 0 | — | 50 | 60 | 60 | 0 | 70 | 0 | 70 | 50 | 40 | 30 | 50 | 40 | 20 | 70 |
| Velvetleaf | 0 | 0 | 0 | — | 20 | 20 | 40 | 0 | 60 | 30 | 40 | 20 | 0 | 0 | 0 | 0 | 20 | 20 |
| Wheat | — | — | — | 0 | — | — | — | — | — | — | — | 10 | — | — | — | — | — | — |
| Wild Oat | — | — | — | 0 | — | — | — | — | — | — | — | 30 | — | — | — | — | — | — |
| Windgrass | — | — | — | 0 | — | — | — | — | — | — | — | 20 | — | — | — | — | — | — |

TABLE C-continued

|  | Rate 62 g/ha COMPOUND | | | Rate 31 g/ha COMPOUND | | | | | |
|---|---|---|---|---|---|---|---|---|---|
|  | 141 | 142 | 143 | 21 | 36 | 37 | 81 | 106 | 109 |
| Barley, Winter | — | — | — |  |  |  |  |  |  |
| Bermudagrass | 40 | 30 | 20 | 50 | 0 | 0 | 0 | 0 | 0 |
| Blackgrass | — | — | — |  |  |  |  |  |  |
| Surinam grass | 20 | 20 | 20 | 0 | 0 | 0 | 0 | 0 | 0 |
| Downy Brome | — | — | — |  |  |  |  |  |  |
| Canarygrass | — | — | — |  |  |  |  |  |  |
| Chickweed | 90 | — | 100 | 30 | 0 | 0 | 0 | — | — |
| Cocklebur | 70 | 30 | 20 | 20 | 0 | 0 | 0 | 30 | 0 |
| Corn | 0 | 0 | 0 | 0 | 0 | 0 | 0 | 0 | 0 |
| Crabgrass | 60 | 40 | 40 | 0 | 0 | 0 | 0 | 0 | 0 |
| Cupgrass, Woolly | 30 | 40 | 40 | 0 | 0 | 0 | 0 | 0 | 0 |
| Foxtail, Giant | — | 90 | 30 | 0 | 0 | 0 | 0 | 0 | 0 |
| Foxtail, Green | — | — | — |  |  |  |  |  |  |
| Goosegrass | 20 | 30 | 30 | 0 | 0 | 0 | 0 | 0 | 0 |
| Johnsongrass | 20 | 20 | 0 | 0 | 0 | 0 | 0 | 0 | 0 |
| Kochia | 10 | 40 | 40 | 30 | 20 | 0 | 40 | 70 | 80 |
| Lambsquarters | 70 | 80 | 90 | 70 | 50 | 20 | 0 | 80 | 70 |
| Morningglory | 70 | 20 | 90 | 0 | 0 | 0 | 50 | 90 | 60 |
| Nutsedge | 0 | 0 | 0 | 0 | 0 | 0 | 0 | 0 | 0 |
| Pigweed | 70 | 80 | 70 | 50 | 30 | 0 | 0 | 70 | 70 |
| Ragweed, Common | 20 | 50 | 20 | 0 | 0 | 0 | 0 | — | 0 |
| Ryegrass | — | — | — |  |  |  |  |  |  |
| Soybean | 90 | 60 | 60 | 0 | 0 | 0 | 50 | 70 | 60 |
| Velvetleaf | 50 | 50 | 40 | 20 | 0 | 0 | 20 | 30 | 20 |
| Wheat | — | — | — |  |  |  |  |  |  |
| Wild Oat | — | — | — |  |  |  |  |  |  |
| Windgrass | — | — | — |  |  |  |  |  |  |

Preemergence

Rate 500 g/ha COMPOUND

|  | 8 | 20 | 22 | 25 | 30 | 31 | 32 | 33 | 38 | 39 | 40 | 44 | 45 | 49 | 50 | 51 | 52 | 56 |
|---|---|---|---|---|---|---|---|---|---|---|---|---|---|---|---|---|---|---|
| Bermudagrass | 100 | 100 | 100 | 100 | 100 | 100 | 100 | 100 | 100 | 100 | 100 | 100 | 100 | 100 | 100 | 100 | 100 | 100 |
| Surinam grass | 60 | 40 | 90 | 80 | 60 | 70 | 90 | 100 | 90 | 80 | 100 | 90 | 70 | 80 | 50 | 70 | 50 | 0 |
| Cocklebur | 0 | 50 | 0 | 70 | 80 | 30 | 0 | 0 | 60 | 0 | 60 | 100 | 90 | 20 | 0 | 0 | 30 | 100 |
| Corn | 0 | 30 | 30 | 50 | 50 | 60 | 60 | 40 | 0 | 70 | 90 | 70 | 0 | 0 | 0 | 0 | 40 | 0 |
| Crabgrass | 100 | 100 | 100 | 100 | 100 | 100 | 100 | 100 | 100 | 100 | 100 | 100 | 100 | 100 | 100 | 100 | 100 | 100 |
| Cupgrass, Woolly | 80 | 100 | 100 | 100 | 100 | 100 | 90 | 100 | 90 | 100 | 100 | 100 | 100 | 100 | 90 | 100 | 100 | 70 |
| Foxtail, Giant | 100 | 0 | 100 | 90 | 100 | 100 | 100 | 30 | 100 | 100 | 100 | 90 | 90 | 100 | 100 | 100 | 30 | 90 |
| Goosegrass | 100 | 100 | 100 | 100 | 100 | 100 | 100 | 100 | 100 | 100 | 100 | 100 | 100 | 100 | 100 | 100 | 100 | 100 |
| Johnsongrass | 0 | 100 | 40 | 100 | 100 | 100 | 90 | 100 | 90 | 90 | 100 | 100 | 100 | 90 | 90 | 90 | 100 | 0 |
| Kochia | 70 | 100 | 100 | 100 | — | — | — | 100 | 100 | 90 | 100 | 100 | 100 | 100 | 20 | 80 | 60 | 100 |
| Lambsquarters | 100 | 100 | 100 | 100 | 100 | 100 | 100 | 100 | 100 | 100 | 100 | 100 | 100 | 100 | 70 | 100 | 100 | 100 |
| Morningglory | 30 | 40 | 0 | 90 | 80 | 50 | 80 | 0 | 0 | 0 | 0 | 40 | 0 | 30 | 30 | 20 | 30 | 0 |
| Nightshade | 0 | 90 | 80 | 100 | 100 | 100 | 100 | 100 | 90 | 0 | 70 | 30 | 40 | 90 | 60 | 60 | 50 | 20 |
| Nutsedge | 0 | 50 | 20 | 0 | 40 | 90 | 60 | 0 | 70 | 40 | 60 | 100 | 100 | 0 | 70 | 30 | 40 | 0 |
| Pigweed | 100 | 60 | 100 | 90 | 100 | 90 | 80 | 100 | 30 | 100 | 100 | 100 | 30 | 100 | 90 | 30 | 100 | 100 |
| Ragweed, Common | 80 | — | — | 100 | 100 | 100 | 100 | 30 | 100 | 20 | 70 | 50 | 60 | 90 | 40 | 0 | 50 | 20 |
| Soybean | 20 | 60 | 40 | 60 | 70 | 0 | 60 | 0 | 0 | 0 | 40 | 30 | 0 | 80 | 40 | 30 | 60 | 0 |
| Sunflower | 30 | 70 | 0 | 70 | 100 | 40 | 70 | 60 | 60 | 0 | 40 | 30 | 70 | 80 | 60 | 30 | 50 | 0 |
| Velvetleaf | 20 | 20 | 0 | 20 | 30 | 30 | 40 | 0 | 0 | 20 | 50 | 60 | 30 | 40 | 0 | 30 | 0 | 20 |

Rate 500 g/ha COMPOUND

|  | 62 | 63 | 64 | 67 | 70 | 71 | 72 | 75 | 76 | 79 | 80 | 82 | 83 | 84 | 85 | 86 | 87 | 88 |
|---|---|---|---|---|---|---|---|---|---|---|---|---|---|---|---|---|---|---|
| Bermudagrass | 100 | 100 | 100 | 100 | 100 | 100 | 100 | 100 | 100 | 100 | 100 | 100 | 100 | 100 | 100 | 100 | 100 | 100 |
| Surinam grass | 80 | 100 | 100 | 100 | 80 | 90 | 50 | 60 | 100 | 100 | 100 | 100 | 100 | 80 | 100 | 30 | 100 | 100 |
| Cocklebur | 0 | 30 | 30 | 50 | 20 | 30 | 70 | 0 | 20 | 30 | 100 | 40 | 0 | 0 | 60 | 0 | 0 | 20 |
| Corn | 20 | 40 | 40 | 100 | 20 | 30 | 0 | 0 | 80 | 0 | 60 | 30 | 10 | 0 | 80 | 30 | 80 | 100 |
| Crabgrass | 100 | 100 | 100 | 100 | 100 | 100 | 100 | 100 | 100 | 100 | 100 | 100 | 100 | 100 | 100 | 100 | 100 | 100 |
| Cupgrass, Woolly | 90 | 100 | 100 | 100 | 100 | 100 | 70 | 100 | 100 | 100 | 100 | 100 | 100 | 100 | 100 | 100 | 100 | 100 |
| Foxtail, Giant | 100 | 100 | 30 | 100 | 100 | 100 | 90 | 100 | 90 | 0 | 50 | 100 | 0 | 100 | 100 | 100 | 100 | 100 |
| Goosegrass | 100 | 100 | 100 | 100 | 100 | 100 | 90 | 100 | 100 | 100 | 100 | 100 | 100 | 100 | 100 | 100 | 100 | 100 |
| Johnsongrass | 100 | 100 | 100 | 100 | 70 | 40 | 40 | 30 | 100 | 0 | 70 | 60 | 30 | 0 | 100 | 50 | 100 | 100 |
| Kochia | 90 | 100 | 100 | 100 | 100 | 100 | 100 | — | 100 | 100 | 100 | 100 | 100 | 100 | 100 | 100 | 100 | 100 |
| Lambsquarters | — | — | — | 100 | 100 | — | 100 | 100 | 100 | 100 | 100 | 100 | 100 | 100 | 100 | 100 | 100 | 100 |
| Morningglory | 0 | 40 | 60 | 20 | 40 | 0 | 100 | 0 | 30 | 70 | 100 | 80 | 0 | 20 | 100 | — | 0 | 30 |
| Nightshade | 0 | 100 | 90 | 60 | 70 | 30 | 60 | 50 | 60 | 90 | 100 | 100 | 100 | 100 | 100 | 10 | 90 | 80 |
| Nutsedge | 70 | 100 | 50 | 20 | 0 | 70 | 20 | 50 | 20 | 0 | 0 | 40 | 0 | 0 | 90 | 0 | 20 | 10 |

TABLE C-continued

| | | | | | | | | | | | | | | | | | | |
|---|---|---|---|---|---|---|---|---|---|---|---|---|---|---|---|---|---|---|
| Pigweed | 100 | 100 | 100 | 80 | 100 | 100 | 100 | 100 | 100 | 100 | 40 | 0 | 100 | 90 | 100 | 100 | 100 | 100 |
| Ragweed, Common | 0 | 90 | 90 | 70 | 100 | 30 | 90 | 60 | 0 | 100 | 100 | 100 | 100 | 0 | 100 | 0 | 0 | 20 |
| Soybean | 0 | 40 | 30 | 0 | 20 | 0 | 20 | 50 | 0 | 50 | 100 | 60 | 10 | 0 | 100 | 0 | 30 | 30 |
| Sunflower | 0 | 60 | 60 | 30 | 60 | 20 | 60 | 50 | 30 | 60 | 60 | 80 | 70 | 30 | 70 | 20 | 30 | 20 |
| Velvetleaf | 20 | 50 | 50 | 30 | 10 | 0 | 40 | 0 | 50 | 50 | 100 | 30 | 40 | 0 | 100 | 70 | 20 | 20 |

Rate 500 g/ha
COMPOUND

| | 89 | 91 | 92 | 93 | 95 | 96 | 99 | 100 | 107 | 111 | 117 | 118 | 119 | 120 | 121 | 122 | 127 | 128 |
|---|---|---|---|---|---|---|---|---|---|---|---|---|---|---|---|---|---|---|
| Bermudagrass | 100 | 100 | 90 | 100 | 100 | 100 | 100 | 100 | 100 | 100 | 100 | 100 | 100 | 100 | 100 | 100 | 100 | 100 |
| Surinam grass | 65 | 80 | 35 | 70 | 100 | 100 | 90 | 30 | 0 | 10 | 100 | 50 | 100 | 100 | 100 | 60 | 100 | 100 |
| Cocklebur | 10 | 10 | 20 | 20 | 0 | 30 | 0 | 0 | 0 | 0 | 85 | 0 | 50 | 30 | 100 | 0 | 20 | 70 |
| Corn | 30 | 10 | 40 | 30 | 40 | 50 | 20 | 20 | 10 | 0 | 50 | 35 | 90 | 60 | 90 | 0 | 30 | 60 |
| Crabgrass | 100 | 100 | 100 | 100 | 100 | 100 | 100 | 100 | 100 | 100 | 100 | 100 | 100 | 100 | 100 | 100 | 100 | 100 |
| Cupgrass, Woolly | 70 | 100 | 50 | 80 | 100 | 100 | 100 | 100 | 80 | 60 | 100 | 100 | 100 | 100 | 100 | 100 | 100 | 100 |
| Foxtail, Giant | 100 | 100 | 100 | 60 | 100 | 100 | 70 | 100 | 100 | 80 | 100 | 100 | 100 | 100 | 100 | 0 | 100 | 100 |
| Goosegrass | 100 | 100 | 100 | 100 | 100 | 100 | 100 | 100 | 100 | 100 | 100 | 100 | 100 | 100 | 100 | 100 | 100 | 100 |
| Johnsongrass | 100 | 100 | 100 | 10 | 90 | 70 | 90 | 100 | 50 | 25 | 90 | 100 | 100 | 100 | 100 | 20 | 0 | 100 |
| Kochia | 100 | 100 | 100 | 80 | 100 | 100 | 100 | 100 | 100 | 0 | 100 | 100 | 100 | 100 | 100 | 100 | 0 | 100 |
| Lambsquarters | 100 | 100 | 100 | 100 | 100 | 100 | 100 | 100 | 100 | 100 | 100 | 100 | 100 | 100 | 100 | 100 | 100 | 100 |
| Morningglory | 0 | 0 | 0 | 20 | 0 | 20 | 20 | 0 | 100 | 0 | 100 | 100 | 100 | 100 | 70 | — | 20 | 80 |
| Nightshade | 30 | 10 | 80 | 10 | 45 | 80 | 10 | 0 | 90 | 0 | 100 | 100 | 100 | 100 | 100 | 90 | 100 | 100 |
| Nutsedge | 0 | 0 | 0 | 0 | 70 | 70 | 90 | 0 | 0 | 0 | 0 | 0 | 30 | 100 | 0 | 0 | 0 | 100 |
| Pigweed | 100 | 100 | 50 | 80 | 60 | 50 | 70 | 100 | 100 | 50 | 30 | 100 | 100 | 70 | 100 | 0 | 0 | 100 |
| Ragweed, Common | 0 | 0 | 40 | 0 | 10 | 70 | 0 | 0 | 70 | 0 | 100 | 100 | 100 | 100 | 100 | 100 | 10 | 100 |
| Soybean | 30 | 0 | 100 | 20 | 30 | 70 | 0 | 0 | 60 | 0 | 100 | 90 | 100 | 100 | 100 | 0 | 0 | — |
| Sunflower | 60 | 10 | 55 | 20 | 10 | 50 | 0 | 0 | 70 | 0 | 65 | 70 | 100 | 100 | 100 | 70 | 30 | 100 |
| Velvetleaf | 10 | 0 | 0 | 20 | 0 | 40 | 0 | 0 | 100 | 0 | 100 | 100 | 100 | 100 | 100 | 20 | 30 | 50 |

| | Rate 500 g/ha COMPOUND | | | | | | | | | | | | Rate 250 g/ha COMPOUND | | | | | |
|---|---|---|---|---|---|---|---|---|---|---|---|---|---|---|---|---|---|---|
| | 129 | 130 | 131 | 132 | 133 | 134 | 140 | 141 | 142 | 143 | 144 | 145 | 8 | 20 | 22 | 25 | 27 | 28 |
| Bermudagrass | 100 | 100 | 100 | 100 | 100 | 100 | 100 | 100 | 100 | 100 | 100 | 100 | 70 | 100 | 100 | 100 | 100 | 100 |
| Surinam grass | 100 | 100 | 100 | 100 | 100 | 100 | 100 | 100 | 100 | 70 | 90 | 100 | 50 | 0 | 60 | 80 | 80 | 60 |
| Cocklebur | 0 | 0 | 30 | 0 | 0 | 0 | — | 100 | 60 | 55 | 60 | 60 | 0 | 0 | 0 | 100 | 0 | 0 |
| Corn | 30 | 100 | 100 | 90 | 100 | 100 | 30 | 30 | 10 | 30 | 60 | 40 | 0 | 30 | 20 | 20 | 30 | 30 |
| Crabgrass | 100 | 100 | 100 | 100 | 100 | 100 | 100 | 100 | 100 | 100 | 100 | 100 | 90 | 100 | 100 | 100 | 100 | 100 |
| Cupgrass, woolly | 100 | 100 | 100 | 100 | 100 | 100 | 100 | 100 | 100 | 100 | 100 | 100 | 50 | 90 | 100 | 100 | 100 | 100 |
| Foxtail, Giant | 100 | 100 | 100 | 100 | 100 | 100 | 100 | 100 | 100 | 100 | 100 | 100 | 90 | 100 | 0 | 100 | 0 | 0 |
| Goosegrass | 100 | 100 | 100 | 100 | 100 | 100 | 100 | 100 | 100 | 100 | 100 | 100 | 90 | 100 | 100 | 100 | 100 | 100 |
| Johnsongrass | 100 | 100 | 100 | 100 | 100 | 100 | 100 | 100 | 100 | 90 | 100 | 90 | 0 | 50 | 40 | 90 | 50 | 70 |
| Kochia | 100 | 100 | 100 | 100 | 100 | 100 | 100 | 100 | 100 | 100 | 100 | 100 | 20 | 100 | 100 | 100 | 100 | 100 |
| Lambsquarters | 100 | 100 | 100 | 100 | 100 | 100 | 100 | 100 | 100 | 100 | 100 | 100 | 100 | 100 | 100 | 100 | 100 | 100 |
| Morningglory | 0 | — | 90 | 0 | 30 | 0 | 100 | 100 | 100 | 100 | 30 | — | 30 | 40 | 0 | 100 | 30 | 0 |
| Nightshade | 60 | 100 | 100 | 20 | 90 | 90 | 100 | 100 | 100 | 100 | 100 | 90 | 0 | 90 | 40 | 90 | 0 | 90 |
| Nutsedge | 90 | 100 | 100 | 90 | 100 | 100 | 70 | 50 | 20 | 0 | 0 | 0 | 0 | 50 | 0 | 40 | 80 | 50 |
| Pigweed | 100 | 100 | 100 | 100 | 100 | 100 | 100 | 100 | 100 | 100 | 100 | 100 | 100 | 100 | 50 | 90 | 100 | 50 |
| Ragweed, Common | 100 | 100 | 100 | 0 | 0 | 40 | 100 | 100 | 100 | 100 | 50 | 20 | — | — | — | 70 | — | — |
| Soybean | 20 | 60 | 40 | 30 | 0 | 20 | 100 | 100 | 100 | 100 | 70 | 60 | 20 | 60 | 40 | 50 | 50 | 40 |
| Sunflower | 10 | 70 | 20 | — | 0 | 20 | 90 | 100 | 80 | 90 | 70 | 50 | 0 | 60 | 0 | 70 | 20 | 40 |
| Velvetleaf | 10 | 60 | 70 | 0 | 30 | 20 | 90 | 100 | 100 | 100 | 20 | 20 | 20 | 20 | 0 | 70 | 0 | 0 |

Rate 250 g/ha
COMPOUND

| | 30 | 31 | 32 | 33 | 34 | 36 | 37 | 38 | 39 | 40 | 44 | 45 | 49 | 50 | 51 | 52 | 56 | 62 |
|---|---|---|---|---|---|---|---|---|---|---|---|---|---|---|---|---|---|---|
| Bermudagrass | 100 | 100 | 100 | 100 | 100 | 100 | 100 | 100 | 100 | 100 | 100 | 100 | 100 | 100 | 100 | 100 | 90 | 100 |
| Surinam grass | 40 | 60 | 80 | 90 | 0 | 100 | 90 | 0 | 0 | 90 | 80 | 40 | 70 | 50 | 70 | 30 | 0 | 60 |
| Cocklebur | 0 | 30 | 0 | 0 | 0 | 30 | 0 | 20 | — | — | 30 | 20 | 0 | 0 | 0 | — | 0 | 0 |
| Corn | 50 | 40 | 50 | 0 | 0 | 80 | 40 | 0 | 0 | 50 | 0 | 0 | 0 | 0 | 0 | 20 | 0 | 0 |
| Crabgrass | 100 | 100 | 100 | 100 | 100 | 100 | 100 | 100 | 100 | 100 | 100 | 100 | 100 | 100 | 100 | 100 | 90 | 100 |
| Cupgrass, Woolly | 90 | 90 | 90 | 100 | 80 | 100 | 100 | 0 | 90 | 90 | 100 | 70 | 70 | 90 | 80 | 60 | 0 | 90 |
| Foxtail, Giant | 90 | 60 | 100 | 0 | 50 | 100 | 100 | 100 | 0 | 100 | 100 | 40 | 100 | 20 | 100 | | | |
| Goosegrass | 100 | 100 | 100 | 100 | 100 | 100 | 100 | 100 | 100 | 100 | 100 | 100 | 100 | 100 | 100 | 100 | 90 | 100 |
| Johnsongrass | 90 | 90 | 90 | 0 | 0 | 100 | 90 | 90 | 70 | 100 | 90 | 50 | 50 | 70 | 60 | 90 | 0 | 60 |
| Kochia | — | — | — | 100 | 0 | 100 | 90 | 90 | 70 | 100 | 90 | 100 | 0 | 50 | 30 | 100 | 0 | 90 |
| Lambsquarters | 100 | 100 | 100 | 100 | 100 | 100 | 100 | 100 | 100 | 100 | 100 | 100 | 70 | 100 | 100 | 100 | | — |
| Morningglory | 80 | 40 | 50 | 0 | 0 | 50 | 30 | 0 | 0 | 0 | 20 | 0 | 0 | 30 | — | 0 | 0 | 0 |
| Nightshade | 100 | 100 | 90 | 0 | 0 | 90 | 0 | 60 | 0 | 40 | 0 | 0 | 50 | 0 | 30 | 0 | 0 | 0 |
| Nutsedge | 40 | 70 | 50 | 0 | 0 | 30 | 30 | 0 | 0 | 50 | 60 | 60 | 0 | 0 | 30 | 20 | 0 | 20 |
| Pigweed | 90 | 80 | 70 | 60 | 40 | 100 | 100 | 0 | 0 | 0 | 20 | 0 | 100 | 20 | 100 | 30 | 0 | 0 |
| Ragweed, Common | 90 | 90 | 90 | 0 | 0 | 50 | 60 | 40 | 0 | 30 | 50 | 30 | 30 | 40 | 0 | 40 | 0 | 0 |
| Soybean | 70 | 0 | 60 | 0 | 0 | 50 | 50 | 0 | 0 | 40 | 30 | 0 | 50 | 0 | 20 | 20 | 0 | 0 |

TABLE C-continued

| | | | | | | | | | | | | | | | | | | |
|---|---|---|---|---|---|---|---|---|---|---|---|---|---|---|---|---|---|---|
| Sunflower | 80 | 40 | 70 | 30 | 0 | 30 | 60 | 60 | 0 | 30 | 20 | 20 | 30 | 30 | 30 | 0 | 0 | 0 |
| Velvetleaf | 0 | 30 | 0 | 0 | 0 | 40 | 20 | 20 | 0 | 30 | 20 | 20 | 30 | 0 | 30 | 0 | 0 | 0 |

Rate 250 g/ha
COMPOUND

| | 63 | 64 | 67 | 70 | 71 | 72 | 73 | 75 | 76 | 79 | 80 | 81 | 82 | 83 | 84 | 85 | 86 | 87 |
|---|---|---|---|---|---|---|---|---|---|---|---|---|---|---|---|---|---|---|
| Bermudagrass | 100 | 100 | 100 | 100 | 100 | 90 | 100 | 100 | 100 | 100 | 100 | 100 | 100 | 100 | 100 | 100 | 90 | 100 |
| Surinam grass | 70 | 90 | 100 | 70 | 50 | 80 | 70 | 60 | 80 | 60 | 100 | 100 | 70 | 90 | 30 | 100 | 20 | 100 |
| Cocklebur | 30 | 20 | 20 | 0 | 30 | 10 | 80 | 0 | 20 | 0 | 0 | 20 | 20 | 30 | 0 | 60 | 0 | 0 |
| Corn | 20 | 30 | 0 | 0 | 0 | 0 | 0 | 0 | 20 | 0 | 0 | 0 | 10 | 0 | 0 | 60 | 0 | 70 |
| Crabgrass | 100 | 100 | 100 | 100 | 100 | 100 | 100 | 100 | 100 | 100 | 100 | 100 | 100 | 100 | 100 | 100 | 100 | 100 |
| Cupgrass, Woolly | 60 | 90 | 100 | 100 | 100 | 80 | 100 | 100 | 100 | 100 | 100 | 100 | 90 | 100 | 90 | 100 | 90 | 100 |
| Foxtail, Giant | 100 | 100 | 70 | 100 | 0 | 70 | 100 | 70 | 20 | 0 | 40 | 100 | 100 | 60 | 100 | 100 | 80 | 100 |
| Goosegrass | 100 | 100 | 100 | 100 | 100 | 80 | 100 | 100 | 100 | 100 | 100 | 100 | 100 | 100 | 90 | 100 | 100 | 100 |
| Johnsongrass | 100 | 90 | 100 | 50 | 0 | 0 | 50 | 30 | 40 | 0 | 60 | 20 | 50 | 30 | 0 | 80 | 40 | 100 |
| Kochia | 100 | 100 | 90 | 100 | 100 | 90 | 100 | 100 | 100 | 100 | 100 | 100 | 100 | 90 | 100 | 100 | 100 | 100 |
| Lambsquarters | — | — | 100 | 100 | — | 100 | — | 100 | 100 | 100 | 100 | 100 | 100 | 100 | 100 | 100 | 100 | 100 |
| Morningglory | 30 | 40 | 0 | 0 | 0 | 10 | 100 | 0 | 30 | 30 | 100 | 20 | 20 | 0 | 20 | 90 | 0 | 0 |
| Nightshade | 60 | 90 | 80 | 70 | 30 | 30 | 100 | 0 | 40 | 50 | 100 | 100 | 30 | 60 | 100 | 100 | 0 | 60 |
| Nutsedge | 20 | 50 | 0 | 0 | 70 | 20 | 50 | 50 | 20 | 0 | 0 | 0 | 10 | 0 | 0 | 70 | 0 | 20 |
| Pigweed | 100 | 100 | 80 | 0 | 100 | 0 | 40 | 100 | 0 | 20 | 0 | 100 | 100 | 100 | 100 | 100 | 0 | 100 |
| Ragweed, Common | 50 | 80 | 70 | 80 | 0 | 70 | 100 | 0 | 0 | 100 | 100 | 100 | 50 | 0 | 0 | 100 | 0 | 0 |
| Soybean | 0 | 20 | 0 | 20 | 0 | 0 | 70 | 0 | 0 | 0 | 0 | 50 | 100 | 0 | 30 | 0 | 40 | 0 | 20 |
| Sunflower | 40 | 50 | 0 | 60 | 0 | 20 | 70 | 0 | 30 | 50 | 60 | 0 | 70 | 0 | 30 | 70 | 20 | 20 |
| Velvetleaf | 30 | 20 | 0 | 0 | 0 | 10 | 60 | 0 | 20 | 20 | 70 | 80 | 10 | 0 | 0 | 80 | 0 | 10 |

Rate 250 g/ha
COMPOUND

| | 88 | 89 | 90 | 91 | 92 | 93 | 95 | 96 | 99 | 100 | 101 | 106 | 107 | 109 | 111 | 117 | 118 | 119 |
|---|---|---|---|---|---|---|---|---|---|---|---|---|---|---|---|---|---|---|
| Bermudagrass | 100 | 90 | 100 | 100 | 85 | 100 | 100 | 100 | 100 | 100 | 100 | 100 | 100 | 100 | 100 | 100 | 100 | 100 |
| Surinam grass | 70 | 30 | 40 | 30 | 20 | 30 | 50 | 100 | 0 | 0 | 40 | 100 | 0 | 90 | 0 | 75 | 30 | 100 |
| Cocklebur | 20 | 10 | 0 | 0 | 20 | 0 | 0 | 30 | 0 | 0 | 50 | 100 | 0 | 30 | 0 | 50 | 0 | 20 |
| Corn | 70 | 30 | 10 | 10 | 30 | 0 | 40 | 40 | 0 | 20 | 60 | 40 | 0 | 0 | 0 | 45 | 10 | 60 |
| Crabgrass | 100 | 100 | 100 | 100 | 100 | 100 | 100 | 100 | 100 | 100 | 100 | 100 | 100 | 100 | 100 | 100 | 100 | 100 |
| Cupgrass, Woolly | 100 | 40 | 60 | 90 | 50 | 70 | 100 | 100 | 10 | 20 | 100 | 100 | 80 | 100 | 60 | 100 | 100 | 100 |
| Foxtail, Giant | 100 | 0 | 40 | 30 | 100 | 20 | 0 | 0 | 20 | 40 | 100 | 100 | 90 | 30 | 100 | 100 | 100 | 90 |
| Goosegrass | 100 | 100 | 100 | 100 | 100 | 100 | 100 | 100 | 90 | 100 | 100 | 100 | 80 | 100 | 100 | 100 | 100 | 100 |
| Johnsongrass | 40 | 70 | 100 | 90 | 70 | 10 | 60 | 50 | 0 | 90 | 90 | 100 | 50 | 50 | 0 | 50 | 70 | 100 |
| Kochia | 100 | 90 | 80 | 90 | 70 | 30 | 100 | 100 | 90 | 90 | 0 | 100 | 85 | 100 | 0 | 100 | 100 | 100 |
| Lambsquarters | 100 | 100 | 100 | 100 | 100 | 90 | 100 | 100 | 100 | 100 | 100 | 100 | 100 | 100 | 100 | 100 | 100 | 100 |
| Morningglory | 30 | 0 | 0 | 0 | 0 | 0 | 0 | 20 | 20 | 0 | 100 | 100 | 0 | 100 | 0 | 100 | 90 | 100 |
| Nightshade | 80 | 0 | 0 | 0 | 20 | 0 | 0 | 60 | 0 | 0 | 100 | 100 | 90 | 100 | 0 | 100 | 100 | 100 |
| Nutsedge | 0 | 0 | 0 | 0 | 0 | 0 | — | 10 | 0 | 0 | 0 | 100 | 0 | 0 | 0 | 0 | 0 | 30 |
| Pigweed | 40 | 50 | 100 | 0 | 100 | 20 | 0 | 0 | 20 | 20 | 10 | 90 | 0 | 80 | 20 | 100 | 100 | 90 |
| Ragweed, Common | 0 | 0 | 0 | 0 | 0 | 0 | 0 | 40 | 0 | 0 | 100 | 100 | 60 | 100 | 0 | 100 | 80 | 100 |
| Soybean | 10 | 0 | 0 | 0 | 30 | 0 | 0 | 50 | 0 | 0 | 50 | 100 | 40 | 90 | 0 | 100 | 65 | 100 |
| Sunflower | 20 | 0 | 10 | 0 | 40 | 0 | 0 | 50 | 0 | 0 | 30 | 90 | 40 | 90 | 0 | 60 | 60 | 40 |
| Velvetleaf | 10 | 0 | 0 | 0 | 0 | 0 | 0 | 30 | 0 | 0 | 90 | 100 | 50 | 100 | 0 | 100 | 100 | 100 |

Rate 250 g/ha
COMPOUND

| | 120 | 121 | 122 | 124 | 127 | 128 | 129 | 130 | 131 | 132 | 133 | 134 | 138 | 140 | 141 | 142 | 143 | 144 |
|---|---|---|---|---|---|---|---|---|---|---|---|---|---|---|---|---|---|---|
| Bermudagrass | 100 | 100 | 100 | 100 | 100 | 100 | 100 | 100 | 100 | 100 | 100 | 100 | 100 | 100 | 100 | 100 | 100 | 100 |
| Surinam grass | 100 | 100 | 20 | 10 | 20 | 100 | 90 | 100 | 100 | 100 | 100 | 100 | 100 | 90 | 20 | 50 | 70 | 0 |
| Cocklebur | 30 | 50 | 0 | 0 | 0 | 40 | 0 | 0 | 30 | 0 | 0 | 0 | 0 | 90 | 70 | 30 | 50 | 60 |
| Corn | 20 | 70 | 0 | 0 | 30 | 40 | 30 | 90 | 100 | 70 | 100 | 100 | 30 | 30 | 30 | 0 | 30 | 50 |
| Crabgrass | 100 | 100 | 100 | 100 | 100 | 100 | 100 | 100 | 100 | 100 | 100 | 100 | 100 | 100 | 100 | 100 | 100 | 100 |
| Cupgrass, Woolly | 100 | 100 | 100 | 60 | 90 | 100 | 100 | 100 | 100 | 100 | 100 | 100 | 100 | 100 | 100 | 100 | 100 | 100 |
| Foxtail, Giant | 60 | 60 | 0 | 85 | 100 | 90 | 80 | 100 | 100 | 100 | 100 | 100 | 100 | 100 | 100 | 100 | 100 | 100 |
| Goosegrass | 100 | 100 | 100 | 60 | 100 | 100 | 100 | 100 | 100 | 100 | 100 | 100 | 100 | 100 | 100 | 100 | 100 | 100 |
| Johnsongrass | 100 | 100 | 0 | 30 | 100 | 100 | 100 | 100 | 80 | 100 | 100 | 100 | 40 | 100 | 0 | 100 | 90 | 100 |
| Kochia | 100 | 100 | 100 | 90 | 0 | 100 | 100 | 100 | 100 | 100 | 100 | 100 | 100 | 100 | 100 | 100 | 100 | 100 |
| Lambsquarters | 100 | 100 | 100 | 100 | 100 | 100 | 100 | 100 | 100 | 100 | 100 | 100 | 100 | 100 | 100 | 100 | 100 | 100 |
| Morningglory | 100 | 50 | 100 | 0 | 0 | 70 | — | 90 | 90 | 0 | 20 | 0 | 80 | 100 | 100 | 100 | 0 | 30 |
| Nightshade | 100 | 100 | 30 | 100 | 0 | 90 | 10 | 100 | 100 | 20 | 20 | 30 | 90 | 100 | 100 | 100 | 100 | 100 |
| Nutsedge | 100 | 0 | 0 | 0 | 0 | 100 | 50 | 100 | 90 | 0 | 90 | 90 | 40 | 60 | 0 | 0 | 0 | 0 |
| Pigweed | 50 | 60 | 20 | 50 | 0 | 80 | 60 | 100 | 100 | 70 | 100 | 100 | 50 | 100 | 100 | 100 | 100 | 100 |
| Ragweed, Common | 100 | 90 | 20 | 0 | 10 | 100 | 100 | 100 | 0 | 0 | 0 | 0 | 30 | 100 | 100 | 100 | 100 | 30 |
| Soybean | 80 | 90 | 0 | 0 | 0 | 60 | 20 | 40 | 40 | 20 | 0 | 0 | 100 | 100 | 100 | 0 | 80 | 70 |
| Sunflower | 100 | 50 | 0 | 0 | 0 | 100 | 10 | 70 | 20 | 20 | 0 | 0 | 50 | 60 | 40 | 80 | 80 | 40 |
| Velvetleaf | 100 | 100 | 20 | 0 | 10 | 30 | 0 | 60 | 70 | 0 | 20 | 20 | 0 | 90 | 70 | 100 | 90 | 20 |

TABLE C-continued

| | Rate 250 g/ha COMPOUND | Rate 125 g/ha COMPOUND | | | | | | | | | | | | | | |
|---|---|---|---|---|---|---|---|---|---|---|---|---|---|---|---|---|
| | 145 | 8 | 20 | 21 | 22 | 25 | 27 | 28 | 30 | 31 | 32 | 33 | 34 | 36 | 37 | 38 |
| Bermudagrass | 100 | 70 | 100 | 100 | 100 | 100 | 100 | 100 | 100 | 100 | 90 | 100 | 90 | 100 | 80 | 90 |
| Surinam grass | 90 | 0 | 0 | 30 | 40 | 80 | 50 | 60 | 40 | 50 | 80 | 0 | 0 | 70 | 0 | 0 |
| Cocklebur | 50 | 0 | 0 | 0 | 0 | 0 | 0 | 0 | 0 | 0 | — | 0 | 0 | — | 0 | 0 |
| Corn | 40 | 0 | 30 | 20 | 20 | 20 | 20 | 30 | 40 | 40 | 50 | 0 | 0 | 40 | 40 | 0 |
| Crabgrass | 100 | 70 | 100 | 100 | 100 | 100 | 100 | 100 | 100 | 100 | 100 | 100 | 70 | 100 | 90 | 100 |
| Cupgrass, Woolly | 100 | 40 | 50 | 80 | 70 | 100 | 80 | 70 | 70 | 60 | 70 | 90 | 20 | 100 | 0 | 0 |
| Foxtail, Giant | 100 | 20 | 70 | 90 | 0 | 70 | 100 | 100 | 60 | 50 | 50 | 100 | 0 | 100 | 70 | 0 |
| Goosegrass | 100 | 20 | 100 | 100 | 90 | 100 | 100 | 100 | 100 | 100 | 100 | 100 | 80 | 100 | 90 | 90 |
| Johnsongrass | 20 | 0 | 20 | 90 | 30 | 90 | 50 | 70 | 40 | 60 | 40 | 0 | 0 | 90 | 30 | 50 |
| Kochia | 100 | 0 | 100 | 90 | 100 | 100 | 100 | 100 | — | — | — | 100 | 100 | 100 | 100 | 70 |
| Lambsquarters | 100 | 100 | 100 | 100 | 100 | 100 | 100 | 100 | 100 | 100 | 100 | 100 | 100 | 100 | 100 | 100 |
| Morningglory | 100 | 30 | 30 | 20 | 0 | 30 | 20 | 0 | 30 | 30 | 40 | 0 | 0 | 0 | 0 | 0 |
| Nightshade | 20 | 0 | 70 | 100 | 0 | 100 | 0 | 70 | 90 | 90 | 50 | 0 | 0 | 50 | 0 | 0 |
| Nutsedge | 0 | 0 | 0 | 60 | 0 | 0 | 60 | 50 | — | 50 | 50 | 0 | 0 | 30 | 20 | 0 |
| Pigweed | 100 | 80 | 30 | 100 | 50 | 100 | 100 | 100 | 50 | 100 | 20 | 0 | 100 | 0 | 0 | 0 |
| Ragweed, Common | 0 | 0 | — | — | — | 70 | — | — | 90 | 90 | 0 | 0 | 0 | 30 | 20 | 20 |
| Soybean | 30 | 0 | 0 | 80 | 40 | 30 | 40 | 40 | 70 | 0 | 50 | 0 | 50 | — | 0 |
| Sunflower | 50 | 0 | 40 | 70 | 0 | 40 | 20 | 40 | 80 | 30 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 20 | 0 |

| | Rate 125 g/ha COMPOUND | | | | | | | | | | | | | | | | |
|---|---|---|---|---|---|---|---|---|---|---|---|---|---|---|---|---|---|
| | 39 | 40 | 42 | 43 | 44 | 45 | 49 | 50 | 51 | 52 | 56 | 62 | 63 | 64 | 67 | 70 | 71 | 72 |
| Bermudagrass | 90 | 100 | — | 60 | 100 | 90 | 100 | 100 | 100 | 100 | 50 | 70 | 100 | 100 | 100 | 100 | 90 | 90 |
| Surinam grass | 0 | 80 | 90 | 0 | 80 | 0 | 0 | 30 | 30 | 20 | 0 | 30 | 20 | 50 | 0 | 70 | 30 | 30 |
| Cocklebur | — | 20 | — | 100 | 0 | 0 | 0 | 0 | 0 | 0 | 0 | 0 | 0 | 0 | 0 | 0 | 0 | 30 |
| Corn | 0 | 20 | 40 | 0 | 0 | 0 | 0 | 0 | — | 0 | 0 | 0 | 0 | 0 | 0 | 0 | 0 | 0 |
| Crabgrass | 100 | 100 | 100 | 90 | 100 | 100 | 100 | 100 | 100 | 100 | 30 | 90 | 100 | 100 | 100 | 100 | 100 | 100 |
| Cupgrass, Woolly | 20 | 90 | 100 | 30 | 90 | 30 | 60 | 20 | 50 | 50 | 0 | 50 | 60 | 50 | 70 | 100 | 80 | 10 |
| Foxtail, Giant | 0 | 0 | 100 | 0 | 100 | 40 | 100 | 0 | 0 | 70 | 0 | 0 | 90 | 50 | 100 | 100 | 90 | 70 |
| Goosegrass | 90 | 100 | — | 90 | 100 | 100 | 100 | 90 | 90 | 90 | 80 | 90 | 100 | 100 | 100 | 100 | 90 | 70 |
| Johnsongrass | 0 | 100 | — | 50 | 60 | 0 | 0 | 40 | 20 | 40 | 0 | 40 | 60 | 70 | 60 | 10 | 0 | 0 |
| Kochia | 50 | 90 | 100 | 100 | 100 | 60 | 90 | 0 | 50 | 20 | 70 | 60 | 100 | 100 | 100 | 90 | 90 | 100 |
| Lambsquarters | 100 | 100 | 100 | 100 | 100 | 100 | 100 | 50 | 100 | 80 | 100 | — | — | — | 100 | 100 | — | 100 |
| Morningglory | 0 | 0 | — | 0 | 0 | 0 | 0 | 30 | 0 | 0 | 0 | 0 | 20 | 40 | 0 | 0 | 0 | 30 |
| Nightshade | 0 | 0 | 100 | 0 | 0 | 0 | 30 | 0 | 0 | 30 | 0 | 0 | 60 | 70 | 70 | 50 | 20 | 10 |
| Nutsedge | 0 | 0 | — | 30 | 30 | 0 | 50 | 0 | 20 | 0 | 0 | 0 | 0 | 0 | 40 | 0 | 30 | 0 |
| Pigweed | 0 | 100 | 100 | 0 | 0 | 0 | 100 | 20 | 0 | 0 | 90 | 0 | 100 | 100 | 90 | 20 | 0 | 100 |
| Ragweed, Common | 0 | 0 | — | 30 | 0 | 0 | 30 | 30 | 0 | 0 | 0 | 0 | 50 | 50 | 20 | 60 | 0 | 0 |
| Soybean | 0 | 20 | 50 | 40 | 0 | 0 | 40 | 0 | 0 | 20 | 0 | 0 | 20 | 0 | 10 | 0 | 0 |
| Sunflower | 0 | 0 | — | 0 | 0 | 20 | 20 | 30 | 0 | 0 | 0 | 0 | 0 | 20 | 0 | 20 | 0 | 20 |
| Velvetleaf | 0 | 0 | — | 0 | 0 | 0 | 0 | 0 | 0 | 0 | 0 | 0 | 0 | 0 | 50 | 0 | 0 | 0 |

| | Rate 125 g/ha COMPOUND | | | | | | | | | | | | | | | | |
|---|---|---|---|---|---|---|---|---|---|---|---|---|---|---|---|---|---|
| | 73 | 75 | 76 | 79 | 80 | 81 | 82 | 83 | 84 | 85 | 86 | 87 | 88 | 89 | 90 | 91 | 92 | 93 |
| Bermudagrass | 100 | 100 | 100 | 100 | 100 | 100 | 90 | 100 | 100 | 100 | 30 | 100 | 100 | 90 | 100 | 100 | 20 | 90 |
| Surinam grass | 70 | 40 | 60 | 20 | 70 | 50 | 80 | 50 | 0 | 30 | 20 | 100 | 30 | 10 | 10 | 30 | 0 | 10 |
| Cocklebur | — | 0 | 0 | 0 | 50 | 0 | 10 | 0 | 0 | 60 | 0 | 0 | 0 | 0 | 0 | 0 | 0 | 0 |
| Corn | 0 | 0 | 20 | 0 | 30 | 0 | 20 | 0 | 0 | 30 | 0 | 70 | 10 | 25 | 0 | 0 | 10 | 0 |
| Crabgrass | 100 | 100 | 100 | 100 | 100 | 100 | 100 | 100 | 100 | 100 | 90 | 100 | 100 | 100 | 100 | 100 | 80 | 100 |
| Cupgrass, Woolly | 80 | 80 | 100 | 90 | 100 | 30 | 90 | 90 | 90 | 100 | 30 | 100 | 90 | 0 | 10 | 70 | 10 | 20 |
| Foxtail, Giant | 100 | 100 | 100 | 0 | 100 | 100 | 0 | 100 | 80 | 100 | 0 | 100 | 100 | 0 | 0 | 30 | 0 | 20 |
| Goosegrass | 100 | 100 | 100 | 90 | 100 | 100 | 100 | 100 | 80 | 100 | 90 | 100 | 100 | 100 | 100 | 100 | 75 | 100 |
| Johnsongrass | 30 | 0 | 30 | 0 | 60 | 20 | 50 | 30 | 0 | 50 | 20 | 90 | 10 | 70 | 70 | 80 | 65 | — |
| Kochia | 100 | 100 | 100 | 100 | 100 | 100 | 90 | 90 | 100 | 100 | 90 | 100 | 90 | 70 | 40 | 90 | 40 | 0 |
| Lambsquarters | — | 100 | 100 | 100 | 100 | 100 | 100 | 100 | 100 | 100 | 100 | 100 | 100 | 100 | 100 | 100 | 100 | 70 |
| Morningglory | 30 | 0 | 30 | 0 | 20 | 20 | 10 | 0 | 20 | 90 | 0 | 0 | 10 | 0 | 0 | 0 | 0 | 0 |
| Nightshade | 80 | 0 | 30 | 50 | 100 | 100 | 10 | 50 | 50 | 90 | 0 | 10 | 20 | 0 | 0 | 0 | 0 | 0 |
| Nutsedge | 30 | 0 | 0 | 0 | 20 | 0 | 0 | 0 | 0 | 70 | 0 | 20 | 0 | 0 | 0 | 0 | 0 | 0 |
| Pigweed | 0 | 100 | 100 | 10 | 0 | 100 | 70 | 50 | 0 | 100 | 100 | 0 | 10 | 0 | 0 | 0 | 0 | 20 |
| Ragweed, Common | 80 | 0 | 0 | 100 | 100 | 100 | 0 | 0 | 0 | 100 | 0 | 0 | 0 | 0 | 0 | 0 | 0 | 0 |
| Soybean | 40 | 0 | 0 | 0 | 30 | — | 10 | 0 | 0 | 40 | 0 | 20 | 10 | 0 | 0 | 0 | 0 | 0 |
| Sunflower | 50 | 0 | 20 | 0 | 30 | 0 | 20 | 30 | 10 | 70 | 20 | 20 | 40 | 0 | 0 | 0 | 0 | 0 |
| Velvetleaf | 50 | 0 | 20 | 0 | 40 | 30 | 10 | 30 | 0 | 70 | 0 | 10 | 10 | 0 | 0 | 0 | 0 | 0 |

TABLE C-continued

| | Rate 125 g/ha COMPOUND | | | | | | | | | | | | | | | | | |
|---|---|---|---|---|---|---|---|---|---|---|---|---|---|---|---|---|---|---|
| | 95 | 96 | 99 | 100 | 101 | 106 | 107 | 109 | 111 | 117 | 118 | 119 | 120 | 121 | 122 | 124 | 127 | 128 |
| Bermudagrass | 100 | 100 | 90 | 90 | 100 | 100 | 100 | 100 | 90 | 100 | 100 | 100 | 100 | 100 | 100 | 80 | 100 | 100 |
| Surinam grass | 40 | 90 | 0 | 0 | 20 | 90 | 0 | 80 | 0 | 10 | 10 | 100 | 100 | 80 | 0 | 0 | 0 | 100 |
| Cocklebur | 0 | 20 | 0 | — | 0 | 90 | 0 | 30 | 0 | 10 | 0 | — | 0 | 20 | 0 | 0 | 0 | 10 |
| Corn | 10 | 20 | 0 | — | 0 | 0 | 0 | 0 | 0 | 30 | 0 | 30 | 0 | 20 | 0 | 0 | 0 | 20 |
| Crabgrass | 100 | 100 | 100 | 100 | 100 | 100 | 100 | 100 | 100 | 100 | 100 | 100 | 100 | 100 | 100 | 100 | 70 | 100 |
| Cupgrass, Woolly | 100 | 95 | 0 | 20 | 20 | 100 | 60 | 90 | 20 | 100 | 90 | 100 | 100 | 100 | 20 | 50 | 50 | 100 |
| Foxtail, Giant | 0 | 0 | 20 | 10 | 40 | 40 | 100 | 20 | 0 | 0 | 100 | 100 | 50 | 100 | 0 | 20 | 0 | 90 |
| Goosegrass | 100 | 100 | 80 | 90 | 100 | 100 | 70 | 100 | 85 | 100 | 100 | 100 | 100 | 100 | 100 | 40 | 30 | 100 |
| Johnsongrass | 30 | 30 | 0 | 90 | 40 | 100 | 20 | 50 | 0 | 50 | 40 | 100 | 80 | 90 | 0 | 20 | 0 | 90 |
| Kochia | 100 | 100 | 90 | 0 | 0 | 100 | 70 | 100 | 0 | 100 | 100 | 100 | 100 | 100 | 100 | 60 | 0 | 100 |
| Lambsquarters | 100 | 100 | 100 | 100 | 100 | 100 | 100 | 100 | 85 | 100 | 100 | 100 | 100 | 100 | 100 | 100 | 80 | 100 |
| Morningglory | 0 | 0 | 20 | 0 | 0 | 100 | 0 | 100 | 0 | 10 | 20 | 90 | 60 | 10 | 0 | 0 | 0 | 60 |
| Nightshade | 0 | 10 | 0 | 0 | 90 | 100 | 90 | 100 | 0 | 100 | 100 | 100 | 100 | 90 | 0 | 20 | 0 | 40 |
| Nutsedge | 0 | 0 | 0 | 0 | 0 | 80 | 0 | 0 | 0 | 0 | 0 | 20 | 80 | 0 | 0 | 0 | 0 | 70 |
| Pigweed | 0 | 0 | 90 | 0 | 0 | 100 | 0 | 70 | 20 | 100 | 100 | 50 | 100 | 50 | 20 | 0 | 0 | 70 |
| Ragweed, Common | 0 | 0 | 0 | 0 | 100 | 100 | 30 | 100 | 0 | 100 | — | 100 | 100 | 90 | 0 | 0 | 0 | 100 |
| Soybean | 0 | 0 | 0 | 0 | 0 | 100 | 30 | 90 | 0 | 100 | 60 | 80 | 70 | 60 | 0 | 0 | 0 | — |
| Sunflower | 0 | 0 | 0 | 0 | 0 | 80 | 0 | 90 | 0 | 40 | 50 | 40 | 90 | 30 | 0 | 0 | 0 | 100 |
| Velvetleaf | 0 | 0 | 0 | 0 | 50 | 100 | 50 | 100 | 0 | 90 | 100 | 100 | 100 | 20 | 10 | 0 | 0 | 20 |

| | Rate 125 g/ha COMPOUND | | | | | | | | | | | | Rate 62 g/ha COMPOUND | | | | | |
|---|---|---|---|---|---|---|---|---|---|---|---|---|---|---|---|---|---|---|
| | 129 | 130 | 131 | 132 | 133 | 134 | 138 | 140 | 141 | 142 | 143 | 144 | 145 | 8 | 20 | 21 | 22 | 25 |
| Bermudagrass | 100 | 100 | 100 | 100 | 100 | 100 | 70 | 100 | 100 | 100 | 100 | 100 | 100 | 0 | 70 | 100 | 30 | 100 |
| Surinam grass | 80 | 100 | 100 | 100 | 100 | 100 | 0 | 0 | 20 | 0 | 0 | 0 | 50 | 0 | 0 | 0 | 0 | 40 |
| Cocklebur | 0 | — | 0 | 0 | 0 | 0 | 0 | 30 | 60 | 30 | 50 | 60 | 20 | 0 | 0 | 0 | 0 | 0 |
| Corn | 20 | 80 | 100 | 10 | — | 20 | 0 | 20 | 30 | 0 | 30 | 50 | 20 | 0 | 0 | 20 | 20 | 0 |
| Crabgrass | 100 | 100 | 100 | 100 | 100 | 100 | 100 | 100 | 100 | 100 | 100 | 100 | 100 | 70 | 0 | 90 | 50 | 100 |
| Cupgrass, Woolly | 100 | 100 | 100 | 100 | 100 | 100 | 60 | 100 | 100 | 100 | 100 | 100 | 100 | 0 | 0 | 80 | 40 | 80 |
| Foxtail, Giant | 60 | 100 | 100 | 70 | 100 | 100 | 100 | 100 | 100 | 100 | 100 | 100 | 100 | 0 | 0 | 80 | 30 | 90 |
| Goosegrass | 100 | 100 | 100 | 100 | 100 | 100 | 90 | 100 | 100 | 100 | 100 | 100 | 100 | 0 | 80 | 80 | 90 | 100 |
| Johnsongrass | 70 | 90 | 70 | 80 | 100 | 100 | 30 | 20 | 0 | 0 | 60 | 90 | 10 | 0 | 0 | 70 | 20 | 70 |
| Kochia | 100 | 100 | 100 | 100 | 100 | 100 | 100 | 100 | 100 | 100 | 100 | 100 | 100 | 0 | 90 | 90 | 100 | 50 |
| Lambsquarters | 100 | 100 | 100 | 100 | 100 | 100 | 100 | 100 | 100 | 100 | 100 | 100 | 100 | 100 | 90 | 100 | 100 | 100 |
| Morningglory | 0 | — | 60 | — | 0 | 0 | 80 | 90 | 100 | 100 | 100 | 0 | 100 | 20 | 0 | 20 | 0 | 20 |
| Nightshade | 0 | 100 | 100 | 0 | 0 | 10 | 50 | 100 | 100 | 100 | 100 | 100 | 10 | 0 | 30 | 90 | 0 | 100 |
| Nutsedge | 0 | 80 | 90 | 0 | — | 70 | 0 | 40 | 0 | 0 | 0 | 0 | 0 | 0 | 0 | 50 | 0 | 0 |
| Pigweed | 100 | 100 | 90 | 30 | 100 | 100 | 50 | 100 | 100 | 100 | 100 | 100 | 100 | 20 | 0 | 80 | 100 | 60 |
| Ragweed, Common | 0 | 100 | 0 | 0 | 0 | 0 | 0 | — | 100 | 100 | 100 | 0 | 0 | 0 | — | — | — | 70 |
| Soybean | 20 | 30 | 0 | 20 | 0 | 0 | 60 | 80 | 100 | 70 | 80 | 50 | 30 | 0 | 0 | 40 | 30 | 0 |
| Sunflower | 0 | 60 | 20 | 20 | 0 | 0 | 0 | 50 | 40 | 20 | 80 | 40 | 0 | 0 | 0 | 60 | 0 | 30 |
| Velvetleaf | 0 | 60 | 30 | — | 20 | 20 | 0 | 70 | 70 | 90 | 70 | 0 | 0 | 0 | 0 | 0 | 0 | 30 |

| | Rate 62 g/ha COMPOUND | | | | | | | | | | | | | | | | | |
|---|---|---|---|---|---|---|---|---|---|---|---|---|---|---|---|---|---|---|
| | 27 | 28 | 30 | 31 | 32 | 33 | 34 | 36 | 37 | 38 | 39 | 40 | 42 | 43 | 44 | 45 | 49 | 50 |
| Bermudagrass | 90 | 50 | 100 | 90 | 50 | 90 | 80 | 100 | 70 | 60 | 90 | 80 | — | 50 | 90 | 50 | 100 | 100 |
| Surinam grass | 50 | 20 | 20 | 50 | 70 | 0 | 0 | 70 | 0 | 0 | 0 | 0 | 70 | 0 | 0 | 0 | 0 | 20 |
| Cocklebur | 0 | — | 0 | 0 | 0 | 0 | 0 | 30 | — | 0 | 0 | 20 | — | 100 | — | — | 0 | — |
| Corn | 20 | 0 | 30 | 40 | 40 | 0 | 0 | 20 | 0 | 0 | 0 | 0 | 20 | 0 | 0 | 0 | 0 | 0 |
| Crabgrass | 100 | 90 | 100 | 100 | 100 | 80 | 60 | 100 | 90 | 90 | 90 | 100 | 90 | 40 | 100 | 90 | 100 | 100 |
| Cupgrass, Woolly | 50 | 50 | 70 | 50 | 60 | 20 | 20 | 60 | 0 | 0 | 0 | 60 | 20 | 30 | 30 | 0 | 30 | 20 |
| Foxtail, Giant | 70 | 0 | 80 | 40 | 70 | 50 | 30 | 0 | 60 | 80 | 0 | 90 | 50 | 0 | 0 | 30 | 0 | 60 |
| Goosegrass | 90 | 80 | 100 | 100 | 100 | 80 | 80 | 100 | 90 | 80 | 80 | 90 | — | 50 | 90 | 90 | 100 | 80 |
| Johnsongrass | 20 | 50 | 30 | 30 | 30 | 0 | 0 | 90 | 30 | 40 | 0 | 50 | — | 0 | 0 | 0 | 0 | 0 |
| Kochia | 100 | 40 | — | — | — | 100 | 100 | 100 | 50 | 30 | 0 | 60 | 50 | 90 | 70 | 20 | 90 | 0 |
| Lambsquarters | 100 | 100 | 100 | 100 | 100 | 100 | 90 | 100 | 100 | 90 | 100 | 100 | 100 | 100 | 100 | 60 | 100 | 20 |
| Morningglory | 20 | 0 | 30 | 30 | 30 | 0 | 0 | 0 | 0 | — | 0 | 0 | — | 0 | 0 | 0 | 0 | 20 |
| Nightshade | 0 | 0 | 80 | 80 | 50 | 0 | 0 | 30 | 0 | 0 | 0 | 0 | 0 | 0 | 0 | 0 | 0 | 0 |
| Nutsedge | 60 | 50 | 20 | 40 | — | 0 | 0 | 0 | 20 | 0 | 0 | 0 | — | 0 | 0 | — | 40 | 0 |
| Pigweed | 0 | 70 | 90 | 30 | 70 | 0 | 100 | 0 | 0 | 0 | 0 | 0 | 60 | 100 | 0 | 0 | 100 | 30 |
| Ragweed, Common | — | — | 0 | 30 | 0 | 0 | 0 | 0 | 0 | 0 | 0 | 0 | — | 0 | 0 | 0 | 0 | 20 |
| Soybean | 30 | 0 | 30 | 0 | 50 | 0 | 0 | 30 | 0 | 0 | 0 | — | 50 | 0 | 0 | 0 | 0 | — |
| Sunflower | 20 | 20 | 0 | 20 | 0 | 0 | 0 | 0 | 0 | 0 | 0 | 0 | — | 0 | 0 | 20 | 20 | 20 |
| Velvetleaf | 0 | 0 | 0 | 0 | 0 | 0 | 0 | 0 | 0 | 0 | 0 | 0 | — | 0 | 0 | 0 | 0 | 0 |

TABLE C-continued

| | Rate 62 g/ha COMPOUND | | | | | | | | | | | | | | | | | |
|---|---|---|---|---|---|---|---|---|---|---|---|---|---|---|---|---|---|---|
| | 51 | 52 | 56 | 62 | 63 | 64 | 67 | 70 | 71 | 72 | 73 | 75 | 76 | 79 | 80 | 81 | 82 | 83 |
| Bermudagrass | 90 | 100 | 40 | 40 | 100 | 100 | 100 | 100 | 30 | 0 | 70 | 100 | 100 | 100 | 100 | 100 | 100 | 100 |
| Surinam grass | 30 | 0 | 0 | 0 | 20 | 0 | 0 | 60 | 30 | 0 | 50 | 10 | 50 | 0 | 20 | 20 | 10 | 40 |
| Cocklebur | 0 | 0 | 0 | 0 | 0 | 0 | 0 | 0 | 0 | 0 | 70 | 0 | 0 | 0 | 0 | 0 | 0 | 0 |
| Corn | 0 | 0 | 0 | 0 | 0 | 0 | 0 | 0 | 0 | 0 | 0 | 0 | 20 | 0 | 0 | 0 | 0 | 0 |
| Crabgrass | 70 | 90 | 30 | 0 | 100 | 100 | 100 | 100 | 40 | 90 | 90 | 90 | 100 | 100 | 100 | 100 | 100 | 100 |
| Cupgrass, Woolly | 50 | 30 | 0 | 30 | 20 | 30 | 90 | 70 | 0 | 0 | 60 | 60 | 50 | 90 | 90 | 30 | 70 | 80 |
| Foxtail, Giant | 70 | 60 | 0 | 0 | 20 | 0 | 100 | 100 | 0 | 30 | 80 | 90 | 100 | 0 | 0 | 90 | 30 | 0 |
| Goosegrass | 80 | 90 | 60 | 80 | 100 | 100 | 100 | 90 | 30 | 20 | 80 | 90 | 100 | 80 | 100 | 100 | 90 | 100 |
| Johnsongrass | 20 | 0 | 0 | 20 | 0 | 30 | 30 | 0 | 0 | 0 | 20 | 0 | 20 | 0 | 20 | 0 | 40 | 20 |
| Kochia | 40 | 0 | 50 | 0 | 70 | 90 | 90 | 80 | 80 | 30 | 80 | 100 | 100 | 100 | 100 | 100 | 0 | 60 |
| Lambsquarters | 60 | 0 | 100 | — | — | — | 100 | 100 | — | 0 | — | 100 | 100 | 100 | 100 | 100 | 100 | 100 |
| Morningglory | — | — | 0 | 0 | 0 | 40 | 0 | 20 | 0 | 0 | 30 | 0 | 10 | 0 | 0 | 0 | 20 | 0 |
| Nightshade | 0 | 30 | 0 | 0 | 30 | 30 | 0 | 30 | 0 | 30 | 60 | 0 | 0 | 20 | 90 | 100 | 0 | 0 |
| Nutsedge | 20 | 0 | 0 | 0 | 0 | 0 | 0 | 0 | 0 | 0 | 0 | 0 | 0 | 0 | 0 | 0 | 0 | 0 |
| Pigweed | 20 | 0 | 0 | 0 | 0 | 0 | 80 | 0 | 0 | 50 | 0 | 100 | 100 | 0 | 0 | 40 | 0 | 90 |
| Ragweed, Common | 0 | 0 | 0 | 0 | 0 | 0 | 0 | 20 | 0 | 30 | 70 | 0 | 0 | 60 | 90 | 30 | 0 | 0 |
| Soybean | — | 20 | 0 | 0 | 0 | 0 | 0 | 0 | 0 | 0 | 0 | 0 | 0 | 0 | — | 100 | 0 | 0 |
| Sunflower | 0 | — | 0 | 0 | 0 | 20 | 0 | 0 | 0 | 0 | 50 | 0 | 20 | 0 | 30 | 0 | 0 | 0 |
| Velvetleaf | 0 | 0 | 0 | 0 | 0 | 0 | 0 | 20 | 0 | 0 | 20 | 0 | 10 | 0 | 0 | 10 | 30 | 0 |

| | Rate 62 g/ha COMPOUND | | | | | | | | | | | | | | | | | |
|---|---|---|---|---|---|---|---|---|---|---|---|---|---|---|---|---|---|---|
| | 84 | 85 | 86 | 87 | 88 | 89 | 90 | 91 | 92 | 93 | 95 | 96 | 99 | 100 | 101 | 106 | 107 | 109 |
| Bermudagrass | 100 | 100 | 10 | 100 | 100 | 10 | 0 | 10 | 20 | 0 | 100 | 100 | 90 | 90 | 40 | 100 | 85 | 100 |
| Surinam grass | 0 | 30 | 20 | 40 | 40 | 0 | 0 | 0 | 0 | 0 | 40 | 50 | 0 | 0 | 0 | 90 | 0 | 0 |
| Cocklebur | 0 | 60 | 0 | 0 | 0 | 0 | 0 | 0 | 0 | 0 | 0 | 0 | 0 | 0 | 0 | 90 | 0 | 0 |
| Corn | 0 | 30 | 0 | 40 | 0 | 10 | 0 | 0 | 0 | 0 | 10 | 0 | 0 | 20 | 0 | 0 | 0 | 0 |
| Crabgrass | 90 | 100 | 0 | 100 | 100 | 20 | 80 | 100 | 60 | 80 | 100 | 100 | 100 | 100 | 100 | 100 | 100 | 100 |
| Cupgrass, Woolly | 60 | 100 | 30 | 90 | 60 | 0 | 0 | 10 | 0 | 0 | 50 | 60 | 0 | 0 | 0 | 100 | 50 | 90 |
| Foxtail, Giant | 10 | 60 | 0 | 30 | 0 | 0 | 40 | 10 | 20 | 0 | 0 | 100 | 10 | 90 | 40 | 0 | 100 | 0 |
| Goosegrass | 20 | 20 | 100 | 100 | 100 | 95 | 100 | 90 | 60 | 20 | 100 | 100 | 80 | 80 | 100 | 100 | 10 | 100 |
| Johnsongrass | 0 | — | 20 | 90 | 10 | 50 | 10 | 20 | 50 | 0 | 30 | 20 | 0 | 0 | 10 | 70 | — | 10 |
| Kochia | 80 | 100 | 70 | 100 | 70 | 20 | 0 | 20 | 0 | 0 | 100 | 100 | 80 | 0 | 0 | 100 | 70 | 100 |
| Lambsquarters | 100 | 100 | 100 | 100 | 100 | 80 | 100 | 90 | 80 | 0 | 100 | 100 | 100 | 90 | 0 | 100 | 90 | 100 |
| Morningglory | 0 | 50 | 0 | 0 | 10 | 0 | 0 | 0 | 0 | 0 | 0 | 0 | 0 | 0 | 0 | 90 | 0 | 90 |
| Nightshade | 30 | 80 | 0 | 0 | 30 | 0 | 0 | 0 | 0 | 0 | 0 | 0 | 0 | 0 | 0 | 100 | 80 | 90 |
| Nutsedge | 0 | 50 | 0 | 20 | 0 | 0 | 0 | 0 | 0 | 0 | 0 | 0 | 0 | 0 | 0 | 10 | 0 | 0 |
| Pigweed | 90 | 100 | 70 | 0 | 0 | 0 | 60 | 0 | 0 | 0 | 100 | 0 | 0 | 0 | 0 | 100 | 90 | 20 |
| Ragweed, Common | 0 | 90 | 0 | 0 | 0 | 0 | 0 | 0 | 0 | 0 | 0 | 0 | 0 | 0 | 0 | 100 | 0 | 90 |
| Soybean | 0 | 20 | 0 | 0 | 0 | 0 | 0 | 0 | 0 | 0 | 0 | 0 | 0 | 0 | 0 | 100 | 30 | 80 |
| Sunflower | 0 | 40 | 0 | 20 | 10 | 0 | 0 | 0 | 0 | 0 | 0 | 0 | 0 | 0 | 0 | 70 | 0 | 70 |
| Velvetleaf | 0 | 70 | 0 | 10 | 0 | 0 | 0 | 0 | 0 | 0 | 0 | 0 | 0 | 0 | 20 | 100 | 40 | 100 |

| | Rate 62 g/ha COMPOUND | | | | | | | | | | | | | | | | | |
|---|---|---|---|---|---|---|---|---|---|---|---|---|---|---|---|---|---|---|
| | 111 | 117 | 118 | 119 | 120 | 121 | 122 | 124 | 127 | 128 | 129 | 130 | 131 | 132 | 133 | 134 | 138 | 140 |
| Bermudagrass | 60 | 100 | 100 | 100 | 100 | 100 | 100 | 60 | 90 | 100 | 100 | 100 | 100 | 100 | 100 | 100 | 70 | 100 |
| Surinam grass | 0 | 10 | 0 | 100 | 90 | 20 | 0 | 0 | 0 | 90 | 80 | 100 | 100 | 90 | 100 | 100 | 0 | 0 |
| Cocklebur | 0 | 0 | 0 | — | 0 | 0 | 0 | 0 | 0 | 0 | 0 | 0 | 0 | — | 0 | 0 | 0 | 30 |
| Corn | 0 | 0 | 0 | 30 | 0 | 0 | 0 | 0 | 0 | 0 | 0 | 40 | 100 | 0 | 100 | — | 0 | 20 |
| Crabgrass | 80 | 100 | 100 | 100 | 100 | 100 | 90 | 90 | 50 | 100 | 100 | 100 | 100 | 100 | 100 | 100 | 70 | 100 |
| Cupgrass, Woolly | 0 | 80 | 40 | 100 | 100 | 80 | 0 | 30 | 0 | 100 | 90 | 100 | 100 | 90 | 100 | 100 | 40 | 100 |
| Foxtail, Giant | 0 | 100 | 0 | 50 | 50 | 20 | 0 | 0 | 0 | 20 | 20 | 90 | 90 | 70 | 90 | 90 | 80 | 100 |
| Goosegrass | 40 | 100 | 100 | 100 | 100 | 100 | 90 | 0 | 10 | 100 | 100 | 100 | 100 | 100 | 100 | 100 | 80 | 100 |
| Johnsongrass | 0 | 45 | 0 | 90 | 20 | 60 | 0 | 15 | 0 | 60 | 20 | 0 | 30 | 50 | 80 | 100 | 0 | 0 |
| Kochia | 0 | 90 | 80 | 100 | 100 | 100 | 100 | 40 | 0 | 100 | 0 | 100 | 0 | — | 100 | 100 | 90 | 100 |
| Lambsquarters | 70 | 100 | 100 | 100 | 100 | 100 | 100 | 50 | 20 | 100 | 100 | 100 | 100 | 100 | 100 | 100 | 100 | 100 |
| Morningglory | 0 | 0 | 0 | 60 | 60 | 0 | 0 | 0 | 0 | 30 | 0 | 70 | 0 | 0 | 0 | 0 | 30 | 70 |
| Nightshade | 0 | 100 | 100 | 100 | 100 | 10 | 0 | 0 | 0 | 20 | 0 | 100 | 90 | 0 | 0 | 0 | 0 | 100 |
| Nutsedge | 0 | 0 | 0 | 0 | 40 | 0 | 0 | 0 | 0 | 20 | 0 | 30 | 0 | 70 | 60 | 0 | 0 | 20 |
| Pigweed | 80 | 100 | 75 | 50 | 100 | 20 | 0 | 0 | 0 | 70 | 20 | 100 | 90 | 0 | 50 | 100 | 30 | 100 |
| Ragweed, Common | 0 | 100 | 60 | 100 | 100 | 0 | 0 | 0 | 100 | 0 | 100 | 0 | 0 | 0 | 0 | 0 | 0 | 100 |
| Soybean | 0 | 100 | 40 | 60 | 60 | 0 | 0 | 0 | 0 | — | 10 | 30 | 0 | 20 | 0 | 0 | 30 | 50 |
| Sunflower | 0 | 35 | 0 | 40 | 60 | 10 | 0 | 0 | 0 | 20 | 0 | 60 | 20 | 0 | 0 | 0 | 0 | 30 |
| Velvetleaf | 0 | 80 | 20 | 60 | 80 | 0 | 0 | 0 | 0 | 10 | 0 | 60 | 20 | 0 | 0 | 20 | 0 | 60 |

TABLE C-continued

|  | Rate 62 g/ha COMPOUND | | | | | Rate 31 g/ha COMPOUND | | | | | | | | | | | | |
|---|---|---|---|---|---|---|---|---|---|---|---|---|---|---|---|---|---|---|
|  | 141 | 142 | 143 | 144 | 145 | 21 | 25 | 27 | 28 | 34 | 36 | 37 | 42 | 43 | 49 | 70 | 73 | 81 |
| Bermudagrass | 100 | 100 | 100 | 100 | 60 | 60 | 90 | 30 | 20 | 0 | 100 | 60 | — | 40 | 0 | 80 | 60 | 100 |
| Surinam grass | 10 | 0 | 0 | 0 | 0 | 0 | 20 | 0 | 20 | 0 | 20 | 0 | 0 | 0 | 0 | 20 | 20 | 0 |
| Cocklebur | 0 | 0 | — | 50 | 0 | 0 | 0 | 0 | 0 | 0 | 0 | 0 | — | 20 | 0 | 0 | 20 | 0 |
| Corn | 0 | 0 | 30 | 30 | 0 | 20 | 0 | 0 | 0 | 0 | 0 | 0 | 0 | 0 | 0 | 0 | 0 | 0 |
| Crabgrass | 100 | 100 | 100 | 100 | 100 | 90 | 100 | 90 | 90 | 0 | 90 | 80 | 40 | 20 | 0 | 30 | 90 | 60 |
| Cupgrass, Woolly | 100 | 90 | 90 | 100 | 20 | 40 | 60 | 50 | 30 | 0 | 30 | 0 | 0 | 0 | 20 | 0 | 20 | 0 |
| Foxtail, Giant | 100 | 100 | 100 | 100 | 100 | 0 | 20 | 0 | 0 | 30 | 90 | 50 | 30 | 0 | 0 | 0 | 20 | 30 |
| Goosegrass | 100 | 100 | 100 | 100 | 90 | 80 | 100 | 40 | 40 | 20 | 90 | 60 | — | 0 | 0 | 30 | 60 | 90 |
| Johnsongrass | 0 | 0 | 0 | 0 | 0 | 30 | 30 | 0 | 0 | 0 | 50 | 20 | — | 0 | 0 | 0 | 0 | 0 |
| Kochia | 100 | 100 | 100 | 90 | 100 | 90 | 60 | 0 | 0 | 100 | 70 | 40 | 20 | 70 | 50 | 0 | 20 | 100 |
| Lambsquarters | 100 | 100 | 100 | 100 | 100 | 90 | 100 | 100 | 100 | 90 | 100 | 100 | 20 | 100 | 100 | — | — | 100 |
| Morningglory | 30 | 90 | 30 | — | 0 | 0 | 0 | 0 | 0 | 0 | 0 | 0 | — | 0 | 0 | 0 | 30 | 0 |
| Nightshade | 100 | 90 | 100 | 100 | 0 | 80 | 20 | 0 | 0 | 0 | 0 | 0 | 0 | 0 | 0 | 20 | 50 | 70 |
| Nutsedge | 0 | 0 | 0 | 0 | 0 | 20 | 0 | 30 | 50 | 0 | 0 | 0 | — | 0 | 30 | 0 | 0 | 0 |
| Pigweed | 100 | 100 | 100 | 100 | 100 | 30 | 100 | 100 | 70 | 0 | 0 | 0 | 0 | 100 | 70 | 0 | 0 | 100 |
| Ragweed, Common | 100 | 0 | 90 | 0 | 0 | — | 0 | — | — | 0 | 0 | 0 | 0 | 0 | 0 | 0 | 30 | 30 |
| Soybean | 70 | 30 | 70 | 50 | 20 | 30 | 20 | 0 | 0 | 0 | 30 | 0 | 20 | 0 | 0 | 0 | 0 | 30 |
| Sunflower | 30 | 10 | 60 | 40 | 0 | 20 | 0 | 0 | 0 | 0 | 0 | 0 | — | 0 | 0 | 0 | 40 | 0 |
| Velvetleaf | 70 | 10 | 70 | 0 | 0 | 0 | 0 | 0 | 0 | 0 | 0 | 0 | — | 0 | 0 | 0 | 20 | 0 |

|  | Rate 31 g/ha COMPOUND | | | | | | Rate 16 g/ha COMPOUND |
|---|---|---|---|---|---|---|---|
|  | 90 | 101 | 106 | 109 | 124 | 138 | 43 |
| Bermudagrass | 0 | 40 | 100 | 100 | 0 | 60 | 20 |
| Surinam grass | 0 | 0 | 30 | 0 | 0 | 0 | 0 |
| Cocklebur | 0 | 0 | 70 | 0 | 0 | 0 | 0 |
| Corn | 0 | 0 | 0 | 0 | 0 | 0 | 0 |
| Crabgrass | 80 | 90 | 100 | 100 | 80 | 20 | 0 |
| Cupgrass, Woolly | 0 | 0 | 60 | 10 | 0 | 0 | 0 |
| Foxtail, Giant | 0 | 0 | 0 | 0 | 0 | 50 | 0 |
| Goosegrass | 20 | 10 | 100 | 90 | 0 | 20 | 0 |
| Johnsongrass | 10 | 0 | 30 | 0 | 0 | 0 | 0 |
| Kochia | 0 | 0 | 100 | 90 | 0 | 60 | 20 |
| Lambsquarters | 10 | 0 | 100 | 100 | 45 | 100 | 100 |
| Morningglory | 0 | 0 | 80 | 30 | 0 | 30 | 0 |
| Nightshade | 0 | 0 | 100 | 50 | 0 | 0 | 0 |
| Nutsedge | 0 | 0 | 10 | 0 | 0 | 0 | 0 |
| Pigweed | 0 | 0 | 70 | 20 | 0 | 0 | 20 |
| Ragweed, Common | 0 | 0 | 80 | 10 | 0 | 0 | 0 |
| Soybean | 0 | 0 | 80 | 20 | 0 | — | 0 |
| Sunflower | 0 | 0 | 70 | 40 | 0 | 0 | 0 |
| Velvetleaf | 0 | 20 | 90 | 50 | 0 | 0 | 0 |

Flooded Paddy

|  | Rate 1000 g/ha COMPOUND | | | | | | | | Rate 500 g/ha COMPOUND | | | | | | | | | | |
|---|---|---|---|---|---|---|---|---|---|---|---|---|---|---|---|---|---|---|---|
|  | 2 | 3 | 4 | 5 | 6 | 7 | 8 | 135 | 1 | 2 | 3 | 4 | 5 | 6 | 7 | 8 | 10 | 11 | 17 | 19 |
| Barnyardgrass | 80 | 100 | 90 | 100 | 100 | 100 | 100 | 30 | 100 | 0 | 100 | 0 | 100 | 100 | 100 | 70 | 80 | 80 | 70 | 0 |
| Ducksalad | 90 | 100 | 60 | 100 | 100 | 100 | 100 | 30 | 100 | 0 | 90 | 20 | 90 | 60 | 90 | 70 | 90 | 30 | 80 | 0 |
| Rice | 70 | 90 | 20 | 90 | 90 | 100 | 80 | 0 | 50 | 0 | 60 | 0 | 70 | 80 | 80 | 60 | 60 | 30 | 0 | 0 |
| Flatsedge | 100 | 100 | 90 | 100 | 100 | 100 | 100 | 100 | 100 | 100 | 100 | 90 | 100 | 100 | 100 | 100 | 100 | 100 | 80 | 30 |

|  | Rate 500 g/ha COMPOUND | | | | | | | | | | | | | | | | | |
|---|---|---|---|---|---|---|---|---|---|---|---|---|---|---|---|---|---|---|
|  | 20 | 21 | 22 | 23 | 24 | 25 | 26 | 27 | 28 | 30 | 31 | 32 | 34 | 36 | 37 | 38 | 39 | 40 |
| Barnyardgrass | 100 | 100 | 100 | 100 | 100 | 100 | 100 | 70 | 70 | 100 | 100 | 100 | 80 | 100 | 100 | 100 | 100 | 100 |
| Ducksalad | 100 | 100 | 100 | 100 | 100 | 100 | 70 | 90 | 100 | 100 | 100 | 80 | 100 | 100 | 100 | 80 | 100 | 100 |
| Rice | 70 | 70 | 40 | 100 | 60 | 80 | 80 | 70 | 20 | 80 | 90 | 100 | 20 | 90 | 90 | 80 | 70 | 90 |
| Flatsedge | 100 | 100 | 100 | 100 | 100 | 100 | 95 | 100 | 100 | 100 | 100 | 100 | 100 | 100 | 100 | 100 | 100 | 100 |

|  | Rate 500 g/ha COMPOUND | | | | | | | | | | | | | | | | | |
|---|---|---|---|---|---|---|---|---|---|---|---|---|---|---|---|---|---|---|
|  | 42 | 43 | 44 | 45 | 46 | 48 | 49 | 50 | 51 | 52 | 53 | 54 | 55 | 56 | 58 | 59 | 62 | 63 | 64 | 65 |
| Barnyardgrass | 100 | 100 | 100 | 100 | 60 | 100 | 100 | 80 | — | 100 | 100 | 20 | 100 | 30 | 20 | 30 | 80 | 100 | 100 | 100 |
| Ducksalad | 100 | 80 | 100 | 100 | 50 | 90 | 100 | 90 | 70 | 100 | 60 | 0 | 50 | 0 | 0 | 0 | 100 | 90 | 90 |

TABLE C-continued

| | | | | | | | | | | | | | | | | | | | |
|---|---|---|---|---|---|---|---|---|---|---|---|---|---|---|---|---|---|---|---|
| Rice | 80 | 30 | 90 | 100 | 40 | 50 | 90 | 50 | 0 | 60 | 0 | 0 | 0 | 0 | 0 | 20 | 50 | 40 | 90 | 90 |
| Flatsedge | 100 | 100 | 100 | 100 | 100 | 100 | 100 | 100 | 100 | 100 | 100 | 80 | 100 | 90 | 30 | 30 | 100 | 100 | 100 | 100 |

Rate 500 g/ha
COMPOUND

| | 66 | 67 | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|---|---|
| Barnyardgrass | 100 | 100 | 100 | 100 | 100 | 80 | 80 | 100 | 0 | 100 | 90 | 20 | 60 | 90 | 90 | 90 | 100 | 100 | 100 | 100 |
| Ducksalad | 100 | 100 | 100 | 20 | 100 | 30 | 90 | 100 | 0 | 90 | 100 | 30 | 0 | 90 | 100 | 100 | 100 | 100 | 100 | 100 |
| Rice | 100 | 90 | 100 | 80 | 90 | 60 | 50 | 60 | 0 | 40 | 80 | 30 | 0 | 50 | 90 | 80 | 80 | 80 | 90 | 90 |
| Flatsedge | 100 | 100 | 100 | 100 | 90 | 100 | 100 | 100 | 40 | 100 | 90 | 80 | 90 | 100 | 90 | 100 | 100 | 100 | 100 | 100 |

Rate 500 g/ha
COMPOUND

| | 86 | 87 | 88 | 89 | 90 | 91 | 92 | 93 | 95 | 96 | 97 | 98 | 99 | 100 | 101 | 102 | 103 | 104 | 105 |
|---|---|---|---|---|---|---|---|---|---|---|---|---|---|---|---|---|---|---|---|
| Barnyardgrass | 100 | 100 | 100 | 100 | 100 | 100 | 100 | 70 | 100 | 100 | 100 | 50 | 60 | 60 | 90 | 0 | 40 | 0 | 60 |
| Ducksalad | — | 100 | 60 | 90 | 90 | 70 | 100 | 100 | 100 | 100 | 0 | 0 | 40 | 100 | 0 | 90 | 0 | 0 |
| Rice | 20 | 80 | 70 | 40 | 20 | 40 | 30 | 80 | 90 | 60 | 20 | 50 | 80 | 80 | 90 | 0 | 20 | 0 | 30 |
| Flatsedge | — | 100 | 100 | 100 | 100 | 100 | 100 | 100 | 100 | 100 | 90 | 90 | 100 | 90 | 100 | 60 | 100 | 0 | 90 |

Rate 500 g/ha
COMPOUND

| | 106 | 107 | 108 | 109 | 110 | 111 | 112 | 113 | 114 | 115 | 116 | 117 | 118 | 119 | 120 | 121 | 122 | 123 |
|---|---|---|---|---|---|---|---|---|---|---|---|---|---|---|---|---|---|---|
| Barnyardgrass | 100 | 80 | 20 | 90 | 80 | 30 | 60 | 0 | 0 | 0 | 0 | 90 | 100 | 80 | — | 80 | 100 | 0 |
| Ducksalad | 100 | 70 | 0 | 90 | 70 | 0 | 30 | 0 | 0 | 0 | 0 | 100 | 100 | 100 | 100 | 90 | 60 | 70 |
| Rice | 90 | 20 | 0 | 20 | 80 | 0 | 70 | 0 | 0 | 0 | 0 | 30 | 30 | 50 | 80 | 0 | 0 | 0 |
| Flatsedge | 100 | 100 | 90 | 100 | 100 | 90 | 100 | 0 | 0 | 0 | 0 | 100 | 100 | 100 | 100 | 100 | 100 | 90 |

Rate 500 g/ha
COMPOUND

| | 124 | 125 | 126 | 127 | 128 | 129 | 130 | 131 | 132 | 133 | 134 | 135 | 136 | 137 | 138 | 140 | 141 | 142 |
|---|---|---|---|---|---|---|---|---|---|---|---|---|---|---|---|---|---|---|
| Barnyardgrass | 0 | 100 | 100 | 50 | 100 | 100 | 100 | 100 | 100 | 100 | 100 | 20 | 0 | 0 | 100 | 100 | 100 | 100 |
| Ducksalad | 80 | 100 | 100 | 80 | 100 | 90 | 100 | 100 | 80 | 100 | 100 | 0 | 0 | 0 | 100 | 95 | 100 | 100 |
| Rice | 0 | 60 | 60 | 0 | 70 | 35 | — | 90 | 90 | 90 | 0 | 0 | 0 | 0 | 70 | 50 | 35 | 55 |
| Flatsedge | 90 | 100 | 100 | 90 | 100 | 90 | 90 | 100 | 90 | 100 | 100 | 0 | 0 | 0 | 100 | 95 | 95 | 95 |

| Rate 500 g/ha COMPOUND | | | | Rate 250 g/ha COMPOUND | | | | | | | | | | | | | | | |
|---|---|---|---|---|---|---|---|---|---|---|---|---|---|---|---|---|---|---|---|
| | 143 | 144 | 145 | 146 | 1 | 2 | 3 | 4 | 5 | 6 | 7 | 8 | 10 | 11 | 17 | 19 | 20 | 21 | 22 | 23 |
| Barnyardgrass | 100 | 100 | 100 | 100 | 30 | 0 | 100 | 0 | 70 | 60 | 100 | 40 | 40 | 30 | 0 | 0 | 100 | 50 | 100 | 100 |
| Ducksalad | 100 | 100 | 80 | 90 | 90 | 0 | 80 | — | 50 | 20 | 70 | 40 | 90 | 20 | 80 | 0 | 100 | 90 | 80 | 100 |
| Rice | 60 | 75 | 60 | 85 | 0 | 0 | 50 | 0 | 70 | 80 | 60 | 60 | 10 | 20 | 0 | 0 | 60 | 70 | 20 | 70 |
| Flatsedge | 100 | 95 | 95 | 95 | 100 | 100 | 100 | 60 | 100 | 90 | 90 | 100 | 100 | 90 | 80 | 0 | 100 | 90 | 100 | 100 |

Rate 250 g/ha
COMPOUND

| | 24 | 25 | 26 | 27 | 28 | 30 | 31 | 32 | 34 | 36 | 37 | 38 | 39 | 40 | 42 | 43 | 44 | 45 | 46 |
|---|---|---|---|---|---|---|---|---|---|---|---|---|---|---|---|---|---|---|---|
| Barnyardgrass | 100 | 100 | 80 | 60 | 40 | 100 | 90 | 100 | 80 | 100 | 100 | 100 | 100 | 100 | 100 | 100 | 100 | 100 | 50 |
| Ducksalad | 100 | 100 | 100 | 0 | 70 | 100 | 100 | 100 | 70 | 100 | 90 | 90 | 70 | 100 | 100 | 30 | 100 | 100 | 20 |
| Rice | 30 | 60 | 80 | 40 | 20 | 80 | 90 | 100 | 0 | 90 | 30 | 50 | 0 | 70 | 70 | 0 | 90 | 70 | 0 |
| Flatsedge | 100 | 100 | 95 | 100 | 100 | 100 | 100 | 100 | 90 | 100 | 100 | 100 | 100 | 100 | 100 | 100 | 100 | 100 | 90 |

Rate 250 g/ha
COMPOUND

| | 48 | 49 | 50 | 51 | 52 | 53 | 54 | 55 | 56 | 58 | 59 | 62 | 63 | 64 | 65 | 66 | 67 | 68 | 69 | 70 | 71 |
|---|---|---|---|---|---|---|---|---|---|---|---|---|---|---|---|---|---|---|---|---|---|
| Barnyardgrass | 100 | 100 | 70 | 90 | 70 | 70 | 20 | 100 | 30 | 0 | 0 | 20 | 70 | 80 | 100 | 100 | 100 | 100 | 100 | 100 | 0 |
| Ducksalad | 70 | 90 | 80 | 40 | 40 | 50 | 0 | 50 | 0 | 0 | 0 | 80 | 90 | 30 | 100 | 100 | 100 | 0 | 100 | 30 |
| Rice | 20 | 30 | 0 | 0 | 0 | 0 | 0 | 0 | 0 | 0 | 50 | 40 | 80 | 90 | 50 | 60 | 30 | 40 | 60 | 0 |
| Flatsedge | 100 | 100 | 90 | 100 | 100 | 90 | 0 | 90 | 90 | 0 | 0 | 90 | 100 | 100 | 100 | 100 | 100 | 100 | 90 | 100 |

TABLE C-continued

| | Rate 250 g/ha COMPOUND | | | | | | | | | | | | | | | | | | | | |
|---|---|---|---|---|---|---|---|---|---|---|---|---|---|---|---|---|---|---|---|---|---|
| | 72 | 73 | 74 | 75 | 76 | 77 | 78 | 79 | 80 | 81 | 82 | 83 | 84 | 85 | 86 | 87 | 88 | 89 | 90 | 91 | 92 |
| Barnyardgrass | 50 | 100 | 0 | 80 | 90 | 0 | 0 | 90 | 90 | 90 | 100 | 70 | 100 | 100 | 100 | 70 | 100 | 100 | 90 | 100 | 100 |
| Ducksalad | 90 | 100 | 0 | — | 80 | 0 | 0 | 90 | 100 | 90 | 90 | 100 | 100 | 100 | 100 | 50 | 60 | 40 | 90 | 90 | 100 |
| Rice | 40 | 50 | 0 | 30 | 80 | 0 | 0 | 20 | 70 | 80 | 60 | 70 | 30 | 80 | 0 | 20 | 30 | 20 | 0 | 20 | 30 |
| Flatsedge | 90 | 100 | 0 | 100 | 90 | 80 | 0 | 90 | 90 | 90 | 90 | 100 | 100 | 100 | 70 | 100 | 100 | 90 | 100 | 100 | 100 |

| | Rate 250 g/ha COMPOUND | | | | | | | | | | | | | | | | | | | |
|---|---|---|---|---|---|---|---|---|---|---|---|---|---|---|---|---|---|---|---|---|
| | 93 | 95 | 96 | 98 | 99 | 100 | 101 | 102 | 103 | 104 | 105 | 106 | 107 | 108 | 109 | 110 | 111 | 112 | 113 |
| Barnyardgrass | 60 | 100 | 100 | 30 | 20 | 0 | 50 | 0 | 20 | 0 | 20 | 90 | 70 | 0 | 70 | 70 | 20 | 20 | 0 |
| Ducksalad | 100 | 100 | 100 | 0 | 0 | 0 | 100 | 0 | 0 | 0 | 0 | 100 | 0 | 0 | 70 | 70 | 0 | 20 | 0 |
| Rice | 20 | 70 | 50 | 50 | 50 | 50 | 80 | 0 | 20 | 0 | 20 | 60 | 0 | 0 | 0 | 70 | 0 | 20 | 0 |
| Flatsedge | 100 | 100 | 100 | 90 | 100 | 70 | 90 | 30 | 100 | 0 | 90 | 100 | 60 | 30 | 80 | 100 | 90 | 100 | 0 |

| | Rate 250 g/ha COMPOUND | | | | | | | | | | | | | | | | | |
|---|---|---|---|---|---|---|---|---|---|---|---|---|---|---|---|---|---|---|
| | 114 | 115 | 116 | 117 | 118 | 119 | 120 | 121 | 122 | 123 | 124 | 125 | 126 | 127 | 128 | 129 | 130 | 131 |
| Barnyardgrass | 0 | 0 | 0 | 90 | 100 | 70 | 80 | 20 | 0 | 0 | 0 | 100 | 100 | 20 | 100 | 80 | 100 | 100 |
| Ducksalad | 0 | 0 | 0 | 100 | 100 | 90 | 100 | 60 | 30 | 60 | 40 | 100 | 100 | 50 | 100 | 90 | 90 | 100 |
| Rice | 0 | 0 | 0 | — | 20 | 50 | 30 | 0 | 0 | 0 | 0 | 40 | 20 | 0 | 30 | 0 | 80 | 80 |
| Flatsedge | 0 | 0 | 0 | 100 | 100 | 100 | 100 | 100 | 80 | 50 | 30 | 100 | 100 | 80 | 100 | 90 | 90 | 100 |

| | Rate 250 g/ha COMPOUND | | | | | | | | | | | | | | Rate 125 g/ha COMPOUND | | | | | |
|---|---|---|---|---|---|---|---|---|---|---|---|---|---|---|---|---|---|---|---|---|---|
| | 132 | 133 | 134 | 135 | 136 | 137 | 138 | 140 | 141 | 142 | 143 | 144 | 145 | 146 | 1 | 2 | 3 | 4 | 5 | 6 |
| Barnyardgrass | 100 | 100 | 100 | 0 | 0 | 0 | 100 | 100 | 100 | 100 | 100 | 100 | 85 | 100 | 80 | 0 | 80 | 0 | 70 | 20 |
| Ducksalad | 40 | 100 | 100 | 0 | 0 | 0 | 100 | 95 | 100 | 100 | 95 | 95 | 80 | 80 | 90 | 0 | 80 | 0 | 0 | 20 |
| Rice | 20 | 90 | 90 | 0 | 0 | 0 | 30 | 35 | 30 | 45 | 50 | 45 | 20 | 50 | 0 | 0 | 0 | 0 | 60 | 30 |
| Flatsedge | 90 | 100 | 100 | 90 | 0 | 0 | 100 | 95 | 95 | 95 | 95 | 95 | 95 | 95 | 100 | 90 | 100 | 0 | 90 | 90 |

| | Rate 125 g/ha COMPOUND | | | | | | | | | | | | | | | | | | | |
|---|---|---|---|---|---|---|---|---|---|---|---|---|---|---|---|---|---|---|---|---|
| | 7 | 8 | 10 | 11 | 17 | 19 | 20 | 21 | 22 | 23 | 24 | 25 | 26 | 27 | 28 | 30 | 31 | 32 | 34 | 36 | 37 | 38 |
| Barnyardgrass | 20 | 0 | 0 | 20 | 0 | 0 | 100 | 50 | 80 | 80 | 100 | 100 | 50 | 60 | 0 | 100 | 80 | 100 | 40 | 100 | 100 | 100 |
| Ducksalad | 0 | 20 | 20 | 20 | 70 | 0 | 100 | 90 | 80 | 80 | 100 | 100 | 80 | 0 | 0 | 100 | 90 | 80 | 50 | 90 | 80 | 90 |
| Rice | 20 | 0 | 0 | 0 | 0 | 0 | 20 | 20 | 20 | 20 | 20 | 20 | 40 | 40 | 20 | 20 | 60 | 30 | 0 | 80 | 0 | 30 |
| Flatsedge | 90 | 90 | 80 | 90 | 70 | 0 | 100 | 90 | 100 | 100 | 100 | 100 | 90 | 90 | 80 | 100 | 100 | 100 | 90 | 100 | 100 | 100 |

| | Rate 125 g/ha COMPOUND | | | | | | | | | | | | | | | | | | | |
|---|---|---|---|---|---|---|---|---|---|---|---|---|---|---|---|---|---|---|---|---|---|
| | 39 | 40 | 42 | 43 | 44 | 45 | 46 | 48 | 49 | 50 | 51 | 52 | 53 | 54 | 55 | 56 | 58 | 59 | 62 | 63 | 64 | 65 |
| Barnyardgrass | 80 | 100 | 100 | 80 | 100 | 100 | 20 | 40 | 100 | 40 | 20 | 60 | 30 | 0 | 50 | 30 | 0 | 0 | 20 | 40 | 80 | 80 |
| Ducksalad | 60 | 100 | 100 | 20 | 90 | 80 | 0 | 20 | 70 | 70 | 0 | — | 40 | 0 | 40 | 0 | 0 | 0 | 0 | 20 | 30 | 0 |
| Rice | 0 | 40 | 40 | 0 | 80 | 50 | 0 | 0 | — | 0 | 0 | 0 | 0 | 0 | 0 | 0 | 0 | 0 | 0 | 20 | 20 | 40 |
| Flatsedge | 100 | 100 | 100 | 100 | 100 | 100 | 90 | 90 | 100 | 90 | 90 | 90 | 90 | 0 | 90 | 80 | 0 | 0 | 90 | 100 | 100 | 100 |

| | Rate 125 g/ha COMPOUND | | | | | | | | | | | | | | | | | | | | | |
|---|---|---|---|---|---|---|---|---|---|---|---|---|---|---|---|---|---|---|---|---|---|---|
| | 66 | 67 | 68 | 69 | 71 | 72 | 73 | 74 | 75 | 76 | 77 | 78 | 79 | 80 | 81 | 82 | 83 | 84 | 85 | 86 | 87 | 88 |
| Barnyardgrass | 100 | 70 | 100 | 30 | 0 | 50 | 70 | 0 | — | 90 | 0 | 0 | 40 | 60 | 80 | 60 | 70 | — | 90 | 30 | 70 | 100 |
| Ducksalad | 90 | 90 | 100 | 0 | 20 | 80 | 90 | 0 | 80 | 80 | 0 | 0 | 30 | 100 | 90 | 30 | 40 | 90 | 100 | 0 | 50 | 10 |
| Rice | 0 | 40 | 30 | 20 | 0 | 20 | 20 | 0 | 0 | 40 | 0 | 0 | 20 | 50 | 0 | 30 | 20 | 0 | 60 | 0 | 20 | 20 |
| Flatsedge | 100 | 100 | 100 | 100 | 100 | 90 | 100 | 0 | 90 | 90 | 70 | 0 | 90 | 90 | 90 | 90 | 100 | 90 | 100 | 0 | 100 | 90 |

| | Rate 125 g/ha COMPOUND | | | | | | | | | | | | | | | | | | | | |
|---|---|---|---|---|---|---|---|---|---|---|---|---|---|---|---|---|---|---|---|---|---|
| | 89 | 90 | 91 | 92 | 93 | 95 | 96 | 97 | 98 | 99 | 100 | 101 | 102 | 103 | 104 | 105 | 106 | 107 | 108 | 109 |
| Barnyardgrass | 70 | 60 | 50 | 100 | 50 | 70 | 80 | 40 | 0 | 0 | 0 | 40 | 0 | 0 | 0 | 50 | 30 | 0 | 0 |
| Ducksalad | 0 | — | 0 | 100 | 90 | 90 | 90 | 0 | 0 | 0 | 90 | 0 | 0 | 0 | 0 | 0 | 0 | 0 | 0 |

TABLE C-continued

| | | | | | | | | | | | | | | | | | | | | |
|---|---|---|---|---|---|---|---|---|---|---|---|---|---|---|---|---|---|---|---|---|
| Rice | 0 | 0 | 20 | 0 | — | 20 | 0 | 20 | 50 | 50 | 50 | 80 | 0 | — | 0 | 0 | 60 | 0 | 0 | 0 |
| Flatsedge | 90 | 100 | 70 | 100 | 100 | 100 | 90 | 90 | 80 | 90 | 70 | 90 | 30 | 80 | 0 | 90 | 90 | 50 | 0 | 50 |

125 g/ha
COMPOUND

| | 110 | 111 | 112 | 113 | 114 | 115 | 116 | 117 | 118 | 119 | 120 | 121 | 122 | 123 | 124 | 125 | 126 | 127 |
|---|---|---|---|---|---|---|---|---|---|---|---|---|---|---|---|---|---|---|
| Barnyardgrass | 0 | 0 | 0 | 0 | 0 | 0 | 0 | 80 | 60 | 70 | 50 | 20 | 0 | 0 | 0 | 100 | 100 | 0 |
| Ducksalad | 20 | 0 | 0 | 0 | 0 | 0 | 0 | 100 | 60 | 20 | 100 | 0 | 20 | 20 | 20 | 95 | 100 | 0 |
| Rice | 30 | 0 | 0 | 0 | 0 | 0 | 0 | 30 | 0 | 40 | 20 | 0 | 0 | 0 | 0 | 10 | 20 | 0 |
| Flatsedge | 50 | 60 | 50 | 0 | 0 | 0 | 0 | 100 | 100 | 100 | 100 | 0 | 80 | 30 | 20 | 100 | 100 | 0 |

Rate 125 g/ha
COMPOUND

| | 128 | 129 | 130 | 131 | 132 | 133 | 134 | 135 | 136 | 137 | 138 | 140 | 141 | 142 | 143 | 144 | 145 | 146 |
|---|---|---|---|---|---|---|---|---|---|---|---|---|---|---|---|---|---|---|
| Barnyardgrass | 100 | 50 | 100 | 100 | 70 | 90 | 100 | 0 | 0 | 0 | 40 | 100 | 100 | 100 | 100 | 100 | 65 | 100 |
| Ducksalad | 70 | 30 | 90 | 100 | 20 | 100 | 90 | 0 | 0 | 0 | 20 | 75 | 95 | 90 | 75 | 50 | 25 | 65 |
| Rice | 30 | 0 | 20 | 15 | 20 | 70 | 60 | 0 | 0 | 0 | 0 | 30 | 25 | 25 | 30 | 20 | 0 | 50 |
| Flatsedge | 90 | 80 | 100 | 100 | 90 | 100 | 100 | 20 | 0 | 0 | 90 | 90 | 90 | 95 | 95 | 85 | 80 | 95 |

Rate 62 g/ha
COMPOUND

| | 1 | 2 | 3 | 4 | 5 | 6 | 7 | 8 | 10 | 11 | 17 | 19 | 20 | 21 | 22 | 23 | 24 | 25 | 26 | 27 | 28 | 30 | 31 | 32 |
|---|---|---|---|---|---|---|---|---|---|---|---|---|---|---|---|---|---|---|---|---|---|---|---|---|
| Barnyardgrass | 20 | 0 | 20 | 0 | 20 | 0 | 0 | 0 | 0 | 0 | 0 | 0 | 70 | 40 | 40 | 80 | 100 | 100 | 0 | 20 | 0 | 100 | 80 | 20 |
| Ducksalad | 60 | 40 | 20 | 0 | 0 | 0 | 0 | 0 | 0 | 30 | 0 | 100 | 80 | 50 | 50 | 60 | 100 | 0 | 0 | 0 | 70 | 70 | 50 |
| Rice | 0 | 0 | 0 | 0 | 20 | 0 | 0 | 0 | 0 | 0 | 0 | 0 | 0 | 0 | 20 | 20 | 0 | 30 | 0 | 0 | 0 | 0 | 30 | 0 |
| Flatsedge | 90 | 70 | 90 | 0 | 90 | 80 | 80 | 30 | 50 | 90 | 20 | 0 | 90 | 80 | 100 | 100 | 100 | 100 | 90 | 90 | 80 | 90 | 100 | 100 |

Rate 62 g/ha
COMPOUND

| | 34 | 36 | 37 | 38 | 39 | 40 | 42 | 43 | 44 | 45 | 46 | 48 | 49 | 50 | 51 | 52 | 53 | 54 | 55 | 56 | 58 | 59 | 62 | 63 |
|---|---|---|---|---|---|---|---|---|---|---|---|---|---|---|---|---|---|---|---|---|---|---|---|---|
| Barnyardgrass | 0 | 100 | 70 | 100 | 80 | 100 | 100 | 30 | 90 | 70 | 0 | 20 | 100 | 0 | 20 | 30 | 20 | 0 | 0 | 0 | 0 | 0 | 0 | 20 |
| Ducksalad | 20 | 80 | 20 | 50 | 20 | 90 | 100 | 0 | 50 | 50 | 0 | 0 | 50 | 0 | 0 | 20 | 20 | 0 | 0 | 0 | 0 | 0 | 0 | 20 |
| Rice | 0 | 30 | 0 | 20 | 0 | 20 | 20 | 0 | 80 | 0 | 0 | 0 | 20 | 0 | 0 | 0 | 0 | 0 | 0 | 0 | 0 | 0 | 0 | 0 |
| Flatsedge | 70 | 100 | 100 | 100 | 90 | 100 | 100 | 90 | 90 | 90 | 80 | 90 | 100 | 80 | 40 | 90 | 80 | 0 | 40 | 80 | 0 | 0 | 0 | 90 |

Rate 62 g/ha
COMPOUND

| | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|
| Barnyardgrass | 20 | 40 | 70 | 60 | 90 | 30 | 60 | 0 | 0 | 30 | 0 | 70 | 40 | 0 | 0 | 30 | 0 | 20 | 30 | 60 | 80 | 40 | 0 | 0 | 30 |
| Ducksalad | 0 | 0 | 30 | 50 | 100 | 0 | 100 | 0 | 40 | 70 | 0 | 70 | 30 | 0 | 0 | 0 | 80 | 80 | 20 | 40 | 90 | 90 | 0 | 0 | 0 |
| Rice | 0 | 0 | 0 | 20 | 20 | 0 | 20 | 0 | 0 | 0 | 0 | 0 | 20 | 0 | 0 | 0 | — | 0 | 0 | 20 | 0 | 30 | 0 | 0 | 0 |
| Flatsedge | 100 | 0 | 100 | 100 | 100 | 100 | 90 | 80 | 60 | 90 | 0 | 90 | 90 | 70 | 0 | 90 | 90 | 90 | 90 | 90 | 90 | 90 | 0 | 0 | 90 |

Rate 62 g/ha
COMPOUND

| | 89 | 90 | 91 | 92 | 93 | 95 | 96 | 97 | 98 | 99 | 100 | 101 | 102 | 103 | 104 | 105 | 106 | 107 | 108 | 109 | 110 |
|---|---|---|---|---|---|---|---|---|---|---|---|---|---|---|---|---|---|---|---|---|---|
| Barnyardgrass | 20 | 30 | 0 | 50 | 0 | 70 | 80 | 0 | 0 | 0 | 0 | 0 | 0 | 0 | 0 | 0 | 30 | 20 | 0 | 0 | 0 |
| Ducksalad | 0 | 80 | 80 | 80 | 0 | 70 | 80 | 0 | 0 | 0 | 0 | 0 | 0 | 0 | 0 | 0 | 0 | 0 | 0 | 0 | 10 |
| Rice | 0 | 0 | 0 | 0 | 0 | 0 | 0 | 0 | 0 | 0 | 0 | 0 | 0 | 0 | 0 | 0 | 20 | 0 | 0 | 0 | 0 |
| Flatsedge | 80 | 100 | 0 | 90 | 0 | 90 | 90 | 30 | 60 | 0 | 70 | 20 | 0 | 0 | 40 | 80 | 30 | 0 | 40 | 50 | |

Rate 62 g/ha
COMPOUND

| | 111 | 112 | 113 | 114 | 115 | 116 | 117 | 118 | 119 | 120 | 121 | 122 | 123 | 124 | 125 | 126 | 127 | 128 |
|---|---|---|---|---|---|---|---|---|---|---|---|---|---|---|---|---|---|---|
| Barnyardgrass | 0 | 0 | 0 | 0 | 0 | 0 | 40 | 50 | 30 | 20 | 0 | 0 | 0 | 0 | 65 | 35 | 0 | 40 |
| Ducksalad | 0 | 0 | 0 | 0 | 0 | 0 | 0 | — | 0 | 70 | 0 | 20 | 20 | 0 | 40 | 60 | 0 | 60 |
| Rice | 0 | 0 | 0 | 0 | 0 | 0 | 20 | 0 | 20 | 0 | — | 0 | 0 | 0 | 0 | 0 | 0 | 0 |
| Flatsedge | 50 | 20 | 0 | 0 | 0 | 0 | 100 | 0 | 0 | 90 | 100 | 0 | 30 | 0 | 100 | 100 | 0 | 90 |

TABLE C-continued

| | Rate 62 g/ha COMPOUND | | | | | | | | | | | | | | | |
|---|---|---|---|---|---|---|---|---|---|---|---|---|---|---|---|---|
| | 129 | 130 | 131 | 132 | 133 | 134 | 135 | 136 | 137 | 138 | 140 | 141 | 142 | 143 | 144 | 145 | 146 |
| Barnyardgrass | 30 | 90 | 100 | 40 | 90 | 100 | 0 | 0 | 0 | 0 | 50 | 70 | 80 | 55 | 100 | 30 | 75 |
| Ducksalad | 20 | 90 | 80 | 0 | 50 | 60 | 0 | 0 | 0 | 0 | 20 | 85 | 30 | 45 | 50 | 20 | 40 |
| Rice | 0 | 50 | 0 | 0 | 60 | 0 | 0 | 0 | 0 | 0 | 0 | 0 | 0 | 0 | 20 | 0 | 15 |
| Flatsedge | 70 | 90 | 90 | 90 | 100 | 90 | 0 | 0 | 0 | 90 | 90 | 90 | 95 | 90 | 85 | 40 | 60 |

| | | | | | | Rate 16 g/ha COMPOUND | | | | | | |
|---|---|---|---|---|---|---|---|---|---|---|---|---|
| | | | 10 | 24 | 30 | 42 | 91 | 130 | 131 | 24 | 30 | 42 | 91 | 130 | 131 |
| | Barnyardgrass | 0 | 100 | 80 | 70 | 0 | 70 | 60 | 80 | 60 | 50 | 0 | 50 | 50 |
| | Ducksalad | 0 | 50 | 50 | 90 | 0 | 70 | 70 | 50 | 0 | 80 | 0 | 20 | 20 |
| | Rice | 0 | 20 | 0 | 0 | 0 | 0 | 0 | 20 | 0 | 0 | 0 | 0 | 0 |
| | Flatsedge | 30 | 100 | 90 | 100 | 0 | 100 | 90 | 100 | 90 | 100 | 0 | 90 | 90 |

Test D

Four plastic pots (ca. 16-cm diameter) per rate were partially filled with sterilized Tama silt loam soil comprised of a 35:50:15 ratio of sand, silt and clay and 2.6% organic matter. Separate plantings for each of the four pots were as follows. Seeds from the U.S. of *Heteranthera limosa* (Hl), *Monochoria vaginalis* (Mv), *Ammania auriculata* (Aa), and *Sphenoclea zeylanica* (Sz) were planted into one 16-cm pot for each rate. Seeds from the U.S. of *Cyperus iria* (Ci), *Leptochloa fascicularis* (Li), one stand of 9 or 10 direct-seeded rice seedlings (*Oryza saliva* cv. 'Japonica—M202'; Oss), and one stand of 6 transplanted rice seedlings (*Oryza sativa* cv. 'Japonica—M202'; Ost) were planted into one 16-cm pot for each rate. Seeds from the U.S. of *Cyperus difformis* (Cd), *Alisma plantago-aquatica* (Ap), and *Scirpus mucronatus* (Sm) were planted into one 16-cm pot for each rate. Seeds from the U.S. of *Echinochloa crus-galli* (Ecg), *Echinochloa oryzicola* (Eor), *Echinochloa oryzoides* (Eoz) and *Echinochloa colonum* (Ecc) were planted into one 16-cm pot for each rate. Plantings were sequential so that crop and weed species were at the 2.0 to 2.5-leaf stage at time of treatment.

Potted plants were grown in a greenhouse with day/night temperature settings of 29.5/26.7° C., and supplemental balanced lighting was provided to maintain a 16-hour photoperiod. Test pots were maintained in the greenhouse until test completion.

Chemical treatments consisting of Compound 1 of Index Table A (Cmpd 1), daimuron (Cmpd D), quinoclamine (Cmpd Q) and combinations thereof were formulated in acetone. At time of treatment, test pots were flooded to 3 cm above the soil surface, treated by application of test compounds directly to the paddy water, and then maintained at that water depth for the duration of the test. Effects of treatments on rice and weeds were visually evaluated by comparison to untreated controls after 21 days. Plant response ratings are reported on a 0 to 100 scale; where 0 is no effect and 100 is complete control. ND means no data.

Colby's equation was used to calculate the expected additive herbicidal effect of the mixtures of Compound 1 with daimuron (Cmpd D) and quinoclamine (Cmpd Q). Colby's equation (Colby, S. R "Calculating Synergistic and Antagonistic Responses of Herbicide Combinations," *Weeds*, 15(1), pp 20–22 (1967)) calculates the expected additive effect of herbicidal mixtures, and for two active ingredients is of the form:

$$P_{a+b} = P_a + P_b - (P_a P_b / 100)$$

wherein $P_{a+b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

Plant response ratings and additive effects expected from the Colby Equation are shown in Table D.

TABLE D

Effect of Compound 1, Daimuron, Quinoclamine and Combinations for Controlling Weeds in Rice in Greenhouse Test*

| Application Rate (g/ha) | | | Oss | | Ost | | Sz | | Hl | | Mv | |
|---|---|---|---|---|---|---|---|---|---|---|---|---|
| Cmpd 1 | Cmpd D | Cmpd Q | Obs. | Exp. | Obs. | Exp. | Obs. | Exp. | Obs. | Exp. | Obs. | Exp. |
| 32 | 0 | 0 | 40 | — | 15 | — | 100 | — | ND | — | 100 | — |
| 64 | 0 | 0 | 40 | — | 0 | — | 100 | — | 40 | — | 100 | — |
| 125 | 0 | 0 | 70 | — | 0 | — | 100 | — | 90 | — | 100 | — |
| 250 | 0 | 0 | 100 | — | 20 | — | 100 | — | 100 | — | 100 | — |
| 500 | 0 | 0 | 100 | — | 60 | — | 100 | — | 100 | — | 100 | — |
| 0 | 500 | 0 | 0 | — | 0 | — | 20 | — | 30 | — | 30 | — |
| 32 | 500 | 0 | 0 | 40 | 0 | 15 | 100 | 100 | 0 | ND | 100 | 100 |
| 64 | 500 | 0 | 35 | 40 | 20 | 0 | 100 | 100 | 40 | 58 | 100 | 100 |
| 125 | 500 | 0 | 45 | 70 | 20 | 0 | 100 | 100 | 80 | 93 | 100 | 100 |

TABLE D-continued

Effect of Compound 1, Daimuron, Quinoclamine and Combinations for Controlling Weeds in Rice in Greenhouse Test*

| 250 | 500 | 0 | 65 | 100 | 40 | 20 | 100 | 100 | 100 | 100 | 100 | 100 |
| 500 | 500 | 0 | 85 | 100 | 50 | 60 | 100 | 100 | 100 | 100 | 100 | 100 |
| 0 | 0 | 500 | 0 | — | 0 | — | 0 | — | 0 | — | 0 | — |
| 32 | 0 | 500 | 20 | 40 | 0 | 15 | 100 | 100 | ND | ND | 100 | 100 |
| 64 | 0 | 500 | 45 | 40 | 20 | 0 | 100 | 100 | ND | 40 | 100 | 100 |
| 125 | 0 | 500 | 65 | 70 | 20 | 0 | 100 | 100 | 85 | 90 | 100 | 100 |
| 250 | 0 | 500 | 85 | 100 | 30 | 20 | 100 | 100 | 100 | 100 | 100 | 100 |
| 500 | 0 | 500 | 100 | 100 | 70 | 60 | 100 | 100 | 100 | 100 | 100 | 100 |

| Application Rate (g/ha) | | | Aa | | Lf | | Ci | | Sm | | Cd | |
|---|---|---|---|---|---|---|---|---|---|---|---|---|
| Cmpd 1 | Cmpd D | Cmpd Q | Obs. | Exp. | Obs. | Exp. | Obs. | Exp. | Obs. | Exp. | Obs. | Exp. |
| 32 | 0 | 0 | 85 | — | 90 | — | 95 | — | 60 | — | 100 | — |
| 64 | 0 | 0 | 95 | — | 100 | — | 100 | — | 100 | — | 100 | — |
| 125 | 0 | 0 | 100 | — | 100 | — | 100 | — | 100 | — | 100 | — |
| 250 | 0 | 0 | 100 | — | 100 | — | 100 | — | 100 | — | 100 | — |
| 500 | 0 | 0 | 100 | — | 100 | — | 100 | — | 100 | — | 100 | — |
| 0 | 500 | 0 | 0 | — | 0 | — | 0 | — | ND | — | 60 | — |
| 32 | 500 | 0 | 95 | 85 | 98 | 90 | 98 | 95 | 95 | ND | 100 | 100 |
| 64 | 500 | 0 | 100 | 95 | 98 | 100 | 100 | 100 | 100 | ND | 100 | 100 |
| 125 | 500 | 0 | 100 | 100 | 100 | 100 | 100 | 100 | 100 | ND | 100 | 100 |
| 250 | 500 | 0 | 100 | 100 | 100 | 100 | 100 | 100 | 100 | ND | 100 | 100 |
| 500 | 500 | 0 | 100 | 100 | 100 | 100 | 100 | 100 | 100 | ND | 100 | 100 |
| 0 | 0 | 500 | 0 | — | 0 | — | 0 | — | 0 | — | 35 | — |
| 32 | 0 | 500 | 90 | 85 | 85 | 90 | 100 | 95 | 90 | 60 | 100 | 100 |
| 64 | 0 | 500 | 100 | 95 | 100 | 100 | 100 | 100 | 100 | 100 | 100 | 100 |
| 125 | 0 | 500 | 100 | 100 | 100 | 100 | 100 | 100 | 100 | 100 | 100 | 100 |
| 250 | 0 | 500 | 100 | 100 | 100 | 100 | 100 | 100 | 100 | 100 | 100 | 100 |
| 500 | 0 | 500 | 100 | 100 | 100 | 100 | 100 | 100 | 100 | 100 | 100 | 100 |

| Application Rate (g/ha) | | | Ap | | Ecg | | Eor | | Eoz | | Ecc | |
|---|---|---|---|---|---|---|---|---|---|---|---|---|
| Cmpd 1 | Cmpd D | Cmpd Q | Obs. | Exp. | Obs. | Exp. | Obs. | Exp. | Obs. | Exp. | Obs. | Exp. |
| 32 | 0 | 0 | 100 | — | 0 | — | 0 | — | 20 | — | 0 | — |
| 64 | 0 | 0 | 100 | — | 85 | — | 30 | — | 100 | — | 100 | — |
| 125 | 0 | 0 | 100 | — | 100 | — | 40 | — | 100 | — | 100 | — |
| 250 | 0 | 0 | 100 | — | 100 | — | 100 | — | 100 | — | 100 | — |
| 500 | 0 | 0 | 100 | — | 100 | — | 100 | — | 100 | — | 100 | — |
| 0 | 500 | 0 | 0 | — | 0 | — | 0 | — | 0 | — | 0 | — |
| 32 | 500 | 0 | 85 | 100 | 0 | 0 | 0 | 0 | 60 | 20 | 60 | 0 |
| 64 | 500 | 0 | 100 | 100 | 100 | 85 | 65 | 30 | 100 | 100 | 100 | 100 |
| 125 | 500 | 0 | 100 | 100 | 100 | 100 | 100 | 40 | 100 | 100 | 100 | 100 |
| 250 | 500 | 0 | 100 | 100 | 100 | 100 | 100 | 100 | 100 | 100 | 100 | 100 |
| 500 | 500 | 0 | 100 | 100 | 100 | 100 | 100 | 100 | 100 | 100 | 100 | 100 |
| 0 | 0 | 500 | 60 | — | 0 | — | 30 | — | 0 | — | 0 | — |
| 32 | 0 | 500 | 100 | 100 | 40 | 0 | 0 | 30 | 100 | 20 | 40 | 0 |
| 64 | 0 | 500 | 100 | 100 | 100 | 85 | 35 | 51 | 100 | 100 | 85 | 100 |
| 125 | 0 | 500 | 100 | 100 | 100 | 100 | 75 | 58 | 100 | 100 | 100 | 100 |
| 250 | 0 | 500 | 100 | 100 | 100 | 100 | 100 | 100 | 100 | 100 | 100 | 100 |
| 500 | 0 | 500 | 100 | 100 | 100 | 100 | 100 | 100 | 100 | 100 | 100 | 100 |

*Obs. is observed effect. Exp. is additive effect expected by calculation according to Colby, S. R. "Calculating Synergistic and Antagonistic Responses of Herbicide Combinations," Weeds, 15(1), pp 20–22 (1967).

As can be seen from the results listed in Table C for this test, mixtures of daimuron and quinoclamine with Compound 1 reduced phytotoxicity on direct-seeded rice (Oss), daimuron being more effective than quinoclamine in this regard. In contrast to the safening on rice, these combinations generally retain excellent effect for controlling weeds. The results suggest some synergism of mixtures of Compound 1 with daimuron on *Ammania auniculata* (Aa) and mixtures of Compound 1 with quinoclamine on *Ammania auriculata* (Aa) and *Scirpus mucronatus* (Sm). Mixtures of Compound 1 with daimuron showed synergism on all four Echinochloa species, *E. crus-galli* (Ecg), *E. oryzicola* (Eor), *E. oryzoides* (Eoz) and *E. colonum* (Ecc), while mixtures of Compound 1 with quinoclamine show synergism on two species, *E. crus-galli* (Ecg) and *E. oryzoides* (Eoz). The synergism on *Echinochloa* species with safening on direct-seeded rice is particularly surprising, as both *Echinochloa* species and rice are grasses.

What is claimed is:

1. A compound selected from Formula 1, an N-oxide or an agriculturally suitable salt thereof,

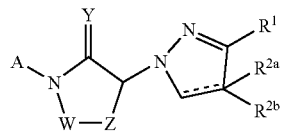

wherein:

A is an optionally substituted aryl or heteroaromatic ring, wherein the optional substituents are selected from halogen, cyano, $C_1$–$C_6$ alkyl, $C_1$–$C_4$ haloalkyl, $C_2$–$C_6$ alkenyl, $C_2$–$C_6$ alkynyl, $OR^8$, —$S(O)_kR^9$, —$C(O)R^{10}$, —$C(O)OR^{11}$ and —$C(O)NR^{12}R^{13}$; two substituents of the group A may combine to form a fused 5- or 6-membered saturated or partially saturated carbocyclic or heterocyclic ring, and said fused ring system is optionally substituted with one or more $R^7$;

Y is O or S;

Z is $CR^3R^4$;

W is $(CR^3R^4)_q$;

$R^1$ is H, $C_1$–$C_{12}$ alkyl, $C_1$–$C_{12}$ haloalkyl, $C_3$–$C_{12}$ cycloalkyl, $C_3$–$C_{12}$ halocycloalkyl, $C_4$–$C_{12}$ alkylcycloalkyl, $C_4$–$C_{12}$ alkylhalocycloalkyl, $C_1$–$C_{12}$ alkoxy, $C_1$–$C_{12}$ alkylthio, di-($C_1$–$C_2$ alkyl)amino, Cl, Br, I, —$C(O)R^5$, —$C(O)OR^5$, —$C(O)NR^5R^6$ or tri($C_1$–$C_4$ alkyl)silyl;

$R^{2a}$ is H, $C_1$–$C_4$ alkyl or $C_1$–$C_4$ haloalkyl; and $R^{2a}$ only exists when the carbon atom to which it is connected is a quaternary carbon center in which case the dotted line in Formula 1, together with the parallel solid line, represents a single bond;

$R^{2b}$ is H, $C_1$–$C_4$ alkyl, $C_1$–$C_4$ haloalkyl, $C_1$–$C_4$ alkoxy, $C_1$–$C_4$ haloalkoxy, F or Cl; or $R^1$ and $R^{2b}$ are taken together as —$C(R^3R^4)CH_2CH_2$—, —$C(R^3R^4)CH_2CH_2$— or —$(CH_2)_mO(CH_2)_t$—;

each $R^3$ and $R^4$ are independently H, $C_1$–$C_6$ alkyl or $C_1$–$C_6$ haloalkyl;

$R^5$ is $C_1$–$C_6$ alkyl, $C_2$–$C_6$ alkenyl, $C_3$–$C_6$ alkynyl, $C_3$–$C_6$ cycloalkyl or $C_1$–$C_6$ haloalkyl;

$R^6$ is H or $C_1$–$C_6$ alkyl;

each $R^7$ is independently $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, halogen, CN, $NO_2$ or hydroxy;

each $R^8$ is independently $C_1$–$C_4$ alkyl or $C_1$–$C_4$ haloalkyl;

each $R^9$ is independently $C_1$–$C_4$ alkyl or $C_1$–$C_4$ haloalkyl;

each $R^{10}$ is independently $C_1$–$C_4$ alkyl or $C_1$–$C_4$ haloalkyl;

each $R^{11}$ is independently $C_1$–$C_4$ alkyl, $C_1$–$C_3$ haloalkyl, $C_2$–$C_4$ alkenyl, $C_2$–$C_3$ haloalkenyl, $C_2$–$C_4$ alkynyl, $C_3$–$C_6$ cycloalkyl, $C_3$–$C_5$ halocycloalkyl, $C_3$–$C_6$ cycloalkenyl or $C_4$–$C_6$ cycloalkylalkyl;

each $R^{12}$ is independently H or $C_1$–$C_2$ alkyl;

each $R^{13}$ is independently $C_1$–$C_4$ alkyl; or $R^{12}$ and $R^{13}$ are taken together as —$(CH_2)_4$—, —$(CH_2)_5$— or —$(CH_2)_2O(CH_2)_2$—;

each k is independently 0, 1 or 2;

q is 1 or 2;

m is 0, 1 or 2;

t is 0, 1 or 2; and m+t is 2 or 3;

provided that:
(a) each position on the aryl or heteroaromatic ring A vicinal (ortho) to the point of attachment of the aryl or heteroaromatic ring to the Formula 1 backbone is independently substituted with fluorine or not substituted;
(b) when A is a phenyl ring with a fluorine substituent meta to the point of attachment of the phenyl ring to the remainder of the Formula 1 backbone, then attached at the other meta position of the phenyl ring is a substituent other than fluorine;
(c) when A is a phenyl ring with at least one —$C(O)NR^{12}R^{13}$ substituent, then the at least one —$C(O)NR^{12}R^{13}$ substituent is at a position other than meta to the point of attachment of the phenyl ring to the remainder of the Formula 1 backbone;
(d) when A is a phenyl ring, the position para to the point of attachment of the phenyl ring to the remainder of the Formula 1 backbone is unsubstituted or substituted by a substituent other than alkoxy,
(e) when A is a phenyl ring with a —$C(O)OR^{11}$ substituent at the position para to the point of attachment of the phenyl ring to the remainder of the Formula 1 backbone, then a substituent is attached to a position on the phenyl ring meta to the point of attachment of the phenyl ring to the remainder of the Formula 1 backbone;
(f) when A is a pyridine ring connected at the 2-position to the remainder of the Formula 1 backbone and methyl is at the 6-position of the pyridine ring, then the pyridine ring is substituted at the 4-position;
(g) when A is a pyrimidine ring connected at the 2-position to the remainder of the Formula 1 backbone, and when the 4-position of the pyrimidine ring is unsubstituted or is substituted with methyl, then the substituent at the 6-position of the pyrimidine ring is other than methyl, and when a methoxy substituent is at the 4-position of the pyrimidine ring, then the substituent at the 6-position of the pyrimidine ring is other than methoxy,
(h) when A is an isothiazole ring connected at the 5-position to the remainder of the Formula 1 backbone, then the isothiazole ring is substituted with a substituent other than alkyl;
(i) when $R^1$ is a $C_3$–$C_{12}$ alkoxy group, then the alkyl moiety of the alkoxy group is branched at the carbon atom attached to the oxygen atom; and
(j) when $R^{2b}$ is connected to a quaternary carbon center, then $R^{2b}$ is H, $C_1$–$C_4$ alkyl or $C_1$–$C_4$ haloalkyl.

2. The compound of claim 1 wherein A is substituted phenyl or 5 or 6-membered heterocyclic ring comprising 0–3 nitrogen atoms, 0–1 oxygen atoms and 0–1 sulfur atoms in said ring.

3. The compound of claim 2 wherein

A is

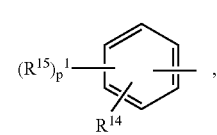

A¹

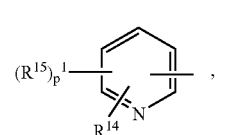

A²

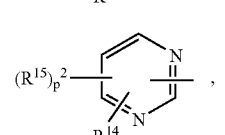

A³

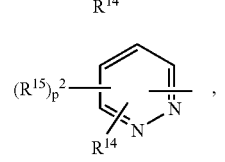

A⁴

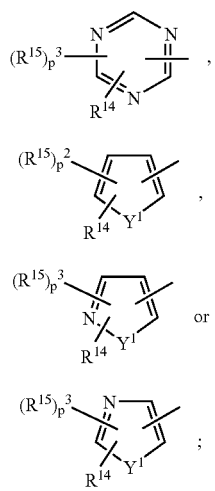

R$^{14}$ is H, halogen, cyano, C$_1$–C$_6$ alkyl, C$_1$–C$_4$ haloalkyl, OR$^8$, —S(O)$_k$R$^9$, —C(O)R$^{10}$ or —C(O)OR$^{11}$; such that R$^{14}$ is bound to a ring atom joined through one intervening ring atom to the ring atom linking the ring to the remainder of Formula 1;

each R$^{15}$ is independently halogen, cyano, C$_1$–C$_4$ alkyl, C$_1$–C$_4$ haloalkyl, C$_1$–C$_4$ alkoxy, C$_1$–C$_4$ alkylthio, C$_1$–C$_4$ haloalkylthio or C$_1$–C$_4$ haloalkoxy; or R$^{14}$ taken together with an adjacent R$^{15}$ is —(CH$_2$)$_3$—, —(CH$_2$)$_4$—, —O(CH$_2$)$_2$—, —O(CH$_2$)$_3$—, —S(CH$_2$)$_2$— or —S(CH$_2$)$_3$—, each optionally substituted with 1–3 substituents selected from CH$_3$, CH$_2$CH$_3$ and F;

Y$^1$ is O, S or N—H; such that when Y$^1$ is N—H, the H of N—H may be replaced by an R$^{14}$ or R$^{15}$ substituent selected from alkyl, or the H of N—H may be replaced by the bond linking the ring to the remainder of Formula 1;

p$^1$ is 0, 1, 2 or 3;
p$^2$ is 0; 1 or 2;
p$^3$ is 0 or 1;
provided that at least one R$^{14}$ or R$^{15}$ is other than H.

4. The compound of claim 3 wherein
Y is O;
Z is CH$_2$;
W is CH$_2$;
R$^1$ is C$_1$–C$_{12}$ alkyl or C$_3$–C$_{12}$ cycloalkyl;
R$^{2a}$ is H; and
R$^{2b}$ is H or C$_1$–C$_4$ alkyl.

5. The compound of claim 4 wherein the dotted line in Formula 1, together with the parallel solid line, represents a double bond; and
R$^{2b}$ is H.

6. The compound of claim 5 wherein
A is A$^1$, A$^2$ or A$^6$;
Y$^1$ is O or S;
R$^{14}$ is halogen, C$_1$–C$_6$ alkyl, C$_1$–C$_4$ haloalkyl, OR$^8$, —S(O)$_k$R$^9$, —C(O)R$^{10}$ or —C(O)OR$^{11}$;
R$^{15}$ is halogen, C$_1$–C$_4$ alkyl, C$_1$–C$_4$ haloalkyl, C$_1$–C$_4$ alkoxy, C$_1$–C$_4$ alkylthio, C$_1$–C$_4$ haloalkylthio or C$_1$–C$_4$ haloalkoxy;

or R$^{14}$ taken together with an adjacent R$^{15}$ is —(CH$_2$)$_3$—, —(CH$_2$)$_4$—, —O(CH$_2$)$_2$—, —O(CH$_2$)$_3$—, —S(CH$_2$)$_2$— or —S(CH$_2$)$_3$—, each optionally substituted with 1–2 CH$_3$, CH$_2$CH$_3$ or F; such that the left-hand bond is connected at the R$^{14}$ position and the right-hand bond is connected at the R$^{15}$ position;

p$^1$ is 0 or 1; and
p$^2$ is 0 or 1.

7. The compound of claim 6 wherein
R$^1$ is branched C$_3$–C$_8$ alkyl or C$_4$–C$_6$ cycloalkyl.

8. The compound of claim 7 wherein
R$^1$ is isopropyl, tert-butyl, sec-butyl or 3-pentyl.

9. The compound of claim 6 wherein
Y$^1$ is S; and
R$^{14}$ is Br, C$_1$–C$_6$ alkyl, CF$_2$H, CF$_3$, C$_1$–C$_4$ alkoxy, OCF$_3$, OCF$_2$H, —C(O)R$^1$ or —C(O)OR$^{11}$;
R$^{15}$ is halogen, C$_1$–C$_2$ alkyl or C$_1$–C$_2$ alkoxy;
R$^{10}$ is C$_1$–C$_2$ alkyl; and
R$^{11}$ is C$_1$–C$_2$ alkyl.

10. The compound of claim 9 wherein
R$^{14}$ is Br, C$_1$–C$_5$ alkyl, CF$_2$H, CF$_3$, C$_1$–C$_4$ alkoxy, OCF$_3$, OCF$_2$H or —C(O)OCH$_3$.

11. The compound of claim 10 wherein
R$^{15}$ is C$_1$–C$_2$ alkyl.

12. The compound of claim 11 wherein
p$^1$ is 0; and
p$^2$ is 0.

13. The compound of claim 6 wherein
R$^{15}$ is CH$_3$.

14. The compound of claim 13 wherein
p$^1$ is 0; and
p$^2$ is 0.

15. The compound of claim 6 wherein
A is A$^1$;
R$^{14}$ is C$_1$–C$_4$ alkoxy,
R$^{15}$ is CH$_3$, F, Cl or Br and is in the para position relative to the bond connecting A to the remainder of Formula 1; and
p$^1$ is 1.

16. The compound of claim 1 which is selected from the group consisting of:
(a) 3-[3-(1-dimethylethyl)-1H-pyrazol-1-yl]-1-[3-(trifluoromethyl)phenyl]-2-pyrrolidinone;
(b) 3-[3-(1,1-dimethylethyl)-1H-pyrazol-1-yl]-1-(3-methoxy-4-methylphenyl)-2-pyrrolidinone;
(c) 1-(4-chloro-3-methoxyphenyl)-3-[3-(1,1-dimethylethyl)-1H-pyrazol-1-yl]-2-pyrrolidinone; and
(d) 1-(4-chloro-3-methoxyphenyl)-3-[3-(1-ethylpropyl)-1H-pyrazol-1-yl]-2-pyrrolidinone.

17. A herbicidal composition comprising a herbicidally effective amount of a compound of claim 1 and at least one of a surfactant, a solid diluent or a liquid diluent.

18. A composition of claim 17 further comprising a herbicidally effective amount of daimuron.

19. A composition of claim 17 further comprising a herbicidally effective amount of quinoclamine.

20. A method for controlling the growth of undesired vegetation comprising contacting the vegetation or its environment with a herbicidally effective amount of a compound of claim 1.

* * * * *